US012343357B2

(12) United States Patent
Freier

(10) Patent No.: US 12,343,357 B2
(45) Date of Patent: Jul. 1, 2025

(54) COMPOSITIONS AND METHODS FOR MODULATING MECP2 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/408,920

(22) Filed: Aug. 23, 2021

(65) Prior Publication Data

US 2022/0226361 A1 Jul. 21, 2022

Related U.S. Application Data

(60) Division of application No. 16/535,888, filed on Aug. 8, 2019, now Pat. No. 11,129,844, which is a continuation-in-part of application No. 15/554,407, filed as application No. PCT/US2016/020610 on Mar. 3, 2016, now abandoned, said application No. 16/535,888 is a continuation-in-part of application No. 15/554,409, filed as application No. PCT/US2016/020771 on Mar. 3, 2016, now abandoned.

(60) Provisional application No. 62/127,693, filed on Mar. 3, 2015, provisional application No. 62/127,682, filed on Mar. 3, 2015.

(51) Int. Cl.

| | |
|---|---|
| ***C12N 15/113*** | (2010.01) |
| ***A61K 31/712*** | (2006.01) |
| ***A61P 25/22*** | (2006.01) |

(52) U.S. Cl.

CPC ............ *A61K 31/712* (2013.01); *A61P 25/22* (2018.01); *C12N 15/113* (2013.01); *C12N 2310/11* (2013.01)

(58) Field of Classification Search

None

See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,185,444 | A | 12/1993 | Summerton et al. |
| 5,276,019 | A | 1/1994 | Cohen et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |

(Continued)

FOREIGN PATENT DOCUMENTS

| | | |
|---|---|---|
| CN | 111150854 A | 5/2020 |
| WO | 1996018736 A2 | 6/1996 |

(Continued)

OTHER PUBLICATIONS

Crooke et al., "Pharmacokinetic Properties of Several Novel Oligonucleotide Analogs in mice" J. Pharmacol. Exp. Ther. (1996) 277, 923-937.

Oberhauser et al., "Effective incorporation of 2'-O-methyl-oligonucleotides into liposomes and enhanced cell association through modification with thiocholesterol" *Nucl. Acids Res.* (1992) 20, 533-538.

Oka et al., "An oxazaphospholidine approach for the stereocontrolled synthesis of oligonucleoside phosphorothioates" J Am Chem Soc (2003) 125: 8307-8317.

(Continued)

*Primary Examiner* — Sean McGarry

(74) *Attorney, Agent, or Firm* — McNeill PLLC

(57) ABSTRACT

Disclosed herein are compounds and methods for decreasing MECP2 mRNA and protein expression. Such compounds and methods are useful to treat, prevent, or ameliorate MECP2 associated disorders and syndromes. Such MECP2 associated disorders include MECP2 duplication syndrome.

25 Claims, 1 Drawing Sheet

Specification includes a Sequence Listing.

(56) References Cited

U.S. PATENT DOCUMENTS 5,403,711 A 4/1995 Walder et al.
5,405,938 A 4/1995 Sumerton et al.
5,405,939 A 4/1995 Suhadolnik et al.
5,432,272 A 7/1995 Benner
5,434,257 A 7/1995 Matteucci
5,446,137 A 8/1995 Maag et al.
5,453,496 A 9/1995 Caruthers et al.
5,455,233 A 10/1995 Spielvogel et al.
5,457,187 A 10/1995 Gmelner et al.
5,457,191 A 10/1995 Cook et al.
5,459,255 A 10/1995 Cook et al.
5,466,677 A 11/1995 Baxter et al.
5,466,786 A 11/1995 Burh et al.
5,470,967 A 11/1995 Huie et al.
5,476,925 A 12/1995 Letsinger et al.
5,484,908 A 1/1996 Froehler et al.
5,489,677 A 2/1996 Sanghvi et al.
5,491,133 A 2/1996 Walder et al.
5,502,177 A 3/1996 Matteucci et al.
5,508,270 A 4/1996 Baxter et al.
5,514,785 A 5/1996 Van Ness et al.
5,519,126 A 5/1996 Hecht
5,519,134 A 5/1996 Acevedo et al.
5,525,711 A 6/1996 Hawkins et al.
5,527,899 A 6/1996 Froehler
5,536,821 A 7/1996 Agrawal et al.
5,541,306 A 7/1996 Agrawal et al.
5,541,307 A 7/1996 Cook et al.
5,550,111 A 8/1996 Suhadolnik et al.
5,552,540 A 9/1996 Haralambidis
5,561,225 A 10/1996 Maddry et al.
5,563,253 A 10/1996 Agrawal et al.
5,565,350 A 10/1996 Kmiec
5,565,555 A 10/1996 Froehler et al.
5,567,811 A 10/1996 Mistura et al.
5,571,799 A 11/1996 Tkachuk et al.
5,576,427 A 11/1996 Cook et al.
5,587,361 A 12/1996 Cook et al.
5,587,469 A 12/1996 Cook et al.
5,587,470 A 12/1996 Cook et al.
5,591,722 A 1/1997 Montgomery et al.
5,594,121 A 1/1997 Froehler et al.
5,596,086 A 1/1997 Matteucci
5,596,091 A 1/1997 Switzer
5,597,909 A 1/1997 Urdea et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,065 A 4/1997 Cook et al.
5,623,070 A 4/1997 Cook et al.
5,625,050 A 4/1997 Beaton et al.
5,627,053 A 5/1997 Usman et al.
5,633,360 A 5/1997 Bishofberger et al.
5,639,873 A 6/1997 Barascut et al.
5,645,985 A 7/1997 Froehler et al.
5,646,265 A 7/1997 McGee
5,646,269 A 7/1997 Matteucci
5,652,355 A 7/1997 Metelev et al.
5,652,356 A 7/1997 Agrawal
5,663,312 A 9/1997 Chaturvedula
5,670,633 A 9/1997 Cook et al.
5,672,697 A 9/1997 Buhr et al.
5,677,437 A 10/1997 Teng et al.
5,677,439 A 10/1997 Weis et al.
5,681,941 A 10/1997 Cook et al.
5,698,685 A 12/1997 Summerton et al.
5,700,920 A 12/1997 Altmann et al.
5,700,922 A 12/1997 Cook
5,721,218 A 2/1998 Froehler
5,750,692 A 5/1998 Cook et al.
5,763,588 A 6/1998 Matteucci et al.
5,792,608 A 8/1998 Swaminathan et al.
5,792,847 A 8/1998 Burh et al.
5,801,154 A 9/1998 Baracchini et al.
5,808,027 A 9/1998 Cook et al.
5,811,534 A 9/1998 Cook et al.
5,830,653 A 11/1998 Froehler et al.
5,859,221 A 1/1999 Cook et al.
5,948,903 A 9/1999 Cook et al.
5,994,517 A 11/1999 Ts'O
6,005,087 A 12/1999 Cook et al.
6,005,096 A 12/1999 Matteucci et al.
6,166,199 A 12/2000 Cook et al.
6,300,319 B1 10/2001 Manoharan
6,426,220 B1 7/2002 Bennett et al.
6,525,191 B1 2/2003 Ramasamy
6,531,584 B1 3/2003 Cook et al.
6,582,908 B2 6/2003 Fodor et al.
6,600,032 B1 7/2003 Manoharan et al.
6,660,720 B2 12/2003 Manoharan
6,770,748 B2 8/2004 Imanishi et al.
7,015,315 B1 3/2006 Cook et al.
7,053,207 B2 5/2006 Wengel et al.
7,101,993 B1 9/2006 Cook et al.
7,262,177 B2 8/2007 Ts'o et al.
7,399,845 B2 7/2008 Seth et al.
7,427,672 B2 9/2008 Imanishi et al.
7,491,805 B2 2/2009 Vargeese et al.
7,547,684 B2 6/2009 Seth et al.
7,569,686 B1 8/2009 Bhat et al.
7,666,854 B2 2/2010 Seth et al.
7,687,616 B1 3/2010 Bentwich et al.
7,696,345 B2 4/2010 Allerson et al.
7,723,509 B2 5/2010 Manoharan et al.
7,741,457 B2 6/2010 Swayze et al.
7,750,131 B2 7/2010 Seth et al.
7,875,733 B2 1/2011 Bhat et al.
7,939,677 B2 5/2011 Bhat et al.
8,022,193 B2 9/2011 Swayze et al.
8,030,467 B2 10/2011 Seth et al.
8,080,644 B2 12/2011 Wengel et al.
8,088,746 B2 1/2012 Seth et al.
8,088,904 B2 1/2012 Swayze et al.
8,106,022 B2 1/2012 Manoharan et al.
8,124,745 B2 2/2012 Allerson et al.
8,153,365 B2 4/2012 Wengel et al.
8,178,503 B2 5/2012 Rigoutsos et al.
8,268,980 B2 9/2012 Seth et al.
8,278,283 B2 10/2012 Seth et al.
8,278,425 B2 10/2012 Prakash et al.
8,278,426 B2 10/2012 Seth et al.
8,440,803 B2 5/2013 Swayze et al.
8,501,805 B2 8/2013 Seth et al.
8,530,640 B2 9/2013 Seth et al.
8,546,556 B2 10/2013 Seth et al.
RE44,779 E 2/2014 Imanishi et al.
8,828,956 B2 9/2014 Manoharan et al.
9,005,906 B2 4/2015 Swayze et al.
9,012,421 B2 4/2015 Migawa et al.
9,127,276 B2 8/2015 Prakash et al.
9,290,760 B2 3/2016 Rajeev et al.
10,655,128 B2 5/2020 Krieg et al.
11,129,844 B2 9/2021 Freier et al.
2001/0053519 A1 12/2001 Fodor et al.
2003/0158403 A1 8/2003 Manoharan et al.
2003/0175906 A1 9/2003 Manoharan et al.
2003/0228597 A1 12/2003 Cowsert et al.
2004/0171570 A1 9/2004 Allerson et al.
2005/0130923 A1 6/2005 Bhat et al.
2006/0148740 A1 7/2006 Platenburg
2007/0009899 A1 1/2007 Mounts
2007/0031844 A1 2/2007 Khvorova et al.
2007/0134697 A1 6/2007 Khvorova et al.
2008/0039618 A1 2/2008 Allerson et al.
2009/0082297 A1 3/2009 Lioy et al.
2010/0190837 A1 7/2010 Migawa et al.
2010/0197762 A1 8/2010 Swayze et al.
2010/0247543 A1 9/2010 Maes et al.
2012/0171279 A1 7/2012 Karelson et al.
2013/0116301 A1 5/2013 Freier et al.
2013/0130378 A1 5/2013 Manoharan et al.

(56) References Cited

U.S. PATENT DOCUMENTS

| | | | | |
|---|---|---|---|---|
| 2013/0296400 | A1 | 11/2013 | Monia et al. | |
| 2014/0094504 | A1 | 4/2014 | Guiducci et al. | |
| 2014/0107330 | A1 | 4/2014 | Freier et al. | |
| 2015/0018540 | A1 | 1/2015 | Prakash et al. | |
| 2015/0099791 | A1 | 4/2015 | Krieg et al. | |
| 2015/0152410 | A1* | 6/2015 | Krieg | C07H 21/04 435/375 |
| 2015/0184153 | A1 | 7/2015 | Freier et al. | |
| 2015/0191727 | A1 | 7/2015 | Migawa et al. | |
| 2015/0267195 | A1 | 9/2015 | Seth et al. | |
| 2015/0275212 | A1 | 10/2015 | Albaek et al. | |
| 2018/0036335 | A1 | 2/2018 | Freier | |
| 2018/0044673 | A1 | 2/2018 | Zoghbi et al. | |
| 2018/0223282 | A1 | 8/2018 | Krieg et al. | |
| 2018/0320175 | A1 | 11/2018 | Lee et al. | |
| 2020/0095579 | A1 | 3/2020 | Lundberg et al. | |

FOREIGN PATENT DOCUMENTS

| | | |
|---|---|---|
| WO | WO 2000/015265 | 3/2000 |
| WO | WO 2005/116204 | 12/2005 |
| WO | 2006006948 A2 | 1/2006 |
| WO | WO 2009/027349 | 3/2009 |
| WO | WO 2010/105096 | 9/2010 |
| WO | 2011079307 A2 | 6/2011 |
| WO | WO 2011/071232 | 6/2011 |
| WO | 2013173635 A1 | 11/2013 |
| WO | WO 2013/173608 | 11/2013 |
| WO | WO 2014/052393 | 4/2014 |
| WO | 2014205445 A1 | 12/2014 |
| WO | 2015089419 A2 | 6/2015 |
| WO | 2016145014 A1 | 9/2016 |
| WO | WO 2016/141145 | 9/2016 |
| WO | WO 2016/141236 | 9/2016 |
| WO | WO 2016/149455 | 9/2016 |
| WO | WO 2017/015555 | 1/2017 |
| WO | 2017189308 A1 | 11/2017 |
| WO | WO 2019/157531 | 8/2019 |
| WO | 2020212448 A1 | 10/2020 |
| WO | 2020227406 A1 | 11/2020 |
| WO | 2021142342 A1 | 7/2021 |

OTHER PUBLICATIONS

Wan et al., "Synthesis, biophysical properties and biological activity of second generation antisense oligonucleotides containing chiral phosphorothioate linkages" Nucl Acid Res (2014) 42: 13456-13468.

Bennett et al., "Antisense oligonucleotides as a tool for gene functionalization and target validation" Biochim Biophys Acta (1999) 1489(1): 19-30.

Branch et al., "A good antisense molecule is hard to find," TIBS (1998) 23:45-50.

Chahrour et al., "MeCP2, a key contributor to neurological disease, activates and represses transcription" Science (2008) 320: 1224-1229.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Dastidar et al. "Isoform-specific toxicity of Mecp2 in postmitotic neurons: Suppression of neurotoxicity of neurotoxcity by FoxG1" J Neurosci. (2012) 32(8): 2846-2855.

Gould et al., "The Open Field Test" Mood and Anxiety Related Phenotypes in Mice (2009) 1-20.

Jin et al., "RNAi-induced down-regulation of Mecp2 expression in the rat brain" Int J Dev Neurosci (2008) 26(5): 457-465.

Jones et al., "Methylated DNA and MeCP2 recruit histone deacetylase to repress transcription" Nat Genet. (1998) 19: 187-191.

Na et al., "GABAA receptor antagonism ameliorates behavioral and synaptic impairments associated with MeCP2 overexpression" Neuropsychopharmacology (2014) 39(8): 1946-1954.

Nan et al., "Transcriptional repression by the methyl-CpG-binding protein MeCP2 involves a histone deacetylase complex" Nature (1998) 393: 386-389.

New England Biolabs 1998/99 Catalog (cover page and pp. 121 and 284).

Pandey et al. "Identification and Characterization of Modified Antisense Oligonucleotides Targeting DMPK in Mice and Nonhuman Primates for the Treatment of Myotonic Dysrophy Type 1" J Pharmacol Exp Ther. (2015) 355(2):329-340.

Ramocki et al., "The MECP2 duplication syndrome" Am J Med Genet A (2010) 152A: 1079-10188.

Reynolds et al., "Rational siRNA design for RNA interference" Nature Biotechnology (2004) 22(3):326-330.

Samaco et al., "Crh and Oprml mediate anxiety-related behavior and social approach in a mouse model of MECP2 duplication syndrome" Nat Genet (2012) 44(2): 206-211.

Sanghvi et al., "Heterocyclic Base Modifications in Nucleic Acids and Their Applications in Antisense Oligonucleotides" Antisense Research and Applications (1993) pp. 273-288.

Sztainbergt et al. "Reversal of phenotypes in MECP2 duplication mice using genetic rescue or antisense oligonucleotides" Nature (2015) 528:123-126.

Walf et al., "The use of the elevated plus maze as an assay of anxiety-related behavior in rodents" Nat Protoc (2007) 2(2): 322-328.

Weaving et al., "Rett syndrome: clinical review and genetic update" J Med Genet (2005) 42: 1-7.

Extended European Search Report for 16759471.2 dated Jul. 26, 2018.

International Search Report for PCT/US16/20610 dated May 20, 2016.

International Search Report for PCT/US2016/020771 dated Aug. 5, 2016.

Collins et al., "Mild overexpression of MeCP2 causes a progressive neurological disorder in mice" Hum Mol Genet (2004) 13: 2679-2689.

Crooke, St., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Gautschi et al., "Activity of a novel bcl-2/bcl-xLbispecific antisense oligonucleotide against tumors of diverse histologic origins" J. Natl. Cancer Inst. (2001) 93:463-471.

Maher et al., "Comparative hybrid arrest by tandem antisense oligodeoxyribonucleotides or oligodeoxyribonucleoside methylphosphonates in a cell-free system" Nucl. Acid. Res. (1988) 16(8):3341-3358.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Shao et al., "Antisense oligonucleotide therapy in a humanized mouse model of MECP2 duplication syndrome" Sci Transl Med (2021) 13: 1-11.

Shao et al., "Antisense oligonucleotide therapy for MECP2 duplication syndrome" Poster Presentation for Society for Neuroscience Annual Meeting 2019 (Oct. 19, 2019) Chicago, IL.

Shao et al., "Antisense oligonucleotide therapy for MECP2 duplication syndrome" Poster Presentation for BCM Graduate Symposium 2017 (Oct. 24, 2017).

Shao et al., "Testing the safety boundaries of MECP2 expression using Antisense Oligonucleotides" Poster Presentation for RNA & Oligocnucleotide Therapeutics (CSHL) 2017 (Mar. 29, 2017).

Shao et al., "Optimizing antisense oligonucleotide therapy in a mouse model that exclusively express two copies of human MECP2" Abstract for Systems Biology: Global Regulation of Gene Expression (CSHL) 2017 (Feb. 26, 2017).

(56) References Cited

OTHER PUBLICATIONS

Sztainberg et al., "Optimization of an antisense oligonucleotide therapy in a novel MECP2 duplication mouse model" Poster Presentation for Society for Neuroscience Annual Meeting 2016 (Nov. 12, 2016) San Diego, CA.
Woolf et al., "Specificity of antisense oligonucleotides in vivo" PNAS (1992) 89: 7305-7309.
Partial Search Report for 16759530.5 date Oct. 1, 2018.
Zhang et al., [Knocking down rat Mecp2 expression by RNAi] Beijing Da Xue Xue Bao Yi Xue Ban (2006) 38: 529-532.

* cited by examiner

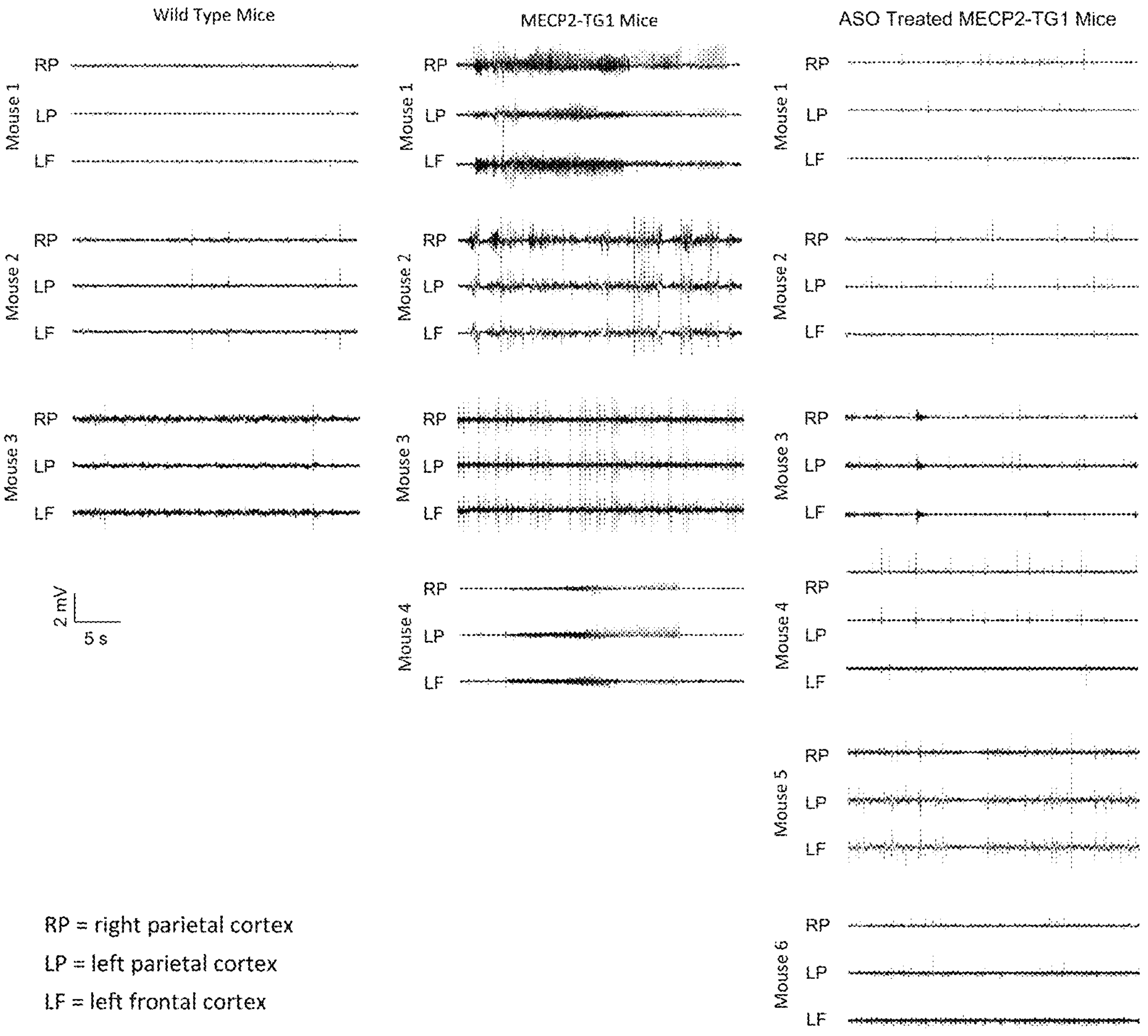
Wild Type Mice
MECP2-TG1 Mice
ASO Treated MECP2-TG1 Mice
Mouse 1
Mouse 2
Mouse 3
Mouse 4
Mouse 5
Mouse 6
RP
LP
LF
2 mV
5 s
RP = right parietal cortex
LP = left parietal cortex
LF = left frontal cortex

SEQUENCE LISTING

```
<160> NUMBER OF SEQ ID NOS: 328

<210> SEQ ID NO 1
<211> LENGTH: 80001
<212> TYPE: DNA
<213> ORGANISM: Homo sapiens

<400> SEQUENCE: 1

gctaccatca actctttctc ctagactgtt ccagggcctt gcaactagcc ttgtgctgta     60

gttttgtttc atcacgtcca gttctccact ctacacctgc aacatagatc agacagctcc    120

tggctcaaaa tcctctgagg gcttctcatc ttagaataaa ctctcggttc tggccgggtg    180
```

-continued

```
cggtggctta cgcctgtagt cccagcactt tgggagtccg aggcgggcgg atcacttgaa    240
ctcaggagtt tgagaccagc ctgggcaaca tggtgaactc ccatctctat caaaaataca    300
aaaacttagc caggcgtggt ggttcgcatc tgtggtccca gctacttagg acgctgagga    360
gggaggatcg cttgagctca gggtggacgt tgcagtgagc caagattgcg ccactgcact    420
gcagcctggg tgacagaatg agaccccatc cccacccccc ccaaaaaaga atgaactccc    480
agttctcata gtggccccag ctgcctttcc aatcacattc cctaccactc tccagcaaca    540
ctgacttcct cgttagtccc caacatgcca ggcatagtct ctcctcatgt cctttgaact    600
tgcctggaat gttctttccc cagatattca tatgagggag taaaatgagg gtgaaaacca    660
gcagatatct aaatagcacc cccttcactt agtttatctt tctcaaagcc cttatcacta    720
tgtgaaatga tatattatac ttatttgtat gctagtatga atcttcccgg caagaatgtt    780
agtttgctgt ctgttcagta ccgtgcatcc agagcctgga agagtgcctg gcacatagca    840
ggtagtcaat aaatgaatgg gggcaagcag ccaaatcaga atcaggtttt cttgctaagc    900
atagaactaa cagaaggatc attgaatgga ttggataatg actggcatca gggtaaggtc    960
cccttaacaa acactcctgt cctgaacacc tggttagcta acagttttct catactctta   1020
ttttcccaaa acacaattgc tggatctcag ctccaaatca actcttctag gaaagtgaaa   1080
aattgctgga tctcagctcc caaatcatat cttccaggca gagctaacat tgccccttat   1140
tcacacctcc accaaaccat ctgatccaac agtgacaggt gtcacgaggc cttggcatgc   1200
actctcttcc cccgccagag ttctgcgaaa gccagggttg cgatttgttg tcagtttatt   1260
ccccgcctct atgagagtgt gagcactggg caggctcgga tgaaataatg cattgagtag   1320
gcctctgaaa ccaaggcccc tcagctgggg caacgtcagg ctccagggtg ggcaactttg   1380
ctgcttctgc cgaagatagt gatattgaga aaatgtgggt gcaatgaaac gcttattgca   1440
gcgcactcgg tgcatctgtg gacagagggt caatcgcccc tcagagcagc gcaaacaggc   1500
gtcccaagcc taggccttca cttgccccag catccgcaag ggtccattaa tccttaacat   1560
tcaaattccg cccactaaac cagtccctcc gcgcccaagc cgcctctttt ccccaaacga   1620
cggccgaaag cagccaatca acagctggag gggtccgccc ccttttccct ggccgaaatg   1680
gacaggaaat ctcgccaatt gacggcatcg ccgctgagac ctccccccctc ccccgtcctc   1740
cccgtcccag cccggccatc acagccaatg acgggcgggc tcgcagcggc gccgagggcg   1800
gggcgcgggc gcgcaggtgc agcagcgcgc gggccggcca agagggcggg gcgcgacgtc   1860
ggccgtgcgg ggtcccggcg tcggcggcgc gcgcgctccc tcctctcgga gagagggctg   1920
tggtaaaagc cgtccggaaa atggccgccg ccgccgccgc cgcgccgagc ggaggaggag   1980
gaggaggcga ggaggagaga ctgtgagtgg gaccgccgtg gccgcgggcg gggacccttg   2040
ccggggggcg ggggtcaggg gcgggacgtg gcgcgggagg ggcccgcggg gtcggacgac   2100
acggctggcg gatggcgtcc ctcctctcta ccctccccct cccgccgccg ccggtggcga   2160
ctctcccctc ggcccgtcac ccgtgctcgc gggtgaccgt cctcggcgcg gcctccctgg   2220
agccgccttc gcctgacgcc cctcttcctc ccgccctcga cgcgcatccc ggcccccggc   2280
cccgcgggcg cccctgtcgc cggggttcgc ctgtcggggc tgcgcgcgct cctgcccttc   2340
tcggggcttt gggccgcggc gccgtcgcgc gcccgcggcc ccggcctctc cctggatcgc   2400
gctctccccc tccctccctc gcgcgccccc tctcccgtta ctcggccccc ccaccggcgc   2460
gcgtgcgcac ttcgcctccc gtcgggagag tgcgccacaa gggctcctga gctctcaccc   2520
```

-continued

```
ccatctctgg gctttgcctc cccctccttc tcgcccattc catgaatttc tgccccccgc   2580

taccccccccg cgagcgagta ggtccaccgg ctcctttccc catctagcag gaacaagtag   2640

gtggggatta ttatccacaa aagggactag acattgtgtt ctgggtccca caactcatca   2700

taaagaggtg gttatagttc ccatcaggag ccgtgggtag ggactgtgc gtccagcagc   2760

acccgaggct cttcggcgcc agaggctcta aggtgcgagc gtgtccccag ggtgctcaga   2820

ggttctttgg agtgctgtgg cctcggaatg tgagcaccct cccatcctac cctccccttc   2880

gccggcgatc ttccagttac ataagtggag tgggacatag taggtaacgg gctctcatcg   2940

ccctggagcg ctcgggatca ccggtaccag atggggcaag ttcatcgcga cgctgtggct   3000

cctgttaatt gtgcctgaaa ggttatcctc tgttcagttt ggtcatgacc gaatcaccca   3060

aactgaaact cagatgactt ttatatggca gtggcaatgt ttctgtggtt ttgcactaaa   3120

gacttaaggt cattatgaag agtgtaaaag gattgctgtc gcaggggaga ccgtttatga   3180

cattgctaag tatggacccc gagggggaaa aagctcattc tggaattgct ctgtggcggt   3240

tgcttctgtt gcgagtgtgt tcgggtgtgg gttggtcaca gcagaaatgg gctccaccac   3300

aaaattgata ttcctgactc atggtcaggc agatgtgtgc ttctggttat ttttccagga   3360

acaggaatgg gctctgccga gcctttcaca cgttgtgtct ctgctgtgcg ggatcagtac   3420

cccagactgt gagataacag gatcgaattc aggggttggt tggtgatcca ggaaccatac   3480

ctacttggat gtgatactga gtggcctaga cgttgtagga ctctcataag ttttagacat   3540

tttgttatac tgtaaaaatg aagcatatac ggcctcagta gtaacattgc actaataggt   3600

aattattact ctagagaatt ttgggttcca tggctggaat gttcatcagt atctcagcaa   3660

tttcagttaa taaccagatt aagctgacct cttgagtctt ttgaaatctg ctgggtccct   3720

ataataagac agggtctgga tttttaatc ttttgggaat ttccaccaag gatttaggga   3780

aataggcttt tatgggcttt tcaggatttc tatttcaaat cccaatgagg aagtctagga   3840

aacacttgct tttattttct tgcctgaata tgtcagaacc ttaaatcacc caatcaatct   3900

agaagtacta cagttgatta aagtaagtca ccacaggtca cccattcgtg gcaggtcagc   3960

taggtggctg atcactggaa tacagtcata tccccaggca tacacacgag cctcacttga   4020

cgatcccaaa gtttgtacat ctgagcttga gacgtgacaa gttgaggtct ctgctttgtt   4080

cttcatagtt ggcagtttgt ctcctcgggt gcccctccgg ttagctgttt atcatacgtc   4140

tagccctatc aacagtgcag gcagcttcca gagtatagtt ttctctgcaa agtgcctggt   4200

ggaggggtac ctccttttcc attgtcctaa tggctccact gggcttccat accagccctt   4260

tccagtgtct taacagctca aagaaaccca tctgtggctt tcttgttagc actggcctat   4320

cacaccttcc tattgcctgt taactaaaat tttgcctgga atgctttaag cttagagtac   4380

tgggtctttg tttcacccga ttgataggag agtgtcatgc agtcagccga actccgactt   4440

ctgtgctgtt taaatcctta ggtaggtctg gggcaaggca caaaccactg tgtattcaaa   4500

gggttatggt gcttgcattc tgtgtgtata tgtttgtaat ttccaaccag agtcgtttcc   4560

cgtgcctgcc ctgcctctgt gcaatctagt ctagtagggt agggaggcaa gctgtggagt   4620

ttgaaaaaaa aaaaaaaagc tagatgagtt taataggctg ttacccccctc cagaacattc   4680

ctcccatgtg gagatgaaac gagaagttca tttctttaac ctaaaataaa gaacaacaga   4740

gataaaattg ttagttcctt attggagcct ggtttccatt gctaatgtac ctgcttggga   4800

ctctgcatga taaatgacgt gtcctggaac ctgaaatctt ttataaaggt taatatcagc   4860

agaaatcttt taattagcta agagcagctt gttctcaagc tgcccgagtt atcttggagg   4920
```

-continued

```
agagaatcac aggaaatgtt tgatatttct agtaaccagt gttttcagtg cgtggggtaa   4980
agcacactcc tagactggcc agtcccaaag agtgtggcag gacacctgct tgttttccct   5040
gccctctgct atggtgacat ccttgcagac cagtcttgcg tggctggcag acgcaatctt   5100
tttttcttgg gtagagcatt atcaccgctg cgatggaagg accttgtcct cggtgcctcc   5160
ataccagccc tttccagtga aactactgct gtcccggcaa gcccctgtgc gtgtgcatca   5220
ttccgggtag gacaagatgt gaacaggtcc ctcttctttg ggcttaagta gaagttgtgc   5280
tcttctgctt ttacctgtgt gctcttctgc ttttacctgt tctcttctgc ctttctcttg   5340
caagaaacct gtcgaaagct tgctttgcat gccattgctt aaatactttg atggtatgta   5400
tggtatgtgg gataactgag tgggagccgg aattgggggg tgggcagggc atccccaccc   5460
ccacccccac atcaaagggg gaatgaccat ttcgttagag aataaagcct gagtcttata   5520
acttcttcaa gcacatgtat gctgggtctc ctggcgtgtg aatgtgttcc cgctgtgctg   5580
tgtggctgtt ttgcagttac tgtagacact gtagtctggg ctctcattat tgcctctgaa   5640
gttgacagga ccaagcctta gtaaggatgc acttgtcttc ctagcccaag agctaggggt   5700
gttttatata tatattaact ttcttttttta gatttcataa actgctctca ttttctcttt   5760
tctttctttc tttttttttt tttttttttg agacagtctc actctgtcac ccatgctgga   5820
gtgcagtggc acgatctcag ctcactgcaa cctctgcctc ccgggctcaa gcagttctct   5880
gcctcagcct cccaagtagc tgggattaca ggcacctgcc accacgcctg gctaattttt   5940
gtattttttt tttttttttt tttttttttt tagtcgagac ggggtttcac catcttggcc   6000
acgctggtct tgaactcctg acctcgtgat ccacccgctt cagcctccca aagtgcaggg   6060
attacaggcg tgagccaccg cacccagcct ctggctcttt tctttttgac atgaaatctt   6120
aagttaatta tcttaaactt taagaactag aaggattctt agtccagcac catcagttta   6180
caaacaaaaa aaacttgtgt ccctgagaag ttgtgacttt tccagggcct cctagccagg   6240
ataccagttt ggtttttatt atatagctag ccgagtaata ctattaactt gacttctggg   6300
atttcaaagt attctatgac ttgactgttt aagggaatta tgaggcctca ctgaacctca   6360
aaagataatt ttaggtacca tcctggtagc tgtagagcag caacagacca gtaaaagact   6420
tggttggtgt tgcccttctt ctgggtttga ttacatgagt aattgtgtga atagtctcta   6480
agttgtatgc tctgagcttt cgtttttagc ttataaaagt gctactcttg ggccagcata   6540
gtatcagaaa ttagctaatt catatggggc agtttaggct ttaactagga aatgatggtt   6600
atcttaatga caaaaaaggt actgacaaaa gtccttttttt gaacatgtgt tcaaaagaaa   6660
aagagaaact atcaaactaa taactgagtt tgttgaacat cgagattgac tgatctgaga   6720
ggcttaaaac tgattgccct gaaatagact tgcatgtttt ggatgatggc tttgggtctc   6780
ccagagcact tggtttccct tggtgctgat tttttctctc aggattaaag cccctttatg   6840
tgatgttgtt acagcagctt attgcaactt cattcagctg cttgaaaaag aagggagact   6900
gcctctaggt tccatgtgtt ctttcaggga tggtattttg atgttgcgta ttctcttgaa   6960
catgtattct tccctgagaa tttctgtgtg ccgtggtaga agaaatactt gccagaaatc   7020
gccactcatg gtatgctttt gtagtgtcga agtgtcccct agaggtgaca aggcttgtga   7080
tagtgttgat tctaacaagc atgaatcttt cctttatttt agcactgtgt gttacgtgcc   7140
agtaatttgc agcttatcct ttgtttctag ctaggtaagc tgggaaatag cctagtactt   7200
tgtctatgtg tttatcttca aaatgtccca aatagccctg ggaaaaaggt cgtgcagctc   7260
```

-continued

```
aatgggggct ttcaacttac aattttcttt gttttaggct ccataaaaat acagactcac   7320
cagttcctgc tttgatgtga catgtgactc cccagaatac accttgcttc tgtagaccag   7380
ctccaacagg attccatggt agctgggatg ttagggctca ggtaagtaac cttccttttt   7440
ttttttttag tatatgtcct ggtttggcca tctgtttttt ttttttttaa aaaaaaaaaa   7500
aaaaggaaaa gaggaaaaaa atatactact cttggacagt ataaaagtac cccaaagact   7560
aaagacataa ctgtgccaaa ctgtgccata taataaaaaa aagtcacttc cctgagccct   7620
gaaaggtcag tgtgtgtagg gttacttggt cgccacagcg tgatctgggg gcgggcgtca   7680
gattagagcc ggaactggtg atctgcaact tcagttcacc ttgaagcagg tcagctgagc   7740
tgagagcgct tgcactgagc ccttttgcgc tgctgctgtt gccttagcgg tcttcagcat   7800
gtgtttgctt tggtttgggg taaatggctt agtggtcaac attagtgagc agtggtaatg   7860
cattttcaga tatgggaact ggtatgtggt tggttcccta gaaggacacc ctcctgaaag   7920
ctgtctcaga acaccggggg ccatggctaa tgtcatgtgc ttgctacact cctcccatgg   7980
taactaaaga gagtacccag atatacatct ggttcttggg actctagagg aggatgagta   8040
ctttgtaaaa acctgggggc cccagtcatt ctaggtctga cactcaggtg ctgtatcagc   8100
tgcagtttga actacttggc accattgtgt ggactttagt tttgtaaaaa tgaatggttc   8160
cttaatttct caaccttcag gctcaacatc tcaagctgtt tgttgttgtt gttgttgttg   8220
ttgttttgtt ttgtcttttt gattagtggt cactccgcat ttgatgtttt gacatgtgga   8280
tttcagaact tctgtgtggt aaagcagaat gttccaattg aattttccca tttttttttcc  8340
cctaagcaaa aatgtgagtt ttcacttatg cggccattgt gattccgact gagaccctaa   8400
gtcgttcttt gttgtctctc tagtggtttc tgacacctca gtgtgaagct gttgtagaca   8460
tccataagaa atagcctgct tagggattat gtgagggcaa ggtttggctg aaggagaata   8520
gaaggtgtgg aaggaagcgg aagaccagaa gagcatcaca ctgcctcaag tcccaaattt   8580
gattctgctc ctgatcctgt gactcaaatt gtcattctct tttactgctg tggggtgtgc   8640
tctgggccca gctgacagga cattctttgt actccacgta tttatgctgg tgggagttgt   8700
atggctagtg ctttgtgctt tgtctcagaa attgtgtgga ctaaatgtaa tatgggcagt   8760
gaatgggttt cttctggaag atgttaggcc tggagggtgg tttgggtttt tacgagtctt   8820
tttctcagat tacagattac gaatggatgt tataaaacag gcagtgttga caccatacag   8880
tttctcctaa gaaatgtaca gagagttcaa cctgaggaag ctaattgaaa ataaactttt   8940
aaaaagaaat gtagaaagag gaaatttaaa aagtatctta tgaatgggaa agatgtagcc   9000
atttgagctt caaagaactt ttgagggaat tctcaaagga cagtacccgt ctttagtaga   9060
taaatgcttg atatctattt ttcttctttt actttttaaa gaattactaa aataatacat   9120
ggatttatag aaaaatcaaa ccacttaaaa attgatcagg tggctgggca aggtggctca   9180
tgcctgtaat cacagcgctt tgggaggcct aggcgggtgg atcacctgaa gtcaggagtt   9240
cgagaccagc ctggctaaca cggcgaaacc ccatctctat taaaaataca aaaattagct   9300
ggccatggtg gcttgagcgt gtagtcccag ctactcggaa ggctgaggca ggagaatcac   9360
ttgaacctgg gaggcggagg ttgcagtgag ccaagatcac accactgcac tcctgcctgg   9420
gtgacagagt gagactcggt ctcaaaaaaa aaaaaaaaaa aaagtatcag gtaaaaaaat   9480
gaaagctccc cgcttaatct ctgctcccac tacccagaat aactgctgtt aatagcttaa   9540
tgtagatcct tctaagtctt ctaagactaa actgtgtact ttttgtgttg taattaacag   9600
gagggttttt gttttgtttt gttttttctt tttttgagat ggagtcttgc tctgtcatcc   9660
```

-continued

```
aggctggagt acagtggcac aatcttggct cactgcaacc tccacctcct gggttcaagt   9720
gattctcctg cctcagcctc ctgagtagct gggattacag gcgcctgcca ccacacccag   9780
ctaatttttg tatttttagt agagatgggt ttcaccatgt tggccaggct ggtgtcgaac   9840
tcctgacctc aggcgatcca cctgccttgg cctcccaaag tgctgggatt acaggcgtga   9900
gccaccgtgc ctggcctcag gatggtgtta tatatacata ttctgcattt ttccatctca   9960
tatattcatc tctgcctcat ttcttttaaa tagcagtgta gtccagggct gacttaccgt  10020
catgcatttc gttgtctctc tatgttatta aaaatgctac aggattgaaa ttcctcatgt  10080
gccagtcatt ttgaagaatg gctgcctaga cttggaattt ctggtggata ccaccacatc  10140
actgtccaaa atggctatcc cagttcccac aacagtctga gaaagtgcca ttttcccata  10200
tcgtcccaga attggatata catcttttaa attggtgccg cttggattat tactgaggct  10260
aaacctcaat aatcattgtc atagctctta atgtattaaa gatgttaact ctttgtcatg  10320
cagatatttt cctgttttgt cttacgtctt gattcttgtc tttctgatat ataaaattta  10380
tgttatgatt tattcttttg ctttcatact taggaaatcc tttttactc ttttttttt  10440
ttttttttt tttttttgag acggagtctc gctctgtcgc ccaggttgga gtgcaatggc  10500
gtgatcttgg ctcactgcaa gctccatctc ccgggttcat tccattctcc tgcctcagcc  10560
tcccgagtag ctgggactac aggcgcccgc caccacgcct ggctaatttt tttgtatttt  10620
tagtagagac agggtttcac catgttagcc aggctggtct cgatctcctg accttgtgat  10680
ccgcccgtct ctgcctccca aagtgctggg attacaggcg tgagccaccg cgccccgcca  10740
ggaaatcctt tcctactctt aacaacagat caatagtcat ctatattttc ttcctaaaaa  10800
acctgatgat gtattatatt catacatacg tatttaatac atacaaaagg gccagatgcg  10860
gtggctcatg cctgtaatcc cagcactttg ggaggctgag gcgggtggat cacctgaggt  10920
caagagttca agaccagcct ggccaagatg gtgaaatccc gtctctacta aaaatacaaa  10980
aattagccag gcgtggtggc gggcacctgt aatctcaact actggggtga ctgaggcagg  11040
agaatcgctt gaacccagga ggcagaagtt tcggtgagcc aagatcacgc cactgcactc  11100
ctgcctgggc gatagagtga ggctctgtct caaaaataaa aaataaaaat aataatttta  11160
tagttaagtt gccctgtgtt tttcctgtga ttaaaaaaaa aaatacctgt tttgtattta  11220
actttggggt gggataaggt atagcccact tagtcagttg tgtctaagcc acttgatgaa  11280
ccagtcaatc cagtcttcac ctttaacaaa tgctgatttc ttcaagtgag caaaatatct  11340
cttaaacttt ttcctatttt ctctataaag ttgctttttt ctgaattttt tctttatgag  11400
gcttgatggg cagccctatc agcagacaat cattcattca cccaacaaat atttgagtat  11460
ctgcttcaag ccaggggcag tgctaagccc tggaagtggt atcttctcct tatccgggag  11520
tggggctaca gtgttcattc cagaagactc aagaaaatag cagatcatca caaaagtagg  11580
ttttacataa atgaggagga atccacaggg ttgtgtatat gtgtgtgtat tttaaattct  11640
gacataagtt ggagctttag ggtagactgt gacataagag tagtttgttt tccaactcat  11700
gtaattgccg gctgattttt gtcttgaatt atgataatgg taacttctgt tgaaacaatt  11760
ctgtattcat cttagcttgg ttgggatgca ataaaagttt tgtactggta aaaatgataa  11820
ttttcttcca tgatgatttt gaagcttttc tgtaacacct gataaaaata gaggggccag  11880
gcatggtggc tcatgcctgt agtcccagct actcgggagg atgaggtgag aggatcccat  11940
gagcccagga gttttaggct acagtgagcc atcatcacac cactgtactc ctgtactcta  12000
```

-continued gcctgggcag cctcgttctt tagagtaaga cactgtctct ttaaaaaaaa aaaaaaagaa 12060
aaaagaaaaa aagaaaaggc ttttagtgaa tatattttta gggtagcaag tgtaattttt 12120
ataaattgca ttatttgaat ctaataaata ccctcaaagc tgaagtcgaa ttctgatttt 12180
gattgaaaat attttttact taaaggaaga gggatagaat aaatgacacg attaaggaaa 12240
agacttcttg tataaggccg gggtttttta aatgattttt tgaatagtta gatggacaat 12300
acggaattaa aaaggtggtg taaaaagtta tacggggctg ggcacagtga ctcacgcctg 12360
caatcccagt actttgggag gccgaggtgg gtggatcacc tgaggtcagg agttcgagac 12420
cagcctagcc aacatgacga aacatcattt ctactaaaaa tacaaaaatt agctgggctt 12480
ggtggtatgc acctgtaatc cagctactcg ggaggctgag gcagaagaat cgtttgaacc 12540
caggaggcag aggttgcagt gagccaagat cgtgccattg cactccagcc tgggcgacag 12600
agtgagactc catctcagaa aaataataat agaaaaaagt tatatggggc tgggcatggt 12660
ggctcatgcc tgtaatccca gcagtttggg aggctgaggc agcttgatca cttgaggtca 12720
ggaattcgag actagcctgg ccaacatggt gaaactccgt ctccactaaa aatacaaaaa 12780
ttagccaagc gtggtggtgc gtgcctgtag tcccagctac ttgggaagct gaggcaggag 12840
aatcgcctga acctgggagg cagaggttgc agtgagccaa gatcatgccg ttgcactcca 12900
gcctggacga caagagcgga actccgtctc aaaaaaaaaa aaaaaagagt tatattgtaa 12960
agtatctctg ctaccctgcc ccaaacattc atttctttcc ctggaggcag ccactattac 13020
ctgtttcttt aaaaaaaaaa aaaaattgtg gccgggcacg gtggctcacg cctgtaatcc 13080
tagcactttg ggaggtggag gtgggtggat catgaggtca agagatcgag accatcttgg 13140
ccaacatggt aaaaccccat ctctactaaa aatacaaaaa attagccggg catggtggcg 13200
ggcacctgta gtcccagcta ctcgggaggc tgaggcagga gaatcgcttg aacctgggag 13260
gcagaggttg cagtgaactg agatcacgcc gctgcactcc agcctggcaa cagaatgaga 13320
ctccatctca aaaaaaaaag cgtgtgtgta cccgtgtgtt aaatttttat tataaaatat 13380
atataacagg ctgggcgtgg tggctcacgc ctgtaatccc agcactttgg gaggccgagg 13440
caggctgatc acgaggtcag gagatcgaga ccatcctggc gagcacggtg aaacctcgtc 13500
tttactaaaa atacaaaaaa ttagccgggc atggtggcgg gcgcctgtag tcccagctac 13560
tctgagagcc tgaggcagga gaatggcgtg aacccaggag gcggagcttg cagtgagccg 13620
agatcgcgtc actgcactcc agcctgggcg acagaccgag actccgtctc aaaaaatata 13680
tatcgatata tataacaatt tacagtttta atcatcttaa ctgtacagtt cagtggcact 13740
gagtacattc acattgttgt acagccatta ctaccatcca tctctacaac ctttcgtctt 13800
gcaaaactga aatttcatac ctattaaaca ctaactccca cttctcccct ttcccccacc 13860
ccaccctctg gcaactacta ttctactctt tgtctctatt ggacatattt ttgtgtgttt 13920
aggtttgtgt atatatttta catgtgtgta taaatacaca agggtatgtg ggcgttgtgt 13980
ttttacacat actataaaat attgtgcaca tttgtttatt ttaatgtatc ctgtagatta 14040
tttagaatcg gttcatacag agccgtatca ttccttttaa gggttgggtt taaatagtct 14100
gttatggatg taccacaatt tatttaacca gtttttaaat tttttactta ttttttttaa 14160
tgttttttta gagacaggat cccactccat cacccagact ggagtgcaac agcatgatca 14220
tagcttactg cagccttgaa ctccggggct gatgtgatcc tcccacctca ggctctcttg 14280
tagctgggac tacagggatg tgccgccatg cctggctaaa tttttttattt ttattttttat 14340
ttttattttt ggtagacacg gggtttcact gtgttgccca ggctggtctt gaactccttg 14400

-continued

```
ggcttgagta atcctcctgc cttggcctcc caaagtgccg agattacaac catgagccat  14460
ggagcccgac aagagtagcc ttttatttgc agaccattag agaaaaagtt gcgtgtaagt  14520
agataagcat acgaatttat cactgcaata ctgtttgtag agatcacaga gctgttaggc  14580
taggaagaag tttttagcag ttagcactag aaagcaaaac tttggaaact tccatttcat  14640
caaaagtgac ctcatctgag tagggcatgt gagggaagga cctttttact cgacaagggg  14700
aacttgccag ttcttgtttg tgaaccttga agaaagtgga gcatttttat tttgggacca  14760
ttctaggttg tggtagttcc ttggtactcg gggttggaga atctccctct gctgctggac  14820
cttctgcctc ctcatgctgt aatatgcata agaggtgtcc tagaagtatt caggaacagg  14880
ctgtggttgc tttgttgttc tgtgactgtt gaactcttta tatagcagta ctttttttaag  14940
ctgtactaat tgagcattta ttatgtgtca gttactgtgc tagctgctgg aaactatcct  15000
accctcagca gtcttctggt ctaatgggag gtacagacag gcaaatgggc tatgacttta  15060
caagaggcta acttctgtga tggagagaag ttccagccac taagggagca cataaaaatc  15120
agaggagatc ctaccaagaa ttgggaggta ggtcagggag gagacttctt tgaaaaatgg  15180
catctaagac ctgaacagca aggaaacatt agctaggtca aggacaaagc atcagtgggg  15240
agagatgcat gagtcttttg gaaggaccag catgtgtaga ggctctgaca ggagagaatc  15300
tctcaggccc attcagagag tccactgtgt gaagacgagg catgaacaac cagccaggac  15360
atgtggagag gagcattttt ctttttttct tttttctttc ttttttttt ttttttttt  15420
ttgagacgtc tttctctgtc acccaggctg gagtgcaatg gcatgatctc ggctcactgc  15480
aacccccact tccagggttc aagcaattct tctgccttag cctcccaagc agctaggatt  15540
acaggcaccc gccaccatgc ccggttaatt tttgtatttt tagtagagac ggagtttcac  15600
catgttggcc tcaaactcct gaccttaggt gatccacccg tctcggcctc ccagagtgct  15660
gggattacag gtgagagccc ccacgcccgg ccaggctcgg ctttctttcc aggccccgtc  15720
acactcttag atgttccctg ggccccagaa ggcagcgtga ggtgctctgc ccatctatgc  15780
tgtccttttc caccccaccc tatccactgg gcccctgggg ctcccactcc actccaggtc  15840
tcttcatgga cccttctttc ccttcacttc tgtcccagga gacctgggag actcatggga  15900
acaggcatca tcttctccag cacagttcat tgtctaatgc acgaaagtgc tgggctgtga  15960
gaaggtcagg agcttacatg gaatgggagt cagctgtggt acaaagtacg ctgcttagtt  16020
ctactgattt tttattttt atttttacat aagactttga tggtaaagga agcagtgtgt  16080
gagcaagctg actcctgtct tgtcaagtac caggtccact ctgatgagcc cctgtggaca  16140
gcactgctgt aactccccaa gcctgggctc aggaggtggg ccctaagcgc tgttcccagc  16200
tcttcctcca tgctgtcagc tcttccacca ttcttcctgg cgtcattcta aggtcctgtc  16260
ttcccccgcc ctcttccttc ctggcttcta cgctcagctc aagtagtagc tgtttgggta  16320
cttttcaccc agacttagga aatgttatca gttggtcgta ttcctgtcag ccctcttact  16380
atggaactca aataggacag attcagctga attcccagcc ctgtggttgc actctttgtc  16440
tgccctgctt ccccaaggta gcctgctccc taaaggtcac cgagatactc cccatgcaag  16500
gtttttgttg tattacacat gacaacatgg aataaagtgt tttgcaaatt tactggatga  16560
tatcctacta tgtggaacat cctacaactt actcttttca ctcaacattt gacttttgaa  16620
cctggtctgt attgctccgt gcagaccaat gttcattcat ttgatatgtc tccttgtgcc  16680
atagaaatag ttttacaata gaagcctgtc cagagccatg agggagaagg ggattgtaga  16740
```

-continued

```
gaaacaagga ttggcatctg gtttatgttt acatccttta gtcctgttaa ccgagaagaa  16800
gatattttta tttccatgtt tgcgaaagct ttccacaaaa aaaagcatcc attttctaga  16860
cttattaata gggcagtcca aaggttttat ttttagattt gaaagaaagc aaagtaggct  16920
tctgagatat gcacatttcc ctgtgtccct gtctcttttg caacattcca cattgctgct  16980
aaaacttgaa catgagcact ttcaagcatg tgcttacttt ctatgtatga ctcatttttt  17040
aaaacattaa agcatttcg gccgggtgtg gtggctcacg cctatattcc tagcacttta  17100
gaaggccgag gcgggtagat cacttgaggt caggagttca agaccagcct agccaatata  17160
gtgaaacccc atctccacta aaaatacaaa aattagccgg gcatggtggc gggcgcctgt  17220
aatcccagct actcgggagg ctgaggcagg agaattgctt gaacccagga ggtggaggtt  17280
gcagtgagca gagatcgagc cactgcactc tagcctaggt gacagagcga gactctgtct  17340
caaaaaaata aaaataaagc attaaagcac tttgtctggt ggtatgtaag ttttggcatt  17400
acttagataa gttgtatttt aagtctttct acacacaata acttattttt aaaatacaag  17460
tttctgtgta cttccgggtt ttgtgttttt gtaaacagca gaaggtatta gtccatatta  17520
agtactaatt tgttctaata ttttcagctg tttttggaat tacacttggc aaaaaaatag  17580
acaaatgtct gcagttgtga cagtttgttt ttttgttctt tttaactcca gaataaataa  17640
ttctagtgag tttttttctt ggcttgtaag aacatgggaa tgattagagt catcataaca  17700
cttaagtagt tatagaaggt tgaacatctg tagtcagttg tataaaattt cctagtcatc  17760
cttccaggtt gtttaagaca aacaaataca tagtatttat taagctctta taaattttaa  17820
ttgtaaaaca tcattgtaca aaactttgaa aatgcgtata ggtacaaaga taaaaaatta  17880
ggccaggcat gccatggctc acgcctgtaa tcccagcact ttgggaggcc aaggtgggag  17940
gatcttttga gcccaggagt tcaagaccag cctgagcaac atattgagac cctatctcta  18000
caaaaatatc ataaaacaaa atagaatcac tctggcgatt ccactatcca aaaaaaaaaa  18060
aaactgctgt taatatttgg tatgtatctt tctagaccaa ggcctccaac tttggttgag  18120
aattcagccg ggtctgtgac cttggatggg aaaaacattc actctttatt ttcactaatg  18180
tctctgaaaa cccagatttt tagctgggca tggtggctcg tgcctgtaat cccagtgctt  18240
tggaagcccg tggagggcag atcacttgag cccaggagtt tgagaccagc ctgggcaaca  18300
tagcaagacc ctgtctttta aaaaaaaaaa aaatccagcc gggtgtggtg gctcatgcct  18360
gtaatcccag cactttgaga ggctgaggca ggcagatcac ctgaggtcag gagtttgaga  18420
ccagcctgac caacatggtg aaatcctgtc tctactaaaa atacaaaaat cagccgggca  18480
tggtggtggg cgcctgtaat cccagctact ccggaggctg aggcaggaga atcacttgaa  18540
cccggaaggt agaggttgca gtgagccaag atcacaccat tgcactccag cctgggcgac  18600
agagcgagac tctgtctcaa aaaaaaaaaa aaaaatccac attttcttca atgacaattg  18660
taagcaacag atcatggtag tattagaata gcagtgactg tcaccagtag agatcaaaga  18720
tactttcata tcatattata gttgttacag atattttgaa atatatatgt ccatcactgc  18780
ttcaaactta aggtaattat tagacccatc tctagatctg gttatttaat gatttactga  18840
agaagcacat attatttgag aacgaactct tgaaatatgt tgttaatttc tgtgcatttt  18900
acacatttca aaacattctt ctgaggaggg gtccagaagg ccaaaagggt ccatggcaga  18960
aaaaggttaa gaacacctgt tctgtacttt gtaccatgtg gctacaaata taaaaacaga  19020
cgttaagccg ggtatggtga tgcacacctg tagttccacc tacttgggag gctgaggtgg  19080
gaaaatcact tgagcccagg agtttgaggc cagcctgggc aacagagcaa gaccccatct  19140
```

-continued

```
cttaaaaacc agtcagcact tgactagtca gttagtgggg gaaaacacag gtacagtaaa  19200
aggagtcaaa attacactta aacttaggtc atcttattat atcaaacatt tattaacatg  19260
tttagtgttt tgtgtatatt atgcaaagtg taatgcaact aaaactgttt aacacttctc  19320
gatatcacat aaatttgttg gtgcataata gcctaaaagt tacttttgct gttggcattt  19380
tattttatta cttacttatt tatttattta tttatttatt ttgagacaga gtcacactgt  19440
cgccaggctg gagtgcagtg gtgcgatctc agctcactgc aacctctgcc tccctggttc  19500
aagcgattct cccgcctcag cctcctgact agctgggact acaggtgcgc gccaccatgc  19560
ccagctaatt tttgtatttt tagtagagat agggtttcgc catgttggcc aggatggtct  19620
tcatctcttg accttgtgat ctgcccacct cggcctccca aagtgctagg attacaggca  19680
tgagccacca cgctgggcct gctgttggca ttttaaacat ccttctagag tctttcttat  19740
ttgcctgtaa gcacgtacac atgttgttgt tgttttgaga caaggtctgt cgcccaagct  19800
ggagcacagt ggtgcaatca cagctcacta cagcttcgac ctcttgggtg caagtgatcc  19860
tcccaatcag cctcccaagt aggtgggact acaggtgtcc gctaccatgc ccagctaatt  19920
tttgtatttt ttttgtagag acggagtttc accatgttgc ccagactggt ctcaaactcc  19980
tttgctcaaa cgatccttcc gcctcggcct cccaaagtgc cgggattaca agtgtgcacc  20040
tctgtgcctg gcccacatat tgttttagat gaatgagatc atatatgtac ttttgtaact  20100
tgctaccttt cctcaacaaa atgttgtaaa tatccatgtc cataaaaata gacgtatatc  20160
ttcacttttc cctaaaatga aaataactta acttgcattt tctttttgt ttttgttttt  20220
gttttgagac aggctcttgc tctgttgctc aggctggagt gcagtgatgt cacagctcac  20280
tacagcctcc acctccagtt tcaagtattc cacctacctc agcctccaag atagctaaga  20340
ctacaggcac atgtcacgac gcctggctaa tttttaaaat attttttgca gaaatgggat  20400
ttcactatgt tgcccaggct ggcctcaaac tgctggcctc aagtgatctt cctgccttgg  20460
cctcccaaag tgctgggatt acagtcgtga gccactgtgc ccagcctgca ttttcttatt  20520
ataaaagtaa tacatgttca atggacaaaa aattttcaga aaatatgcaa agatgaaaag  20580
taaaaattgt ccataaatct gtcatctaca gataaagata acttctggat aatgtttttc  20640
taccatcatt tttagtaatc acataacatt tcgttgtatg tctatgcctt catttaatta  20700
agaggcattt ccattatttc tgcatgttca tgactctgaa tgatgatatg tctgcctgct  20760
gatggctaca accctgtttc tgcatttcaa acctctctct tgagctccag atttgatggc  20820
ctcgtcagca tttacttgag ttgctcataa gtgtctcaaa tttaacaagt cccagtcttg  20880
atttttttcc cccttcaaac ctattcctca tgttgtctct atttcagtaa acaatatcaa  20940
catccaccca gttactcagt ccaaaattct aggagtcatc cttgattctg ctctttcttt  21000
tttttttttt ttttgagacg gagtctcgct ctgtcgccca ggccggactg cggactgcag  21060
tggcgcgatc tcggctcact gcaagctccg cttcccgggt tcacgccatt ctcctgcctc  21120
agcctcccga gtagctggga ctacaggcgc ccgccaccgc gcccggctaa ttttttgtat  21180
ttttagtaga gacggggttt caccttgtta gccaggatgg tctcgatctc ctgacctcat  21240
gatccacccg cctcggcctc ccaaagtgct gggattacag gcgtgagcca ccgcgcccgg  21300
cctctttttt ttttttgata cggagtctca ttctcgtcat ccaggctgga gtgcagtggt  21360
gcaatcttgg ctcactgcaa cctccgcctc ccgggttcaa gcaattcttc tgccccaacc  21420
tcctgagtag ctgggcctgg ctaatttttt gtatttttag tagagatggg gtttcaccat  21480
```

-continued

```
gttggccagg ctggtcctga actcctgacc ttgtgatccg cccacctcag cctcccaaag  21540
tgctgggatt acaggcgtga gccactgcac ccgccctgat tctgctcttt ctctcatcat  21600
ccctgatctg tcagcaagtc ctgttaggcc aaccacttct cagcatctgc actgccagta  21660
tgctagtcca agccacaaaa cacctctcag aggtacgcaa caggactttg ttgttgttgt  21720
gtgtgtgtgt gttttttttt tttttacggt agaattattt tataacttga agtgtaggga  21780
tgaccttcct tttaaaattt tatttatttt cttaattttt tattcccata gattttaggg  21840
gaacaggtgg tatttggtga catgagtaag ttctttaatg gtgatttctg agattttggt  21900
gcacccatca cccgagcagt gtacactgaa cccaatttgt agtcttttat ccctcacccc  21960
ctcccaccct ttccctcaag tccccaaagt ccattgtatc attctgatgc ctttgcatcc  22020
tcatagctta gctcccactt atgagtgaga acatacggtg tttggttttc cattcctgag  22080
ttacttcact tagaataata gtctctagtt ccatccaggt tgctgtgaat gccattaagt  22140
cattcctttt tatggctgag tagtattcct ttgtatatat atgccacaat ttctctattc  22200
actttctgat tgatgggcat ttgggctggt tctatatttt tgtaattgtg aattgtgctg  22260
ctataagcat gcgtgtgcaa gtatcattat gcaacgggac ttcggatgac atattgaaca  22320
acttcctcac tgatatcctt gtgaaacgct acatatttca tgggtctgtt tgttatacca  22380
acactcaatt ctgaatgatg gaattatttc acatttagtc tctttttcat ctagccatta  22440
tagtttagtt taaacaccaa gttccattcc tgctgcatgc tgaaggattt gcagtacatc  22500
aggctatagt ccatcaattc attccacaat tgagtaagta aggtatctat agtacctcag  22560
gccctgtgtt aggcagggat ggggtaacct agacagattt ggtacctgtc ctcatggagc  22620
ttgactttag cggcagagac agatcttaga taattgtacc agtacttaag tgttcagaag  22680
gacaagtatg gaggtgggag ccactccagt cctctacagt cacgtgctgc acaacaacgt  22740
ttcaaccgac aacagagcac acatacagtg gtgttcccat aagattagaa tgccatattt  22800
ttactgtacc ttttctatgt ttagatatac aaatacttac cattgtgttc cagtgatcta  22860
cagtattcag tatagtacca tgctgtacag ttttatagcc caggagcaat aggctatata  22920
ccgtatagcc taggtgtgta gtatgctaca ccatctagat ttgtgtaaga acactctctg  22980
atgttagcac aaataaatcg cccaatgaca catttctcag aacatatccc tgttgttgag  23040
cgactcatga ctgtacaatg ggggaacagc tcagcctgcc ttccccaagg aggcaacgcc  23100
gatgcaggga accgagggtt gaacagaagt gggcaaggtg cagagaggaa aaaggctttc  23160
cagatggaga agagcatgtg tgaaggccct cagtctggca agagcttagt cctgtgtggc  23220
aggagctgaa cgaggggtta ggggagagtg gcaaagggtc cgggccatca gagaggtcaa  23280
caggggctgg atcatgcagg attttgaatg ttaacatcag agcgatagaa aacatgaagg  23340
gtaaggtggt ttgggttttg aatttttatc aaaatattgc aactactcgg caacaagtta  23400
gatataacaa aagaggtcat cgtaaaaaca gcagtctacc ccttcccctt cccttccctg  23460
actcagacat gacagctttt aactgtttct gattttagtt cctttgatgg ttacctccaa  23520
aattaaatca tatgcttata catctttctt gatttgccaa ctttagggaa ctgtgttaac  23580
tccctgaaat gaaagagaat gacttagctt acgttacctc cccatgttga aattcatatt  23640
cacatttctc tgtaattttt tttttgagat ggagtctcac tctgtcgccc aggctggagt  23700
gcagtgatgt gatctcggct cactgaaacc tctgcctccc gggttcaagc aattctcgtg  23760
cctcagcctc ctgagtagct gggactacag gcgcacacca gtgcactggg ctaatttttg  23820
tatttttagt agaggcgggg tttcaccatg ttggccaggc tggtcttaaa ctcctgacct  23880
```

caggtgatct gcctgccttg gcctcccaaa gtgctgggat tacaggtgtg agctaccatg 23940
ccaagcccac atttctctgt aaattttaaa cagtatttta gtccatatgt cagttcccct 24000
ctttttaaga taaggatatt aataacccta cttttccttc cactttccct ccttaacttc 24060
tgcgtcttaa aagctgtact tgaccatacc cattcttgca tttgttaaca tgtgtgttct 24120
gccctgcaac cacagccaag ttgtagctta attctaaagt cgaaaataac attatttaca 24180
ttattacaca tgtgagtatt gttcttggcg agaccaaata atgaatgtgc ccaggattac 24240
atttccttct ttacagatct ggaccactca aaggagaatg accaatcaag gtcaaatgga 24300
ttccctttc ttagactctg tcacctgctt aaaatccttg ctaggattta atctacttca 24360
tattcaaacc ttggcttgct tatatagctc tttgttttgc ccaccatttc tagttgcctt 24420
tttattttgt ttactattcc tccttgatta tgttgtaaaa tgctattagc agtgctgttt 24480
atttcgtacg attcggcttt ttccccactg aagacctttc tcttggaagg cctctgccct 24540
tctgcaatct gggcaagtat ctgctctttg atttaaggtt gcatatacag ctgtacctgg 24600
accttctcct cactgggctc ttgggttgga gcccgtgtct taaaacccat atcttccttt 24660
cacatggttt actccctcgt tttctggact gcatccttaa ataatgtgct cagatagagt 24720
gcatggggag taaactgtag tggataccgt tgtcacctac cccatatcca tttcttcttt 24780
gcccattcct aacagaatcc tgatattatt cacctttcta ccttattccc aacttcagaa 24840
aggatcctta agtcattcca cacattgcat tcctttggca actgttactg gtcaaggatg 24900
gacatacgat ctaagttggt tcactcagac tgaagggaag gacttccatg gcacgttcag 24960
ggaagacttt ctctttttct ctcactggag taagtgagaa aggtgttgct gggggctctt 25020
ctgtaacctc agactgaggg acaaagcctg aggataaagc ctgctcacca aggaaggcgg 25080
agcagagaaa cgggaagaac ctgggtcttg atgccgttgc ttagctggtg attgcactgt 25140
ggctggggcc tgtcctacct gagctaggga ctcagatagg atggactttc ttactgaatg 25200
agccagcttc agttttcttt tctgttactt gtaaccaaaa gcattgtaac agataggtct 25260
tctgagtcac tgcatgcctg aaataccttt cttctactct tacacttgat tggctgagta 25320
tagggttcca agttgaaaat catttttct cctaactttg gaggcatctc ttctagtatg 25380
cagagtaaca aatgcaacaa atgcctgatg ccaatcttat tatggttctt ttgtaggtgc 25440
ccttcttttc tcttccttcc ctggaagttt ttaggatttc gtctccttat ttttagtgtc 25500
ctgaaatctc atgagaatat gtctagagtt gtgtcttgtt cactcgttgt actgtggtca 25560
ttcaatctga atacttttgt caactctttt ttttaaaaaa aaattactaa tttacatgct 25620
ttcattttct ctatggggac tactgtttaa ctttggacct cttatattgg tcttctgtct 25680
tctctcatat ttttcattta ttgggcggtg gggggtgctc tgaattttgg aagatctcct 25740
gcatttattt tctttttcct tttttctttt tttttgaggc agagtcttgc tctgtcaccc 25800
aggctggagt gcagtagcct gatctcggct cactgcaacc tctgccttcc aggttcaagc 25860
aattctgcct ctgcctccca cgtagctggg attacagacc tgcaccacca cgcccggcta 25920
atttttgtat ttttaataga gatggggttt caccatgttg ccaggctggt ctcgaactcc 25980
tgacctcaag tgatccgccc gcctcagcct cccaaagtgg tgtgagccac cgcacccagc 26040
ctcctgactt tattttctat cccttctgtt aaattcttta tttcagccaa accttttttt 26100
ttttttttt aacttactgt gaagcctgtg tgcctactgc ctagattaga caattgttaa 26160
cattttggcg tattttcctg gtctgtatag atagggtgca tttttatacc tttttgctca 26220

-continued

```
ccatttaaaa ggaactcaca gatgtcacga catttcaccc ctaagtactt cagtatacat  26280
ctcctaaaaa taaggacatt ttccaatata agcacaatac cccgatcaca tctttaaaag  26340
ttaacaataa ttctctaatg ttatcaggca cccactttaa attcagattt cctccaaatg  26400
tctcttatcg ctgttgaggg gctccaaagc aattaagatt tatacattgc atttgaatat  26460
gcttcctttg tctcttattt atttatttat tttattttga gacagagtct cgctgtctcc  26520
caggctggag tgcagtggtg tgatctcagc tcactgcaac ctccgccttc caggttcaag  26580
cgattctcct gcctcagcct cccaaatagc tgggattaca ggtacgcacc accacgccca  26640
gctaactttt ttgtattttt agtagagaca gggtttctac taaaccatgt tggccaggct  26700
ggttttgaac tcctgacctc aagtgatctg cccgcctcgg cctcccaaag ttctaggatt  26760
ataggcgtga gccaccatgc ccagcccctt tgtctctttt aacaagaaca gcctacccac  26820
ctctccttca cttgtgatac tgactttttg aagcagtcag cccaattgtc atctagaagg  26880
gcccacattt taagatacat atttttagag atggcgtgtc actatgttgc ctaggctggc  26940
cttgaactcc tggcctcaag taatcctcct gcctcagcct cccaggtagc tgggactaca  27000
ggcttgtgcc accacgacta gctggcccac attttagatg tctctctttt cttgtgatat  27060
aatttaactt gtttgtccat atatattact tgtagacaag aagttaggtc tacaggcatg  27120
ttcaggttaa acattttggg caagaatatt tcataggcag tactgtgtac ttcatatagc  27180
atcagctcac caggcactta atggttggtt accctgtggt ttgtgatgct acgttttaac  27240
acttgattaa agaaggaggt gactgccaaa tctccccatt gtagacatac agttttcctg  27300
tggtaattga tatataatct gtgatgtgat gctttggcac catacaaata tcctattgcc  27360
caacagccat ttgcataatt attttagcat tcattgatcc ttgcctgaaa ccattattac  27420
attgggggtt gcaaaatgat agttttttta attgtcacct cttctacatt tagtactgtc  27480
attcctctgt aatgaatttt ccctcatcaa ataaggaggc attatatttc ctcctaaaaa  27540
gacagtatag atgcttaatc tttgccttta ttacatttca gagtaaggag ttggtagaat  27600
aatcacctca aatggtggca aaatatttgc tgttgtgttt ccttttctct ttcatgtcaa  27660
tatggactca tagggattta tttattaaat gttttacaat tcaaattggg tcaacaagag  27720
tcccttcatg ttggttccta tattctcctg gcataccctc attaattagt ctttgagcaa  27780
tttcttgttt tctggcacaa gatattccat cccaatatgt gcttttcgtg tcctagaact  27840
gattccaagg agctctggtt ccttatagtg gcaacggtat ttagaatcca acatgtgggt  27900
actaaatgtg ctgattctta ctggggtaac attatatcta ggcactttca gaggacatcg  27960
ctagaaaata tattcagttt ttattttta tttttaattt ttttgtagag acaaggtctc  28020
actatgttgc ccaagctggt ttcgaactga gctcaagcga tcctcccacc tcagcctccc  28080
aaagtgctgg gattacatct gtcagggcaa actgctggta aatattttca caaaagaaaa  28140
ataaaaaaac caaagtgctg ggattacaga tgtgagccac tgtgccctcc attttttttt  28200
taagtcataa atacataatg atgtcttcta tggcaattta acattacagg gttcttcctt  28260
aacttttttt ttttttttc tttttttga ggcagggtct tgctctattg cccaggctgg  28320
agtggtgcag tggtacaatc ctaattcact gcagcttcaa atgcctaggc ttcaaacaat  28380
cctcctccct cagcctcccg agtagctaag actacaggtg catatcacca tgcccagcta  28440
atttttaaaa attttttgta gagatggggg gtctcgttgc gttgcccagg ctggtctcga  28500
actcctggcc tcaagtgatc ctcccatctc gatttcccaa agtgctggga ttacaggtgt  28560
gagccaccat gcctggccaa cttttatttg atctgtatat atcttttcct tacactgaaa  28620
```

-continued atgttgggtc ttactaatgt taacatagtt acttatttgc tttatcttgt aatagacata 28680
aaattacaaa attataatac caatattacg ataaatagct gggcatggcg gcgctcgcct 28740
gtagtcccag ctactcagga agctgaggtg gagggactgc ttgaacctaa gagtttgaag 28800
ctgcagtgag ctgtggttgt gccactgtac tcctacccgg acaacagagt gagtgggggg 28860
aaaaaaaaga aataatggaa gatccagaga aagccccaaa tatttaaaaa ttaaacaata 28920
cactttgcag cttcctcacc tctctcagcc ttcatagaat tgaagagagt tagggccttg 28980
cactagatta ggctttgcct taaggaaatg ttgtgtttga tttgatcttt tatccagacc 29040
attaaaactt ccttaacgtt tattagtaat aaggctattt cactttcata tcatttgtgt 29100
gttcactgga gtagcacttt tagtttcctt caagaacttt gattcacaac ttggctaact 29160
ttggtacaag aggcctagct tttggcttct cggctttcaa catgcctctc actaagcctg 29220
atcatttggt ttttggttta aagagaaaga catatgactc ttccttttac ttgaatgctt 29280
agaggccatt gtagggttat taattggcct aatttcagta ctgtcttgtc caagggaata 29340
gggaggccca aggagagaga gagagatggg ggaacagctg attggtggag tagtcagaat 29400
atacacattt atcacttaag ttttgccatc ttttcttttt ctttttcttt tttttttttg 29460
agacagtctt gctctgtcac ccaggctggc atgcagtggc atgatctcag ttcactgcaa 29520
cctctgcctc ctgggctcaa gcaattctcc tgcctcaacc tcccgagtag ctggtattac 29580
aagcgtgcgc caccataccc agctaatttt tatatttttt agtagagaca gggtttgcca 29640
tgttggccag gctggtctcg aattcctgac ctcaagtgat ccacccgcct tggcctccca 29700
aagtgcgggg attacaggcg taagccactg ccgcctggcc aagtttgcca ccttttttat 29760
ttttttattt ttttgagatg gagtctcact ccatcaccca ggctggagtg cagtgatgca 29820
atctcggctc actgcagtct ctgcctcctg gattcaagcg attctcctgc ctcagcctcc 29880
cgagtagctg ggactacagg catgtgccag cacgcccagc ttgttttttg tatttttagt 29940
agagacgggg tttcaccatg ttggccaggc tggtctccaa ctcctgacct caggtgatct 30000
gcccggctca gcctcccaaa gtgctgggat tacaggcgtg agccaccccg cccggccaag 30060
tttgccatct tttatgggtg cagtttgtgg tgccgcaaaa tgatgatagt agtaacatca 30120
gagagcattg atcacagatc accataacaa atataataat gagaaatttg aaacattgtg 30180
aaaattacca aaatgtgaca gagacatgaa gtaagcacat gctattggaa aaatggcact 30240
ggtaaacttg cttgatgcag ggttgccaca caccttcaat ttgttaaaaa ctcagtatct 30300
gcgaagtaca gtaaagcaaa gcacaatcaa atgaggtgcg cctgcatatt acaaccaaga 30360
ggcttttcgc agaaacacga gtgtgcttca acattcaaaa atcagttggt gtaattcacc 30420
acattaagat aataaaggag gccgggtgcg gtggctcaca cctgtaatcc cagcactttc 30480
agaagccgag gtggacagat cacttgaggc caggagtttg agagcagcct ggccaacata 30540
gtgaaatcct gtctctacta aaaatagaaa aattagccgg gcagggtggc acgcaccttt 30600
agtcccagct attcgggagg ctgaggcagg tgaatccttg aaaccaagag gcggaggttg 30660
cagtaagctg agatcacgcc aatgcattct agcctgggca acagtgagac ccagtatcca 30720
aaaaaaaaaa aaaaaaaaaa aaagataata aaggagaaaa accatatagt ctattcaata 30780
aatacagaaa acgcatctga caaaattcag tgccctttca tgataaaaat tcagcagatt 30840
agaaatagag gaagtgcatg tatgaaagag ctacagatag attgtactta attgtgaaat 30900
attgaacatg ttaccccgaa aatcaggaaa aaggcaaaga tgtccactct aaccacttct 30960

-continued

```
attcaacatt atactagagg tcatagccag tataatgagg caagaaaaaa cataagaggc  31020
attaatattt aaaggaagta aaactgtttc tatttgtagg taatgtcgaa aatgtgaaag  31080
aaactatcag aacctgctag aactaaaaag tgaattcagc aaggtctcag ggtacgagat  31140
cattcaaaaa ctaatcagaa atgaaatttc aaatgcaata tcgttaggaa taatttaata  31200
agaaatgtac aagatttaca cgctgaaact gaaaatgttg ctgaaagaaa ttaaagacct  31260
aaataaatgg aatgttgtac catgttcatc agctgaaaga ctaagtgtct ttacagtgtc  31320
agttctccct tcattgaact gtagattcat aaccccagtc ataactgcag ggtttttttt  31380
gtagaaattg attgtaaaat gtatatggaa gctgggcacg gtggcttatg cctgtaaacc  31440
agcactttgg gaggctgagg cagacagatg acttgaggtc aggaatttga gaccagcctg  31500
gctaacatga cgaaaccccg tctctacaaa aaatacaaaa attagccaga catggtggca  31560
cacacctgta atcccagcta cttgggaggc tgaggcatga gaatcacttg aacccggagg  31620
tggaggttgc agtgagccaa gatcatgcca ctgcacgccc gcctgggcaa cagagtgaga  31680
ctttgcctca aataaataaa taaataaaac gtatatggaa atgcaaagga cctagaacat  31740
ccaaagtaaa cttgaaagag aacaaaatta aggggcttat gtgatgtgac tttatagtca  31800
tttgattttt aacagaggca ccagaacagt ccggtgcggg aaaggaaagt cttttagcac  31860
gtgccggatg atggcaaatg acatccatac cagacaaaaa tgaaccttga ccttacccta  31920
aatattagtt tcttagagtt gccacaaact aggtggctta aaaccacaga aatttggctg  31980
ggtgcggtgg ctgacgcctg taatcccggc ctttgggagg ccgagtcggg cagatcacct  32040
gaggtcagga gtgcaagact agcctggcca acgtggtgaa actttgtctc tactaaaaat  32100
acaaaaaact tagtcaggtg tagtggtgca cacatataat cccagctagc caggaggctg  32160
aggcaggaga attgcatgaa cctgggaggt tgcactgagc caagattgca ccactgcact  32220
ccagcctggg tgacagagtg agactccgtc tcaaaacaaa accacagaaa tttgctgtct  32280
cataattcca gagtctagaa gtccaaaatc aactgtcatc agggccatgg tctctgtgaa  32340
acctgtaggg gagtccttcc ttgcctcttc ctagcttcca gtggttggca acctttggca  32400
ttctttgatt tgcagctgca ttacttcaat atctgtcttc ctcatcacac agcattctcc  32460
atgtatgtct ctgtctttac atggcctcct tcttgtaaga acaacagtaa tattggattg  32520
gggcctgccc tactccagtg tgacctcacc ttaactaatt acacctgcaa caacgctgtt  32580
tccaactaag gtctcagtgt gaggtactga gggttaggac ttcaacatat ctttttttggg  32640
ggacatagtc caacccatga cactacttca caccatacat aaaaattaat tcatgagaga  32700
ttatagacct aaatgtttta aaagctaaaa atataaagct tctgcaagaa aacataggag  32760
aatatctgtg cagtccaaag aataaggttt tttttaaaca caatttcact ctgttgccca  32820
ggctggagtg cagtggtgcg atctcagctc actgcaacct ctgcctcccg agttcaagcg  32880
attcccatgc ctcagccttc caagtagctg ggattacagg tgtgcgccac catgcctggc  32940
taatttttgt atttttagta gaggcagggt tttgccatgt tggccaggct ggtctcaaac  33000
tcctgacctc aagtgatctg cctgcctcgg cctcccaaag tgctgggatt acaggtatga  33060
gccaccgtgc caggccaaaa aaagatttat taggatacat gaagcaatag ctattaaaag  33120
aaaaaataaa ttggacttca ttaaaattta aaactttttgg tcctcaaaag ataccattaa  33180
gaaaatgaaa agacagagct gggcgtggtg aggcttgcct gtagtcacta ctgggtactt  33240
gagaggctga ggcaggagga tcacttgagc ccaggagttc taggccaaca taggcaatat  33300
agtgagacag tgtctcttaa aaaaaaaaag aaaaagaaaa aacaaaagaa aataggctga  33360
```

-continued

```
gagctgtggc tcatgcttgt aatcccagca ctttgggagt acaaggcaga tggattgctt  33420
gagctcagga gttcaagacc agcctgggca acagtgaaat cccatctcta caaaagatac  33480
aaaaaattag ccaaccatgg tggcgtgcac ccgtagtcca tagtcccagc tactcgggaa  33540
gcagaggcag gaggattgct tgatcccaag gaggtcaagg ctgcagtgag ctgaggtcgc  33600
gccaccgcac cccagcctgg gtgactgagt gagaccctgt ctcaaagaaa atgaaaagac  33660
aagtccacca agaaaacagt tgagaccagt catagaaaaa atagaaagtc atatctgaca  33720
aaggatttgt attcagaaga attcctataa ctcggtaata aaaagacaac ctgattttta  33780
aagggtgaaa atattttaat ggatactttt tttttttttt ttgagacaga gtctcactgt  33840
gtcacctagg ctggagtgca gtggtgccat catacatagc tcactgcaga ctcgaactcc  33900
tgggctcaag tggtcttcct gcctcagcct cctgcgtagc taggactaca agcacgtgcc  33960
actatgcctg gctaattttt aaatttttttg tagacatggg ctggtgtgtg tctgtgttgt  34020
ctaggctggt cttgaactcc tgggctcaag tgatcctccc acctctgccc cccaaagtgc  34080
tgggccacca cgcctggtgt ggtgtcacca gagatgagcc accatgccct gcctgatact  34140
tttcttttat catctgttta tttcttgttt atgggtgttt ctgttctgat tttatgacta  34200
ttctgtattc taagatttct ctgagaatat tatttgtttc ctctaaggac agacttggtc  34260
tctcttccat ggggctggtt cttgagccgc cagggatggg gggaggacct gggtagctgc  34320
tgcgctgccc cttctctgct gtggtggagt ggcccgttgc ctgcggggtc tgtctctgaa  34380
gggtggtttg gagaagttct gtggaggcga ggcaggggtc agctcttgcc ccatggaccc  34440
tcagagactg ggaaaaggta ggcatcacct gggctgctgc cagccacatc aagagccttt  34500
ggggtgggtg gggtgggggc cggggaaggg aaggttctag ctgttgattt agaaaagacc  34560
cattgatttc ttgcctgagg gaagaagtgg caccttgcca ctccaagttt gctctgctca  34620
ccagccccaa cagcatcagc ctcacctggg agcttattga aggtgccctg ccccaaagct  34680
tgtgggtcgg gatctggcag tcagcagccc ccaggtgttg cacacatgac agcactgctt  34740
gcccctcctc tcgtctggtc tggtctggtc tggtctggtc tggtctgaga gcttctttgg  34800
ggctctgaca ggtatacagg ctctcatctg ctctacagct ctcttgtagt acattcctct  34860
ctgttccatt agtcaacatg ttcttgccta cttccagcat ctagaaattt gctgagtgta  34920
tcttatccgt tcagaggtcc tctcctgcta ttgcctctgt tagaaatttc ttccctttca  34980
tatgtctgta cttcggtttc tttgaggttt gaagggtcaa gtggcaatta catgtaggca  35040
gttggccatc ctctggtgaa ggctttaaag cccaggaata acaagatcca ttatgtctaa  35100
aactagcaaa aaccctacct gtcacatggt gaactgaatt agaggtgatg gggacagaag  35160
ccagattgga gtgagtggaa ggtgagggag tggagattgg gtatagacaa ctctctttaa  35220
gaagttttgt tgtgatggtg accagaaaaa taggagtggg gtagaggggg atgagggtgt  35280
ttttcacgtg ggtgaatatg agagcatgtt tacatccttc tgggaatggc ccaggagaga  35340
ggggagcgtg agaaggagga aatggggacc tggaggagca gactccttgt gtggaggggg  35400
gaagcggcat ctagagctgt tgcaggaggt gggctttgag taaatgcttc ctctttggta  35460
aagacgggga acgggaacgg tagaagttgc acggaccctt tgttaaagct cagaagctga  35520
gcgagaatta gagcttaagt ttatggagta gtcagaataa agtacccccta actgtattct  35580
tgcacagtgc aggaagccag ggtctgaaa tcaagatgtt gcagggctcc attcccccca  35640
gagcctctag catggatcct tccttgcctc ttccagcttt tggtggctgc ctggcagtcc  35700
```

-continued tagactttcc ttggcttgca gttgcattgc tccattctct gcttgtgtct tcacatggcc 35760
ttctctgtgt ccccgtattc ttctctggat gcttgtcact gtattaggcc caccctaaat 35820
ccaggatgat ctcatatcaa gatccttcac ttaattacag aagcaaagac cttccaaata 35880
aggtcagagc cacagggtct gggggttaag acatacacct aactattcgg ggctaccatc 35940
gaacccctgt agaagcctgt ccatttccag gatagcagag cccaaggaag ggccagaagt 36000
ccccccaaaa cagttgtttg cattcaccag attctaagct ataagcagat gggcagtggc 36060
agtcggtcct aatccatata ccattggcaa caatagttta gttcactgta gacataatga 36120
gatgcttatc ttctgctaag tagtcctcat ggtaacagcc atattactcc tggctttgag 36180
tgacagcgct gtgctcttgt ctggtgccca tatacttcag cagctggaaa caagacagtg 36240
ctcatgattc accggaaagt ttctgtagtt aaaatcaagt gatcccttga gtctattcta 36300
atatttgtct gtaccatgtt ctgtgacgag acatggaaac aaaacattaa gaagtgaaag 36360
tatctttgat tatgctcttg aagacaactt tttgtttgtt tgttttgttt gagacggagt 36420
ttcactcttg ttgcccaggc tggagtgcaa tggtgtgatc tcggctcact gcaacctccg 36480
cattcccggg ttcaagcgat tctcctgcct cagcctccca agtagccagg attacaggca 36540
tgcaccacca cgcctggcta attttttta ttttagtaga gacggggttt caccatgcta 36600
gtcagactgg tctcaaactc ctgacctcag gtgatccgcc tgcctctgcc tcccaaagtg 36660
ccgggattac aggtgtgagc caccgtgcct ggccgaagac aactttttaa agatgcatat 36720
gctctgggct gggtgtggtg gctcacacct gtaatcccag cactttggga ggccaaggcg 36780
ggcagatcac ctgaggtcag ggttcaaga ccagcctggc caacatggtg aaacaccgtc 36840
tctactaaaa gtataaaaat tagccgggtg tggtggcggg tgcctgtaat cacagctact 36900
caggaggctg aggcaggaga atcgcttgaa ccccagaggc ggaggttgca gtgaattgag 36960
actgtgccac tgcactccag cctgggcgac agagtgagac ttggtctcaa taaataaaat 37020
aaaataaaga tgcatatatg ctctgaaggc tggctacatt ttatttttc tcaaacaact 37080
tttacagtgg atagtgctgt aaaagttgtt tagctctggt cattttatct tttttgtgat 37140
ctgcaaaagg agatcctttt ccttttcact gcctctaata cccaactcca atactccttt 37200
gacctcacag gcacttagaa tccatcagtg gctccatctt ttctcagact tcacctcctt 37260
cgtatcctta ttcctctcct ttgtagcttc agtgccagtc agacgtcgtt actccctggc 37320
acactacctc agcccttcgg cactttcttg ctttgttata ttcagtcgac aaagccccag 37380
cctcatgaaa ttcagtcatg tctgccccat gcctgctccg tcctgaagct gaatgtgact 37440
ccttcattga ttccccttt aagttcatgt ctaccccagg taaacttctt gccgccaagc 37500
ccacctgcat actgcagttc cccggtctct cctagcccct cccaccctcc tcatcagctg 37560
tcacacctcc ttgcagctga tatcttagtt cccagagagc acagaagcaa gctcaagaga 37620
gtgtctacag gccagcgtct actccttcgc tctgcctccc tcatgctgtc acggagcgcc 37680
tgtcccaggc cctcactcct gttctaaggc atctctccag tcctctactg cactctcccc 37740
catcagagat tcctccctcg cctgccctag aaacttgttg ctacttctcc caccttgaca 37800
aaagctgctc ccaaccccc acctgtctag catctctgtt ttcctttacc agcaagactc 37860
cagtccctgt ctccacaccc tcttcaacct tctccagttg ttcctttgct gccacagctc 37920
tgccaagctg ctccatgagg tctccagtga tgaccttcat gttgttaaat ctgggagctg 37980
cttgtcactt cttttcccag agctgtcgtc gtcagttaac cccaataccc atacgagaca 38040
atcctttccc tcccttgagt ctctgcactg atgtgcacct tctcagtgca aaccacagct 38100

-continued

```
tttgtctctt tctagctgaa tacatgactg actgtgctta tcttagctgt caccccctgct  38160
ggagcagaag ctccacagga caggattgtc tccttgattc acagatgtag ctcaagctcc  38220
tagaacagtg cctggtgtct gtgggtcctc aggaagtcct aggtgagtgt gtgaatgtct  38280
gtcctcctcg gtcttttctg tttcgcatgt gatgttggaa ggcctcaggt tcaggctttt  38340
cttctccacc ctcactcccg aagtgattcc gtccagcctc atggctccca aatttatgtc  38400
tccaggctga ctgggtcacg ggaactcctt atcctcccta gaccttctct ttccctggtc  38460
ttctcctttc cagtaaacag caactccaac tcctgctcct caggccagaa acctggcgct  38520
ggttacctca tttgttcaca aatactgtta ctccacctgc aagatggata caaaatctca  38580
tgagttcccc tgcctccatg gcccccaccc tggtccaggt gtccagcttc cctgcctctg  38640
cccttgcccc ctggttcttt gtttagtcct gcaatattgt gctcttctgt tcagaaccct  38700
ccagtgggtc cctgcttgct cagagtcaca gcccaacagg atcacctctc ttgccactct  38760
cccaccactc atgcactgcg gcctcactgg cctcctggct cctccctgga ccctccaagt  38820
atgcccctgc ctcaaggcct tgacctctcc tctgccctct gtcccaggta tcacacatgt  38880
ctgctcaagt gtcaccttcc caatgtggcc ttccccgagc acacccatgt ctgtaagtca  38940
ggcagcctgc ctctgcccca ccagttcccc ctgcctagca taggacttgt caccatctgc  39000
cacaagctgt gttactgctt ggttttgttt gtgctctccc actcccttcc cctccctccc  39060
tctccccacc cctatagaat ctgagtccca tgaggacaga gatttttttt tttgcctctt  39120
cctcaatata tccccagtgc ctagaatcat gcatatttta atttattgag tgaattaaca  39180
aataaattct gcagtgggac attgctctaa ggttttgtct tataagaggg acagaagaac  39240
atgcagcctg ctctgctgtt ggctccttag cttctccatg gctaacagga acaatattgt  39300
ttatgagata atcaaagcca tagtcatgag ttagaaggta catataaagg caaatatgtg  39360
gagattgagt tactttggcg ggggcggagg ggtgtgtagt tatctgaaaa catggaacaa  39420
atcaatgaga gtctaaatag cacccacata tttgcccctc ttttaaaaca tacctccttt  39480
atgagtgtag aatttaacag cacagtttcc cagtgcagct ttgcgaaaca agagaaatga  39540
attttaaagg ctgtcaggtg cctttgcaat ctgtggctta gtatttgtgt aacaacattt  39600
gtgttttgcc aacagatgta ctgcttaaag tacccatgag aatggcctct gtggttttct  39660
actttctcgg atggaacctt aggaactgat tattgagaag aggctgatac tgcccacctc  39720
agctcccagg caggcttcag ggccttggtt actactcctt tgggccctca ctgacccttg  39780
cagacgtctt ttgcaacctc tgtagccaga agagacaact gctttctggc atgttgctct  39840
ttccctaatg gctttatgag cttcttgaac accaaagcat gtgtgacttc ctcacgcctt  39900
cccctgtata gtatagcacc cctaactgta tgtgtaagga gaaggagtga gcaattgatg  39960
gcgtccccct ggatctccaa gggaatggga aggggcaggg tttctggatt cagtcatgtg  40020
gaatctggtc gttggtgtct aaatgtgcct gttacttgtg cccaatgtcc aggttcacca  40080
ggaggcttag cctgctcatt tccctgctag tagctatatt ttgggagagc attttttatg  40140
ctctaattga actttgtggg tctcagcaat ttgaacaatg ttttgttttt cttctggtca  40200
ggttacaaag gaaagaaaag gaatctggtg ttgtaggagg tggtgtgttg tgtaattact  40260
tgtttttttt ttttaagttt ttttatattt ttgcaacaag gcaagttttc tttgaataaa  40320
taatgctggg agcttatcac atagaaggca tatgtgttgt actcagtaca ttctgaatta  40380
tctgggttta tttttatctc ttgaattcac ttataaacaa ttcaaaggct gctttttttag  40440
```

-continued

```
ctaacagaaa taggaagaga atctcagaat ctgttttgtc attttttcaa tgggttgagt  40500
tatagtgatt atgctaactc ggtggaaaag cagtgtagtg agtaaacccc acatacggca  40560
tatcatgaac attttgttgc ttttttggct tctgaccatc ttcatacctt tttttgtgtt  40620
aaaagtctcc ccattgtgta tatcttagta agaggcaggt ggaccctagt ttctacctaa  40680
gaaaacctga agatggggtt gggggcctgt ggtgtacttc cttctcatgc tgtccatgac  40740
cactgcagtg gctttgtaag gatccaggac ccagggcccc tcagtgggtg tcttccattt  40800
ctcaagattg cctcttggtt gtgagatgac ggttgctgct ctagtcattg catccactcc  40860
tccaggtagg aagaaagagg tcatagggga aaggcaaaat ggcacttgac atcttaactt  40920
ctaggcccat tcaatatttc catttccatc ttcacaccca tcatcttgtc ctagggaaca  40980
aacagcacca gcagctcagt agctataaca gcaattatta tttctcacac atgggtctgg  41040
gtcagctgca agatgggatt cagatctgtt ctcaagcctg tcgttccagg acccaggagg  41100
gagaagcagc tgccagggga agtctcttcg taggcggagg tcaggagtcc aagaggagtg  41160
agcagagtca cagaagcctc ttaaagcctc ttcttccccc atcccatcaa cacgtgagca  41220
agcccagagt cagtgggtgg gaggtgtgct ccgcccatag tcagtagaac aagagcaagc  41280
ttgaaagaga acgatgaaca ggagtgcact cggccactgt ctccttagcc ataacgtagt  41340
cccatggtct gctgggaagc ggggaataac tctccttagc tgagcgcagg gtctcattag  41400
taaggcagat ggagaacatg gatgttgggg gacaactggc agtgcctgcc acaggggaat  41460
ggatatattc cctccccttg ctctctggaa actaggggat ggcgatgaag cctaggtttg  41520
gccaaaccca ttctgccttc agggactttg actcttgagg gacagtgagg gattagtcat  41580
ggtggtggca gttgagtcac aaaaccagca gtggtggcta atgtccagtg atgacatgca  41640
acagtgccca gggtgggtgt cccaaccagc aggtccctgc agtataacct tggctgtgtt  41700
tgcagtggtg cagcctctat tcctgctgct tttctgagcc tagttctcta gttctctctc  41760
catttccaga tctgctgccc aagaactcct ttgtgattga atttaaccag agttgatttc  41820
tgttgcttga aactcaggac cttgatgcag tgtgcagggt ctgggcaagg taaaaacaca  41880
ctttcatgat ttcgcctcaa gtatagtaga tgagcttagg ctttttgagc caggtagcct  41940
tgggattaat tctcagctct tgcacctagc aggtgacctc agcaatcaag tcacttgccc  42000
tccttgagcc tcagtgttgc cctcagttaa acattgctct cgtgtgttgc tgagcattca  42060
gtgagattgt atataaagtg atcattgtga aggtattggg acataatttg ggaaagcgtc  42120
ctggtctaag cttttgattg gctctccatc atttgggtaa tgggatagtg atttaggagt  42180
atcatagcag ctcaaggggc ccttctggaa agggtatgag gaaggtcagg gacaagtctg  42240
aaatgaatca tcctaggctt aatgcctgtg actgggcagt gggtacaatt atctcaggct  42300
agtcagtagt catttattgt gagaatacat gggcagattt tttaatttcc ttctcagtct  42360
agacttgaat gcaaacagtt cttattgcta acttaccact agtcaccact aatgaacaaa  42420
gactatgaac aggaaattca taaaagaaga gatacagatg gccaatgaag ataggaaaag  42480
agttctgcct gctggtaatc aaagagatgc aaacgagaac aaaaatgatg ccttttcacc  42540
taccaaattt gtcaagatta aaaagaaagc aaagagccag cgtcagctga tgttcatacc  42600
tgcacctgct cggtagcttg ctaatgttct gcctgctcca cacgccaggc cagcctccac  42660
ggcgcagcca ggtgaggcct ttccttgtat acaggcacgt ttggattcac tgttgcataa  42720
gtgagacatg tgcatgcttc acaattcagg aagtgcaaac tccagagtga tgcaaggtct  42780
gagtgtccct gctgccctgg tctcccagct gcctaggcct ctcttcaggg aacggctgca  42840
```

tccagggtct tgtctgtgtc ttttgaggtg ttctatgtac acgcagacac atctaaacct 42900
atttttattt tccctgcacc tgcttgggct actgtaagct gttaaatttt tttttctagg 42960
aatttgtcca ttttgtctga ctagcataaa gttgttcatg ttatagttta tacatttgca 43020
acatctgtaa ttatgtctgc tttttcattc ctagtgtttg ttgtttactt gtaccttctc 43080
ccgtttttcc ttgtcttggt aaaagctcat taggttcatt ggtcttacaa gaagcagaca 43140
tgtaggcatt attgccctgt attactctgt gtctcttttc tagttcatta aattctgctt 43200
ttgcttttat ctttattatt ttttctatgg tcttagagta cattctctgt gttttgttgt 43260
tgttgttgtt gttgtttgtt ttttgttttg agagagagag tcttgctctg tcgcccaggc 43320
tggagtgcag tagtgcaatc tcagctcact gcaacctcca cctcctgggt tcaagtgatt 43380
ctcgtgcctc aacctcccga gtagctgaga tttacaggca tttgccccac acccggcaaa 43440
ttttttgtat ttttagtaga gatggggttt tggcatgttg accaggcggg tctcgaactg 43500
ctgacgccag gtgctccacc cgccttggcc tcccaaagtg ctgggattac aggcatgagc 43560
caccacgcct ggccctaact tcttaagtta taaatttggt tcattgattt ttctaccctt 43620
ttttcaaatg taaacattta aggctaaccc tctggaacta cttcaactgt atctagcaag 43680
ttctgatagt attgtcactt taagttagcc caaagatatt ttaaattttc tttgtttctt 43740
cctttgactc acatattatt ttaaaatgtg tttttcaatt tccaagcaca tggctttggg 43800
tttgtttttt ttttttccta gttgctctag aaaaaaaaat tgactgcatg aggtggctca 43860
tgcctgtaat cccagcactt tgggaggccg aggcgggcag atcacctgag gtcaggagtt 43920
cgagaccagc ctggccaaca tgccaaaacc tcgtctctac taaaaataca aaattagccg 43980
ggcatggtgg cacacacctg tagttccagc tactcgggag gctgaggcag gagaatcact 44040
tgaaccggga ggcagtggtc acagtgagcc aagattgtgc cagtgtactc cagcctgggc 44100
aacaagagca atactccgtc tcaaaaaaaa aaaagaaaaa aagaaaaaat caacttctaa 44160
ctaaatggca ctgtgatcaa agaacttggt ctgtgtgaca ccagttcttg cagttggttg 44220
agaagtgctc catgacacat tatccacaac cagtggacag aatatgtcac caccaagcat 44280
gggtgcagga ttctacatat attcattacc tctgtcttat ccgtttgttg tgaaagtatt 44340
ttctcttctt actgtcattt tgtttacttg atttatcaac tgatggaata cgtgttaaaa 44400
cctactgtgg tgatggacac atcagtttct ccacagagtt tggtcatttt cattttatta 44460
tttattttga ggccacattt tcagttttag atacagtttc acattcctgg tgtattgaac 44520
cctttggtat tatgaagcga ccatactaat atgttatttt tttttaaatt attatttatt 44580
ttatttattt ttctttcttt tttttttttt tgagacaggg tctccctctg tcacccagtc 44640
tggagtgcag tggtgcaatc tcagctcact gcaacctccg cctcctgggc tcaagtggtc 44700
ctcccacctc agcctcctga gtagctggga ttacaggctt gcaccagcgc gcctggctaa 44760
gtttttgtat ttttagtaga gacagggttt tgccatgttg cccagactgg tctcaaactc 44820
ctgggctcaa gcagttcacc agccttggcc tctaaaagtg ttgggattac aggtgtgagc 44880
caccacgccc ggccatccca gtttttttatt ttcctccttt ctgtgtcttt atgcatcagt 44940
gaggtggagc ttttgaaaat gtcagatagc tagattttttt tttttgaga cggagttttg 45000
ctcttgttgc ccaggctgga gtgcaatggc gtgatctcgg ctcactgcaa cctccacctc 45060
ccaggttcaa aacaattctc ctgccgcagc ctcctgagta gctgggacta caggcacgtg 45120
ccaccacacc cggctaattt tgtattttta gtagagatgt ggtttcacca tgttggccag 45180

-continued

```
gctggtctca aactcctcac ctcagctgat cacccgcctc agcctcccaa agtgttggaa  45240
ttacagacgt gagccaccat gcccagctga tagctagatt ttttttttt ttttttttt  45300
gagacggagt cttgctctgt cgcccaggct ggagtgcggt ggcgcgatct cggctcactg  45360
caagctccgc cccccgggtt catgccattc tcctgcttca gcctccagag tagctgggac  45420
tacaggtgcc cgccaccacg cgtggctgat ttttttttt ttttttttt tgtattttta  45480
gtagagacgg ggtttcaccg tgtcagccag gatggtctcg atctcctgac ctcgtgatcc  45540
gcccgcctca gcctcccaaa gtgctgggat tacaggcgtg agccaccgca cccggcctcg  45600
agatttttta aaaaatccat tgtctgtttc gtcctttaac atctatttga tttctgatgt  45660
atttagattc atttatagca tatttgtgca ttctattttt ccatattttc tgttctttta  45720
aattttcctt ctcctttctt gccttctctt agacttttaa aaaaattgta gtaaaataca  45780
catcacctaa aatttaccat ttttaaatgt acagttcagt ggcattaaat acaaattgga  45840
ggccaggcat ggtggctcat gcctggaatc ccagcacttt gagaggctga ggtgggagga  45900
ttgcttgaac ctggaggtcg aggttgcagt gaggtgtgat cacactactg ctatagccca  45960
ggcaacagag tgagaaccta tctaaaaaaa caaacaaaca aacaaacaaa cagattggca  46020
tcacacagtg tgtgtgctgc tgtgctgtgc tgttatcatt taacattaaa acataaacat  46080
cagcactgtt atggactgaa tgtttgtgtc ccccaaaatt ccagtgttga agctcaaacc  46140
tccaatgtga tgttatttgg agatggggta tttgagaggt ggttaggttt agatgaaatc  46200
aggagggagg gtgggtttcg catgatgaga ttagtgtcct tataacaaga gacagcagag  46260
agcttgcttt ctccaccatg tgagtatgca atgagaaggc agccatctcc aagtcagaaa  46320
gagagccctc accaggggct gaatgtgctg acaccttgat cttggacttc tagcctccag  46380
aactgtgaga aatttcagtt gaataggccc cccagtctgt actattttgt tatagcttga  46440
gcagactaat acacccatgt tatgaaaagc tataaacatc cctttaaagg ccacctaacg  46500
cgtcgtatta cctcatgcat cttctctgct gagctttcca aaagagtggc ttaggctggg  46560
cctggtggct catgcctgta atcccagcac tttgggaggc caaggcaggt ggatcacctg  46620
aggtcaggag ttcaagacca gcctgaccaa catggagaaa tcccgtccct actaaaaata  46680
caaaattagc tgggcgtggt ggcgcatgcc tgtaatccca gctacttggg aggctgagcc  46740
aggagaatca cttgaacctg ggagatggag ggtgcagtga gccgagatcg tgccattgca  46800
ttccagcccg gccaacaaga gcgaaactcc atctcaaaaa aaaagagtgg ctggccgggc  46860
gcagtggctc acgcctgtaa tccccgcact gtgggaggcc gaggtgggtg gatcacgagg  46920
tcaggagttc aaaaccagcc tggccgagat ggtgaaaccc cgtctctact aaaaatagaa  46980
aaactagcca ggcgcagtgg caggcgcctg taatcccagc tacttgggtg gctgaggcag  47040
gagaatcgct tgaacctggg gggcggaggt tgcagtgagc caagatggtg ccactgcact  47100
ccagcctggg tgacacagtg agaccccgtc tcaaaaaaaa aaaaaaaaaa aaaaaaagtg  47160
gcgtatgttc ccggtctcca cctctcattc gccagcccct gtgaccaaac ccctgggatt  47220
agatctccat cgggtccctc ccctcaccct aacctcacat gcagtggttc ctgagaagct  47280
gctgtttatc tgatcacggg atccagcagg atctgagggc tcattcactg aatctgtact  47340
acccaacaag gcaggcttgt ccttacccac acttttcagg tgaaaactta atcagattca  47400
agcgtttatc ttagtggcct cttcgtggtg tgtgatttcc ttcttgcagc tctttactgg  47460
ctaaaactct tcactgggag ttaaaccagg tgtggtcctt gaccctcatc attttgtccc  47520
atctcctatg ctgggctctg tatccttgtc tccaagcagt ctcgtgtgac agggaagtta  47580
```

-continued

```
cctattattg tatggtcccc tcttcttgtc acctctggtg tggcacttgt tccatttctt  47640
gttcaatgaa tgtgatttgt gaatgtgcca catctgtggg aggaaggcag ttcgcagcaa  47700
gagttgtagt tcccttgctt tgccctgagg gccaggactt tacactagat tttttgttg  47760
cattcctgca ctcataaagt acacgtaaac ttagaggtgg tgtgttaaat gctagaactt  47820
aaaactgagt tcagctaggc tcaagtgccc cacaattttt gtcccaccag acaatttcat  47880
gaatatctac agattgttcc ctcaatatgc ctcaatattg aggcatattg atttggggag  47940
cacagacaag tcaaggttga tgtgcatccg ctgaacatga tcttaagttg ttgaagtagg  48000
tattattaat gaacgaacgt ctattttagc tccaagagcc cctggtcttc cagaagagac  48060
tcccaatgat cttccagaag cagctgggct tcttttggtc ctcccccacc caggtgcagt  48120
cccgttctcc ctgcctgggt gagtttgatt cctctgccgt ggaataggct aggctgctac  48180
ctcttgagcc tcttccacca ggccatccat taggtggcga cagagagcac taaaaggaac  48240
tactatggaa ataaaacttg ttttgcttct tggggggaaa aaaaaagaaa aaggcttgtg  48300
gggcgtgtgt gcattttagt cagattttac tgtgcaaaac atttgagaga tttctgccct  48360
ctttctccct tccattcttc tcaacccact gggcgcccta ccacccctgt ctccttcaag  48420
ataaggtaga tcagaagacc aaatagacaa atgccatgtc cactgttttc tgtcacagtt  48480
gatagccata ccagtcaccc aagctggaaa cccaacaggc ccctgccctt cactgcccac  48540
atccaaggga gccaccaagt cccacaaatt gttcctttaa ctgtttgtcc ctcttttgtc  48600
ttctgtcatc ccttctaccg ctgtcctggt tcaatccctc atcttgctct gggactccca  48660
tgataactta tgatctttcc tccacctctc tatcttccac acaatcccta tcatcaatct  48720
cattcccctg ctttaaaccc aagagtggca ccctgtgttt gagtgacatc agggcccctc  48780
atgtggctcc tgcttctctt tgtggcccct tctgttgctg ctgcttttct tatggacata  48840
gccctcagca gtccaggact gcttgtagtt cctcccaggt accatgtttc ttgcactcct  48900
ggcctttgtc attggctccc ctgcccaagt ccccttctct tctcctttcc ttcccctgtg  48960
gccttgcctt gtcgtgctta tccttgaaga ccctgtcagg tatctcttcc ccaaagagcc  49020
ctgcctaacc accgcccccc tcccccccgc gacacacaca cctgggttag gccctgcctc  49080
tccacgcctg tgcctcctgc caagtcctca gaggtctctg atcccatgtg cctccaggca  49140
tggcataggg ggactgtgac acagcctctc ggcccacaga cccctgattg tgggcttgct  49200
cactgcccca gtcagtcctc ttattgagga ttccgtgcca gttcctgact ccagcacaca  49260
cacgcatgta ggccgccctc ctagtgcctg gctccttccc tgtctcttct gccactcatt  49320
cccatggtcg tatcctggag ttggtcatct ctggaactcc acccacggag ttctaactta  49380
gctctgccta tgatgaggac ttactgtctt cccagcttgc agtgtcaacc actgtttgat  49440
gcccctggga ctccattggt cttccctcct cttgtgaact gtgcccatca ccagacgaac  49500
ttgttttaga atttaccatc gtaactgagc tcccttcagc gcatacctcc ttggctcctg  49560
ctcagtctct gtttctcctt ttagccaaac tctctaagag ttctctccac tcatgggccc  49620
tcttccttgc ctgctgctcc ttgctcagct tgctccatga acacttgctt ttccacattc  49680
catgaaataa tcttaacagt catcagtggc tgtcactcct tctcagccct ttccttgtgt  49740
ctcttctggt acctcatact ctccaggtgg ccatctcacc tcacatcttg aaccctctgg  49800
gtttgggaga attctcacct cacgagttga tgggaggcct ggcgacctct gattgtagtc  49860
actgcaaatg ccagatgctt atttgcctag cttccctttc ggtcagggca gcagttggca  49920
```

-continued

```
aacggtatct caagggccaa gtccggccca ctgcctgttt tcgtaaatga agctttacca  49980
ggacccagtt ccaccccgtc ctttgtgcat tgtccaagac tgctctcctg tacaacagca  50040
ggtgggctgg ttgtgacaga tactgtctgg cccacaaggt ggaaaatact atctggcccc  50100
ttacagaaag aaattacctg agttctacac gagggtgtag gtatgtaccc tggcctctgc  50160
cagtcagact cacatgctag gaggagcagg gccaggcagg agagccgtgt ctcctggcat  50220
tggggctgca ggaaagacga gctcctaggc cacagtgcca gtggccagtg ctgctgcctt  50280
gcagggtcgc acaggcagtg ctggctgttt ggactggctt ggcagaagga tttgaagtat  50340
tgttcctagc caactggact caaacctgtt cctccaaccc tctagggatt ctcttatcac  50400
ccagtagcct tttcccccta gttttaaaaa ttgcagtaaa atacacaaaa gataaaatgt  50460
actgccttaa ccatttttaa gtgtacaatt ctgtggtatt gagcacattt atattgtgca  50520
accatcacca catgcatctt caatagcttt tcatcagtcc ttgtctgcat aaatcagcta  50580
gagttggttt ctattgattg ccaccaataa tcttgacaga tatgtctgat cttccttctc  50640
tgcactgact cctctttctc tgtctcctct gctgattctt tctcctcatc acaactccaa  50700
atagcagggg gagggttgtt tacacttata ttcagcacgc cctcacgcac tcgcctggct  50760
cttcagacct ctcccctgaa ctccagattc atacatccag ctgcccttta ggcctctaga  50820
aagctaaata cctcagtatc aaaaacatga gaaacggaag ccagagtcct ggatctctcg  50880
ccctttcgct gtcccggtgc ccatgccctt cagggatggc acctagacca gctccctgca  50940
tccctgccta gactctgcag tagtctcacg tggcagaccc ggaggtcact ctcctctctg  51000
gatgccctgc ggacactccg gttagcctca gctgcaagag cctcctcacc caaggtcacg  51060
ccatttccag gacagcaccc tggtgactga gcgaggtaag ggtacaaggc ccttataggg  51120
ccttctcttt gacttcttcc cacctccctt tatggatgtc agttcctgat gaacatctta  51180
cacctcaaac cgtgacccaa catctgcttc tgcagagccc ccctgtggca tcttgtgccc  51240
tcctgcccca ctccctctac tctatatctt cccatagtta gaatgggctt ttttttttt  51300
tttttgagat aaggtctccc tttgtcaccc aggctggaat gcaatggcac agtcacgact  51360
cactgcagcc tcaacctcct gggctcaagc agtcctccca cctcagcctc ccaagtagct  51420
gagactacag gtatgcacca ccacacctgg ctaattttta tattttttgt agagactggg  51480
gtctccctat gttgcccggg ctggtctcga actcccaggc tcaagcaatc ctcccgcctt  51540
ggcctcccaa aatgcaggat tacaggcgtg taccagtgtg cccagcctca gatgggctct  51600
ttgaaaaatg tttattagat caggttactc ccttgagaaa aaccctctca gaataaaacc  51660
cgaagtccat tacttgaaag cagagccagc ttcatgggcc tttgtaactg cccatgggct  51720
tgctggaacc caggcttggt ttaatactct actctcacca tctcaaaatt cttaattttt  51780
gaacaagagg ccctgcattt tcattttgca ccaggctcca caaattgtgt aactgggcct  51840
gcctcagcag ccacatggaa catgatccct ccttgcctat ttgagctcat tctctaccat  51900
tctctccctt gctcacctgg ctcccactgc tcttgctctt cctggaactt gccataatgt  51960
tgctagagtc agagccttgg ctcttgctgc tcctcattgg ctggacccct ctttacttga  52020
cctgctccct caccactcac ttccttcaga tctgtgttca gatttcgtct tctcagagag  52080
gcttttggcc cctgtccatc tctctgaatt tacctctgac ctctccccca ccaccactgc  52140
gctaagctgc ctcagaactt tgtagacatt ctgtctggtc ttctgatgtt tccccccttgg  52200
aagaatccca aggtgcctga agaatgcttt ctttatcctt gaagttgagt aggttgacta  52260
gagtctggct tgctattgag cattctttat caaattgtcc tgggaacatg gtgtattctt  52320
```

tcagtctgca gatgtagtcg ttgctgtttc aggtcagctc tcttatggat ctttgacagc 52380
atcttctgtt ccatttgttg agttctgtac ttcagggaca caaattcctc atgttggatt 52440
gtctttgtct ctcttccaat gctattagct ttgccgtaat tggtttagct tttgtctttt 52500
tcatctgcat tcactttgtc taatttgatt ttcagctatg tatattctgt ttctggctgt 52560
ttttcaatgt atttattagt ttcataatga tgtgttttgg tctgcagttt gtttctctag 52620
gttggaaatt tgtcttttca tcttattctg ttttatcatc ccatctttga actcttttat 52680
tgggaacatg ttcttatgaa gttgtgggga attttttcc cttccttgtg tattctcttc 52740
ttggtgggag actttgcctt tctcgtgcca tctccctccc tgggcctctt ttttttcttc 52800
tggccataat atgtttgcct agttaccatg tcacttcttt tcgtcttggc tcaggcttgg 52860
atggctctgc atagtcgttc tgtttgcttt gagacagtgg aggaattctt ggctctctct 52920
tcccagtttc ttggcatctt ctcttgctgt tttcccctct gagctatcgc gtgcaggctt 52980
gttatcttgt atccggagag aatttgcacg ctggagggag ctgcagccat gtagtcttca 53040
gccctatctg gattcttctc tttgttctaa gaactgtgtt ggatgtctta ctaaggctca 53100
ctctagctgc acgagggatg tgtgtgccat ttccatgggg atagggggca cctcagtctc 53160
tgggtggttc cataatctgt gtatacctaa gagcagttgc ttcccacaga gctgggctgg 53220
ctcactgggc actttgccat ttctcctgca cctcccagct ggagtttctg ggtctaaaag 53280
gaaaaagtga aggactccca cttggttgct tctctccagc ttactgactg caaattccca 53340
gggcgttgcc cgctccctag ggtggtttct gggggacggg gcaggagcct ggctttgctg 53400
ctgctttgtc ctctggagtc ttttctcaga ctgctttgaa ttacacccct ttcctttgtg 53460
tgctgaaatc ttcccttcac actctccttc cctgcctttc ttttgtgtct tatcttacta 53520
ggactggaag agggcagttg tgcaggaggt ctgcatctaa ttccctaatc catgtgagag 53580
tgctcctgtt gtgtgctttg tgacatgatg gtgagaaata ctccctagag cagtggctac 53640
cagaaggaag ccatcccccc ccctgcacac acacacacac acacacacac acacacacac 53700
acacacacac actccttctg gctgtcctca gatgcctatt ctaggtaaat gtcagattcc 53760
aaagaaaatc cagttgagat cttttttctt tttttgagac gagagtcttg ctgtgttgcc 53820
caggctggag tgcagtggca caatctcggc tcactgtaac ctccgcctcc tgggttcaag 53880
cgattctcct gcctcagcct cccaagtagc tgggactaca ggcgcgcacc accacaccag 53940
gctaaaattt ttttgtattt ttagtagaga cagggtttca ctgtgttggc caggctggtc 54000
tcgaactcct gacctcgtgt tctgcccgcc tcagcctccc agagtgctgg gattacaggc 54060
ttgagccatc gcgcccggcc tccagttggg atcttgactg gaatgactgg tgttcaatca 54120
ttatagtttc cacctaattt gtatttgtac acaggacagt tactaatttg ttggtacttg 54180
tttgatcccc agtccctaga gttgtttatg gggtggagct tcagtccctg ctgcttcccc 54240
tgtggcagca gctggagtca gggtggggac ccagggtgct gctggcagat tcttgagaca 54300
ggtagaatct cctctatatt ggtgtctctc tctgtcccag cagtgcccag gaaaacctgg 54360
ccagcctgtc actgacctct ccacctaggg cactggtggt tcaggtcctt ctatttgcca 54420
ccggcaaacc gtacttctgc cagtctggct cttaggccca gtttctctga tcttgcagat 54480
tttcttgggc tctgctacgg aatcctcata cctccggcag gtccctcctt tgcccatgtg 54540
tttaactgtg gtggaatcgt gtgagagctg cttctctcgc atggatccca gccacaccac 54600
attctacagc ggttcctctg aaggcattga tagagatatt tcctcctgtt ttgcatttcg 54660
ttggtcattt cagtagaatc agggtgaaat aaacatgggg gctcagatgt cagcattacg 54720
aaccaagtac gtcaggcagg ctgatgtgga ctgacctaca ctagtgagac gcaagatgac 54780
gaaaacaagg gcactcactc caagttactg atgagatgtt tggatcaaat gagccagtcc 54840
ttaagcagag ttctctagta aaagagatct cctttctgcc ctttcttgtt ccccaaaatg 54900
tgttgccttc atggtgaaaa tttattttgg cagattttct cttctttgat aaaagcagcc 54960
aacactttgt taaaagtctg tgaaacttat ttacatgaag tatgtaaagg taagaaaaaa 55020
acattatcaa caagaaatgg agaaagccag cagctgagga cagaaaagtc atgcacagtg 55080
tcagtgtcta tggaaacagg ccacttggac cttgaggact aggtatttgg aattggaggt 55140
gagcttggcc tggtgagtct ctaaccactt gtgtgtagga tcagtgtgag aaccctgcta 55200
gaatatagtg gcagagatgc aaggggaaat cattggagaa gttaccaggg aatgatgagc 55260
taatctgaaa aaaatacatg tttctaagtt gggcgtggta gctcatctgt agtcccagct 55320
acttgagagc ctgaggcagg aggatcgctt gagcccagcc tgggcagcac agcgagaccc 55380
tatctcccta aaaaaaactt tttcgttgtt tagttttggg attttttttt ttcctggtct 55440
tttttccccc tttttgtgaa taacgggatc tcactatgtt gcccaggcag atctcgaact 55500
cctgggccca agcaatcctc ctgcctctgc cttcctaaga ttacaggtat gagccactgt 55560
gttaagcaaa aaaacttttt taaatgaaaa tcattttttta aaagacaggc tttccagggg 55620
agggtattat tccacttata tgaagtgtca acagtaggca gatttgtgga gacaaataga 55680
ttagtggtta ccaggggctg agaggagtgg gagtggggag caactgctta atgggtaaag 55740
ggttgtcttt ggaactagag agtagtgatg gtcgcatgac attgtgaatg tactaaatgc 55800
tattaatgat aaattttatg ttatgtgtat tttaccacaa ttaaaaaaaa aagatcaaat 55860
gtcctcagaa tagccaacaa ccttccactt ggctaaatgc ctactcatta aacttcttga 55920
actaaattcc tttctgattg tcatggttat tgtgtcctgg gcttcagagt ttcacattca 55980
ggttggcttg gtccagtctg tcatgtatca ctataggtcc ccacattggc ctcttcctca 56040
gacggacagc ccatctatct gccggggctc tgtgccacag ccagatagac ttgctctgag 56100
acagctgtgt gggctctgag cactggccag gcatcacaaa acctatcttt atgatttaga 56160
ataattggtg gtcagctgct gttttaatgt tgttgttttt tttaatttag atataattca 56220
cataccatga aatttactca tttaaagtgt acaattcatt cttcagtata attcataggc 56280
tcacagaaaa aattgtttaa aaataaaatg tgcaattcag tgtcttttag tacattcaca 56340
gagttgtgca accatcgcct ctgtgtcatt ccagaacact ttcagcaccc aaaagaaacc 56400
ccagacacag gagcagtcac ctcttattac ccgcagcccc tggcaacaac tcatccactt 56460
cctgtctcta tggatttgcc tattctggac atttcctata aatggaatta tgcactattt 56520
ggccttttgt gtctggcctc tttcactgag cgtaatgtcc tcaaggttca tctgcattgt 56580
agcatgtgtc agaatttctt tcctttttga ggctgaatga tattatatcc tatagataat 56640
gaggttttga ttatccaccc atcccttggg aatgcatatt tgggttgccc ccaccatttg 56700
gctgttgtaa actgtgctgc catgaacact ggtgtacgga tatctgtttg gttactggtt 56760
ttggtttttt gtttgtttgt tttggttttt tgagacaagg tcttgctctg tcgcccaggc 56820
tggattacag tggcacgatc tctgctcact gcaacctcca cctcccaggt tcaagcaatt 56880
ctcctgcctc agtctcctga gtagctggga ctacaggtag cactcaccac catgcccggc 56940
taaatttttt tgtattttta gtagagacaa ggtttcgcca tattggccag gctggtctca 57000
aactcctgac ctcaggtgat ccacccacct cagcctccca aagtgctggg attacagacg 57060
tgagccaccg cacccggcat agttgtggct ttttgagagt gtatggctag gagtaaaatt 57120
gccaggtcat atggtaactc catgtttaac atttgagaaa ctgccaaact gttctccaca 57180
gcaggaattt tttaacctgt atgtggtggg cttgtgtttc ggttttcatt ttacacatct 57240
ataaagatga gatttgctgt atggcactgg ttgcctgtat ttggggaggg ttctgctttt 57300
ggttggcaag aactgcattt tatttaagct tagcaaaaca taactggttt ctcgcatctt 57360
ctcaaaagtg gaggattaag aaatggactg cgaattcaga gcagggcagc tgaacctcag 57420
gctccaccct tgtagccttc aagctgaacc tcattctctc ttgctccctg gagaccactg 57480
agacactctg cctgtgccag tttgatttct cacattttta aagggccaaa gcttgtgtct 57540
caaagtgcta tagcctttat tgattcatgc agagaagcct ccttgattcc gtaattctgc 57600
agctaatact ggaagtagaa agaattggaa acaccatctg gatgacactt tagggtggaa 57660
gcagccagta caaggggggg ctcattattt cctctggtcc cagactgttc acctggagct 57720
gtagccacca ccctgccctt aggttaactg cctcgagtgg tagtttagct ctttgtgctg 57780
tgccgaggga taactggaag tgaaaggtgc tgagaaatgc catctcctga aagtggcgag 57840
catgagtgaa tttacgaaag gttgggatat tgctggggct ctggaagttt ctctggagct 57900
cactccaggg gacagggagg gggctggatt ccaattcaag tgaaaaatac ctttcatctg 57960
ccttgttcac ctggcttttt tgccttttttg taaaatctga aaacctcagg gattgagtag 58020
tctttcctta actgcagttg cctgtctggc cacacctgcc agctgttgct tgtacccctg 58080
taatttgcac ggccttccgg gcctttctca caagatcact gcaggtcaca ttcatgagga 58140
aaatgcaggc agttcctgcc atcagacccc tcaggatgtc atggtttggc ctgaaaacaa 58200
gattcctgca actctaattt tcctttgcta gatcaaatga aggatttgat ctaatgtttg 58260
cattctagca gcaaaatcat tgaatatttt atttcttaag agccttactt catattttgt 58320
aggtatttta agattttgta aaggcctttc tgcttcaacg tgtgatgtgt gcattcttag 58380
aaaaagatct tgtgttctgt aaatcacaca ataaaaacat gagttcgtgc aggaaaaact 58440
ggggcggggt ggatcactcc aaacttgtgt ggtgtggtaa ctggagctca ctgatgaaac 58500
catgaacagt tctggctgaa agaaccccac agtacactga ggtctgttgg catcgccgcc 58560
agcaccgccc cggtcccttt gtgcgcgcca ccacacctgg ctaatttttt atttttagta 58620
gagagggggt ttcaccatgt tggtcaggat ggcctcgaac tgacctcgtg atccgcccac 58680
ctcagcctcc caaagtgctg ggattacagg tgtgagcctc cgtgcccagc cttcagcttt 58740
ttttcttaat gtctttgtgt aatatgaagg cattctcttt aattgttaaa aagcttgcct 58800
accactgctt caaaatatta ctgtcagttg gcatagcttc tgattatatt gatgtcatct 58860
cccttctttt aaacatgtta ccatattggc actgtatttc ccctagccca ttgatcactt 58920
gagagttagt catagtcctc gtgctgtttc actcctaaac gtttaagcat gcctttccta 58980
agagcagaca gtacagttaa gacactcagg aagtttagca atgagctaac acagaacctt 59040
acatttctcc acatacccca taaatgcctt ttttagagcc tttgagcctg gaatgcagag 59100
tccaggactg tgtgttgtat tcgattgtgt catcccttca gtctccttta tcagaaatgt 59160
tcccccaccc ccttgttttc tctcatcatc ttgagtccag accgtggttg catggcacgc 59220
cctctctgga ctcttcctgc tgtctcctca cggtaagctt cagtctccta ctcgtgatgc 59280
tggttcatct cagcagcact gaggggcctg agctcagttt ggtcgtgtgt taaggtggtg 59340
cctgccagat ttctccacag aaaagggccc cgtactttta tttgctcttc agcctgtgta 59400

-continued ttccttcctt tcttgccagc ttgtgggtgg cttctctagc agcttctgta agatactcag 59460
tttggcagtt gtagttgttt cagcaggaga ggtgtctgca tacctgacca ccacatggct 59520
agaagtcgat ccatcctctg gcgtaaccat cctccatgct actgtccctg gggcactgag 59580
gccctcctca gtgacttcct ccacctcatc ttccgccatc tccaagccac cagtgtccaa 59640
cggactactg atatgtccca aactcatcat ttgtttattc accaattcag agcccacctt 59700
tttttcagca ctgagctagc ctctccttgc tagaagctta cggtcgaagg tctccagcca 59760
tcagaagaag cacgtggagc gctgcgtccg tgttgtggtt attcatccag catgtgttga 59820
gtaagggttg cacctgtgcc tggcattatg cattgagcgg ggagatgggg gttggcacgc 59880
acagtggggt gttctaagta cactgagggc tcgggtgccc tggctcatag agcagggagg 59940
gaggcaggag cagggaaggt gtctcagaag tgccatcttt tttttttttt ttttgggaag 60000
tggaatcttg ttctatcgcc tggtctggag tgcaatggca ctatctcaac tcactgcagc 60060
ctccgcctcc caggttcaag cgattctcat gcctcagtcc ccgagtagct gggaccacag 60120
gcgcacacca ccacacccgg caaatatttt gtatttttag tagaggcgga gttttgccat 60180
gttggccagg ctggtcttaa actcctggcc tcaagtgatc tgctcacctc ggcctcctaa 60240
ggtgttggga ttacaggcat gagccactgc gcccggtcta gaagtgccat cctaactgaa 60300
cctgaaagat gaaagttctc cagatgaacc tgaaagttct ccaaatgaaa aggtgggagg 60360
gggtgacagg gttaggccca gagcctctgg tgacacaggg tgggcatcat tggtcacttt 60420
ttcctcgagg gaggggcgtc acacgggtga tagggtggga gctataacca tgttgatagt 60480
gccgcctctg cccatctggc ctggcatgcc ctgagccctc tgtcccacct gtggaactca 60540
taagccctga cagcccactc actcctgatt cattatccac acccctgtgc ttccgctgtg 60600
cctggagcaa gctttcttca gggggaaggg aggctggaac tatgttgtag ttacctattt 60660
gtcctccctt ccaaactgtg agttcttgga ggtggaagga tgctgcagga tctggctcag 60720
gacgaaggca gttggtgaac agacacgtgt gtttttgact cacggtgatc tcagacaagt 60780
tcctctgtct agtcgaactt ctttttttcc atctgtaaca ctcaggagtt gaataggtgg 60840
tttttctgag gatacttcaa ctgtaaaatg tatgaacttg tgaactagct atttagttct 60900
cctcataatc aagattgtgt gtgtgtgggg ggttctgatt agagggagga tgaagagagg 60960
tgtatggggt ttttttgtt ttgttttctg tttgtttgtt tgtttttgag atggagtctc 61020
actctgtcac ccaggctgga gtgcagtggc acgatttcgg ttcactgcaa cctctgcctc 61080
ctgggttcaa gtgattctcc tgcctcagcc tcctgagtaa ctgggattac aggcatgcac 61140
caccatgccc agctaatttt tgtattttta atagagatgg ggttttcgcc atgttggcca 61200
ggctggtctc gaactcctga cctcaggtga tccacctgcc tcggcctccc aaagtgctgg 61260
gattataggc atgagccacc acacctggca ggtttctttg aaaaagtttg tgtttcggca 61320
aacaccataa accccctggg ggacagcctt ggggagtcac ctggcaccct agcccagcct 61380
ccctcccttg ggtcctgcag tgaaggctta gtgagggtgt gcaaatgccc aggtcaccct 61440
gggactgggc aggccctctg ggctaagggt aaactcattt ggaatacctg ttttctatca 61500
ttgtttttta tttgttaaat ttaaagggta caagtgcagt tttgttgcgt ggatatattg 61560
tatagtagtg aagtctgagc tttcagtgta accatcacct gaatagtgga cattgtaccc 61620
gttaagtaat gtctcatccc tcacccccctc ccacccttcc cagtctctcc agtgtctgcc 61680
attcctcact ctgtccatgt gcacatgcta ttcagctcct gcttctaagt gagaacgtac 61740
ggtatttgac tttctgtgtc tgagctgtgt cactgaagac aatggactcc agctccatcc 61800

-continued

```
acgtttttta tcatttttac ctgcactcca cacccagcac aatccaggct tctttgtggg  61860
tttttgaaa tttgtcttta attataaaag tagcagccag caaattaaca aacacccatg  61920
tgcctttcat tgcacagaat tgaaaatcat catactatat ttgcttcaag taatttccat  61980
tagaaagaac tagaatatta cagtagagtt aaagaccctt tatttcccat cttcagtgct  62040
cttaaaagtt catttagggc caggcatggt ggctcacacc tataatccca gcactttgag  62100
aggcccaggt gggtggatca cctgaggtca ggagttcaag accagcctgg ccaacatggc  62160
gaaaccccat ctctactaaa aatacaaaaa ttagctgggc gtggtggtgc gcatctgtaa  62220
tctcagctac tcgggaggct gaggcaggag aatcgcttga actcaggagg gaggcagagc  62280
ctgtatgcag taagccgaga ttgcgccacc acaccccagc atgggtgaca gagcaagact  62340
ccgtctcaaa aaaaaaaaaa aaaaagttca ttcattgtac acttagaaat agttaaaaag  62400
gtaaactttg ttttgtgtgt gtgtgtatat atatatatat atatatatat atatatatat  62460
atatatatgt attttttttt gagacatata tgtgtctggt ttgttcgccc aggcaggagt  62520
gcagtggcat gatcaacggc tcactgcagc ctcaacttcc taggctcaag tgatcctcct  62580
gcctcagcct cccgagtagc taggattaca ggcacacacc accatgccca gctaattttt  62640
ttttttttt tttttttttg tagagacagg gttttgctat gttgcccagg ctggtctcaa  62700
actcctgagc tcaagcgatc cacctgcctc acctcccaaa gtgctgggat tacaagtgta  62760
agccaccaca cctgacctgt tttgtatatt ttaccacaat aaaaagcctt taaaacccca  62820
agcagacagt tcattttcat tcaggcccaa ctcagaatct gatcacagcg gggtttcccc  62880
cctttctagc gagtagctga agaactgttt tctctccttg atggtataac tgtctctgtg  62940
ggtgttgctc ccctgccgct ccagtggttt tgtttttgtt tttgtttttt tgagacggag  63000
tcttgcgatc tcagctcact gcgacctctg cctcctgggt tcaggcgatt cttctccctc  63060
agccttccat gtagctggga cttacaggca cctgccacca cgcccggctc atttttgtat  63120
ttttagtaga gacggagttt caccatgttg gccaggttgg gctcgaactc cagacctcag  63180
gtgatccacc tgcctcagcc tcccacagtg ctgggattac aggtgagagc cactgcaccc  63240
agccggcccc tcagtctttt ccttctcaat cagtggcacc accatcttcc caggctttgg  63300
acatggtccc tgactcaccc ttgcccctca cccccacact aatccacctg cgagctctgt  63360
tgcttcacca cctagaccag ccccaaatcc tcaactgccc ccaccctggg ccacacctgg  63420
accactgcta gaggcctctc atgggccctc cctgtttttc tcttgcactc cccgggcttt  63480
ctggcacaag atgccccaga agcagaatca catatctctc ctgggagcca atctagtgtg  63540
tttactgccc ctggagtgtt attgttggcc ttagaatatg tcccactaca ggtttgcaga  63600
gcactgtagt caaaagtcat ttgaaataaa tcttttctct gtggtatatt gtcaatttga  63660
tatagaatta aatttgtttc ttttcttttt tcttttcttt tttttttttt ttaagagaca  63720
gggtcttggc caggcgtggt gtctcatgcc tgtaatcccg gcactttggg aagccaaggt  63780
gggtggatcg cctgaggtca ggaattcaag accaacctgg ccagcatggt gaaaccccgt  63840
ctctgctaaa aatacaaaaa ttagccgggc gtgatggcag gtacctgtaa tcccagctac  63900
tcgggaagct gaggcaggag aaggcttgaa ctcaggagtc ggaggttgca gtgagccaag  63960
atcacgccat ggcactctag caagactctg tctcaaaaaa aaaaaaagag agagagagag  64020
acagggtctt gctctgtcac tcaggctgga gtgcagtgat gtagtcatgg ctcactgcag  64080
cctcatactc ctgacctcag gtgatcgacc cgcctcggcc tcccaaagtg ctgggatcgt  64140
```

-continued

```
aggctgaagc caccatgcct ggcccgaact catttgtttt tatttgcatt aagtgtaata  64200
aggttttgtt acttttagtt tgaattttat tttgggtaat ataaacattt acatgattca  64260
gaagtcagaa ttacactgag gcatgttcag ctaggcctca ctcctgtgcc tgtaccctta  64320
ccttttttccc cctaccccat gcagggaatc aatttcatta gttcctggtg tgtccttcct  64380
taatacccccc ccttctttct ttggtagaat gcagtagata tgtttgcgct ttgctccctt  64440
tgcttcacag tggatcctgg aaatgactcc atcgcagttc ttagagctct tgtttagtcc  64500
ctttggatct gcacagtact ccagtgtgtg ggcgcaccat aagtttattc agcaagtgcc  64560
ctggtgatag ggatcggggg tattggaagc ctttggctgg taaaaataat gttgtagcaa  64620
ataacatcat gcatatgttc tttgagattt ctggaggtgt ctctttagca tagatttcta  64680
gaaggcattc cttacgtcac gtttaggttt atagtttgac ctcatggtga ttaaggtatt  64740
tgggaaatgc aaatgagagt ttcgaagaag ccagatcttt cccattagtt cactgttttt  64800
ctctgacatt aggaccgtcc gggttctagg gagcagccct ggcgttaggc agtgccatga  64860
tggattgtgt agaagtagcg attcccatct gtctgctttc ttggcccact ctgctggtgg  64920
ctccccttcc ctccctcctt tatggggagc tggggagctg cctaggggtc cattctcaaa  64980
ggctgatctc tggtgggcaa caggccacac ctagctttcc agggttcttc gtcatttccc  65040
attgagagct gtaagactca gagacatgaa aaggaagctc tggctgggca cggtggctca  65100
cgcctgtaat cccagcactt tgggaggctg aggcgggtcg atcacctgag gtcaggagtt  65160
cgagaccagc ctgcccaaca tggtgaaacc ccgtctccac taaacataca aaaattagcc  65220
tggcgtggta gcacacgcct gtgatcccag ctactccgga ggctgaggca ggagaataac  65280
ttgaacccgg caggcggagg ttgcgatgag ccgatattat gccatcggca acagagcgag  65340
actccatctc aaaaaaaaaa caaaaaacaa aacaaggcga gctctgtgct gggacagatt  65400
agggacccct ctttacagca agaaagactg ctctgtgggt tgtaggatgc ctttgtgtat  65460
gcagtggctc taggtgactc tggcagccac actctgggcc ctaaacttct ggaggaagat  65520
acaggatagg gaggaactca ggggtgagtc atggtgggga caagacattc cctcactcta  65580
agaccttgtc actagattgg aacatctctt gcctccctac acctgacctg atggttctgg  65640
agagatacgt ccttgcagct tctgagtccc agcactaagc agcctttggt aacttcccta  65700
catcatttga gttctggttt cctaaggatg cttgccagtg agtgccatgg tgccctcatt  65760
gcacagtctg tgcagtgtag acaagagggg aagtctcttg gggtagacca gccgcaaggc  65820
ggtgactagc actgatgtga accacatggg acaggggagt tgtggggctg agaacacgga  65880
gggtgggagt agtcatgctc ttttccagaa tgaactgcta acgaagggac tcgcaggtgg  65940
ctgctgcttc tttccaagct gcccctgttg ttgcagaggc tctggagtcc taggaggttt  66000
cacggtggca tactcgacag agtactagag catcatggcc agatagtgat gctggggtgt  66060
ggggcctcac ggtggccatt tctgacgaga ccccaccggg ccaaagtgat gtgtagagaa  66120
ggagctgctt cggtcaccag aaaagaacgg ggaagcctcc cacactagaa taggtagggt  66180
gctcttctcc accggcagga aggggatgta tggctctgcc tggaccacac ctttttcctt  66240
gctcttccct ccgcatctgc tgtggccgag gccattcctc atcagggaac atgtgttaga  66300
ggctcacgcc acctgggacc acttgtctta tcacccccag gaccctaggc ggtagtttcc  66360
tgtggcctga gttagctgat atttatatag tgccattgtg ccttttctcc tgtgatgctc  66420
acagtaagga tgcctagatg gggttacctg ttgtcaagat aaggaaactg aagcacagaa  66480
tgctgaggtc atttgctggg ttcatgtttg gaaagcggca aaggatttca gtgcaggttg  66540
```

-continued

```
gctggctcca aacctgtgtg tgctttccat gacactgtac tgtgtgcctc attgagcctc  66600
attctagaaa accaaaaaca cacccaaggc ccggccttca caaaggagac ccctccccca  66660
tttggctccc tttccagcag tcgacggcct cttgtcagcc atcgagccca gagtcccttg  66720
aagtgcgact catgctgggg tggtatgctc aggagccgca gtgtttccgc tcagaggaaa  66780
gggctctgat tctcctgcag tgctaggaga cttgtgggtg gccacagtgc aggtcaggca  66840
caccggccag caccacccac agcccaaatt cctaaagaaa tatttgggtc ccagcttggc  66900
ccgagtctct gttgtcctgg ggaaggacat caagatctga gtgtatgatg gcctggggcc  66960
ttgcatgtgg tgggggtcca agcctgcctc tgctcacttg ttctgcagac tggcatgttc  67020
tctgtgatac ttacatactt gtttaacact tcagggaaga aaagtcagaa gaccaggacc  67080
tccagggcct caaggacaaa cccctcaagt ttaaaaaggt gaagaaagat aagaaagaag  67140
agaaagaggg caagcatgag cccgtgcagc catcagccca ccactctgct gagcccgcag  67200
aggcaggcaa agcagagaca tcagaagggt caggctccgc cccggctgtg ccggaagctt  67260
ctgcctcccc caaacagcgg cgctccatca tccgtgaccg gggacccatg tatgatgacc  67320
ccaccctgcc tgaaggctgg acacggaagc ttaagcaaag gaaatctggc cgctctgctg  67380
ggaagtatga tgtgtatttg atcaagtaag taagagcaac tcctatctct acagggcagg  67440
gagggcaggg acaaggatcc ctcatggagc aggaaaatgt atgtgcccag ggtggggtcg  67500
gggggaacat aaacaatgaa cactgagacc aggtgtgctt gaaatgaccg tgtacagagg  67560
tcgctgccct gagtgggaag ttctcaaggt agcaggccct ctatcctctc cacacctcaa  67620
gtctttatct ggggatggaa tagctgcgga agcagaggaa cttgcagagc taggggttca  67680
gaggggtgaa gaagcatgtt tcagttctgc cttttaaatg atcccaaaaa ggttagcagt  67740
tttcaaatga catttgcaga cagcctcatt taattccatg agaagggtga gcaaaggatt  67800
atcttgttga aactgattcc tggagagact gagcaccgta cctgagttca aacttgggaa  67860
tgttctagat ggtgactcag gcccaggcac caaccagcag aatgggcctc agcctgacaa  67920
cccttctgta ccaggcctga ctctttggtt gctgaacttt ggagaggcct ggggggggtca  67980
gcggcaggca gacgagtgag tggctttggt gacaggtcct caggggcagc caggcagtgt  68040
gactctcgtt caatagtaac gtttgtcaga gcgttgtcac caccatccgc tctgccctat  68100
ctctgacatt gctatggaga gcctctaatt gttccttgtg tctttctgtt tgtccccaca  68160
gtccccaggg aaaagccttt cgctctaaag tggagttgat tgcgtacttc gaaaaggtag  68220
gcgacacatc cctggaccct aatgattttg acttcacggt aactgggaga gggagcccct  68280
cccggcgaga gcagaaacca cctaagaagc ccaaatctcc caaagctcca ggaactggca  68340
gaggccgggg acgccccaaa gggagcggca ccacgagacc caaggcggcc acgtcagagg  68400
gtgtgcaggt gaaaagggtc ctggagaaaa gtcctgggaa gctccttgtc aagatgcctt  68460
ttcaaacttc gccagggggc aaggctgagg ggggtggggc caccacatcc acccaggtca  68520
tggtgatcaa acgccccggc aggaagcgaa aagctgaggc cgaccctcag gccattccca  68580
agaaacgggg ccgaaagccg gggagtgtgg tggcagccgc tgccgccgag gccaaaaaga  68640
aagccgtgaa ggagtcttct atccgatctg tgcaggagac cgtactcccc atcaagaagc  68700
gcaagacccg ggagacggtc agcatcgagg tcaaggaagt ggtgaagccc ctgctggtgt  68760
ccaccctcgg tgagaagagc gggaaaggac tgaagacctg taagagccct gggcggaaaa  68820
gcaaggagag cagccccaag gggcgcagca gcagcgcctc ctcacccccc aagaaggagc  68880
```

-continued

```
accaccacca tcaccaccac tcagagtccc caaaggcccc cgtgccactg ctcccacccc  68940
tgcccccacc tccacctgag cccgagagct ccgaggaccc caccagcccc cctgagcccc  69000
aggacttgag cagcagcgtc tgcaaagagg agaagatgcc cagaggaggc tcactggaga  69060
gcgacggctg ccccaaggag ccagctaaga ctcagcccgc ggttgccacc gccgccacgg  69120
ccgcagaaaa gtacaaacac cgaggggagg gagagcgcaa agacattgtt tcatcctcca  69180
tgccaaggcc aaacagagag gagcctgtgg acagccggac gcccgtgacc gagagagtta  69240
gctgacttta cacggagcgg attgcaaagc aaaccaacaa gaataaaggc agctgttgtc  69300
tcttctcctt atgggtaggg ctctgacaaa gcttcccgat taactgaaat aaaaaatatt  69360
tttttttctt tcagtaaact tagagtttcg tggcttcagg gtgggagtag ttggagcatt  69420
ggggatgttt ttcttaccga caagcacagt caggttgaag acctaaccag ggccagaagt  69480
agctttgcac ttttctaaac taggctcctt caacaaggct tgctgcagat actactgacc  69540
agacaagctg ttgaccaggc acctcccctc ccgcccaaac ctttccccca tgtggtcgtt  69600
agagacagag cgacagagca gttgagagga cactcccgtt ttcggtgcca tcagtgcccc  69660
gtctacagct cccccagctc cccccacctc ccccactccc aaccacgttg ggacagggag  69720
gtgtgaggca ggagagacag ttggattctt tagagaagat ggatatgacc agtggctatg  69780
gcctgtgcga tcccacccgt ggtggctcaa gtctggcccc acaccagccc caatccaaaa  69840
ctggcaagga cgcttcacag gacaggaaag tggcacctgt ctgctccagc tctggcatgg  69900
ctaggagggg ggagtccctt gaactactgg gtgtagactg gcctgaacca caggagagga  69960
tggcccaggg tgaggtggca tggtccattc tcaagggacg tcctccaacg ggtggcgcta  70020
gaggccatgg aggcagtagg acaaggtgca ggcaggctgg cctggggtca ggccgggcag  70080
agcacagcgg ggtgagaggg attcctaatc actcagagca gtctgtgact tagtggacag  70140
gggagggggc aaagggggag gagaagaaaa tgttcttcca gttactttcc aattctcctt  70200
tagggacagc ttagaattat ttgcactatt gagtcttcat gttcccactt caaaacaaac  70260
agatgctctg agagcaaact ggcttgaatt ggtgacattt agtccctcaa gccaccagat  70320
gtgacagtgt tgagaactac ctggatttgt atatatacct gcgcttgttt taaagtgggc  70380
tcagcacata gggttcccac gaagctccga aactctaagt gtttgctgca attttataag  70440
gacttcctga ttggtttctc ttctcccctt ccatttctgc cttttgttca tttcatcctt  70500
tcacttcttt cccttcctcc atcctcctcc ttcctagttc atcccttctc ttccaggcag  70560
ccgcggtgcc caaccacact tgtcggctcc agtccccaga actctgcctg ccctttgtcc  70620
tcctgctgcc agtaccagcc ccaccctgtt ttgagccctg aggaggcctt gggctctgct  70680
gagtccgacc tggcctgtct gtgaagagca agagagcagc aaggtcttgc tctcctaggt  70740
agccccctct tccctggtaa gaaaaagcaa aaggcatttc ccaccctgaa caacgagcct  70800
tttcaccctt ctactctaga gaagtggact ggaggagctg ggcccgattt ggtagttgag  70860
gaaagcacag aggcctcctg tggcctgcca gtcatcgagt ggcccaacag gggctccatg  70920
ccagccgacc ttgacctcac tcagaagtcc agagtctagc gtagtgcagc agggcagtag  70980
cggtaccaat gcagaactcc caagacccga gctgggacca gtacctgggt ccccagccct  71040
tcctctgctc cccctttcc ctcggagttc ttcttgaatg gcaatgtttt gcttttgctc  71100
gatgcagaca gggggccaga acaccacaca tttcactgtc tgtctggtcc atagctgtgg  71160
tgtaggggct tagaggcatg ggcttgctgt gggtttttaa ttgatcagtt ttcatgtggg  71220
atcccatctt tttaacctct gttcaggaag tccttatcta gctgcatatc ttcatcatat  71280
```

-continued tggtatatcc ttttctgtgt ttacagagat gtctcttata tctaaatctg tccaactgag 71340
aagtacctta tcaaagtagc aaatgagaca gcagtcttat gcttccagaa acacccacag 71400
gcatgtccca tgtgagctgc tgccatgaac tgtcaagtgt gtgttgtctt gtgtatttca 71460
gttattgtcc ctggcttcct tactatggtg taatcatgaa ggagtgaaac atcatagaaa 71520
ctgtctagca cttccttgcc agtctttagt gatcaggaac catagttgac agttccaatc 71580
agtagcttaa gaaaaaaccg tgtttgtctc ttctggaatg gttagaagtg agggagtttg 71640
ccccgttctg tttgtagagt ctcatagttg gactttctag catatatgtg tccatttcct 71700
tatgctgtaa aagcaagtcc tgcaaccaaa ctcccatcag cccaatccct gatccctgat 71760
cccttccacc tgctctgctg atgacccccc cagcttcact tctgactctt ccccaggaag 71820
ggaagggggg tcagaagaga gggtgagtcc tccagaactc ttcctccaag gacagaaggc 71880
tcctgccccc atagtggcct cgaactcctg gcactaccaa aggacactta tccacgagag 71940
cgcagcatcc gaccaggttg tcactgagaa gatgtttatt ttggtcagtt gggtttttat 72000
gtattatact tagtcaaatg taatgtggct tctggaatca ttgtccagag ctgcttcccc 72060
gtcacctggg cgtcatctgg tcctggtaag aggagtgcgt ggcccaccag gccccccctgt 72120
cacccatgac agttcattca gggccgatgg ggcagtcgtg gttgggaaca cagcatttca 72180
agcgtcactt tatttcattc gggccccacc tgcagctccc tcaaagaggc agttgcccag 72240
cctctttccc ttccagttta ttccagagct gccagtgggg cctgaggctc cttagggttt 72300
tctctctatt tccccctttc ttcctcattc cctcgtcttt cccaaaggca tcacgagtca 72360
gtcgcctttc agcaggcagc cttggcggtt tatcgccctg gcaggcaggg gccctgcagc 72420
tctcatgctg cccctgcctt ggggtcaggt tgacaggagg ttggagggaa agccttaagc 72480
tgcaggattc tcaccagctg tgtccggccc agttttgggg tgtgacctca atttcaattt 72540
tgtctgtact tgaacattat gaagatgggg gcctctttca gtgaatttgt gaacagcaga 72600
attgaccgac agctttccag tacccatggg gctaggtcat taaggccaca tccacagtct 72660
cccccaccct tgttccagtt gttagttact acctcctctc ctgacaatac tgtatgtcgt 72720
cgagctcccc ccaggtctac ccctcccggc cctgcctgct ggtgggcttg tcatagccag 72780
tgggattgcc ggtcttgaca gctcagtgag ctggagatac ttggtcacag ccaggcgcta 72840
gcacagctcc cttctgttga tgctgtattc ccatatcaaa agacacaggg gacacccaga 72900
aacgccacat cccccaatcc atcagtgcca aactagccaa cggccccagc ttctcagctc 72960
gctggatggc ggaagctgct actcgtgagc gccagtgcgg gtgcagacaa tcttctgttg 73020
ggtggcatca ttccaggccc gaagcatgaa cagtgcacct gggacaggga gcagccccaa 73080
attgtcacct gcttctctgc ccagcttttc attgctgtga cagtgatggc gaaagagggt 73140
aataaccaga cacaaactgc caagttgggt ggagaaagga gtttctttag ctgacagaat 73200
ctctgaattt taaatcactt agtaagcggc tcaagcccag gagggagcag agggatacga 73260
gcggagtccc ctgcgcggga ccatctggaa ttggtttagc ccaagtggag cctgacagcc 73320
agaactctgt gtcccccgtc taaccacagc tccttttcca gagcattcca gtcaggctct 73380
ctgggctgac tgggccaggg gaggttacag gtaccagttc tttaagaaga tctttgggca 73440
tatacatttt tagcctgtgt cattgcccca aatggattcc tgtttcaagt tcacacctgc 73500
agattctagg acctgtgtcc tagacttcag ggagtcagct gtttctagag ttcctaccat 73560
ggagtgggtc tggaggacct gcccggtggg ggggcagagc cctgctccct ccgggtcttc 73620

-continued

```
ctactcttct ctctgctctg acgggatttg ttgattctct ccattttggt gtctttctct  73680
tttagatatt gtatcaatct ttagaaaagg catagtctac ttgttataaa tcgttaggat  73740
actgcctccc ccagggtcta aaattacata ttagagggga aaagctgaac actgaagtca  73800
gttctcaaca atttagaagg aaaacctaga aaacatttgg cagaaaatta catttcgatg  73860
tttttgaatg aatacgagca agcttttaca acagtgctga tctaaaaata cttagcactt  73920
ggcctgagat gcctggtgag cattacaggc aaggggaatc tggaggtagc cgacctgagg  73980
acatggcttc tgaacctgtc ttttgggagt ggtatggaag gtggagcgtt caccagtgac  74040
ctggaaggcc cagcaccacc ctccttccca ctcttctcat cttgacagag cctgccccag  74100
cgctgacgtg tcaggaaaac acccagggaa ctaggaaggc acttctgcct gaggggcagc  74160
ctgccttgcc cactcctgct ctgctcgcct cggatcagct gagccttctg agctggcctc  74220
tcactgcctc cccaaggccc cctgcctgcc ctgtcaggag gcagaaggaa gcaggtgtga  74280
gggcagtgca aggagggagc acaaccccca gctcccgctc cgggctccga cttgtgcaca  74340
ggcagagccc agaccctgga ggaaatccta cctttgaatt caagaacatt tggggaattt  74400
ggaaatctct ttgcccccaa acccccattc tgtcctacct ttaatcaggt cctgctcagc  74460
agtgagagca gatgaggtga aaaggccaag aggtttggct cctgcccact gatagcccct  74520
ctccccgcag tgtttgtgtg tcaagtggca aagctgttct tcctggtgac cctgattata  74580
tccagtaaca catagactgt gcgcataggc ctgctttgtc tcctctatcc tgggcttttg  74640
ttttgctttt tagttttgct tttagttttt ctgtcccttt tatttaacgc accgactaga  74700
cacacaaagc agttgaattt ttatatatat atctgtatat tgcacaatta taaactcatt  74760
ttgcttgtgg ctccacacac acaaaaaaag acctgttaaa attatacctg ttgcttaatt  74820
acaatatttc tgataaccat agcataggac aagggaaaat aaaaaaagaa aaaaaagaaa  74880
aaaaaacgac aaatctgtct gctggtcact tcttctgtcc aagcagattc gtggtctttt  74940
cctcgcttct ttcaagggct ttcctgtgcc aggtgaagga ggctccaggc agcacccagg  75000
ttttgcactc ttgtttctcc cgtgcttgtg aaagaggtcc caaggttctg ggtgcaggag  75060
cgctcccttg acctgctgaa gtccggaacg tagtcggcac agcctggtcg ccttccacct  75120
ctgggagctg gagtccactg gggtggcctg actcccccag tccccttccc gtgacctggt  75180
cagggtgagc ccatgtggag tcagcctcgc aggcctccct gccagtaggg tccgagtgtg  75240
tttcatcctt cccactctgt cgagcctggg ggctggagcg gagacgggag gcctggcctg  75300
tctcggaacc tgtgagctgc accaggtaga acgccaggga ccccagaatc atgtgcgtca  75360
gtccaagggg tcccctccag gagtagtgaa gactccagaa atgtcccttt cttctccccc  75420
atcctacgag taattgcatt tgcttttgta attcttaatg agcaatatct gctagagagt  75480
ttagctgtaa cagttctttt tgatcatctt tttttaataa ttagaaacac caaaaaaatc  75540
cagaaacttg ttcttccaaa gcagagagca ttataatcac cagggccaaa agcttccctc  75600
cctgctgtca ttgcttcttc tgaggcctga atccaaaaga aaaacagcca taggcccttt  75660
cagtggccgg gctacccgtg agcccttcgg aggaccaggg ctggggcagc ctctgggccc  75720
acatccgggg ccagctccgg cgtgtgttca gtgttagcag tgggtcatga tgctctttcc  75780
cacccagcct gggatagggg cagaggaggc gaggaggccg ttgccgctga tgtttggccg  75840
tgaacaggtg ggtgtctgcg tgcgtccacg tgcgtgtttt ctgactgaca tgaaatcgac  75900
gcccgagtta gcctcacccg gtgacctcta gccctgcccg gatggagcgg ggcccacccg  75960
gttcagtgtt tctggggagc tggacagtgg agtgcaaaag gcttgcagaa cttgaagcct  76020
```

-continued

```
gctccttccc ttgctaccac ggcctccttt ccgtttgatt tgtcactgct tcaatcaata  76080
acagccgctc cagagtcagt agtcaatgaa tatatgacca aatatcacca ggactgttac  76140
tcaatgtgtg ccgagccctt gcccatgctg ggctcccgtg tatctggaca ctgtaacgtg  76200
tgctgtgttt gctccccttc cccttccttc tttgcccttt acttgtcttt ctggggtttt  76260
tctgtttggg tttggtttgg tttttatttc tccttttgtg ttccaaacat gaggttctct  76320
ctactggtcc tcttaactgt ggtgttgagg cttatatttg tgtaattttt ggtgggtgaa  76380
aggaattttg ctaagtaaat ctcttctgtg tttgaactga agtctgtatt gtaactatgt  76440
ttaaagtaat tgttccagag acaaatattt ctagacactt tttctttaca aacaaaagca  76500
ttcggaggga gggggatggt gactgagatg agaggggaga gctgaacaga tgacccctgc  76560
ccagatcagc cagaagccac ccaaagcagt ggagcccagg agtcccactc caagccagca  76620
agccgaatag ctgatgtgtt gccactttcc aagtcactgc aaaaccaggt tttgttccgc  76680
ccagtggatt cttgttttgc ttcccctccc cccgagatta ttaccaccat cccgtgcttt  76740
taaggaaagg caagattgat gtttccttga ggggagccag gaggggatgt gtgtgtgcag  76800
agctgaagag ctggggagaa tggggctggg cccacccaag caggaggctg ggacgctctg  76860
ctgtgggcac aggtcaggct aatgttggca gatgcagctc ttcctggaca ggccaggtgg  76920
tgggcattct ctctccaagg tgtgccccgt gggcattact gtttaagaca cttccgtcac  76980
atcccacccc atcctccagg gctcaacact gtgacatctc tattccccac cctccccttc  77040
ccagggcaat aaaatgacca tggagggggc ttgcactctc ttggctgtca cccgatcgcc  77100
agcaaaactt agatgtgaga aaaccccttc ccattccatg gcgaaaacat ctccttagaa  77160
aagccattac cctcattagg catggttttg ggctcccaaa acacctgaca gcccctccct  77220
cctctgagag gcggagagtg ctgactgtag tgaccattgc atgccgggtg cagcatctgg  77280
aagagctagg cagggtgtct gccccctcct gagttgaagt catgctcccc tgtgccagcc  77340
cagaggccga gagctatgga cagcattgcc agtaacacag gccaccctgt gcagaaggga  77400
gctggctcca gcctggaaac ctgtctgagg ttgggagagg tgcacttggg gcacagggag  77460
aggccgggac acacttagct ggagatgtct ctaaaagccc tgtatcgtat tcaccttcag  77520
tttttgtgtt ttgggacaat tactttagaa aataagtagg tcgttttaaa aacaaaaatt  77580
attgattgct tttttgtagt gttcagaaaa aaggttcttt gtgtatagcc aaatgactga  77640
aagcactgat atatttaaaa acaaaaggca atttattaag gaaatttgta ccatttcagt  77700
aaacctgtct gaatgtacct gtatacgttt caaaaacacc cccccccac tgaatccctg  77760
taacctattt attatataaa gagtttgcct tataaattta cataaaaatg tccgtttgtg  77820
tcttttgttg taaaaatcaa gtgatttttt cataaggttc ttttactatt ggaaaagatg  77880
ggcagcacgc agttttattt tatttttgta agttttttaa tacatgtgaa agcaaagaat  77940
actcagcatg cctttctaag tgacgcgttt gcaccttttg ttgggaagta ctgtatcctg  78000
tgctgttagc attctcgata aatctctctg tgaaagtgac tcaaggtctg ggctttcatt  78060
ataagacaga agtccccctc cagctcacat gacagcatgg tgctgcgttt cctcattgga  78120
tctggctgtc cctggacaca ggtagctgcc ttcaggcctg ccacgagcgg ccaagggaag  78180
cctcctccat atgctggcct cgctggcccc tcagcttctt ccaagccagt gctctccagg  78240
cacactgctc cagcgtgtga cgggaagggc ctggcatgag tcagcctgca gcacaacctc  78300
cctgctccag acccgtatgg taggggcacc ccctaggtct ggatgtgctg tggtgctttt  78360
```

```
ggacaccccc acccccgcag gctgtggctc ctcctgtgtc tcattctggc caggaccctc  78420
acgtgccctc tgttgactgc taacgtggtt ctctgaccag gcaagggcag gctgaggggt  78480
ttgcccaaag ggggccccct tgttactggc ttccttggct ctcaggagca gcctcaccag  78540
gttggtaagg ggctggagga gacaactgct caaaggagtc cagcttcaca tgcacatgct  78600
agaaggtacc ctcggaaggc ctggccttca aaggtagatc ccagggttga aaagtcaact  78660
tgtatgcatt gagcatctcg tatgccagcc ctgttccgtg agctgatggg cctttgtgtg  78720
taagtaggac caagtgcccc cgtggaggtt agcatgggtg tgcagtcatt tcagatactt  78780
gagttggtac atctcagtaa agtctgtccc gtgagaagcc atgggtttca tggtatggtt  78840
ggcatcttcc ttgggagtgg ccacagtggt ggtggcttca ggaaagagac tccaacaggg  78900
gccagctgtg ggccttgggc acttctcgtt tctaggaaaa gtcctaagtc tgtagggcta  78960
ggggtgggga acccccttcgc tgtcaggatc aagagggcaa ggggaactgt cgctggagga  79020
gacatccagc tggagaaaca aaagagtaag tctgcgttgc tgcttgtggg gtcttcccca  79080
tctcagggcg gggaccgggg gtggcggtcc agacaagtaa tcaaggacga tgcccaggag  79140
gggacaggta cggggtggca ggagctctgc cggcgggctc aggaagcctt caccacagct  79200
gcctgagctc acccttgcca aatgagggct ggggcagcag caacgcatac actcacggct  79260
gtggcgggca gcgttctcgg catatttcag gacacctaag gagactgaat ggctcaaggc  79320
tgctgccgtg tgcagggggc tagacgtggg gcgggcaggc agggctcctg gtaacagccc  79380
tgcaggccgc agtggagagc agggttccgg cagggccgcc caggagcttt cggaaggccc  79440
ggccccggcc cctttccgag cagcccgggc ctccgccctg ccctctgtcc ccaacgccgg  79500
gagccgccgt tcgtcctcca gagccccgcc cgggcgagcc cgggaggccg atcgccgctc  79560
gcggaacccg ccgggacccg ggccctcccc ggcgcggggc gcccccgtgt gacccagcgc  79620
gcggccgcgg cgcgcaagat ggcggcgggc ccgggcaccg cccccttccgc cccgccgggc  79680
gtcgcacgag gccggctcga aggggaagtg agtcagtgtc cgcggacccg gccggcccag  79740
gcccgcgccc gccgcggccc tgagaggccc cggcaggtcc cggcccggcg gcggcagcca  79800
tggccggggg gccgggcccg ggggagcccg cagccccccgg cgcccagcac ttcttgtacg  79860
aggtgccgcc ctgggtcatg tgccgcttct acaaagtgat ggacgccctg gagcccgccg  79920
actggtgcca gttcggtggg tggcggcggg ctgccggggg gcgggaggcg cgcgggctcc  79980
tggcgccgac gcctgacgcc c                                           80001
```

<210> SEQ ID NO 2
<211> LENGTH: 10241
<212> TYPE: DNA
<213> ORGANISM: Homo sapiens

<400> SEQUENCE: 2

```
ccggcgtcgg cggcgcgcgc gctccctcct ctcggagaga gggctgtggt aaaagccgtc     60
cggaaaatgg ccgccgccgc cgccgccgcg ccgagcggag gaggaggagg aggcgaggag    120
gagagactgc tccataaaaa tacagactca ccagttcctg ctttgatgtg acatgtgact    180
ccccagaata caccttgctt ctgtagacca gctccaacag gattccatgg tagctgggat    240
gttagggctc agggaagaaa agtcagaaga ccaggacctc cagggcctca aggacaaacc    300
cctcaagttt aaaaaggtga agaaagataa gaaagaagag aaagagggca agcatgagcc    360
cgtgcagcca tcagcccacc actctgctga gcccgcagag gcaggcaaag cagagacatc    420
agaagggtca ggctccgccc cggctgtgcc ggaagcttct gcctccccca aacagcggcg    480
```

-continued

```
ctccatcatc cgtgaccggg gacccatgta tgatgacccc accctgcctg aaggctggac    540
acggaagctt aagcaaagga aatctggccg ctctgctggg aagtatgatg tgtatttgat    600
caatccccag ggaaaagcct ttcgctctaa agtggagttg attgcgtact tcgaaaaggt    660
aggcgacaca tccctggacc ctaatgattt tgacttcacg gtaactggga gagggagccc    720
ctcccggcga gagcagaaac cacctaagaa gcccaaatct cccaaagctc caggaactgg    780
cagaggccgg ggacgcccca aagggagcgg caccacgaga cccaaggcgg ccacgtcaga    840
gggtgtgcag gtgaaaaggg tcctggagaa aagtcctggg aagctccttg tcaagatgcc    900
ttttcaaact tcgccagggg gcaaggctga ggggggtggg gccaccacat ccacccaggt    960
catggtgatc aaacgccccg gcaggaagcg aaaagctgag gccgaccctc aggccattcc   1020
caagaaacgg ggccgaaagc cggggagtgt ggtggcagcc gctgccgccg aggccaaaaa   1080
gaaagccgtg aaggagtctt ctatccgatc tgtgcaggag accgtactcc ccatcaagaa   1140
gcgcaagacc cgggagacgg tcagcatcga ggtcaaggaa gtggtgaagc ccctgctggt   1200
gtccaccctc ggtgagaaga gcgggaaagg actgaagacc tgtaagagcc ctgggcggaa   1260
aagcaaggag agcagcccca aggggcgcag cagcagcgcc tcctcacccc ccaagaagga   1320
gcaccaccac catcaccacc actcagagtc ccccaaggcc cccgtgccac tgctcccacc   1380
cctgccccca cctccacctg agcccgagag ctccgaggac cccaccagcc cccctgagcc   1440
ccaggacttg agcagcagcg tctgcaaaga ggagaagatg cccagaggag gctcactgga   1500
gagcgacggc tgccccaagg agccagctaa gactcagccc gcggttgcca ccgccgccac   1560
ggccgcagaa aagtacaaac accgagggga gggagagcgc aaagacattg tttcatcctc   1620
catgccaagg ccaaacagag aggagcctgt ggacagccgg acgcccgtga ccgagagagt   1680
tagctgactt tacacggagc ggattgcaaa gcaaaccaac aagaataaag gcagctgttg   1740
tctcttctcc ttatgggtag ggctctgaca aagcttcccg attaactgaa ataaaaaata   1800
tttttttttc tttcagtaaa cttagagttt cgtggcttca gggtgggagt agttggagca   1860
ttggggatgt tttcttacc gacaagcaca gtcaggttga agacctaacc agggccagaa    1920
gtagctttgc acttttctaa actaggctcc ttcaacaagg cttgctgcag atactactga   1980
ccagacaagc tgttgaccag gcacctcccc tcccgcccaa acctttcccc catgtggtcg   2040
ttagagacag agcgacagag cagttgagag gacactcccg ttttcggtgc catcagtgcc   2100
ccgtctacag ctcccccagc tccccccacc tcccccactc ccaaccacgt tgggacaggg   2160
aggtgtgagg caggagagac agttggattc tttagagaag atggatatga ccagtggcta   2220
tggcctgtgc gatcccaccc gtggtggctc aagtctggcc ccacaccagc cccaatccaa   2280
aactggcaag gacgcttcac aggacaggaa agtggcacct gtctgctcca gctctggcat   2340
ggctaggagg ggggagtccc ttgaactact gggtgtagac tggcctgaac cacaggagag   2400
gatggcccag ggtgaggtgg catggtccat tctcaaggga cgtcctccaa cgggtggcgc   2460
tagaggccat ggaggcagta ggacaaggtg caggcaggct ggcctggggt caggccgggc   2520
agagcacagc ggggtgagag ggattcctaa tcactcagag cagtctgtga cttagtggac   2580
aggggagggg gcaaaggggg aggagaagaa aatgttcttc cagttacttt ccaattctcc   2640
tttagggaca gcttagaatt atttgcacta ttgagtcttc atgttcccac ttcaaaacaa   2700
acagatgctc tgagagcaaa ctggcttgaa ttggtgacat ttagtccctc aagccaccag   2760
atgtgacagt gttgagaact acctggattt gtatatatac ctgcgcttgt tttaaagtgg   2820
```

-continued

```
gctcagcaca tagggttccc acgaagctcc gaaactctaa gtgtttgctg caattttata   2880
aggacttcct gattggtttc tcttctcccc ttccatttct gccttttgtt catttcatcc   2940
tttcacttct ttcccttcct ccgtcctcct ccttcctagt tcatcccttc tcttccaggc   3000
agccgcggtg cccaaccaca cttgtcggct ccagtcccca gaactctgcc tgccctttgt   3060
cctcctgctg ccagtaccag ccccaccctg ttttgagccc tgaggaggcc ttgggctctg   3120
ctgagtccga cctggcctgt ctgtgaagag caagagagca gcaaggtctt gctctcctag   3180
gtagccccct cttccctggt aagaaaaagc aaaaggcatt tcccaccctg aacaacgagc   3240
cttttcaccc ttctactcta gagaagtgga ctggaggagc tgggcccgat ttggtagttg   3300
aggaaagcac agaggcctcc tgtggcctgc cagtcatcga gtggcccaac aggggctcca   3360
tgccagccga ccttgacctc actcagaagt ccagagtcta gcgtagtgca gcagggcagt   3420
agcggtacca atgcagaact cccaagaccc gagctgggac cagtacctgg gtccccagcc   3480
cttcctctgc tccccctttt ccctcggagt tcttcttgaa tggcaatgtt ttgcttttgc   3540
tcgatgcaga caggggggcca gaacaccaca catttcactg tctgtctggt ccatagctgt   3600
ggtgtagggg cttagaggca tgggcttgct gtgggttttt aattgatcag ttttcatgtg   3660
ggatcccatc tttttaacct ctgttcagga agtccttatc tagctgcata tcttcatcat   3720
attggtatat ccttttctgt gtttacagag atgtctctta tatctaaatc tgtccaactg   3780
agaagtacct tatcaaagta gcaaatgaga cagcagtctt atgcttccag aaacacccac   3840
aggcatgtcc catgtgagct gctgccatga actgtcaagt gtgtgttgtc ttgtgtattt   3900
cagttattgt ccctggcttc cttactatgg tgtaatcatg aaggagtgaa acatcataga   3960
aactgtctag cacttccttg ccagtcttta gtgatcagga accatagttg acagttccaa   4020
tcagtagctt aagaaaaaac cgtgtttgtc tcttctggaa tggttagaag tgagggagtt   4080
tgccccgttc tgtttgtaga gtctcatagt tggactttct agcatatatg tgtccatttc   4140
cttatgctgt aaaagcaagt cctgcaacca aactcccatc agcccaatcc ctgatccctg   4200
atcccttcca cctgctctgc tgatgacccc cccagcttca cttctgactc ttccccagga   4260
agggaagggg ggtcagaaga gagggtgagt cctccagaac tcttcctcca aggacagaag   4320
gctcctgccc ccatagtggc ctcgaactcc tggcactacc aaaggacact tatccacgag   4380
agcgcagcat ccgaccaggt tgtcactgag aagatgttta ttttggtcag ttgggttttt   4440
atgtattata cttagtcaaa tgtaatgtgg cttctggaat cattgtccag agctgcttcc   4500
ccgtcacctg ggcgtcatct ggtcctggta agaggagtgc gtggcccacc aggccccccct   4560
gtcacccatg acagttcatt cagggccgat ggggcagtcg tggttgggaa cacagcattt   4620
caagcgtcac tttatttcat tcgggcccca cctgcagctc cctcaaagag gcagttgccc   4680
agcctctttc ccttccagtt tattccagag ctgccagtgg ggcctgaggc tccttagggt   4740
tttctctcta tttccccctt tcttcctcat tccctcgtct ttcccaaagg catcacgagt   4800
cagtcgcctt tcagcaggca gccttggcgg tttatcgccc tggcaggcag gggccctgca   4860
gctctcatgc tgcccctgcc ttggggtcag gttgacagga ggttggaggg aaagccttaa   4920
gctgcaggat tctcaccagc tgtgtccggc ccagttttgg ggtgtgacct caatttcaat   4980
tttgtctgta cttgaacatt atgaagatgg gggcctcttt cagtgaattt gtgaacagca   5040
gaattgaccg acagctttcc agtacccatg gggctaggtc attaaggcca catccacagt   5100
ctcccccacc cttgttccag ttgttagtta ctacctcctc tcctgacaat actgtatgtc   5160
gtcgagctcc ccccaggtct acccctcccg gccctgcctg ctggtgggct tgtcatagcc   5220
```

-continued

```
agtgggattg ccggtcttga cagctcagtg agctggagat acttggtcac agccaggcgc   5280
tagcacagct cccttctgtt gatgctgtat tcccatatca aaagacacag gggacaccca   5340
gaaacgccac atcccccaat ccatcagtgc caaactagcc aacggcccca gcttctcagc   5400
tcgctggatg gcggaagctg ctactcgtga gcgccagtgc gggtgcagac aatcttctgt   5460
tgggtggcat cattccaggc ccgaagcatg aacagtgcac ctgggacagg gagcagcccc   5520
aaattgtcac ctgcttctct gcccagcttt tcattgctgt gacagtgatg gcgaaagagg   5580
gtaataacca gacacaaact gccaagttgg gtggagaaag gagtttcttt agctgacaga   5640
atctctgaat tttaaatcac ttagtaagcg gctcaagccc aggagggagc agagggatac   5700
gagcggagtc ccctgcgcgg gaccatctgg aattggttta gcccaagtgg agcctgacag   5760
ccagaactct gtgtccccccg tctaaccaca gctccttttc cagagcattc cagtcaggct   5820
ctctgggctg actgggccag gggaggttac aggtaccagt tctttaagaa gatctttggg   5880
catatacatt tttagcctgt gtcattgccc caaatggatt cctgtttcaa gttcacacct   5940
gcagattcta ggacctgtgt cctagacttc agggagtcag ctgtttctag agttcctacc   6000
atggagtggg tctggaggac ctgcccggtg ggggggcaga gccctgctcc ctccgggtct   6060
tcctactctt ctctctgctc tgacgggatt tgttgattct ctccattttg gtgtctttct   6120
cttttagata ttgtatcaat ctttagaaaa ggcatagtct acttgttata aatcgttagg   6180
atactgcctc ccccagggtc taaaattaca tattagaggg gaaaagctga acactgaagt   6240
cagttctcaa caatttagaa ggaaaaccta gaaaacattt ggcagaaaat tacatttcga   6300
tgtttttgaa tgaatacgag caagctttta caacagtgct gatctaaaaa tacttagcac   6360
ttggcctgag atgcctggtg agcattacag gcaaggggaa tctggaggta gccgacctga   6420
ggacatggct tctgaacctg tcttttggga gtggtatgga aggtggagcg ttcaccagtg   6480
acctggaagg cccagcacca ccctccttcc cactcttctc atcttgacag agcctgcccc   6540
agcgctgacg tgtcaggaaa acacccaggg aactaggaag gcacttctgc ctgaggggca   6600
gcctgccttg cccactcctg ctctgctcgc ctcggatcag ctgagccttc tgagctggcc   6660
tctcactgcc tccccaaggc cccctgcctg ccctgtcagg aggcagaagg aagcaggtgt   6720
gagggcagtg caaggaggga gcacaacccc cagctcccgc tccgggctcc gacttgtgca   6780
caggcagagc ccagaccctg gaggaaatcc tacctttgaa ttcaagaaca tttggggaat   6840
ttggaaatct ctttgccccc aaaccccccat tctgtcctac ctttaatcag gtcctgctca   6900
gcagtgagag cagatgaggt gaaaaggcca agaggtttgg ctcctgccca ctgatagccc   6960
ctctccccgc agtgtttgtg tgtcaagtgg caaagctgtt cttcctggtg accctgatta   7020
tatccagtaa cacatagact gtgcgcatag gcctgctttg tctcctctat cctgggcttt   7080
tgttttgctt tttagttttg cttttagttt ttctgtccct tttatttaac gcaccgacta   7140
gacacacaaa gcagttgaat ttttatatat atatctgtat attgcacaat tataaactca   7200
ttttgcttgt ggctccacac acacaaaaaa agacctgtta aaattatacc tgttgcttaa   7260
ttacaatatt tctgataacc atagcatagg acaagggaaa ataaaaaaag aaaaaaaaga   7320
aaaaaaaacg acaaatctgt ctgctggtca cttcttctgt ccaagcagat tcgtggtctt   7380
ttcctcgctt ctttcaaggg ctttcctgtg ccaggtgaag gaggctccag gcagcaccca   7440
ggttttgcac tcttgtttct cccgtgcttg tgaaagaggt cccaaggttc tgggtgcagg   7500
agcgctccct tgacctgctg aagtccggaa cgtagtcggc acagcctggt cgccttccac   7560
```

ctctgggagc tggagtccac tggggtggcc tgactccccc agtccccttc ccgtgacctg 7620
gtcagggtga gcccatgtgg agtcagcctc gcaggcctcc ctgccagtag ggtccgagtg 7680
tgtttcatcc ttcccactct gtcgagcctg ggggctggag cggagacggg aggcctggcc 7740
tgtctcggaa cctgtgagct gcaccaggta gaacgccagg gaccccagaa tcatgtgcgt 7800
cagtccaagg ggtcccctcc aggagtagtg aagactccag aaatgtccct ttcttctccc 7860
ccatcctacg agtaattgca tttgcttttg taattcttaa tgagcaatat ctgctagaga 7920
gtttagctgt aacagttctt tttgatcatc tttttttaat aattagaaac accaaaaaaa 7980
tccagaaact tgttcttcca aagcagagag cattataatc accagggcca aaagcttccc 8040
tccctgctgt cattgcttct tctgaggcct gaatccaaaa gaaaaacagc cataggccct 8100
ttcagtggcc gggctacccg tgagcccttc ggaggaccag ggctggggca gcctctgggc 8160
ccacatccgg ggccagctcc ggcgtgtgtt cagtgttagc agtgggtcat gatgctcttt 8220
cccacccagc ctgggatagg ggcagaggag gcgaggaggc cgttgccgct gatgtttggc 8280
cgtgaacagg tgggtgtctg cgtgcgtcca cgtgcgtgtt ttctgactga catgaaatcg 8340
acgcccgagt tagcctcacc cggtgacctc tagccctgcc cggatggagc ggggcccacc 8400
cggttcagtg tttctgggga gctggacagt ggagtgcaaa aggcttgcag aacttgaagc 8460
ctgctccttc ccttgctacc acggcctcct ttccgtttga tttgtcactg cttcaatcaa 8520
taacagccgc tccagagtca gtagtcaatg aatatatgac caaatatcac caggactgtt 8580
actcaatgtg tgccgagccc ttgcccatgc tgggctcccg tgtatctgga cactgtaacg 8640
tgtgctgtgt ttgctcccct tccccttcct tctttgccct ttacttgtct ttctggggtt 8700
tttctgtttg ggtttggttt ggtttttatt tctccttttg tgttccaaac atgaggttct 8760
ctctactggt cctcttaact gtggtgttga ggcttatatt tgtgtaattt ttggtgggtg 8820
aaaggaattt tgctaagtaa atctcttctg tgtttgaact gaagtctgta ttgtaactat 8880
gtttaaagta attgttccag agacaaatat ttctagacac tttttcttta caaacaaaag 8940
cattcggagg gagggggatg gtgactgaga tgagagggga gagctgaaca gatgacccct 9000
gcccagatca gccagaagcc acccaaagca gtggagccca ggagtcccac tccaagccag 9060
caagccgaat agctgatgtg ttgccacttt ccaagtcact gcaaaaccag gttttgttcc 9120
gcccagtgga ttcttgtttt gcttcccctc cccccgagat tattaccacc atcccgtgct 9180
tttaaggaaa ggcaagattg atgtttcctt gaggggagcc aggaggggat gtgtgtgtgc 9240
agagctgaag agctggggag aatggggctg ggcccaccca agcaggaggc tgggacgctc 9300
tgctgtgggc acaggtcagg ctaatgttgg cagatgcagc tcttcctgga caggccaggt 9360
ggtgggcatt ctctctccaa ggtgtgcccc gtgggcatta ctgtttaaga cacttccgtc 9420
acatcccacc ccatcctcca gggctcaaca ctgtgacatc tctattcccc accctcccct 9480
tcccagggca ataaaatgac catggagggg gcttgcactc tcttggctgt cacccgatcg 9540
ccagcaaaac ttagatgtga gaaaacccct tcccattcca tggcgaaaac atctccttag 9600
aaaagccatt accctcatta ggcatggttt tgggctccca aaacacctga cagcccctcc 9660
ctcctctgag aggcggagag tgctgactgt agtgaccatt gcatgccggg tgcagcatct 9720
ggaagagcta ggcagggtgt ctgccccctc ctgagttgaa gtcatgctcc cctgtgccag 9780
cccagaggcc gagagctatg gacagcattg ccagtaacac aggccaccct gtgcagaagg 9840
gagctggctc cagcctggaa acctgtctga ggttgggaga ggtgcacttg gggcacaggg 9900
agaggccggg acacacttag ctggagatgt ctctaaaagc cctgtatcgt attcaccttc 9960

-continued agtttttgtg ttttgggaca attactttag aaaataagta ggtcgtttta aaaacaaaaa 10020
ttattgattg cttttttgta gtgttcagaa aaaaggttct ttgtgtatag ccaaatgact 10080
gaaagcactg atatatttaa aaacaaaagg caatttatta aggaaatttg taccatttca 10140
gtaaacctgt ctgaatgtac ctgtatacgt ttcaaaaaca cccccccccc actgaatccc 10200
tgtaacctat ttattatata aagagtttgc cttataaatt t 10241

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
tatttgatca atccccaggg 20

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
ctccctctcc cagttaccgt 20

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
aggagagact ggaagaaaag tc 22

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
cttgaggggt ttgtccttga 20

<210> SEQ ID NO 7
<211> LENGTH: 23
<212> TYPE: DNA
<213> ORGANISM: Artificial sequence
<220> FEATURE:
<223> OTHER INFORMATION: Primer

<400> SEQUENCE: 7
ctcaccagtt cctgctttga tgt 23

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
aggagagact ggaggaaaag tc 22

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
cttaaacttc agtggcttgt ctctg 25

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
cgggggacat aaaagttatt g 21

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
tgcattgttt taccagtgtc aa 22

<210> SEQ ID NO 12
<211> LENGTH: 25
<212> TYPE: DNA
<213> ORGANISM: Artificial sequence
<220> FEATURE:
<223> OTHER INFORMATION: Primer

<400> SEQUENCE: 12
tgaaggagtc ttctatccga tctgt 25

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
cacttccttg acctcgatgc t 21

<210> SEQ ID NO 14
<211> LENGTH: 26
<212> TYPE: DNA
<213> ORGANISM: Artificial sequence
<220> FEATURE:
<223> OTHER INFORMATION: Probe

<400> SEQUENCE: 14
agaccgtact ccccatcaag aagcgc 26

<210> SEQ ID NO 15
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 15
gtgcgcgcga gcccgaaatc 20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
ctctccgaga ggagggagcg 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gccattttcc ggacggcttt 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
tctctcctcc tcgcctcctc 20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
acccccgccc cccggcaagg 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agagacctca acttgtcacg 20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21

-continued cattaagata accatcattt 20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ggaactggtg agtctgtatt 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
gaagcaaggt gtattctggg 20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
ctaccatgga atcctgttgg 20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ttttctataa atccatgtat 20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tagccccact cccggataag 20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
actcaagccc aaggagttca 20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
gctttaatgc tttattttta 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
tgccaacagc aggcccagcg 20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
gatatcagtg aggaagttgt 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
cgtgccatgg aagtccttcc 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ggtgagctga tgctatatga 20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
aggcggcagt ggcttacgcc 20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
agccccttaa ttttgttctc 20

-continued

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tggcggctca agaaccagcc 20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
caaatattag aatagactca 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
tgggactcag attctatagg 20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gtcctggaac gacaggcttg 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ccaaatttat aacttaagaa 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
ggtgatgtgt attttactac 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tggtgggaca aaaattgtgg 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
aaataagcat ctggcatttg 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tacattgaaa aacagccaga 20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ggatccatgc gagagaagca 20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tataatatca ttcagcctca 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
cagcaggaag agtccagaga 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
agaaacctgc caggtgtggt 20

<210> SEQ ID NO 48

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ccaggtgtgg cccagggtgg 20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggcatcctac aacccacaga 20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tgacttttct tccctgagcc 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
gggtttgtcc ttgaggccct 20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
ctcttctttc ttatctttct 20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
cttgccctct ttctcttctt 20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
tggctgcacg ggctcatgct 20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
gtggtgggct gatggctgca 20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
ctgctttgcc tgcctctgcg 20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
aagcttccgg cacagccggg 20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ggtcacggat gatggagcgc 20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
ttccgtgtcc agccttcagg 20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
cagcagagcg gccagatttc 20

<210> SEQ ID NO 61
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 61
tgtccctgcc ctccctgccc 20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
gcgaaaggct tttccctggg 20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gaagtacgca atcaactcca 20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
gggatgtgtc gcctaccttt 20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
cgtgaagtca aaatcattag 20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ttaggtggtt tctgctctcg 20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
cggcctctgc cagttcctgg 20

-continued

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
acccttttca cctgcacacc 20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
aaggagcttc ccaggacttt 20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
tggcgaagtt tgaaaaggca 20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
agccttgccc cctggcgaag 20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
tggatgtggt ggccccaccc 20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
gcttttcgct tcctgccggg 20

<210> SEQ ID NO 74
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 74
gtttcttggg aatggcctga 20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
ggctgccacc acactccccg 20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
ttcacggctt tctttttggc 20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
ctcctgcaca gatcggatag 20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
tctcccgggt cttgcgcttc 20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
cttcaccact tccttgacct 20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
tcagtccttt cccgctcttc 20

-continued

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
cttgcttttc cgcccagggc 20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
ggtgatggtg gtggtgctcc 20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
gctgctgctc aagtcctggg 20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
ctccagtgag cctcctctgg 20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
aaccgcgggc tgagtcttag 20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
tggcggcggt ggcaaccgcg 20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
ttttctgcgg ccgtggcggc 20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
ctctccctcc cctcggtgtt 20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
cttggcatgg aggatgaaac 20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
tccggctgtc cacaggctcc 20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
aatccgctcc gtgtaaagtc 20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
cagctgcctt tattcttgtt 20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
gtcagagccc tacccataag 20

<210> SEQ ID NO 94
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 94
agcgcgcgcg ccgccgacgc 20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
cttttaccac agccctctct 20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
ccgctcggcg cggcggcggc 20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
tcagtttggg tgattcggtc 20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
cagcacagcg ggaacacatt 20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
tatttttatg gagcagtctc 20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100

-continued atgtcacatc aaagcaggaa 20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
ttggagctgg tctacagaag 20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
agccctaaca tcccagctac 20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
cacactgacc tttcagggct 20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
taaaaaagga tttcctaagt 20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
gtacacacac gctttttttt 20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
gaaagccgag cctggccggg 20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
gaagaaaatg tggatttttt 20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
cgagaatgag actccgtatc 20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
aaacccaaac caccttaccc 20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
aaaataaagt caggaggctg 20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
aaaaatggag ggcacagtgg 20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
ggtttttctc ctttattatc 20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
tatgttggcc tagaactcct 20

-continued

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
tgctctcata ttcacccacg 20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
gtgcagagac tcaagggagg 20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
gctaagcctc ctggtgaacc 20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
gtatgaacat cagctgacgc 20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
aggcgcgctg gtgcaagcct 20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
cagccactct tttttttga 20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
gtacctggga ggaactacaa 20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
agggcgagag atccaggact 20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
ggattaggga attagatgca 20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
ggaaagcctg tcttttaaaa 20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
ccagatggtg tttccaattc 20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
acttctagac cgggcgcagt 20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
gtacaatgaa tgaacttttt 20

<210> SEQ ID NO 127

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
caaacatatc tactgcattc 20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
acaggtaacc ccatctaggc 20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
ggaggtcctg gtcttctgac 20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
ttatctttct tcaccttttt 20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
ctctttctct tctttcttat 20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
cacgggctca tgcttgccct 20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
ggctgatggc tgcacgggct 20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
tgcgggctca gcagagtggt 20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
gacccttctg atgtctctgc 20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
aggcagaagc ttccggcaca 20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
tcatacatgg gtccccggtc 20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
tttcctttgc ttaagcttcc 20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
tacacatcat acttcccagc 20

<210> SEQ ID NO 140
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 140
tcaactccac tttagagcga 20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
gcctaccttt tcgaagtacg 20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
ggtccaggga tgtgtcgcct 20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
tccctctccc agttaccgtg 20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
tggagctttg ggagatttgg 20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
cgtggccgcc ttgggtctcg 20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146 aggactttc tccaggaccc 20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
aggcatcttg acaaggagct 20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
gccccctggc gaagtttgaa 20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
ccccaccccc ctcagccttg 20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
ccatgacctg ggtggatgtg 20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
ctgagggtcg gcctcagctt 20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
cccggctttc ggccccgttt 20

<210> SEQ ID NO 153
<211> LENGTH: 20
<212> TYPE: DNA
<213> ORGANISM: Artificial sequence
<220> FEATURE:

-continued

<223> OTHER INFORMATION: Synthetic oligonucleotide

<400> SEQUENCE: 153
tggcctcggc ggcagcggct 20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
tcggatagaa gactccttca 20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
tacggtctcc tgcacagatc 20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
acctcgatgc tgaccgtctc 20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
cttctcaccg agggtggaca 20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
gggctcttac aggtcttcag 20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
ctgctgctgc gccccttggg 20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
tcgggctcag gtggaggtgg 20

<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
ctgggcatct tctcctcttt 20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
gtcttagctg gctccttggg 20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
ggtggcaacc gcgggctgag 20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
cggccgtggc ggcggtggca 20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
tgtttgtact tttctgcggc 20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide -continued

<400> SEQUENCE: 166
aaacaatgtc tttgcgctct 20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
ctcctctctg tttggccttg 20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
agtcagctaa ctctctcggt 20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
tgttggtttg ctttgcaatc 20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
taaggagaag agacaacagc 20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
ttaatcggga agctttgtca 20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
gaggagggag cgcgcgcgcc 20

<210> SEQ ID NO 173
<211> LENGTH: 20

-continued

<212> TYPE: DNA
<213> ORGANISM: Artificial sequence
<220> FEATURE:
<223> OTHER INFORMATION: Synthetic oligonucleotide

<400> SEQUENCE: 173
ccggacggct tttaccacag 20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
ctcctcctcc gctcggcgcg 20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 175
atgcttcatt tttacagtat 20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
gagccagagg ctgggtgcgg 20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
tgagtctgta tttttatgga 20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
ggagtcacat gtcacatcaa 20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179

-continued gaatcctgtt ggagctggtc 20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
cttccctgag ccctaacatc 20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
cccacagcag taaaagagaa 20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 182
accccagtag ttgagattac 20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
atagtagttg ccagagggtg 20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
ggcttctatt gtaaaactat 20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
actggttttt aagagatggg 20

<210> SEQ ID NO 186
<211> LENGTH: 20
<212> TYPE: DNA
<213> ORGANISM: Artificial sequence -continued
<220> FEATURE:
<223> OTHER INFORMATION: Synthetic oligonucleotide

<400> SEQUENCE: 186
taaaatctat gggaataaaa 20

<210> SEQ ID NO 187
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 187
gaaatgtggg cttggcatgg 20

<210> SEQ ID NO 188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 188
aacatggttt agtagaaacc 20

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189
ggtattataa ttttgtaatt 20

<210> SEQ ID NO 190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 190
caacattcca tttatttagg 20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
attttcaccc tttaaaaatc 20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 192
taatacagtg acaagcatcc 20

<210> SEQ ID NO 193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 193
tccatcttgc aggtggagta 20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
gaagccaaaa aagcaacaaa 20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 195
ccaagacaag gaaaaacggg 20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
ctagctatca gctgggcatg 20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
tgccttgttg ggtagtacag 20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
gctaagttag aactccgtgg 20

<210> SEQ ID NO 199
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 199
acacgcctgt aatcctgcat 20

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 200
caactggagg ccgggcgcga 20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
agcccacaca gctgtctcag 20

<210> SEQ ID NO 202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
ttcctcatga atgtgacctg 20

<210> SEQ ID NO 203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 203
gaggaacttg tctgagatca 20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
cagctactcg ctagaaaggg 20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
ctccccataa aggagggagg 20

<210> SEQ ID NO 206

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 206
ccatcataca ctcagatctt 20

<210> SEQ ID NO 207
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207
ttgaggccct ggaggtcctg 20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
ttctttctta tctttcttca 20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209
gccctctttc tcttctttct 20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
ctgcacgggc tcatgcttgc 20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
gtgggctgat ggctgcacgg 20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 212
cctgcctctg cgggctcagc 20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 213
cggagcctga cccttctgat 20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
gggaggcaga agcttccggc 20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
ccagccttca ggcagggtgg 20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
cggccagatt tcctttgctt 20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
tgatcaaata cacatcatac 20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
gtacgcaatc aactccactt 20

<210> SEQ ID NO 219
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 219
tgtgtcgcct accttttcga 20

<210> SEQ ID NO 220
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 220
caaaatcatt agggtccagg 20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
tttctgctct cgccgggagg 20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
ccagttcctg gagctttggg 20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
cacctgcaca ccctctgacg 20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
gagcttccca ggacttttct 20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
gtttgaaaag gcatcttgac 20

-continued

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
cttgccccct ggcgaagttt 20

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
tgtggtggcc ccaccccccct 20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
tttgatcacc atgacctggg 20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
ggaatggcct gagggtcggc 20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
ccacactccc cggctttcgg 20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
tttctttttg gcctcggcgg 20

<210> SEQ ID NO 232
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 232
ctgcacagat cggatagaag 20

<210> SEQ ID NO 233
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 233
gtcttgcgct tcttgatggg 20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
cttccttgac ctcgatgctg 20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
ttcccgctct tctcaccgag 20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
tccgcccagg gctcttacag 20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
tggtggtgct ccttcttggg 20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238
cggagctctc gggctcaggt 20

-continued

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
agcctcctct gggcatcttc 20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
cgggctgagt cttagctggc 20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
ggcggtggca accgcgggct 20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
tctgcggccg tggcggcggt 20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
cccctcggtg tttgtacttt 20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
ggaggatgaa acaatgtctt 20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide -continued

<400> SEQUENCE: 245
tccacaggct cctctctgtt 20

<210> SEQ ID NO 246
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 246
ccgtgtaaag tcagctaact 20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
tttattcttg ttggtttgct 20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
cctacccata aggagaagag 20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
tatttcagtt aatcgggaag 20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
acagccctct ctccgagagg 20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
cggcggcggc cattttccgg 20

<210> SEQ ID NO 252
<211> LENGTH: 20

-continued

<212> TYPE: DNA
<213> ORGANISM: Artificial sequence
<220> FEATURE:
<223> OTHER INFORMATION: Synthetic oligonucleotide

<400> SEQUENCE: 252
tggagcagtc tctcctcctc 20

<210> SEQ ID NO 253
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 253
ttcatggaat gggcgagaag 20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
acagaggcag ggcaggcacg 20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
aagattcatg cttgttagaa 20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
tcaaagcagg aactggtgag 20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
ggtctacaga agcaaggtgt 20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258

-continued catcccagct accatggaat 20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 259
caccatcctg aggccaggca 20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
taactttttt ctattattat 20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
acagtcacag aacaacaaag 20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
ggcctaattt tttatctttg 20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
acagggttgt agccatcagc 20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
gatcactgga acacaatggt 20

<210> SEQ ID NO 265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 265
ggaagagaaa agaagggcac 20

<210> SEQ ID NO 266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 266
catttaataa ataaatccct 20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
tttaccagtg ccatttttcc 20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
cagcaaattt ctgtggtttt 20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
gctctcagac cagaccagac 20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
acagctgatg aggagggtgg 20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
tacacaaata ctaagccaca 20

-continued

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
actgccacca ccatgactaa 20

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
gttagaagtt gattttttct 20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
atactcacat ggtggagaaa 20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
gagaagaatg gaagggagaa 20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
tagagggttg gaggaacagg 20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
cttagaacaa agagaagaat 20

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide -continued

<400> SEQUENCE: 278
gacactgaca ctgtgcatga 20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
ggagttacca tatgacctgg 20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
cgtaagcttc tagcaaggag 20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
ggtaaaaatg ataaaaaacg 20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
agccttctcc tgcctcagct 20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
agaagcagca gccacctgcg 20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
tggtcttctg acttttcttc 20

<210> SEQ ID NO 285

-continued

<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 285
caccttttta aacttgaggg 20

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
tttctcttct ttcttatctt 20

<210> SEQ ID NO 287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 287
tcatgcttgc cctctttctc 20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
tgatggctgc acgggctcat 20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
cagcagagtg gtgggctgat 20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
tgatgtctct gctttgcctg 20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 291

-continued cagaagcttc cggcacagcc 20

<210> SEQ ID NO 292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 292
gggtccccgg tcacggatga 20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
gcttaagctt ccgtgtccag 20

<210> SEQ ID NO 294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 294
atacttccca gcagagcggc 20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
agcaaccaaa gagtcaggcc 20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
actttagagc gaaaggcttt 20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
ttttcgaagt acgcaatcaa 20

<210> SEQ ID NO 298
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 298
ccagggatgt gtcgcctacc 20

<210> SEQ ID NO 299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 299
ccagttaccg tgaagtcaaa 20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
tgggcttctt aggtggtttc 20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
gtggtgccgc tccctttggg 20

<210> SEQ ID NO 302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 302
tctccaggac ccttttcacc 20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
gacaaggagc ttcccaggac 20

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
ccctggcgaa gtttgaaaag 20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
cccctcagcc ttgccccctg                                              20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
tgggtggatg tggtggcccc                                              20

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
cggcctcagc ttttcgcttc                                              20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
tcggccccgt ttcttgggaa                                              20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
gcggcagcgg ctgccaccac                                              20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
aagactcctt cacggctttc                                              20

<210> SEQ ID NO 311
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 311
ggtctcctgc acagatcgga 20

<210> SEQ ID NO 312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 312
gctgaccgtc tcccgggtct 20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
cgagggtgga caccagcagg 20

<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
acaggtcttc agtcctttcc 20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
ctgctctcct tgcttttccg 20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
ctgagtggtg gtgatggtgg 20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 317
cttctcctct ttgcagacgc 20

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 318
ccgtcgctct ccagtgagcc 20

<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
ggcaaccgcg ggctgagtct 20

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
ccgtggcggc ggtggcaacc 20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
tacttttctg cggccgtggc 20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
tctttgcgct ctccctcccc 20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
tgtttggcct tggcatggag 20

<210> SEQ ID NO 324
<211> LENGTH: 20
<212> TYPE: DNA
<213> ORGANISM: Artificial sequence
<220> FEATURE:
<223> OTHER INFORMATION: Synthetic oligonucleotide -continued

```
<400> SEQUENCE: 324

aactctctcg gtcacgggcg                                                  20


<210> SEQ ID NO 325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 325

tgctttgcaa tccgctccgt                                                  20


<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326

agagacaaca gctgccttta                                                  20


<210> SEQ ID NO 327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 327

gaagctttgt cagagcccta                                                  20


<210> SEQ ID NO 328
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 328

ccttccctga aggttccctc cc                                               22
```

COMPOSITIONS AND METHODS FOR MODULATING MECP2 EXPRESSION

SEQUENCE LISTING

The present application is being filed along with a Sequence Listing in electronic format. The Sequence Listing is provided as a file entitled BIOL0264WOSEQ_ST25.txt created Mar. 2, 2016, which is 180 Kb in size. The information in the electronic format of the sequence listing is incorporated herein by reference in its entirety.

FIELD

Provided are compositions and methods for modulating expression of methyl CpG binding protein 2 (MECP2) mRNA and protein in an animal. Such methods are useful to treat, prevent, or ameliorate neurological disorders, including MECP2 duplication syndrome, by reducing expression and amount of MECP2 mRNA and protein in an animal.

BACKGROUND

Methyl CpG binding protein 2 (MECP2) is located on chromosome Xq28 and plays a fundamental role in epigenetics, controlling chromatin states, and expression of thousands of genes (Chahrour et al., *Science,* 2008, 320:1224-1229; Nan et al., *Nature,* 1998, 393:386-389; Jones et al., *Nat. Genet.,* 1998, 19:187-191). MECP2 expression must be maintained within a fairly narrow range to assure proper gene expression and neuronal function (Nan et al., *Nature,* 1988, 393:386-389). MECP2 duplication syndrome caused by overexpression of MECP2 is characterized by autism, intellectual disability, motor dysfunction, anxiety, epilepsy, recurrent respiratory tract infections, and early death, typically in males (Ramocki et al., *Am J Med Genet A,* 2010, 152A:1079-1088). Underexpression of MECP2 is associated with Rett Syndrome, which is characterized by normal early growth and development followed by a slowing of development, loss of purposeful use of the hands, distinctive hand movements, slowed brain and head growth, problems with walking, seizures, and intellectual disability, typically in females (Weaving et al., *J Med Genet,* 2005, 42:1-7).

Currently there is a lack of acceptable options for treating such neurological disorders. It is therefore an object herein to provide compositions and methods for the treatment of such disorders.

SUMMARY

Provided herein are compositions and methods for modulating expression and amount of methyl CpG binding protein 2 (MECP2) mRNA and protein. In certain embodiments, compounds useful for modulating expression and amount of MECP2 mRNA and protein are antisense compounds. In certain embodiments, the antisense compounds are modified antisense oligonucleotides. In certain embodiments, the antisense compounds are single-stranded antisense oligonucleotides. In certain embodiments, the antisense compounds are not siRNA compounds.

In certain embodiments, modulation can occur in a cell or tissue. In certain embodiments, the cell or tissue is in an animal. In certain embodiments, the animal is a human. In certain embodiments, MECP2 mRNA levels are reduced. In certain embodiments, MECP2 protein levels are reduced. Such reduction can occur in a time-dependent manner or in a dose-dependent manner.

Also provided are compositions and methods useful for preventing, treating, and ameliorating disorders and syndromes associated with MECP2 overexpression. In certain embodiments, a disorder associated with MECP2 overexpression is a neurological disorder. In certain embodiments, the neurological disorder is MECP2 duplication syndrome. In certain embodiments, MECP2 duplication syndrome is characterized by having additional copies of MECP2, which leads to overexpression of MECP2.

In certain embodiments, MECP2 duplication syndrome is characterized by autism, intellectual disability, motor dysfunction, anxiety, epilepsy, recurrent respiratory tract infections, and early death. In certain embodiments, MECP2 duplication syndrome is inherited in an X-linked pattern.

In certain embodiments, methods of treatment include administering a MECP2 antisense compound to an individual in need thereof. In certain embodiments, methods of treatment include administering a MECP2 modified antisense oligonucleotide to an individual in need thereof.

In certain embodiments, MECP2 levels are reduced sufficiently to prevent, treat, and ameliorate symptoms of MECP2 duplication syndrome, but not enough to cause symptoms of Rett Syndrome.

BRIEF DESCRIPTION OF THE DRAWINGS

FIG. 1 displays representative EEG traces for WT mice, MECP2-TG1 mice without Isis No. 628785 treatment, and MECP2-TG1 mice that received treatment with Isis No. 628785.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-$OCH_2CH_2$—$OCH_3$ and MOE) refers to an O-methoxyethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a syndrome or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" or "inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Constrained ethyl nucleoside" (also cEt nucleoside) means a nucleoside comprising a bicyclic sugar moiety comprising a 4'-$CH(CH_3)$—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to an individual in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Hotspot region" is a range of nucleobases on a target nucleic acid amenable to antisense compounds for reducing the amount or activity of the target nucleic acid as demonstrated in the examples hereinbelow.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having a MECP2 associated disorder" means identifying an animal having been diagnosed with a MECP2 associated disorder or predisposed to develop a MECP2 associated disorder. Individuals predisposed to develop a MECP2 associated disorder include those having one or more risk factors for developing a MECP2 associated disorder, including, having a personal or family history or genetic predisposition to one or more MECP2 associated disorders. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting MECP2" means reducing the level or expression of a MECP2 mRNA and/or protein. In certain embodiments, MECP2 mRNA and/or protein levels are inhibited in the presence of an antisense compound targeting MECP2, including an antisense oligonucleotide targeting MECP2, as compared to expression of MECP2 mRNA and/or protein levels in the absence of a MECP2 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"MECP2 antisense compound" means an antisense compound targeting MECP2.

"MECP2" means the mammalian gene methyl CpG binding protein 2 (MECP2), including the human gene methyl CpG binding protein 2 (MECP2). Human MECP2 has been mapped to human chromosome Xq28.

"MECP2 associated disorder" means any disorder or syndrome associated with any MECP2 nucleic acid or expression product thereof. Such disorders may include a neurological disorder. Such neurological disorders may include MECP2 duplication syndrome.

"MECP2 nucleic acid" means any nucleic acid encoding MECP2. For example, in certain embodiments, a MECP2 nucleic acid includes a DNA sequence encoding MECP2, an RNA sequence transcribed from DNA encoding MECP2 (including genomic DNA comprising introns and exons), and an mRNA sequence encoding MECP2.

"MECP2 mRNA" means any messenger RNA expression product of a DNA sequence encoding MECP2.

"MECP2 protein" means the polypeptide expression product of a MECP2 nucleic acid.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified antisense oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to MECP2 is a pharmaceutical agent.

"Pharmaceutical composition" means a mixture of substances suitable for administering to an individual. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disorder or syndrome for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salt" means a physiologically and pharmaceutically acceptable salt(s) of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded antisense oligonucleotide" means an oligonucleotide which is not hybridized to a complementary strand. A single-stranded antisense oligonucleotide is not a siRNA.

"Sites" as used herein, are defined as unique nucleobase positions within a target nucleic acid.

"Slows progression" means decrease in the development of the disorder or syndrome.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Standard cell assay" means the assay described in Example 1 and reasonable variations thereof.

"Stringent hybridization conditions" or "stringent conditions" refer to conditions under which an oligomeric compound will hybridize to its target sequence, but to a minimal number of other sequences.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds. In certain embodiments, the target nucleic acid is a MECP2 nucleic acid.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" refers administering a composition to effect an alteration or improvement of the disorder or syndrome.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

CERTAIN EMBODIMENTS

Certain embodiments provide methods, compounds, and compositions for inhibiting MECP2 mRNA and protein expression. Certain embodiments provide methods, compounds, and compositions for decreasing MECP2 mRNA and protein levels.

Certain embodiments provide antisense compounds targeted to a MECP2 nucleic acid. In certain embodiments, the MECP2 nucleic acid is the sequence set forth in GENBANK Accession No. NM_004992.3 (incorporated herein as SEQ ID NO: 2) and the complement of GENBANK Accession No. NT_167198.1 truncated from nucleotides 4203000 to 4283000 (incorporated herein as SEQ ID NO: 1).

Certain embodiments provide methods, compounds, and compositions for the treatment, prevention, or amelioration of disorders and syndromes associated with MECP2 in an individual in need thereof. Also contemplated are methods for the preparation of a medicament for the treatment, prevention, or amelioration of a disorder or syndrome associated with MECP2. MECP2 associated disorders and syndromes include neurological disorders. In certain embodiments, MECP2 associated disorders include MECP2 duplication syndrome.

The present disclosure provides the following non-limiting numbered embodiments:

Embodiment 1

A compound, comprising a modified antisense oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 16-327.

Embodiment 2

The compound of embodiment 2, wherein the nucleobase sequence of the modified antisense oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1 or SEQ ID NO: 2.

Embodiment 3

The compound of any preceding embodiment, consisting of a single-stranded modified antisense oligonucleotide.

Embodiment 4

The compound of any preceding embodiment, wherein at least one internucleoside linkage is a modified internucleoside linkage.

Embodiment 5

The compound of embodiment 4, wherein at least one modified internucleoside linkage is a phosphorothioate internucleoside linkage.

Embodiment 6

The compound of embodiment 4, wherein each modified internucleoside linkage is a phosphorothioate internucleoside linkage.

Embodiment 7

The compound of any preceding embodiment, wherein at least one internucleoside linkage is a phosphodiester internucleoside linkage.

Embodiment 8

The compound of any preceding embodiment, wherein at least one internucleoside linkage is a phosphorothioate linkage and at least one internucleoside linkage is a phosphodiester linkage.

Embodiment 9

The compound of any preceding embodiment, wherein at least one nucleoside comprises a modified nucleobase.

Embodiment 10

The compound of embodiment 9, wherein the modified nucleobase is a 5-methylcytosine.

Embodiment 11

The compound of any preceding embodiment, wherein at least one nucleoside of the modified antisense oligonucleotide comprises a modified sugar.

Embodiment 12

The compound of embodiment 11, wherein the at least one modified sugar is a bicyclic sugar.

Embodiment 13

The compound of embodiment 12, wherein the bicyclic sugar comprises a 4'-CH(R)—O-2' bridge wherein R is, independently, H, $C_1$-$C_{12}$ alkyl, or a protecting group.

Embodiment 14

The compound of embodiment 13, wherein R is methyl.

Embodiment 15

The compound of embodiment 13, wherein R is H.

Embodiment 16

The compound of embodiment 11, wherein the at least one modified sugar comprises a 2'-O-methoxyethyl group.

Embodiment 17

The compound of any preceding embodiment, wherein the modified antisense oligonucleotide comprises:

a gap segment consisting of 10 linked deoxynucleosides;

a 5' wing segment consisting of 5 linked nucleosides; and a 3' wing segment consisting of 5 linked nucleosides;

wherein the gap segment is positioned between the 5' wing segment and the 3' wing segment and wherein each nucleoside of each wing segment comprises a modified sugar.

Embodiment 18

The compound of any preceding embodiment, wherein the modified antisense oligonucleotide consists of 20 linked nucleosides.

Embodiment 19

A composition comprising the compound of any preceding embodiment or salt thereof and at least one of a pharmaceutically acceptable carrier or diluent.

Embodiment 20

A method comprising administering to an animal the compound or composition of any preceding embodiment.

Embodiment 21

The method of embodiment 20, wherein the animal is a human.

Embodiment 22

The method of embodiment 20, wherein administering the compound prevents, treats, ameliorates, or slows progression of a MECP2 associated disorder or syndrome.

Embodiment 23

The method of embodiment 22, wherein the disease, disorder or condition is MECP2 duplication syndrome.

Embodiment 24

Use of the compound or composition of any preceding embodiment for the manufacture of a medicament for treating a neurological disorder.

Embodiment 25

A method comprising administering a MECP2 antisense compound to an animal for treating a MECP2 associated disorder.

Embodiment 26

A method comprising:

identifying an animal having a MECP2 associated disorder; and administering a MECP2 antisense compound.

Embodiment 27

The method of embodiment 25 or embodiment 26, wherein MECP2 associated disorder is a neurological disorder.

Embodiment 28

The method of any one of embodiments 25-27, wherein the MECP2 associated disorder is MECP2 duplication syndrome.

Embodiment 29

The method of any one of embodiments 25-28, wherein the animal is a human.

Embodiment 30

The method of any one of embodiments 25-29, wherein the administering is parenteral administration.

Embodiment 31

The method of embodiment 30, wherein the parenteral administration is any of intracerebroventricular administration or intrathecal administration.

Embodiment 32

The method of any one of embodiments 25-31, wherein the administering reduces MECP2 mRNA and or protein levels.

Embodiment 33

The method of embodiment 32, wherein the administering reduces MECP2 mRNA and or protein levels by 15, 20, 25, 30, 35, 40, 45, 50, 55, 60, or 65 percent.

Embodiment 34

The method of any one of embodiments 25-33, wherein the administering improves motor function.

Embodiment 35

The method of embodiment 34, wherein motor function is improved by 10, 15, 20, 25, 30, or 35 percent.

Embodiment 36

The method of any one of embodiments 25-35, wherein the administering improves anxiety.

Embodiment 37

The method of embodiment 36, wherein the administering improves anxiety by 5, 10, 15, 20, 25, 30, 35, 40, 45, or 50 percent.

Embodiment 38

The method of any one of embodiments 25-37, wherein the administering improves social interaction.

Embodiment 39

The method of embodiment 38, wherein the administering improves social interaction by 5, 10, 15, 20, 25, 30, 35, 40, 45, or 50 percent.

Embodiment 40

The method of any one of embodiments 25-39, wherein the administering improves activity.

Embodiment 41

The method of embodiment 40, wherein the administering improves activity by 5, 10, 15, 20, 25, 30, 35, 40, 45, 50, 55, 60, 65, 70, 75, or 80 percent.

Embodiment 42

The method of any one of embodiments 25-41, wherein the administering reduces seizures.

Embodiment 43

The method of any one of embodiments 25-42, wherein the administering normalizes EEG discharges.

Embodiment 44

The method of any one of embodiments 25-43, wherein at least one symptom of a MECP2 associated disorder is ameliorated, treated, prevented, or slowed.

Embodiment 45

The method of any one of embodiments 25-44, wherein the antisense compound is a modified antisense oligonucleotide.

Embodiment 46

The method of embodiment 45, wherein the modified antisense oligonucleotide has the nucleobase sequence of SEQ ID NO: 324, 103, 264, 31, or 112.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a target nucleic acid is 12 to 30 subunits in length. In certain embodiments, an antisense compound targeted to a target nucleic acid is 12 to 25 subunits in length. In certain embodiments, an antisense compound targeted to a target nucleic acid is 12 to 22 subunits in length. In certain embodiments, an antisense compound targeted to a target nucleic acid is 14 to 20 subunits in length. In certain embodiments, an antisense compound targeted to a target nucleic acid is 15 to 25 subunits in length. In certain embodiments, an antisense compound targeted to a target nucleic acid is 18 to 22 subunits in length. In certain embodiments, an antisense compound targeted to a target nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to a target nucleic acid is 12 subunits in length. In certain embodiments, an antisense compound targeted to a target nucleic acid is 13 subunits in length. In certain embodiments, an antisense compound targeted to a target nucleic acid is 14 subunits in length. In certain embodiments, an antisense compound targeted to a target nucleic acid is 15 subunits in length. In certain embodiments, an antisense compound targeted to a target nucleic acid is 16 subunits in length. In certain embodiments, an antisense compound targeted to a target nucleic acid is 17 subunits in length. In certain embodiments, an antisense compound targeted to a target nucleic acid is 18 subunits in length. In certain embodiments, an antisense compound targeted to a target nucleic acid is 19 subunits in length. In certain embodiments, an antisense compound targeted to a target nucleic acid is 20 subunits in length. In certain embodiments, an antisense compound targeted to a target nucleic acid is 21 subunits in length. In certain embodiments, an antisense compound targeted to a target nucleic acid is 22 subunits in length. In certain embodiments, an antisense compound targeted to a target nucleic acid is 23 subunits in length. In certain embodiments, an antisense compound targeted to a target nucleic acid is 24 subunits in length. In certain embodiments, an antisense compound targeted to a target nucleic acid is 25 subunits in length. In certain embodiments, an antisense compound targeted to a target nucleic acid is 26 subunits in length. In certain embodiments, an antisense compound targeted to a target nucleic acid is 27 subunits in length. In certain embodiments, an antisense compound targeted to a target nucleic acid is 28 subunits in length. In certain embodiments, an antisense compound targeted to a target nucleic acid is 29 subunits in length. In certain embodiments, an antisense compound targeted to a target nucleic acid is 30 subunits in length. In certain embodiments, the antisense compound targeted to a target nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is an antisense oligonucleotide, and the linked subunits are nucleosides.

In certain embodiments antisense oligonucleotides targeted to a target nucleic acid may be shortened or truncated. For example, a single subunit may be deleted from the 5' end (5' truncation), or alternatively from the 3' end (3' truncation). A shortened or truncated antisense compound targeted to a target nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a target nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)$n-O-2' bridge, where n=1 or n=2 and 4'-$CH_2$—O—$CH_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X-Y-Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5. In certain embodiments, gapmers provided herein include, for example 19-mers having a motif of 5-9-5. In certain embodiments, gapmers provided herein include, for example 18-mers having a motif of 5-8-5. In certain embodiments, gapmers provided herein include, for example 18-mers having a motif of 4-8-6. In certain embodiments, gapmers provided herein include, for example 18-mers having a motif of 6-8-4. In certain embodiments, gapmers provided herein include, for example 18-mers having a motif of 5-7-6.

Target Nucleic Acids, Target Regions and Nucleotide Sequences

Nucleotide sequences that encode MECP2 include, without limitation, the following: GENBANK Accession No. NM_004992.3 (incorporated herein as SEQ ID NO: 2) and the complement of GENBANK Accession No. NT_167198.1 truncated from nucleotides 4203000 to 4283000 (incorporated herein as SEQ ID NO: 1).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for MECP2 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in MECP2 mRNA levels are indicative of inhibition of MECP2 expression. Reductions in levels of an MECP2 protein are also indicative of inhibition of target mRNA expression. Phenotypic changes are indicative of inhibition of MECP2 expression. Improvement in neurological function is indicative of inhibition of MECP2 expression. Improved motor function, activity, social behavior, and memory are indicative of inhibition of MECP2 expression. Reduction of anxiety-like behaviors is indicative of inhibition of MECP2 expression.

Hybridization

In some embodiments, hybridization occurs between an antisense compound disclosed herein and an MECP2 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a MECP2 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a MECP2 nucleic acid).

Non-complementary nucleobases between an antisense compound and a target nucleic acid may be tolerated provided that the antisense compound remains able to specifically hybridize to a target nucleic acid. Moreover, an antisense compound may hybridize over one or more segments of a target nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a MECP2 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a MECP2 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a MECP2 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(═O)—$N(R_m)(R_n)$, and O—$CH_2$—C(═O)—$N(R_1)$—$(CH_2)_2$—$N(R_m)(R_n)$, where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' and 4'-$CH(CH_2OCH_3)$—O-2' (and analogs thereof see U.S. Pat. No. 7,399,845, issued on Jul. 15, 2008); 4'-$C(CH_3)(CH_3)$—O-2' (and analogs thereof see published International Application WO/2009/006478, published Jan. 8, 2009); 4'-$CH_2$—$N(OCH_3)$-2' (and analogs thereof see published International Application WO/2008/150729, published Dec. 11, 2008); 4'-$CH_2$—O—$N(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—$C(H)(CH_3)$-2' (see Chattopadhyaya et al., *J. Org. Chem.,* 2009, 74, 118-134); and 4'-$CH_2$—C—(=$CH_2$)-2' (and analogs thereof see published International Application WO 2008/154401, published on Dec. 8, 2008).

Further reports related to bicyclic nucleosides can also be found in published literature (see for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2007, 129(26) 8362-8379; Elayadi et al., *Curr. Opinion Invest. Drugs,* 2001, 2, 558-561; Braasch et al., *Chem. Biol.,* 2001, 8, 1-7; and Orum et al., *Curr. Opinion Mol. Ther.,* 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$=$C(R_b)$—, —$C(R_a)$=N—, —C(=O)—, —C(=$NR_a$)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —$[C(R_a)(R_b)]_n$—, —$[C(R_a)(R_b)]_n$—O—, —$C(R_aR_b)$—N(R)—O— or —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-$(CH_2)_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, and (J) propylene carbocyclic (4'-$(CH_2)_3$-2') BNA as depicted below.

(A)

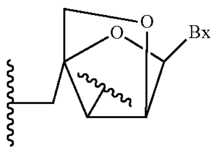

(B)

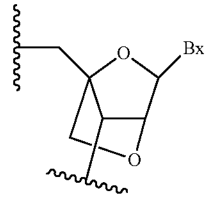

(C)

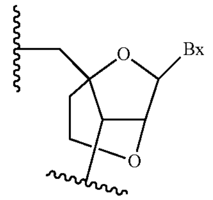

(D)

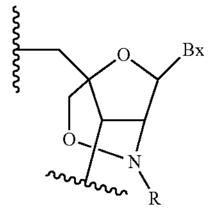

(E)

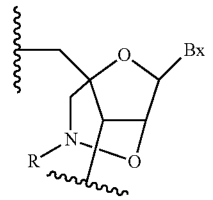

-continued (F)

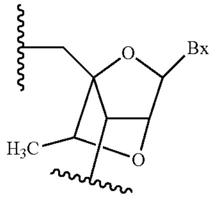

(G)

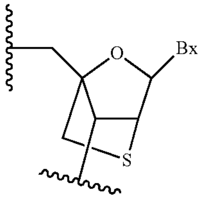

(H)

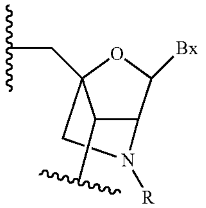

(I)

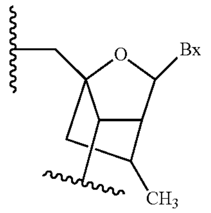

(J)

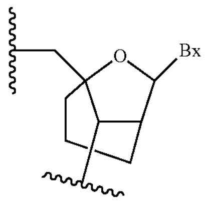

wherein Bx is the base moiety and R is independently H, a protecting group or $C_1$-$C_{12}$ alkyl.

In certain embodiments, bicyclic nucleosides are provided having Formula I:

I

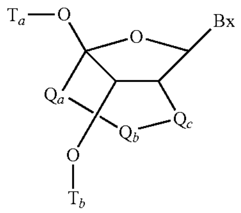

wherein:

Bx is a heterocyclic base moiety;

$Q_a$-$Q_b$-$Q_c$- is —$CH_2$—N($R_c$)—$CH_2$—, —C(═O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II

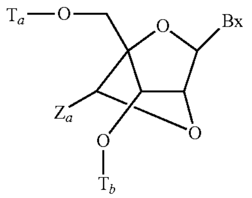

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(═X)$J_c$, and $NJ_e$C(═X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III

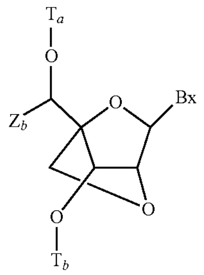

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(═O)—).

In certain embodiments, bicyclic nucleosides are provided having Formula IV:

IV

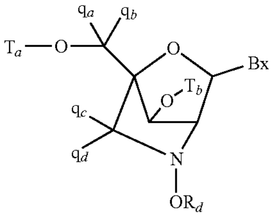

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

V

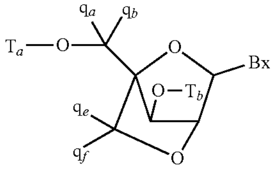

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

VI

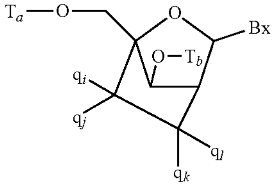

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.,* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a “modified tetrahydropyran nucleoside” or “modified THP nucleoside” means a nucleoside having a six-membered tetrahydropyran “sugar” substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854), fluoro HNA (F-HNA) or those compounds having Formula VII:

VII

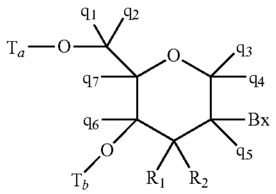

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, “2'-modified” or “2'-substituted” refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modifed nucleosides may further comprise other modifications, for example at other positions of the sugar and/or at the nucleobase.

As used herein, “2'-F” refers to a nucleoside comprising a sugar comprising a fluoro group at the 2' position.

As used herein, “2'-OMe” or “2'-$OCH_3$” or “2'-O-methyl” each refers to a nucleoside comprising a sugar comprising an —$OCH_3$ group at the 2' position of the sugar ring.

As used herein, “MOE” or “2'-MOE” or “2'-$OCH_2CH_2OCH_3$” or “2'-O-methoxyethyl” each refers to a nucleoside comprising a sugar comprising a —$OCH_2CH_2OCH_3$ group at the 2' position of the sugar ring.

As used herein, “oligonucleotide” refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.,* 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disorder, or dose to be administered.

An antisense compound targeted to a MECP2 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a MECP2 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of MECP2 nucleic acids can be tested in vitro in a variety of cell types. Cell types used for such analyses are available from commerical vendors (e.g. American Type Culture Collection, Manassus, VA; Zen-Bio, Inc., Research Triangle Park, NC; Clonetics Corporation, Walkersville, MD) and are cultured according to the vendor's instructions using commercially available reagents (e.g. Invitrogen Life Technologies, Carlsbad, CA). Illustrative cell types include, but are not limited to, HepG2 cells, Hep3B cells, and primary hepatocytes. In certain embodiments, cells are patient cells, such as B-lymphoblast cells.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, CA). Antisense oligonucleotides may be mixed with LIPOFECTIN in OPTI-MEM 1 (Invitrogen, Carlsbad, CA) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPOFECTAMINE concentration that may range from 2 to 12 ug/mL per 100 nM antisense oligonucleotide.

Another reagent used to introduce antisense oligonucleotides into cultured cells includes TURBOFECT (Thermo Scientific, Carlsbad, CA).

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, CA) according to the manufacturer's recommended protocols.

Analysis of Inhibition of Target Levels or Expression

Inhibition of levels or expression of a MECP2 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, CA). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, CA). Cyclophilin A expression is quantified by real time PCR, by being run simultaneously with the target, multiplexing, or separately. Total RNA is quantified using RIBOGREEN RNA quantification reagent (Invetrogen, Inc. Eugene, OR). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a MECP2 nucleic acid. Methods for designing real-time PCR probes and primers are well known in the art, and may include the use of software such as PRIMER EXPRESS Software (Applied Biosystems, Foster City, CA).

Analysis of Protein Levels

Antisense inhibition of MECP2 nucleic acids can be assessed by measuring MECP2 protein levels. Protein levels of MECP2 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of MECP2 and produce phenotypic changes, such as, improved behavior, motor function, and cognition. In certain embodiments, motor function is measured by walking initiation analysis, rotarod, grip strength, pole climb, open field performance, balance beam, hindpaw footprint testing in the animal. In certain embodiments, behavior is measured by elevated plus maze and three-chamber social interaction. Testing may be performed in normal animals, or in experimental models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in MECP2 nucleic acid expression are measured.

Certain Indications

In certain embodiments, provided herein are methods of treating an individual comprising administering one or more pharmaceutical compositions described herein. In certain embodiments, the individual has a neurological disorder. In certain embodiments, the individual is at risk for developing a neurological disorder, including, but not limited to, MECP2 duplication syndrome. In certain embodiments, the individual has been identified as having a MECP2 associated disorder. In certain embodiments, provided herein are methods for prophylactically reducing MECP2 expression in an individual. Certain embodiments include treating an individual in need thereof by administering to an individual a therapeutically effective amount of an antisense compound targeted to a MECP2 nucleic acid.

In one embodiment, administration of a therapeutically effective amount of an antisense compound targeted to a MECP2 nucleic acid is accompanied by monitoring of MECP2 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a MECP2 nucleic acid results in reduction of MECP2 mRNA and or protein expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in improved motor function in an animal. In certain embodiments, administration of a MECP2 antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in improved anxiety in an animal. In certain embodiments, administration of a MECP2 antisense compound improves anxiety by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in improved social interaction in an animal. In certain embodiments, administration of a MECP2 antisense compound improves social interaction by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in improved activity in an animal. In certain embodiments, administration of a MECP2 antisense compound improves activity by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in reduction of seizures. In certain embodiments, administration of a MECP2 antisense compound reduces seizures by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, administration of an antisense compound targeted to a MECP2 nucleic acid results in normalized EEG discharges.

In certain embodiments, pharmaceutical compositions comprising an antisense compound targeted to MECP2 are used for the preparation of a medicament for treating a patient suffering or susceptible to a neurological disorder including MECP2 duplication syndrome.

Certain Amplicon Regions

Certain antisense oligonucleotides described herein may target the amplicon region of the primer probe set. Additional assays may be used to measure the potency and efficacy of these compounds.

Certain Hotspot Regions

1. Nucleobases 28-382, 386-437, 439-464, 478-513, 519-602, 606-716, 720-789, 797-973, 977-1126, 1130-1189, 1192-1275, 1310-1337, 1440-1509, and 1514-1793

In certain embodiments, modified antisense oligonucleotides are complementary to nucleobases 28-382, 386-437, 439-464, 478-513, 519-602, 606-716, 720-789, 797-973, 977-1126, 1130-1189, 1192-1275, 1310-1337, 1440-1509, and 1514-1793 of SEQ ID NO: 2. In certain embodiments, nucleobases 28-382, 386-437, 439-464, 478-513, 519-602, 606-716, 720-789, 797-973, 977-1126, 1130-1189, 1192-1275, 1310-1337, 1440-1509, and 1514-1793 of SEQ ID NO: 2 are hotspot regions. In certain embodiments, such modified antisense oligonucleotides are 20 nucleobases in length. In certain embodiments, such modified antisense oligonucleotides are gapmers. In certain such embodiments, the gapmers are 5-10-5 MOE gapmers. In certain embodiments, the nucleosides of the modified antisense oligonucleotides are linked by phosphorothioate and phosphodiester internucleoside linkages.

The nucleobase sequences of SEQ ID Nos: 17, 18, 22-24, 50-60, 62-84, 86-93, 95-96, 99-102, 129-131, 133, 135-158, 161-171, 173-174, 177-180, 207-213, 215-237, 239-244, 246-252, 256-258, 284-288, 290, 292, 293, 296-305, 307-315, and 317-327 are complementary to nucleobases 28-382, 386-437, 439-464, 478-513, 519-602, 606-716, 720-789, 797-973, 977-1126, 1130-1189, 1192-1275, 1310-1337, 1440-1509, and 1514-1793 of SEQ ID NO: 2.

In certain embodiments, modified antisense oligonucleotides complementary to nucleobases 28-382, 386-437, 439-464, 478-513, 519-602, 606-716, 720-789, 797-973, 977-1126, 1130-1189, 1192-1275, 1310-1337, 1440-1509, and 1514-1793 of SEQ ID NO: 2 achieve at least 25% reduction of MECP2 RNA in vitro in the standard cell assay.

2. Nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785

In certain embodiments, modified antisense oligonucleotides are complementary to nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785 of SEQ ID NO: 2. In certain embodiments, nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785 of SEQ ID NO: 2 are hotspot regions. In certain embodiments, such modified antisense oligonucleotides are 20 nucleobases in length. In certain embodiments, such modified antisense oligonucleotides are gapmers. In certain such embodiments, the gapmers are 5-10-5 MOE gapmers. In certain embodiments, the nucleosides of the modified antisense oligonucleotides are linked by phosphorothioate and phosphodiester internucleoside linkages.

The nucleobase sequences of SEQ ID Nos: 17, 18, 22-24, 50, 52, 54, 58, 63-65, 68-73, 77-79, 81, 83, 88, 90, 91, 93, 100, 102, 133, 137, 141-143, 146, 147, 154-156, 158, 161-163, 165-169, 171, 173, 174, 177-179, 210, 216, 218-220, 223, 224, 226-228, 232-234, 236, 239-242, 244, 246, 247, 251, 257, 258, 284, 287, 288, 292, 293, 298, 303, 307, 310, 311, 314, 315, 317-319, and 321-327 are complementary to nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785 of SEQ ID NO: 2.

In certain embodiments, modified antisense oligonucleotides complementary to nucleobases 44-79, 87-126, 131-273, 321-376, 478-513, 535-570, 630-716, 834-928, 930-973, 977-1004, 1081-1126, 1130-1189, 1224-1275, 1440-1509, 1514-1745, and 1750-1785 of SEQ ID NO: 2 achieve at least 50% reduction of MECP2 RNA in vitro in the standard cell assay.

3. Nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351

In certain embodiments, modified antisense oligonucleotides are complementary to nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351 of SEQ ID NO: 1. In certain embodiments, nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351 of SEQ ID NO: 1 are hotspot regions. In certain embodiments, such modified antisense oligonucleotides are 20 nucleobases in length. In certain embodiments, such modified oligonucleotides are gapmers. In certain such embodiments, the gapmers are 5-10-5 MOE gapmers. In certain embodiments, the nucleosides of the modified oligonucleotides are linked by phosphorothioate and phosphodiester internucleoside linkages.

The nucleobase sequences of SEQ ID Nos: 17, 18, 22-24, 56-60, 62-84, 86-93, 95-96, 100-102, 135-156, 158, 161-171, 173-174, 177-179, 212-213, 215-237, 239-244, 246-251, 256-258, 290-293, 296-305, 307-315, and 317-327 are complementary to nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351 of SEQ ID NO: 1.

In certain embodiments, modified oligonucleotides complementary to nucleobases 1902-2000, 7300-7418, 67188-67239, 67241-67266, 67280-67315, 67321-67404, 68164-68274, 68278-68347, 68355-68531, 68535-68684, 68688-68747, 68750-68833, 68868-68895, 68998-69067, and 69072-69351 of SEQ ID NO: 1 achieve at least 25% reduction of MECP2 RNA in vitro in the standard cell assay.

4. Nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343

In certain embodiments, modified antisense oligonucleotides are complementary to nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343 of SEQ ID NO: 1. In certain embodiments, nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343 of SEQ ID NO: 1 are hotspot regions. In certain embodiments, such modified oligonucleotides are 20 nucleobases in length. In certain embodiments, such modified oligonucleotides are gapmers. In certain such embodiments, the gapmers are 5-10-5 MOE gapmers. In certain embodiments, the nucleosides of the modified oligonucleotides are linked by phosphorothioate and phosphodiester internucleoside linkages.

The nucleobase sequences of SEQ ID Nos: 17, 18, 22-24, 52, 54, 58, 63-65, 68-73, 77-79, 81, 83, 88, 90, 91, 93, 100, 102, 133, 137, 141-143, 146, 147, 154-156, 158, 161-163, 165-169, 171, 173, 174, 177-179, 210, 216, 218-220, 223, 224, 226-228, 232-234, 236, 239, 240-242, 244, 246, 247, 251, 257, 258, 287, 288, 292, 293, 298, 303, 307, 310, 311, 314, 315, 317-319, and 321-327 are complementary to nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343 of SEQ ID NO: 1.

In certain embodiments, modified antisense oligonucleotides complementary to nucleobases 1918-1953, 1961-2000, 7300-7418, 67123-67178, 67280-67315, 67337-67372, 68188-68274, 68392-68486, 68488-68531, 68535-68562, 68639-68684, 68688-68747, 68782-68833, 68998-69067, 69072-69303, and 69308-69343 of SEQ ID NO: 1 achieve at least 50% reduction of MECP2 RNA in vitro in the standard cell assay.

EXAMPLES

Non-limiting Disclosure and Incorporation By Reference

While certain methods described herein have been described with specificity in accordance with certain embodiments, the following examples serve only to illustrate the compounds described herein and are not intended to limit the same. Each of the references recited in the present application is incorporated herein by reference in its entirety.

Example 1: Screening of Antisense Oligonucleotides Targeting MECP2

Antisense oligonucleotides (ASOs) that target human Methyl CpG Binding Protein 2 (MECP2), the complement of GENBANK accession number NT_167198.1 truncated from 4203000 to 4283000, SEQ ID NO: 1, were synthesized using standard solid phase oligonucleotide synthetic methods. They are chimeric oligonucleotides ("gapmers"), composed of a central "gap" region consisting of 2'-deoxynucleotides, which is flanked on both sides (5' and 3') by "wings" that are composed of modified nucleotides. The internucleoside (backbone) linkages are phosphorothioate or phosphodiester throughout the oligonucleotides. The sequences and structures of the antisense oligonucleotides and their start and stop sites along SEQ ID NO: 1 are shown in the tables below. ASOs were designed to target exons and introns along the MECP2 pre-mRNA and some ASOs also target the mRNA. Isis Numbers 628567 (Table 1), 628553 (Table 2), 628566 (Table 3), and 628552 (Table 4) have mismatches to SEQ ID NO: 1 but are 100% complementary to human MECP2 mRNA, GENBANK accession number NM_004992.3 (SEQ ID NO: 2), with start sites of 246, 123, 238, and 115, respectively, on SEQ ID NO: 2. Isis Number 18078 does not target MECP2 and was used as a negative control.

The antisense oligonucleotides were analyzed for their effects on target mRNA levels. HepG2 cells were plated at a density of 20,000 cells per well in 96-well plates and were electroporated with 4.00 μM oligonucleotide or with no oligonucleotide for untreated controls. After approximately 24 hours, RNA was isolated from the cells, and MECP2 mRNA levels were measured by quantitative real-time PCR using primer probe set RTS4253 (forward: 5'-TGAAGGAGTCTTCTATCCGATCTGT-3', SEQ ID NO: 12; reverse: 5'-CACTTCCTTGACCTCGATGCT-3', SEQ ID NO: 13; probe: 5'-AGACCGTACTCCCCATCAAGAAGCGC-3', SEQ ID NO: 14). MECP2 mRNA levels were adjusted according to total RNA content, as measured by RIBOGREEN®. Results are presented as average percent inhibition of MECP2 mRNA expression level, relative to untreated control cells, in the tables below. The levels of MECP2 mRNA in untreated control cells (UTC) represents 0% inhibition, and an undetectable level of MECP2 mRNA represents 100% inhibition. A negative inhibition value means that the level of MECP2 mRNA detected was greater than that detected in untreated control cells. The results show that many of the antisense oligonucleotides inhibited MECP2 mRNA levels. The antisense oligonucleotides marked with an asterisk (*) target the region of the primer probe set. Additional assays may be used to measure the potency and efficacy of these antisense oligonucleotides.

TABLE 1

Inhibition of human MECP2 by antisense oligonucleotides in vitro

| Isis No. | Sequence (5' to 3') | Start site | Stop site | % Inhi-bition | SEQ ID NO: |
|---|---|---|---|---|---|
| 18078 | $G_{es}$ $T_{es}$ $G_{es}$ ${}^{m}C_{es}$ $G_{es}$ $C_{ds}$ $G_{ds}$ $C_{ds}$ $G_{ds}$ $A_{ds}$ $G_{ds}$ $C_{ds}$ $C_{ds}$ $C_{ds}$ $G_{es}$ $A_{es}$ $A_{es}$ $A_{es}$ $T_{es}$ ${}^{m}C_{e}$ | n/a | n/a | 0.5 | 15 |
| 628543 | ${}^{m}C_{es}$ $T_{eo}$ ${}^{m}C_{eo}$ $T_{eo}$ ${}^{m}C_{eo}$ ${}^{m}C_{ds}$ $G_{ds}$ $A_{ds}$ $G_{ds}$ $A_{ds}$ $G_{ds}$ $G_{ds}$ $A_{ds}$ $G_{ds}$ $G_{ds}$ $G_{eo}$ $A_{eo}$ $G_{es}$ ${}^{m}C_{es}$ $G_{e}$ | 1894 | 1913 | -1.7 | 16 |
| 628547 | $G_{es}$ ${}^{m}C_{eo}$ ${}^{m}C_{eo}$ $A_{eo}$ $T_{eo}$ $T_{ds}$ $T_{ds}$ $T_{ds}$ ${}^{m}C_{ds}$ ${}^{m}C_{ds}$ $G_{ds}$ $G_{ds}$ $A_{ds}$ ${}^{m}C_{ds}$ $G_{ds}$ $G_{eo}$ ${}^{m}C_{eo}$ $T_{es}$ $T_{es}$ $T_{e}$ | 1926 | 1945 | 61.8 | 17 |
| 628551 | $T_{es}$ ${}^{m}C_{eo}$ $T_{eo}$ ${}^{m}C_{eo}$ $T_{eo}$ ${}^{m}C_{ds}$ ${}^{m}C_{ds}$ $T_{ds}$ ${}^{m}C_{ds}$ ${}^{m}C_{ds}$ $T_{ds}$ ${}^{m}C_{ds}$ $G_{ds}$ ${}^{m}C_{d}$ ${}^{m}C_{ds}$ $T_{eo}$ ${}^{m}C_{eo}$ ${}^{m}C_{eo}$ ${}^{m}C_{es}$ $T_{es}$ ${}^{m}C_{e}$ | 1981 | 2000 | 54.2 | 18 |
| 628739 | $A_{es}$ ${}^{m}C_{eo}$ ${}^{m}C_{eo}$ ${}^{m}C_{eo}$ ${}^{m}C_{eo}$ ${}^{m}C_{ds}$ $G_{ds}$ ${}^{m}C_{ds}$ ${}^{m}C_{ds}$ ${}^{m}C_{ds}$ ${}^{m}C_{ds}$ ${}^{m}C_{ds}$ ${}^{m}C_{ds}$ $G_{ds}$ $G_{ds}$ ${}^{m}C_{eo}$ $A_{eo}$ $A_{es}$ $G_{es}$ $G_{e}$ | 2036 | 2055 | 33.6 | 19 |
| 628743 | $A_{es}$ $G_{eo}$ $A_{eo}$ $G_{eo}$ $A_{eo}$ ${}^{m}C_{ds}$ ${}^{m}C_{ds}$ $T_{ds}$ ${}^{m}C_{ds}$ $A_{ds}$ $A_{ds}$ ${}^{m}C_{ds}$ $T_{ds}$ $T_{ds}$ $G_{ds}$ $T_{eo}$ ${}^{m}C_{eo}$ $A_{es}$ ${}^{m}C_{es}$ $G_{e}$ | 4053 | 4072 | 36.6 | 20 |
| 628747 | ${}^{m}C_{es}$ $A_{eo}$ $T_{eo}$ $T_{eo}$ $A_{eo}$ $A_{ds}$ $G_{ds}$ $A_{ds}$ $T_{ds}$ $A_{ds}$ $A_{ds}$ ${}^{m}C_{ds}$ ${}^{m}C_{ds}$ $A_{ds}$ $T_{ds}$ ${}^{m}C_{eo}$ $A_{eo}$ $T_{es}$ $T_{es}$ $T_{e}$ | 6590 | 6609 | 43.4 | 21 |
| 628555 | $G_{es}$ $G_{eo}$ $A_{eo}$ $A_{eo}$ ${}^{m}C_{eo}$ $T_{ds}$ $G_{ds}$ $G_{ds}$ $T_{ds}$ $G_{ds}$ $A_{ds}$ $G_{ds}$ $T_{ds}$ ${}^{m}C_{ds}$ $T_{ds}$ $G_{eo}$ $T_{eo}$ $A_{es}$ $T_{es}$ $T_{e}$ | 7308 | 7327 | 60.7 | 22 |
| 628559 | $G_{es}$ $A_{eo}$ $A_{eo}$ $G_{eo}$ ${}^{m}C_{eo}$ $A_{ds}$ $A_{ds}$ $G_{ds}$ $G_{ds}$ $T_{ds}$ $G_{ds}$ $T_{ds}$ $A_{ds}$ $T_{ds}$ $T_{ds}$ ${}^{m}C_{eo}$ $T_{eo}$ $G_{es}$ $G_{es}$ $G_{e}$ | 7351 | 7370 | 62.7 | 23 |
| 628563 | ${}^{m}C_{es}$ $T_{eo}$ $A_{eo}$ ${}^{m}C_{eo}$ ${}^{m}C_{eo}$ $A_{ds}$ $T_{ds}$ $G_{ds}$ $G_{ds}$ $A_{ds}$ $A_{ds}$ $T_{ds}$ ${}^{m}C_{ds}$ ${}^{m}C_{ds}$ $T_{ds}$ $G_{eo}$ $T_{eo}$ $T_{es}$ $G_{es}$ $G_{e}$ | 7383 | 7402 | 63.1 | 24 |
| 628751 | $T_{es}$ $T_{eo}$ $T_{eo}$ $T_{eo}$ ${}^{m}C_{eo}$ $T_{ds}$ $A_{ds}$ $T_{ds}$ $A_{ds}$ $A_{ds}$ $A_{ds}$ $T_{ds}$ ${}^{m}C_{ds}$ ${}^{m}C_{ds}$ $A_{ds}$ $T_{eo}$ $G_{eo}$ $T_{es}$ $A_{es}$ $T_{e}$ | 9115 | 9134 | 78.3 | 25 |
| 628755 | $T_{es}$ $A_{eo}$ $G_{eo}$ ${}^{m}C_{eo}$ ${}^{m}C_{ds}$ ${}^{m}C_{ds}$ ${}^{m}C_{ds}$ $A_{ds}$ ${}^{m}C_{ds}$ $T_{ds}$ ${}^{m}C_{ds}$ ${}^{m}C_{ds}$ ${}^{m}C_{ds}$ $G_{ds}$ $G_{ds}$ $A_{eo}$ $T_{eo}$ $A_{es}$ $A_{es}$ $G_{e}$ | 11509 | 11528 | 62.1 | 26 |
| 628759 | $A_{es}$ ${}^{m}C_{eo}$ $T_{eo}$ ${}^{m}C_{eo}$ $A_{eo}$ $A_{ds}$ $G_{ds}$ ${}^{m}C_{ds}$ ${}^{m}C_{ds}$ ${}^{m}C_{ds}$ $A_{ds}$ $A_{ds}$ $G_{ds}$ $G_{ds}$ $A_{ds}$ $G_{eo}$ $T_{eo}$ $T_{es}$ ${}^{m}C_{es}$ $A_{e}$ | 14390 | 14409 | 39.1 | 27 |
| 628763 | $G_{es}$ $C_{eo}$ $T_{eo}$ $T_{eo}$ $T_{eo}$ $A_{ds}$ $A_{ds}$ $T_{ds}$ $G_{ds}$ $C_{ds}$ $T_{ds}$ $T_{ds}$ $T_{ds}$ $A_{ds}$ $T_{ds}$ $T_{eo}$ $T_{eo}$ $T_{es}$ $T_{es}$ $A_{e}$ | 17349 | 17368 | 89.3 | 28 |
| 628767 | $T_{es}$ $G_{eo}$ ${}^{m}C_{eo}$ ${}^{m}C_{eo}$ $A_{eo}$ $A_{ds}$ ${}^{m}C_{ds}$ $A_{ds}$ $G_{ds}$ ${}^{m}C_{ds}$ $A_{ds}$ $G_{ds}$ $G_{ds}$ ${}^{m}C_{ds}$ ${}^{m}C_{ds}$ ${}^{m}C_{eo}$ $A_{eo}$ $G_{es}$ ${}^{m}C_{es}$ $G_{e}$ | 19691 | 19710 | 82.2 | 29 |
| 628771 | $G_{es}$ $A_{eo}$ $T_{eo}$ $A_{eo}$ $T_{eo}$ ${}^{m}C_{ds}$ $A_{ds}$ $G_{ds}$ $T_{ds}$ $G_{ds}$ $A_{ds}$ $G_{ds}$ $G_{ds}$ $A_{ds}$ $A_{ds}$ $G_{eo}$ $T_{eo}$ $T_{es}$ $G_{es}$ $T_{e}$ | 22318 | 22337 | 69.0 | 30 |
| 628775 | ${}^{m}C_{es}$ $G_{eo}$ $T_{eo}$ $G_{eo}$ ${}^{m}C_{eo}$ ${}^{m}C_{ds}$ $A_{ds}$ $T_{ds}$ $G_{ds}$ $G_{ds}$ $A_{ds}$ $A_{ds}$ $G_{ds}$ $T_{ds}$ ${}^{m}C_{ds}$ ${}^{m}C_{eo}$ $T_{eo}$ $T_{es}$ ${}^{m}C_{es}$ ${}^{m}C_{e}$ | 24936 | 24955 | 82.8 | 31 |
| 628779 | $G_{es}$ $G_{eo}$ $T_{eo}$ $G_{eo}$ $A_{eo}$ $G_{ds}$ ${}^{m}C_{ds}$ $T_{ds}$ $G_{ds}$ $A_{ds}$ $T_{ds}$ $G_{ds}$ ${}^{m}C_{ds}$ $T_{ds}$ $A_{ds}$ $T_{eo}$ $A_{eo}$ $T_{es}$ $G_{es}$ $A_{e}$ | 27172 | 27191 | 75.8 | 32 |
| 628783 | $A_{es}$ $G_{eo}$ $G_{eo}$ ${}^{m}C_{eo}$ $G_{eo}$ $G_{ds}$ ${}^{m}C_{ds}$ $A_{ds}$ $G_{ds}$ $T_{ds}$ $G_{ds}$ $G_{ds}$ ${}^{m}C_{ds}$ $T_{ds}$ $T_{ds}$ $A_{eo}$ ${}^{m}C_{eo}$ $G_{es}$ ${}^{m}C_{es}$ ${}^{m}C_{e}$ | 29717 | 29736 | 35.2 | 33 |
| 628787 | $A_{es}$ $G_{eo}$ ${}^{m}C_{eo}$ ${}^{m}C_{eo}$ ${}^{m}C_{eo}$ ${}^{m}C_{ds}$ $T_{ds}$ $T_{ds}$ $A_{ds}$ $A_{ds}$ $T_{ds}$ $T_{ds}$ $T_{ds}$ $T_{ds}$ $G_{ds}$ $T_{eo}$ $T_{eo}$ ${}^{m}C_{es}$ $T_{es}$ ${}^{m}C_{e}$ | 31758 | 31777 | 81.2 | 34 |
| 628791 | $T_{es}$ $G_{eo}$ $G_{eo}$ ${}^{m}C_{eo}$ $G_{eo}$ $G_{ds}$ ${}^{m}C_{ds}$ $T_{ds}$ ${}^{m}C_{ds}$ $A_{ds}$ $A_{ds}$ $G_{ds}$ $A_{ds}$ $A_{ds}$ ${}^{m}C_{ds}$ ${}^{m}C_{eo}$ $A_{eo}$ $G_{es}$ ${}^{m}C_{es}$ ${}^{m}C_{e}$ | 34273 | 34292 | 39.2 | 35 |
| 628795 | ${}^{m}C_{es}$ $A_{eo}$ $A_{eo}$ $A_{eo}$ $T_{eo}$ $A_{ds}$ $T_{ds}$ $T_{ds}$ $A_{ds}$ $G_{ds}$ $A_{ds}$ $A_{ds}$ $T_{ds}$ $A_{ds}$ $G_{ds}$ $A_{eo}$ ${}^{m}C_{eo}$ $T_{es}$ ${}^{m}C_{es}$ $A_{e}$ | 36288 | 36307 | 62.8 | 36 |
| 628799 | $T_{es}$ $G_{eo}$ $G_{eo}$ $G_{eo}$ $A_{eo}$ ${}^{m}C_{ds}$ $T_{ds}$ ${}^{m}C_{ds}$ $A_{ds}$ $G_{ds}$ $A_{ds}$ $T_{ds}$ $T_{ds}$ ${}^{m}C_{ds}$ $T_{ds}$ $A_{eo}$ $T_{eo}$ $A_{es}$ $G_{es}$ $G_{e}$ | 39071 | 39090 | 67.2 | 37 |
| 628803 | $G_{es}$ $T_{eo}$ ${}^{m}C_{eo}$ ${}^{m}C_{eo}$ $T_{eo}$ $G_{ds}$ $G_{ds}$ $A_{ds}$ $A_{ds}$ ${}^{m}C_{ds}$ $G_{ds}$ $A_{ds}$ ${}^{m}C_{ds}$ $A_{ds}$ $G_{ds}$ $G_{eo}$ ${}^{m}C_{eo}$ $T_{es}$ $T_{es}$ $G_{e}$ | 41073 | 41092 | 66.0 | 38 |
| 628807 | ${}^{m}C_{es}$ ${}^{m}C_{eo}$ $A_{eo}$ $A_{eo}$ $A_{eo}$ $T_{ds}$ $T_{ds}$ $T_{ds}$ $A_{ds}$ $T_{ds}$ $A_{ds}$ $A_{ds}$ ${}^{m}C_{ds}$ $T_{ds}$ $T_{ds}$ $A_{eo}$ $A_{eo}$ $G_{es}$ $A_{es}$ $A_{e}$ | 43580 | 43599 | 18.3 | 39 |

TABLE 1-continued

| Isis No. | Sequence (5' to 3') | Start site | Stop site | % Inhi-bition | SEQ ID NO: |
|---|---|---|---|---|---|
| Inhibition of human MECP2 by antisense oligonucleotides in vitro | | | | | |
| 628811 | $G_{es}$ $G_{eo}$ $T_{eo}$ $G_{eo}$ $A_{eo}$ $T_{ds}$ $G_{ds}$ $T_{ds}$ $G_{ds}$ $T_{ds}$ $A_{ds}$ $T_{ds}$ $T_{ds}$ $T_{ds}$ $T_{ds}$ $A_{eo}$ $^{m}C_{eo}$ $T_{es}$ $A_{es}$ $^{m}C_{e}$ | 45768 | 45787 | 86.2 | 40 |
| 628815 | $T_{es}$ $G_{eo}$ $G_{eo}$ $T_{eo}$ $G_{eo}$ $G_{ds}$ $G_{ds}$ $A_{ds}$ $^{m}C_{ds}$ $A_{ds}$ $A_{ds}$ $A_{ds}$ $A_{ds}$ $A_{ds}$ $T_{ds}$ $T_{eo}$ $G_{eo}$ $T_{es}$ $G_{es}$ $G_{e}$ | 47850 | 47869 | 64.6 | 41 |
| 628819 | $A_{es}$ $A_{eo}$ $A_{eo}$ $T_{eo}$ $A_{eo}$ $A_{ds}$ $G_{ds}$ $^{m}C_{ds}$ $A_{ds}$ $T_{ds}$ $^{m}C_{ds}$ $T_{ds}$ $G_{ds}$ $G_{ds}$ $^{m}C_{ds}$ $A_{eo}$ $T_{eo}$ $T_{es}$ $T_{es}$ $G_{e}$ | 49865 | 49884 | 52.8 | 42 |
| 628823 | $T_{es}$ $A_{eo}$ $^{m}C_{eo}$ $A_{eo}$ $T_{eo}$ $T_{ds}$ $G_{ds}$ $A_{ds}$ $A_{ds}$ $A_{ds}$ $A_{ds}$ $A_{ds}$ $^{m}C_{ds}$ $A_{ds}$ $G_{ds}$ $^{m}C_{eo}$ $^{m}C_{eo}$ $A_{es}$ $G_{es}$ $A_{e}$ | 52552 | 52571 | 17.2 | 43 |
| 628827 | $G_{es}$ $G_{eo}$ $A_{eo}$ $T_{eo}$ $^{m}C_{eo}$ $^{m}C_{ds}$ $A_{ds}$ $T_{ds}$ $G_{ds}$ $^{m}C_{ds}$ $G_{ds}$ $A_{ds}$ $G_{ds}$ $A_{ds}$ $G_{ds}$ $A_{eo}$ $A_{eo}$ $G_{es}$ $^{m}C_{es}$ $A_{e}$ | 54569 | 54588 | 29.1 | 44 |
| 628831 | $T_{es}$ $A_{eo}$ $T_{eo}$ $A_{eo}$ $A_{eo}$ $T_{ds}$ $A_{ds}$ $T_{ds}$ $^{m}C_{ds}$ $A_{ds}$ $T_{ds}$ $T_{ds}$ $^{m}C_{ds}$ $A_{ds}$ $G_{ds}$ $^{m}C_{eo}$ $^{m}C_{eo}$ $T_{es}$ $^{m}C_{es}$ $A_{e}$ | 56608 | 56627 | 61.7 | 45 |
| 628835 | $^{m}C_{es}$ $A_{eo}$ $G_{eo}$ $^{m}C_{eo}$ $A_{eo}$ $G_{ds}$ $G_{ds}$ $A_{ds}$ $A_{ds}$ $G_{ds}$ $A_{ds}$ $G_{ds}$ $T_{ds}$ $^{m}C_{ds}$ $^{m}C_{ds}$ $A_{eo}$ $G_{eo}$ $A_{es}$ $G_{es}$ $A_{e}$ | 59223 | 59242 | 15.9 | 46 |
| 628839 | $A_{es}$ $G_{eo}$ $A_{eo}$ $A_{eo}$ $A_{eo}$ $^{m}C_{ds}$ $^{m}C_{ds}$ $T_{ds}$ $G_{ds}$ $^{m}C_{ds}$ $^{m}C_{ds}$ $A_{ds}$ $G_{ds}$ $G_{ds}$ $T_{ds}$ $G_{eo}$ $T_{eo}$ $G_{es}$ $G_{es}$ $T_{e}$ | 61278 | 61297 | 64.4 | 47 |
| 628843 | $^{m}C_{es}$ $^{m}C_{eo}$ $A_{eo}$ $G_{eo}$ $G_{eo}$ $T_{ds}$ $G_{ds}$ $T_{ds}$ $G_{ds}$ $G_{ds}$ $^{m}C_{ds}$ $^{m}C_{ds}$ $^{m}C_{ds}$ $A_{ds}$ $G_{ds}$ $G_{eo}$ $G_{eo}$ $T_{es}$ $G_{es}$ $G_{e}$ | 63401 | 63420 | 20.5 | 48 |
| 628847 | $G_{es}$ $G_{eo}$ $^{m}C_{eo}$ $A_{eo}$ $T_{eo}$ $^{m}C_{ds}$ $^{m}C_{ds}$ $T_{ds}$ $A_{ds}$ $^{m}C_{ds}$ $A_{ds}$ $A_{ds}$ $^{m}C_{ds}$ $^{m}C_{ds}$ $^{m}C_{ds}$ $A_{eo}$ $^{m}C_{eo}$ $A_{es}$ $G_{es}$ $A_{e}$ | 65432 | 65451 | 58.1 | 49 |
| 628567 | $T_{es}$ $G_{eo}$ $A_{eo}$ $^{m}C_{eo}$ $T_{eo}$ $T_{ds}$ $T_{ds}$ $T_{ds}$ $^{m}C_{ds}$ $T_{ds}$ $T_{ds}$ $^{m}C_{ds}$ $^{m}C_{ds}$ $^{m}C_{ds}$ $T_{ds}$ $G_{ds}$ $A_{eo}$ $G_{es}$ $^{m}C_{es}$ $^{m}C_{e}$ | 67048 | 67067 | 51.8 | 50 |
| 628571 | $G_{es}$ $G_{eo}$ $G_{eo}$ $T_{eo}$ $T_{eo}$ $T_{ds}$ $G_{ds}$ $T_{ds}$ $^{m}C_{ds}$ $^{m}C_{ds}$ $T_{ds}$ $T_{ds}$ $G_{ds}$ $A_{ds}$ $G_{ds}$ $G_{eo}$ $^{m}C_{eo}$ $^{m}C_{es}$ $^{m}C_{es}$ $T_{e}$ | 67084 | 67103 | 40.4 | 51 |
| 628575 | $^{m}C_{es}$ $T_{eo}$ $^{m}C_{eo}$ $T_{eo}$ $T_{eo}$ $^{m}C_{ds}$ $T_{ds}$ $T_{ds}$ $T_{ds}$ $^{m}C_{ds}$ $T_{ds}$ $T_{ds}$ $A_{ds}$ $T_{ds}$ $^{m}C_{ds}$ $T_{eo}$ $T_{eo}$ $T_{es}$ $^{m}C_{es}$ $T_{e}$ | 67123 | 67142 | 55.4 | 52 |
| 628579 | $^{m}C_{es}$ $T_{eo}$ $T_{eo}$ $G_{eo}$ $^{m}C_{eo}$ $^{m}C_{ds}$ $^{m}C_{ds}$ $T_{ds}$ $^{m}C_{ds}$ $T_{ds}$ $T_{ds}$ $T_{ds}$ $T_{ds}$ $^{m}C_{ds}$ $T_{ds}$ $^{m}C_{ds}$ $T_{eo}$ $T_{eo}$ $^{m}C_{es}$ $T_{es}$ $T_{e}$ | 67135 | 67154 | 49.6 | 53 |
| 628583 | $T_{es}$ $G_{eo}$ $G_{eo}$ $^{m}C_{eo}$ $T_{eo}$ $G_{ds}$ $^{m}C_{ds}$ $A_{ds}$ $^{m}C_{ds}$ $G_{ds}$ $G_{ds}$ $G_{ds}$ $^{m}C_{ds}$ $T_{ds}$ $^{m}C_{ds}$ $A_{eo}$ $T_{eo}$ $G_{es}$ $^{m}C_{es}$ $T_{e}$ | 67153 | 67172 | 57.4 | 54 |
| 628587 | $G_{es}$ $T_{eo}$ $G_{eo}$ $G_{eo}$ $T_{eo}$ $G_{ds}$ $G_{ds}$ $G_{ds}$ $^{m}C_{ds}$ $T_{ds}$ $G_{ds}$ $A_{ds}$ $T_{ds}$ $G_{ds}$ $G_{ds}$ $^{m}C_{eo}$ $T_{eo}$ $G_{es}$ $^{m}C_{es}$ $A_{e}$ | 67165 | 67184 | 30.9 | 55 |
| 628591 | $^{m}C_{es}$ $T_{eo}$ $G_{eo}$ $^{m}C_{eo}$ $T_{eo}$ $T_{ds}$ $T_{ds}$ $G_{ds}$ $^{m}C_{ds}$ $^{m}C_{ds}$ $T_{ds}$ $G_{ds}$ $^{m}C_{ds}$ $^{m}C_{ds}$ $T_{ds}$ $^{m}C_{eo}$ $T_{eo}$ $G_{es}$ $^{m}C_{es}$ $G_{e}$ | 67196 | 67215 | 50.0 | 56 |
| 628595 | $A_{es}$ $A_{eo}$ $G_{eo}$ $^{m}C_{eo}$ $T_{eo}$ $T_{ds}$ $^{m}C_{ds}$ $^{m}C_{ds}$ $G_{ds}$ $G_{ds}$ $^{m}C_{ds}$ $A_{ds}$ $^{m}C_{ds}$ $A_{ds}$ $G_{ds}$ $^{m}C_{eo}$ $^{m}C_{eo}$ $G_{es}$ $G_{es}$ $G_{e}$ | 67241 | 67260 | 47.3 | 57 |
| 628599 | $G_{es}$ $G_{eo}$ $T_{eo}$ $^{m}C_{eo}$ $A_{eo}$ $^{m}C_{ds}$ $G_{ds}$ $G_{ds}$ $A_{ds}$ $T_{ds}$ $G_{ds}$ $A_{ds}$ $T_{ds}$ $G_{ds}$ $G_{ds}$ $A_{eo}$ $G_{eo}$ $^{m}C_{es}$ $G_{es}$ $^{m}C_{e}$ | 67280 | 67299 | 50.6 | 58 |
| 628603 | $T_{es}$ $T_{eo}$ $^{m}C_{eo}$ $^{m}C_{eo}$ $G_{eo}$ $T_{ds}$ $G_{ds}$ $T_{ds}$ $^{m}C_{ds}$ $^{m}C_{ds}$ $A_{ds}$ $G_{ds}$ $^{m}C_{ds}$ $^{m}C_{ds}$ $T_{ds}$ $T_{eo}$ $^{m}C_{eo}$ $A_{es}$ $G_{es}$ $G_{e}$ | 67329 | 67348 | 28.8 | 59 |
| *628607 | $^{m}C_{es}$ $A_{eo}$ $G_{eo}$ $^{m}C_{eo}$ $A_{eo}$ $G_{ds}$ $A_{ds}$ $G_{ds}$ $^{m}C_{ds}$ $G_{ds}$ $G_{ds}$ $^{m}C_{ds}$ $^{m}C_{ds}$ $A_{ds}$ $G_{ds}$ $A_{eo}$ $T_{eo}$ $T_{es}$ $T_{es}$ $T_{e}$ | 67361 | 67380 | 33.0 | 60 |
| 628851 | $T_{es}$ $G_{eo}$ $T_{eo}$ $^{m}C_{eo}$ $^{m}C_{eo}$ $^{m}C_{ds}$ $T_{ds}$ $G_{ds}$ $^{m}C_{ds}$ $^{m}C_{ds}$ $^{m}C_{ds}$ $T_{ds}$ $^{m}C_{ds}$ $^{m}C_{ds}$ $^{m}C_{ds}$ $T_{eo}$ $G_{eo}$ $^{m}C_{es}$ $^{m}C_{es}$ $^{m}C_{e}$ | 67434 | 67453 | 20.0 | 61 |
| 628611 | $G_{es}$ $^{m}C_{eo}$ $G_{eo}$ $A_{eo}$ $A_{eo}$ $A_{ds}$ $G_{ds}$ $G_{ds}$ $^{m}C_{ds}$ $T_{ds}$ $T_{ds}$ $T_{ds}$ $T_{ds}$ $^{m}C_{ds}$ $^{m}C_{ds}$ $^{m}C_{eo}$ $T_{eo}$ $G_{es}$ $G_{es}$ $G_{e}$ | 68164 | 68183 | 71.0 | 62 |
| 628615 | $G_{es}$ $A_{eo}$ $A_{eo}$ $G_{eo}$ $T_{eo}$ $A_{ds}$ $^{m}C_{ds}$ $G_{ds}$ $^{m}C_{ds}$ $A_{ds}$ $A_{ds}$ $T_{ds}$ $^{m}C_{ds}$ $A_{ds}$ $A_{ds}$ $^{m}C_{eo}$ $T_{eo}$ $^{m}C_{es}$ $^{m}C_{es}$ $A_{e}$ | 68191 | 68210 | 65.9 | 63 |

TABLE 1-continued

Inhibition of human MECP2 by antisense oligonucleotides in vitro

| Isis No. | Sequence (5' to 3') | Start site | Stop site | % Inhi-bition | SEQ ID NO: |
|---|---|---|---|---|---|
| 628619 | $G_{es}$ $G_{eo}$ $G_{eo}$ $A_{eo}$ $T_{eo}$ $G_{ds}$ $T_{ds}$ $G_{ds}$ $T_{ds}$ $^{m}C_{ds}$ $G_{ds}$ $^{m}C_{ds}$ $^{m}C_{ds}$ $T_{ds}$ $A_{ds}$ $^{m}C_{eo}$ $^{m}C_{eo}$ $T_{es}$ $T_{es}$ $T_{e}$ | 68213 | 68232 | 62.3 | 64 |
| 628623 | $^{m}C_{es}$ $G_{eo}$ $T_{eo}$ $G_{eo}$ $A_{eo}$ $A_{ds}$ $G_{ds}$ $T_{ds}$ $^{m}C_{ds}$ $A_{ds}$ $A_{ds}$ $A_{ds}$ $A_{ds}$ $T_{ds}$ $^{m}C_{ds}$ $A_{eo}$ $T_{eo}$ $T_{es}$ $A_{es}$ $G_{e}$ | 68239 | 68258 | 68.7 | 65 |
| 628627 | $T_{es}$ $T_{eo}$ $A_{eo}$ $G_{eo}$ $G_{eo}$ $T_{ds}$ $G_{ds}$ $G_{ds}$ $T_{ds}$ $T_{ds}$ $T_{ds}$ $^{m}C_{ds}$ $T_{ds}$ $G_{ds}$ $^{m}C_{ds}$ $T_{eo}$ $^{m}C_{eo}$ $T_{es}$ $^{m}C_{es}$ $G_{e}$ | 68286 | 68305 | 43.0 | 66 |
| 628631 | $^{m}C_{es}$ $G_{eo}$ $G_{eo}$ $^{m}C_{eo}$ $^{m}C_{eo}$ $T_{ds}$ $^{m}C_{ds}$ $T_{ds}$ $G_{ds}$ $^{m}C_{ds}$ $^{m}C_{ds}$ $A_{ds}$ $G_{ds}$ $T_{ds}$ $T_{ds}$ $^{m}C_{eo}$ $^{m}C_{eo}$ $T_{es}$ $G_{es}$ $G_{e}$ | 68328 | 68347 | 36.5 | 67 |
| 628635 | $A_{es}$ $^{m}C_{eo}$ $^{m}C_{eo}$ $^{m}C_{eo}$ $T_{eo}$ $T_{ds}$ $T_{ds}$ $T_{ds}$ $^{m}C_{ds}$ $A_{ds}$ $^{m}C_{ds}$ $^{m}C_{ds}$ $T_{ds}$ $G_{ds}$ $^{m}C_{ds}$ $A_{eo}$ $^{m}C_{eo}$ $A_{es}$ $^{m}C_{es}$ $^{m}C_{e}$ | 68400 | 68419 | 53.2 | 68 |
| 628639 | $A_{es}$ $A_{eo}$ $G_{eo}$ $G_{eo}$ $A_{eo}$ $G_{ds}$ $^{m}C_{ds}$ $T_{ds}$ $T_{ds}$ $^{m}C_{ds}$ $^{m}C_{ds}$ $^{m}C_{ds}$ $A_{ds}$ $G_{ds}$ $G_{ds}$ $A_{eo}$ $^{m}C_{eo}$ $T_{es}$ $T_{es}$ $T_{e}$ | 68428 | 68447 | 60.0 | 69 |
| 628643 | $T_{es}$ $G_{eo}$ $G_{eo}$ $^{m}C_{eo}$ $G_{eo}$ $A_{ds}$ $A_{ds}$ $G_{ds}$ $T_{ds}$ $T_{ds}$ $T_{ds}$ $G_{ds}$ $A_{ds}$ $A_{ds}$ $A_{ds}$ $A_{eo}$ $G_{eo}$ $G_{es}$ $^{m}C_{es}$ $A_{e}$ | 68455 | 68474 | 57.8 | 70 |
| 628647 | $A_{es}$ $G_{eo}$ $^{m}C_{eo}$ $^{m}C_{eo}$ $T_{eo}$ $T_{ds}$ $G_{ds}$ $^{m}C_{ds}$ $^{m}C_{ds}$ $^{m}C_{ds}$ $^{m}C_{ds}$ $^{m}C_{ds}$ $T_{ds}$ $G_{ds}$ $G_{ds}$ $^{m}C_{eo}$ $G_{eo}$ $A_{es}$ $A_{es}$ $G_{e}$ | 68467 | 68486 | 59.3 | 71 |
| 628651 | $T_{es}$ $G_{eo}$ $G_{eo}$ $A_{eo}$ $T_{eo}$ $G_{ds}$ $T_{ds}$ $G_{ds}$ $G_{ds}$ $T_{ds}$ $G_{ds}$ $G_{ds}$ $^{m}C_{ds}$ $^{m}C_{ds}$ $^{m}C_{ds}$ $^{m}C_{eo}$ $A_{eo}$ $^{m}C_{es}$ $^{m}C_{es}$ $^{m}C_{e}$ | 68492 | 68511 | 50.3 | 72 |
| 628655 | $G_{es}$ $^{m}C_{eo}$ $T_{eo}$ $T_{eo}$ $T_{eo}$ $T_{ds}$ $^{m}C_{ds}$ $G_{ds}$ $^{m}C_{ds}$ $T_{ds}$ $T_{ds}$ $^{m}C_{ds}$ $^{m}C_{ds}$ $T_{ds}$ $G_{ds}$ $^{m}C_{eo}$ $^{m}C_{eo}$ $G_{es}$ $G_{es}$ $G_{e}$ | 68535 | 68554 | 67.2 | 73 |
| 628659 | $G_{es}$ $T_{eo}$ $T_{eo}$ $T_{eo}$ $^{m}C_{eo}$ $T_{ds}$ $T_{ds}$ $G_{ds}$ $G_{ds}$ $G_{ds}$ $A_{ds}$ $A_{ds}$ $T_{ds}$ $G_{ds}$ $G_{ds}$ $^{m}C_{eo}$ $^{m}C_{eo}$ $T_{es}$ $G_{es}$ $A_{e}$ | 68567 | 68586 | 41.1 | 74 |
| 628663 | $G_{es}$ $G_{eo}$ $^{m}C_{eo}$ $T_{eo}$ $G_{eo}$ $^{m}C_{ds}$ $^{m}C_{ds}$ $A_{ds}$ $^{m}C_{ds}$ $^{m}C_{ds}$ $A_{ds}$ $^{m}C_{ds}$ $A_{ds}$ $^{m}C_{ds}$ $T_{ds}$ $^{m}C_{eo}$ $^{m}C_{eo}$ $^{m}C_{es}$ $^{m}C_{es}$ $G_{e}$ | 68599 | 68618 | 40.4 | 75 |
| *628667 | $T_{es}$ $T_{eo}$ $^{m}C_{eo}$ $A_{eo}$ $^{m}C_{eo}$ $G_{ds}$ $G_{ds}$ $^{m}C_{ds}$ $T_{ds}$ $T_{ds}$ $T_{ds}$ $^{m}C_{ds}$ $T_{ds}$ $T_{ds}$ $T_{ds}$ $T_{eo}$ $T_{eo}$ $G_{es}$ $G_{es}$ $^{m}C_{e}$ | 68631 | 68650 | 38.2 | 76 |
| *628671 | $^{m}C_{es}$ $T_{eo}$ $^{m}C_{eo}$ $^{m}C_{eo}$ $T_{eo}$ $G_{ds}$ $^{m}C_{ds}$ $A_{ds}$ $^{m}C_{ds}$ $A_{ds}$ $G_{ds}$ $A_{ds}$ $T_{ds}$ $^{m}C_{ds}$ $G_{ds}$ $G_{eo}$ $A_{eo}$ $T_{es}$ $A_{es}$ $G_{e}$ | 68659 | 68678 | 76.9 | 77 |
| *628675 | $T_{es}$ $^{m}C_{eo}$ $T_{eo}$ $^{m}C_{eo}$ $^{m}C_{eo}$ $^{m}C_{ds}$ $G_{ds}$ $G_{ds}$ $G_{ds}$ $T_{ds}$ $^{m}C_{ds}$ $T_{ds}$ $T_{ds}$ $G_{ds}$ $^{m}C_{ds}$ $G_{eo}$ $^{m}C_{eo}$ $T_{es}$ $T_{es}$ $^{m}C_{e}$ | 68696 | 68715 | 85.3 | 78 |
| *628679 | $^{m}C_{es}$ $T_{eo}$ $T_{eo}$ $^{m}C_{eo}$ $A_{eo}$ $^{m}C_{ds}$ $^{m}C_{ds}$ $A_{ds}$ $^{m}C_{ds}$ $T_{ds}$ $T_{ds}$ $^{m}C_{ds}$ $^{m}C_{ds}$ $T_{ds}$ $T_{ds}$ $G_{eo}$ $A_{eo}$ $^{m}C_{es}$ $^{m}C_{es}$ $T_{e}$ | 68728 | 68747 | 74.5 | 79 |
| 628683 | $T_{es}$ $^{m}C_{eo}$ $A_{eo}$ $G_{eo}$ $T_{eo}$ $^{m}C_{ds}$ $^{m}C_{ds}$ $T_{ds}$ $T_{ds}$ $T_{ds}$ $^{m}C_{ds}$ $^{m}C_{ds}$ $^{m}C_{ds}$ $G_{ds}$ $^{m}C_{ds}$ $T_{eo}$ $^{m}C_{eo}$ $T_{es}$ $T_{es}$ $^{m}C_{e}$ | 68774 | 68793 | 43.0 | 80 |
| 628687 | $^{m}C_{es}$ $T_{eo}$ $T_{eo}$ $G_{eo}$ $^{m}C_{eo}$ $T_{ds}$ $T_{ds}$ $T_{ds}$ $T_{ds}$ $^{m}C_{ds}$ $^{m}C_{ds}$ $G_{ds}$ $^{m}C_{ds}$ $^{m}C_{ds}$$^{m}C_{ds}$ $A_{eo}$ $G_{eo}$ $G_{es}$ $G_{es}$ $^{m}C_{e}$ | 68806 | 68825 | 69.2 | 81 |
| 628691 | $G_{es}$ $G_{eo}$ $T_{eo}$ $G_{eo}$ $A_{eo}$ $T_{ds}$ $G_{ds}$ $G_{ds}$ $T_{ds}$ $G_{ds}$ $G_{ds}$ $T_{ds}$ $G_{ds}$ $G_{ds}$ $T_{ds}$ $G_{eo}$ $^{m}C_{eo}$ $T_{es}$ $^{m}C_{es}$ $^{m}C_{e}$ | 68876 | 68895 | 49.4 | 82 |
| 628695 | $G_{es}$ $^{m}C_{eo}$ $T_{eo}$ $G_{eo}$ $^{m}C_{eo}$ $T_{ds}$ $G_{ds}$ $^{m}C_{ds}$ $T_{ds}$ $^{m}C_{ds}$ $A_{ds}$ $A_{ds}$ $G_{ds}$ $T_{ds}$ $^{m}C_{ds}$ $^{m}C_{eo}$ $T_{eo}$ $G_{es}$ $G_{es}$ $G_{e}$ | 68998 | 69017 | 62.3 | 83 |
| 628699 | $^{m}C_{es}$ $T_{eo}$ $^{m}C_{eo}$ $^{m}C_{eo}$ $A_{eo}$ $G_{ds}$ $T_{ds}$ $G_{ds}$ $A_{ds}$ $G_{ds}$ $^{m}C_{ds}$ $^{m}C_{ds}$ $T_{ds}$ $^{m}C_{ds}$ $^{m}C_{ds}$ $T_{eo}$ $^{m}C_{eo}$ $T_{es}$ $G_{es}$ $G_{e}$ | 69040 | 69059 | 45.7 | 84 |
| 628703 | $A_{es}$ $A_{eo}$ $^{m}C_{eo}$ $^{m}C_{eo}$ $G_{eo}$ $^{m}C_{ds}$ $G_{ds}$ $G_{ds}$ $G_{ds}$ $^{m}C_{ds}$ $T_{ds}$ $G_{ds}$ $A_{ds}$ $G_{ds}$ $T_{ds}$ $^{m}C_{eo}$ $T_{eo}$ $T_{es}$ $A_{es}$ $G_{e}$ | 69085 | 69104 | 23.7 | 85 |
| 628707 | $T_{es}$ $G_{eo}$ $G_{eo}$ $^{m}C_{eo}$ $G_{eo}$ $G_{ds}$ $^{m}C_{ds}$ $G_{ds}$ $G_{ds}$ $T_{ds}$ $G_{ds}$ $G_{ds}$ $^{m}C_{ds}$ $A_{ds}$ $A_{ds}$ $^{m}C_{eo}$ $^{m}C_{eo}$ $G_{es}$ $^{m}C_{es}$ $G_{e}$ | 69098 | 69117 | 43.7 | 86 |
| 628711 | $T_{es}$ $T_{eo}$ $T_{eo}$ $T_{eo}$ $^{m}C_{eo}$ $T_{ds}$ $G_{ds}$ $^{m}C_{ds}$ $G_{ds}$ $G_{ds}$ $^{m}C_{ds}$ $^{m}C_{ds}$ $G_{ds}$ $T_{ds}$ $G_{ds}$ $G_{eo}$ $^{m}C_{eo}$ $G_{es}$ $G_{es}$ $^{m}C_{e}$ | 69111 | 69130 | 44.4 | 87 |

TABLE 1-continued

Inhibition of human MECP2 by antisense oligonucleotides in vitro

| Isis No. | Sequence (5' to 3') | Start site | Stop site | % Inhi-bition | SEQ ID NO: |
|---|---|---|---|---|---|
| 628715 | $^{m}C_{es}\ T_{eo}\ ^{m}C_{eo}\ T_{eo}\ ^{m}C_{eo}\ ^{m}C_{ds}\ ^{m}C_{ds}\ T_{ds}\ ^{m}C_{ds}\ ^{m}C_{ds}\ ^{m}C_{ds}\ ^{m}C_{ds}\ T_{ds}\ ^{m}C_{ds}\ G_{ds}\ G_{eo}\ T_{eo}\ G_{es}\ T_{es}\ T_{e}$ | 69136 | 69155 | 54.7 | 88 |
| 628719 | $^{m}C_{es}\ T_{eo}\ T_{eo}\ G_{eo}\ G_{eo}\ ^{m}C_{ds}\ A_{ds}\ T_{ds}\ G_{ds}\ G_{ds}\ A_{ds}\ G_{ds}\ G_{ds}\ A_{ds}\ T_{ds}\ G_{eo}\ A_{eo}\ A_{es}\ A_{es}\ ^{m}C_{e}$ | 69168 | 69187 | 41.5 | 89 |
| 628723 | $T_{es}\ ^{m}C_{eo}\ ^{m}C_{eo}\ G_{eo}\ G_{eo}\ ^{m}C_{ds}\ T_{ds}\ G_{ds}\ T_{ds}\ ^{m}C_{ds}\ ^{m}C_{ds}\ A_{ds}\ ^{m}C_{ds}\ A_{ds}\ G_{ds}\ G_{eo}\ ^{m}C_{eo}\ T_{es}\ ^{m}C_{es}\ ^{m}C_{e}$ | 69200 | 69219 | 59.6 | 90 |
| 628727 | $A_{es}\ A_{eo}\ T_{eo}\ ^{m}C_{eo}\ ^{m}C_{eo}\ G_{ds}\ ^{m}C_{ds}\ T_{ds}\ ^{m}C_{ds}\ ^{m}C_{ds}\ G_{ds}\ T_{ds}\ G_{ds}\ T_{ds}\ A_{ds}\ A_{eo}\ A_{eo}\ G_{es}\ T_{es}\ ^{m}C_{e}$ | 69244 | 69263 | 50.4 | 91 |
| 628731 | $^{m}C_{es}\ A_{eo}\ G_{eo}\ ^{m}C_{eo}\ T_{eo}\ G_{ds}\ ^{m}C_{ds}\ ^{m}C_{ds}\ T_{ds}\ T_{ds}\ T_{ds}\ A_{ds}\ T_{ds}\ T_{ds}\ ^{m}C_{ds}\ T_{eo}\ T_{eo}\ G_{es}\ T_{es}\ T_{e}$ | 69276 | 69295 | 43.3 | 92 |
| 628735 | $G_{es}\ T_{eo}\ ^{m}C_{eo}\ A_{eo}\ G_{eo}\ A_{ds}\ G_{ds}\ ^{m}C_{ds}\ ^{m}C_{ds}\ ^{m}C_{ds}\ T_{ds}\ A_{ds}\ ^{m}C_{ds}\ ^{m}C_{ds}\ ^{m}C_{ds}\ A_{eo}\ T_{eo}\ A_{es}\ A_{es}\ G_{e}$ | 69308 | 69327 | 70.7 | 93 |

Superscript "m" indicates 5-methylcytosine. Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

TABLE 2

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 18078 | $G_{es}\ T_{es}\ G_{es}\ ^{m}C_{es}\ G_{es}\ C_{ds}\ G_{ds}\ C_{ds}\ G_{ds}\ A_{ds}\ G_{ds}\ C_{ds}\ C_{ds}\ C_{ds}\ G_{es}\ A_{es}\ A_{es}\ A_{es}\ T_{es}\ ^{m}C_{e}$ | n/a | n/a | 3.8 | 15 |
| 628541 | $A_{es}\ G_{eo}\ ^{m}C_{eo}\ G_{eo}\ ^{m}C_{eo}\ G_{ds}\ ^{m}C_{ds}\ G_{ds}\ ^{m}C_{ds}\ G_{ds}\ ^{m}C_{ds}\ ^{m}C_{ds}\ G_{ds}\ ^{m}C_{ds}\ ^{m}C_{ds}\ G_{eo}\ A_{eo}\ ^{m}C_{es}\ G_{es}\ ^{m}C_{e}$ | 1878 | 1897 | 15.3 | 94 |
| 628545 | $^{m}C_{es}\ T_{eo}\ T_{eo}\ T_{eo}\ T_{eo}\ A_{ds}\ ^{m}C_{ds}\ ^{m}C_{ds}\ A_{ds}\ ^{m}C_{ds}\ A_{ds}\ G_{ds}\ ^{m}C_{ds}\ ^{m}C_{ds}\ ^{m}C_{ds}\ T_{eo}\ ^{m}C_{eo}\ T_{es}\ ^{m}C_{es}\ T_{e}$ | 1910 | 1929 | 48.4 | 95 |
| 628549 | $^{m}C_{es}\ ^{m}C_{eo}\ G_{eo}\ ^{m}C_{eo}\ T_{eo}\ ^{m}C_{ds}\ G_{ds}\ G_{ds}\ ^{m}C_{ds}\ G_{ds}\ ^{m}C_{ds}\ G_{ds}\ G_{ds}\ ^{m}C_{ds}\ G_{ds}\ G_{eo}\ ^{m}C_{eo}\ G_{es}\ G_{es}\ ^{m}C_{e}$ | 1953 | 1972 | 32.9 | 96 |
| 628741 | $T_{es}\ ^{m}C_{eo}\ A_{eo}\ G_{eo}\ T_{eo}\ T_{ds}\ T_{ds}\ G_{ds}\ G_{ds}\ G_{ds}\ T_{ds}\ G_{ds}\ A_{ds}\ T_{ds}\ T_{ds}\ ^{m}C_{eo}\ G_{eo}\ G_{es}\ T_{es}\ ^{m}C_{e}$ | 3047 | 3066 | 45.7 | 97 |
| 628745 | $^{m}C_{es}\ A_{eo}\ G_{eo}\ ^{m}C_{eo}\ A_{eo}\ ^{m}C_{ds}\ A_{ds}\ G_{ds}\ ^{m}C_{ds}\ G_{ds}\ G_{ds}\ G_{ds}\ A_{ds}\ A_{ds}\ ^{m}C_{ds}\ A_{eo}\ ^{m}C_{eo}\ A_{es}\ T_{es}\ T_{e}$ | 5561 | 5580 | 42.2 | 98 |
| 628553 | $T_{es}\ A_{eo}\ T_{eo}\ T_{eo}\ T_{eo}\ T_{ds}\ T_{ds}\ A_{ds}\ T_{ds}\ G_{ds}\ G_{ds}\ A_{ds}\ G_{ds}\ ^{m}C_{ds}\ A_{ds}\ G_{eo}\ T_{eo}\ ^{m}C_{es}\ T_{es}\ ^{m}C_{e}$ | 7292 | 7311 | 36.6 | 99 |
| 628557 | $A_{es}\ T_{eo}\ G_{eo}\ T_{eo}\ ^{m}C_{eo}\ A_{ds}\ ^{m}C_{ds}\ A_{ds}\ T_{ds}\ ^{m}C_{ds}\ A_{ds}\ A_{ds}\ A_{ds}\ G_{ds}\ ^{m}C_{ds}\ A_{eo}\ G_{eo}\ G_{es}\ A_{es}\ A_{e}$ | 7324 | 7343 | 70.2 | 100 |
| 628561 | $T_{es}\ T_{eo}\ G_{eo}\ G_{eo}\ A_{eo}\ G_{ds}\ ^{m}C_{ds}\ T_{ds}\ G_{ds}\ G_{ds}\ T_{ds}\ ^{m}C_{ds}\ T_{ds}\ A_{ds}\ ^{m}C_{ds}\ A_{eo}\ G_{eo}\ A_{es}\ A_{es}\ G_{e}$ | 7367 | 7386 | 43.4 | 101 |
| 628565 | $A_{es}\ G_{eo}\ ^{m}C_{eo}\ ^{m}C_{eo}\ ^{m}C_{eo}\ T_{ds}\ A_{ds}\ A_{ds}\ ^{m}C_{ds}\ A_{ds}\ T_{ds}\ ^{m}C_{ds}\ ^{m}C_{ds}\ ^{m}C_{ds}\ A_{ds}\ G_{eo}\ ^{m}C_{eo}\ T_{es}\ A_{es}\ ^{m}C_{e}$ | 7399 | 7418 | 72.5 | 102 |
| 628749 | $^{m}C_{es}\ A_{eo}\ ^{m}C_{eo}\ A_{eo}\ ^{m}C_{eo}\ T_{ds}\ G_{ds}\ A_{ds}\ ^{m}C_{ds}\ ^{m}C_{ds}\ T_{ds}\ T_{ds}\ T_{ds}\ ^{m}C_{ds}\ A_{ds}\ G_{eo}\ G_{eo}\ G_{es}\ ^{m}C_{es}\ T_{e}$ | 7615 | 7634 | 96.4 | 103 |
| 628753 | $T_{es}\ A_{eo}\ A_{eo}\ A_{eo}\ A_{eo}\ A_{ds}\ A_{ds}\ G_{ds}\ G_{ds}\ A_{ds}\ T_{ds}\ T_{ds}\ T_{ds}\ ^{m}C_{ds}\ ^{m}C_{ds}\ T_{eo}\ A_{eo}\ A_{es}\ G_{es}\ T_{e}$ | 10408 | 10427 | 12.3 | 104 |
| 628757 | $G_{es}\ T_{eo}\ A_{eo}\ ^{m}C_{eo}\ A_{eo}\ ^{m}C_{ds}\ A_{ds}\ ^{m}C_{ds}\ A_{ds}\ ^{m}C_{ds}\ G_{ds}\ ^{m}C_{ds}\ T_{ds}\ T_{ds}\ T_{ds}\ T_{eo}\ T_{eo}\ T_{es}\ T_{es}\ T_{e}$ | 13332 | 13351 | 85.5 | 105 |
| 628761 | $G_{es}\ A_{eo}\ A_{eo}\ A_{eo}\ G_{eo}\ ^{m}C_{ds}\ ^{m}C_{ds}\ G_{ds}\ A_{ds}\ G_{ds}\ ^{m}C_{ds}\ ^{m}C_{ds}\ T_{ds}\ G_{ds}\ G_{ds}\ ^{m}C_{eo}\ ^{m}C_{eo}\ G_{es}\ G_{es}\ G_{e}$ | 15686 | 15705 | 51.4 | 106 |

TABLE 2-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628765 | $G_{es} A_{eo} A_{eo} G_{eo} A_{eo} A_{ds} A_{ds} A_{ds} T_{ds} G_{ds} T_{ds} G_{ds} G_{ds} A_{ds} T_{ds} T_{eo} T_{eo} T_{es} T_{es} T_{e}$ | 18630 | 18649 | 78.3 | 107 |
| 628769 | ${}^{m}C_{es} G_{eo} A_{eo} G_{eo} A_{eo} A_{ds} T_{ds} G_{ds} A_{ds} G_{ds} A_{ds} {}^{m}C_{ds} T_{ds} {}^{m}C_{ds} {}^{m}C_{ds} G_{eo} T_{eo} A_{es} T_{es} {}^{m}C_{e}$ | 21317 | 21336 | 63.6 | 108 |
| 628773 | $A_{es} A_{eo} A_{eo} {}^{m}C_{eo} {}^{m}C_{eo} {}^{m}C_{ds} A_{ds} A_{ds} A_{ds} {}^{m}C_{ds} {}^{m}C_{ds} A_{ds} {}^{m}C_{ds} {}^{m}C_{ds} T_{ds} T_{eo} A_{eo} {}^{m}C_{es} {}^{m}C_{es} {}^{m}C_{e}$ | 23339 | 23358 | 48.9 | 109 |
| 628777 | $A_{es} A_{eo} A_{eo} A_{eo} T_{eo} A_{ds} A_{ds} A_{ds} G_{ds} T_{ds} {}^{m}C_{ds} A_{ds} G_{ds} G_{ds} A_{ds} G_{eo} G_{eo} {}^{m}C_{es} T_{es} G_{e}$ | 26037 | 26056 | 65.5 | 110 |
| 628781 | $A_{es} A_{eo} A_{eo} A_{eo} A_{eo} T_{ds} G_{ds} G_{ds} A_{ds} G_{ds} G_{ds} G_{ds} {}^{m}C_{ds} A_{ds} {}^{m}C_{ds} A_{eo} G_{eo} T_{es} G_{es} G_{e}$ | 28177 | 28196 | 12.2 | 111 |
| 628785 | $G_{es} G_{eo} T_{eo} T_{eo} T_{eo} T_{ds} T_{ds} {}^{m}C_{ds} T_{ds} {}^{m}C_{ds} {}^{m}C_{ds} T_{ds} T_{ds} T_{ds} A_{ds} T_{eo} T_{eo} A_{es} T_{es} {}^{m}C_{e}$ | 30744 | 30763 | 92.2 | 112 |
| 628789 | $T_{es} A_{eo} T_{eo} G_{eo} T_{eo} T_{ds} G_{ds} G_{ds} {}^{m}C_{ds} {}^{m}C_{ds} T_{ds} A_{ds} G_{ds} A_{ds} A_{ds} {}^{m}C_{eo} T_{eo} {}^{m}C_{es} T_{e}$ | 33273 | 33292 | 52.4 | 113 |
| 628793 | $T_{es} G_{eo} {}^{m}C_{eo} T_{eo} {}^{m}C_{eo} T_{ds} {}^{m}C_{ds} A_{ds} T_{ds} A_{ds} T_{ds} T_{ds} {}^{m}C_{ds} A_{ds} {}^{m}C_{ds} {}^{m}C_{eo} {}^{m}C_{eo} A_{es} {}^{m}C_{es} G_{e}$ | 35287 | 35306 | 79.3 | 114 |
| 628797 | $G_{es} T_{eo} G_{eo} {}^{m}C_{eo} A_{eo} G_{ds} A_{ds} G_{ds} A_{ds} {}^{m}C_{ds} T_{ds} {}^{m}C_{ds} A_{ds} A_{ds} G_{ds} G_{eo} G_{eo} A_{es} G_{es} G_{e}$ | 38049 | 38068 | 21.7 | 115 |
| 628801 | $G_{es} {}^{m}C_{eo} T_{eo} A_{eo} A_{eo} G_{ds} {}^{m}C_{ds} {}^{m}C_{ds} T_{ds} {}^{m}C_{ds} {}^{m}C_{ds} T_{ds} G_{ds} G_{ds} T_{ds} G_{eo} A_{eo} A_{es} {}^{m}C_{es} {}^{m}C_{e}$ | 40072 | 40091 | 65.0 | 116 |
| 628805 | $G_{es} T_{eo} A_{eo} T_{eo} G_{eo} A_{ds} A_{ds} {}^{m}C_{ds} A_{ds} T_{ds} {}^{m}C_{ds} A_{ds} G_{ds} {}^{m}C_{ds} T_{ds} G_{eo} A_{eo} {}^{m}C_{es} G_{es} {}^{m}C_{e}$ | 42580 | 42599 | 69.6 | 117 |
| 628809 | $A_{es} G_{eo} G_{eo} {}^{m}C_{eo} G_{eo} {}^{m}C_{ds} G_{ds} {}^{m}C_{ds} T_{ds} G_{ds} G_{ds} T_{ds} G_{ds} {}^{m}C_{ds} A_{ds} A_{eo} G_{eo} {}^{m}C_{es} {}^{m}C_{es} T_{e}$ | 44735 | 44754 | 16.5 | 118 |
| 628813 | ${}^{m}C_{es} A_{eo} G_{eo} {}^{m}C_{eo} {}^{m}C_{eo} A_{ds} {}^{m}C_{ds} T_{ds} {}^{m}C_{ds} T_{ds} T_{ds} T_{ds} T_{ds} T_{ds} T_{ds} T_{eo} T_{eo} T_{es} G_{es} A_{e}$ | 46834 | 46853 | 59.1 | 119 |
| 628817 | $G_{es} T_{eo} A_{eo} {}^{m}C_{eo} {}^{m}C_{eo} T_{ds} G_{ds} G_{ds} G_{ds} A_{ds} G_{ds} G_{ds} A_{ds} A_{ds} {}^{m}C_{ds} T_{eo} A_{eo} {}^{m}C_{es} A_{es} A_{e}$ | 48863 | 48882 | 68.0 | 120 |
| 628821 | $A_{es} G_{eo} G_{eo} G_{eo} {}^{m}C_{eo} G_{ds} A_{ds} G_{ds} A_{ds} G_{ds} A_{ds} T_{ds} {}^{m}C_{ds} {}^{m}C_{ds} A_{ds} G_{eo} G_{eo} A_{es} {}^{m}C_{es} T_{e}$ | 50865 | 50884 | 80.7 | 121 |
| 628825 | $G_{es} G_{eo} A_{eo} T_{eo} T_{eo} A_{ds} G_{ds} G_{ds} G_{ds} A_{ds} A_{ds} T_{ds} T_{ds} A_{ds} G_{ds} A_{eo} T_{eo} G_{es} {}^{m}C_{es} A_{e}$ | 53552 | 53571 | 59.3 | 122 |
| 628829 | $G_{es} G_{eo} A_{eo} A_{eo} A_{eo} G_{ds} {}^{m}C_{ds} {}^{m}C_{ds} T_{ds} G_{ds} T_{ds} {}^{m}C_{ds} T_{ds} T_{ds} T_{ds} T_{eo} A_{eo} A_{es} A_{es} A_{e}$ | 55596 | 55615 | 54.0 | 123 |
| 628833 | ${}^{m}C_{es} {}^{m}C_{eo} A_{eo} G_{eo} A_{eo} T_{ds} G_{ds} G_{ds} T_{ds} G_{ds} T_{ds} T_{ds} T_{ds} {}^{m}C_{ds} {}^{m}C_{ds} A_{eo} A_{eo} T_{es} T_{es} {}^{m}C_{e}$ | 57622 | 57641 | 85.3 | 124 |
| 628837 | $A_{es} {}^{m}C_{eo} T_{eo} T_{eo} {}^{m}C_{eo} T_{ds} A_{ds} G_{ds} A_{ds} {}^{m}C_{ds} {}^{m}C_{ds} G_{ds} G_{ds} G_{ds} {}^{m}C_{ds} G_{eo} {}^{m}C_{eo} A_{es} G_{es} T_{e}$ | 60266 | 60285 | 48.3 | 125 |
| 628841 | $G_{es} T_{eo} A_{eo} {}^{m}C_{eo} A_{eo} A_{ds} T_{ds} G_{ds} A_{ds} A_{ds} T_{ds} G_{ds} A_{ds} A_{ds} {}^{m}C_{ds} T_{eo} T_{eo} T_{es} T_{es} T_{e}$ | 62361 | 62380 | 69.7 | 126 |
| 628845 | ${}^{m}C_{es} A_{eo} A_{eo} A_{eo} {}^{m}C_{eo} A_{ds} T_{ds} A_{ds} T_{ds} {}^{m}C_{ds} T_{ds} A_{ds} {}^{m}C_{ds} T_{ds} G_{ds} {}^{m}C_{eo} A_{eo} T_{es} T_{es} {}^{m}C_{e}$ | 64407 | 64426 | 27.4 | 127 |
| 628849 | $A_{es} {}^{m}C_{eo} A_{eo} G_{eo} G_{eo} T_{ds} A_{ds} A_{ds} {}^{m}C_{ds} {}^{m}C_{ds} {}^{m}C_{ds} {}^{m}C_{ds} A_{ds} T_{ds} {}^{m}C_{ds} T_{eo} A_{eo} G_{es} G_{es} {}^{m}C_{e}$ | 66432 | 66451 | 68.5 | 128 |
| 628569 | $G_{es} G_{eo} A_{eo} G_{eo} G_{eo} T_{ds} {}^{m}C_{ds} {}^{m}C_{ds} T_{ds} G_{ds} G_{ds} T_{ds} {}^{m}C_{ds} T_{ds} T_{ds} {}^{m}C_{eo} T_{eo} G_{es} A_{es} {}^{m}C_{e}$ | 67064 | 67083 | 41.4 | 129 |
| 628573 | $T_{es} T_{eo} A_{eo} T_{eo} {}^{m}C_{eo} T_{ds} T_{ds} T_{ds} {}^{m}C_{ds} T_{ds} T_{ds} {}^{m}C_{ds} A_{ds} {}^{m}C_{ds} {}^{m}C_{ds} T_{eo} T_{eo} T_{es} T_{es} T_{e}$ | 67113 | 67132 | 27.1 | 130 |
| 628577 | ${}^{m}C_{es} T_{eo} {}^{m}C_{eo} T_{eo} T_{eo} T_{ds} {}^{m}C_{ds} T_{ds} {}^{m}C_{ds} T_{ds} T_{ds} {}^{m}C_{ds} T_{ds} T_{ds} T_{ds} {}^{m}C_{eo} T_{eo} T_{es} A_{es} T_{e}$ | 67129 | 67148 | 43.9 | 131 |

TABLE 2-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628581 | $^{m}C_{es}A_{eo}$ $^{m}C_{eo}$ $G_{eo}$ $G_{eo}$ $G_{ds}$ $^{m}C_{ds}$ $T_{ds}$ $^{m}C_{ds}$ $A_{ds}$ $T_{ds}$ $G_{ds}$ $^{m}C_{ds}$ $T_{ds}$ $T_{ds}$ $G_{eo}$ $^{m}C_{eo}$ $^{m}C_{es}$ $^{m}C_{es}$ $T_{e}$ | 67147 | 67166 | 15.0 | 132 |
| 628585 | $G_{es}$ $G_{eo}$ $^{m}C_{eo}$ $T_{eo}$ $G_{eo}$ $A_{ds}$ $T_{ds}$ $G_{ds}$ $G_{ds}$ $^{m}C_{ds}$ $T_{ds}$ $G_{ds}$ $^{m}C_{ds}$ $A_{ds}$ $^{m}C_{ds}$ $G_{eo}$ $G_{eo}$ $G_{es}$ $^{m}C_{es}$ $T_{e}$ | 67159 | 67178 | 73.7 | 133 |
| 628589 | $T_{es}$ $G_{eo}$ $^{m}C_{eo}$ $G_{eo}$ $G_{eo}$ $G_{ds}$ $^{m}C_{ds}$ $T_{ds}$ $^{m}C_{ds}$ $A_{ds}$ $G_{ds}$ $^{m}C_{ds}$ $A_{ds}$ $G_{ds}$ $A_{ds}$ $G_{eo}$ $T_{eo}$ $G_{es}$ $G_{es}$ $T_{e}$ | 67180 | 67199 | 22.6 | 134 |
| 628593 | $G_{es}$ $A_{eo}$ $^{m}C_{eo}$ $^{m}C_{eo}$ $^{m}C_{eo}$ $T_{ds}$ $T_{ds}$ $^{m}C_{ds}$ $T_{ds}$ $G_{ds}$ $A_{ds}$ $T_{ds}$ $G_{ds}$ $T_{ds}$ $^{m}C_{ds}$ $T_{eo}$ $^{m}C_{eo}$ $T_{es}$ $G_{es}$ $^{m}C_{e}$ | 67212 | 67231 | 47.4 | 135 |
| 628597 | $A_{es}$ $G_{eo}$ $G_{eo}$ $^{m}C_{eo}$ $A_{eo}$ $G_{ds}$ $A_{ds}$ $A_{ds}$ $G_{ds}$ $^{m}C_{ds}$ $T_{ds}$ $T_{ds}$ $^{m}C_{ds}$ $^{m}C_{ds}$ $G_{ds}$ $G_{eo}$ $^{m}C_{eo}$ $A_{es}$ $^{m}C_{es}$ $A_{e}$ | 67247 | 67266 | 48.6 | 136 |
| 628601 | $T_{es}$ $^{m}C_{eo}$ $A_{eo}$ $T_{eo}$ $A_{eo}$ $^{m}C_{ds}$ $A_{ds}$ $T_{ds}$ $G_{ds}$ $G_{ds}$ $G_{ds}$ $T_{ds}$ $^{m}C_{ds}$ $^{m}C_{ds}$ $^{m}C_{ds}$ $^{m}C_{eo}$ $G_{eo}$ $G_{es}$ $T_{es}$ $^{m}C_{e}$ | 67296 | 67315 | 53.7 | 137 |
| 628605 | $T_{es}$ $T_{eo}$ $T_{eo}$ $^{m}C_{eo}$ $^{m}C_{eo}$ $T_{ds}$ $T_{ds}$ $T_{ds}$ $G_{ds}$ $^{m}C_{ds}$ $T_{ds}$ $T_{ds}$ $A_{ds}$ $A_{ds}$ $G_{ds}$ $^{m}C_{eo}$ $T_{eo}$ $T_{es}$ $^{m}C_{es}$ $^{m}C_{e}$ | 67345 | 67364 | 46.5 | 138 |
| 628609 | $T_{es}$ $A_{eo}$ $^{m}C_{eo}$ $A_{eo}$ $^{m}C_{eo}$ $A_{ds}$ $T_{ds}$ $^{m}C_{ds}$ $A_{ds}$ $T_{ds}$ $A_{ds}$ $^{m}C_{ds}$ $T_{ds}$ $T_{ds}$ $^{m}C_{ds}$ $^{m}C_{eo}$ $^{m}C_{eo}$ $A_{es}$ $G_{es}$ $^{m}C_{e}$ | 67377 | 67396 | 40.1 | 139 |
| 628613 | $T_{es}$ $^{m}C_{eo}$ $A_{eo}$ $A_{eo}$ $^{m}C_{eo}$ $T_{ds}$ $^{m}C_{ds}$ $^{m}C_{ds}$ $A_{ds}$ $^{m}C_{ds}$ $T_{ds}$ $T_{ds}$ $T_{ds}$ $A_{ds}$ $G_{ds}$ $A_{eo}$ $G_{eo}$ $^{m}C_{es}$ $G_{es}$ $A_{e}$ | 68180 | 68199 | 42.9 | 140 |
| 628617 | $G_{es}$ $^{m}C_{eo}$ $^{m}C_{eo}$ $T_{eo}$ $A_{eo}$ $^{m}C_{ds}$ $^{m}C_{ds}$ $T_{ds}$ $T_{ds}$ $T_{ds}$ $T_{ds}$ $^{m}C_{ds}$ $G_{ds}$ $A_{ds}$ $A_{ds}$ $G_{eo}$ $T_{eo}$ $A_{es}$ $^{m}C_{es}$ $G_{e}$ | 68203 | 68222 | 65.5 | 141 |
| 628621 | $G_{es}$ $G_{eo}$ $T_{eo}$ $^{m}C_{eo}$ $^{m}C_{eo}$ $A_{ds}$ $G_{ds}$ $G_{ds}$ $G_{ds}$ $A_{ds}$ $T_{ds}$ $G_{ds}$ $T_{ds}$ $G_{ds}$ $T_{ds}$ $^{m}C_{eo}$ $G_{eo}$ $^{m}C_{es}$ $^{m}C_{es}$ $T_{e}$ | 68219 | 68238 | 62.9 | 142 |
| 628625 | $T_{es}$ $^{m}C_{eo}$ $^{m}C_{eo}$ $^{m}C_{eo}$ $T_{eo}$ $^{m}C_{ds}$ $T_{ds}$ $^{m}C_{ds}$ $^{m}C_{ds}$ $^{m}C_{ds}$ $A_{ds}$ $G_{ds}$ $T_{ds}$ $T_{ds}$ $A_{ds}$ $^{m}C_{eo}$ $^{m}C_{eo}$ $G_{es}$ $T_{es}$ $G_{e}$ | 68255 | 68274 | 65.6 | 143 |
| 628629 | $T_{es}$ $G_{eo}$ $G_{eo}$ $A_{eo}$ $G_{eo}$ $^{m}C_{ds}$ $T_{ds}$ $T_{ds}$ $T_{ds}$ $G_{ds}$ $G_{ds}$ $G_{ds}$ $A_{ds}$ $G_{ds}$ $A_{ds}$ $T_{eo}$ $T_{eo}$ $T_{es}$ $G_{es}$ $G_{e}$ | 68311 | 68330 | 28.3 | 144 |
| 628633 | $^{m}C_{es}$ $G_{eo}$ $T_{eo}$ $G_{eo}$ $G_{eo}$ $^{m}C_{ds}$ $^{m}C_{ds}$ $G_{ds}$ $^{m}C_{ds}$ $^{m}C_{ds}$ $T_{ds}$ $T_{ds}$ $G_{ds}$ $G_{ds}$ $G_{ds}$ $T_{eo}$ $^{m}C_{eo}$ $T_{es}$ $^{m}C_{es}$ $G_{e}$ | 68374 | 68393 | 25.5 | 145 |
| 628637 | $A_{es}$ $G_{eo}$ $G_{eo}$ $A_{eo}$ $^{m}C_{eo}$ $T_{ds}$ $T_{ds}$ $T_{ds}$ $T_{ds}$ $^{m}C_{ds}$ $T_{ds}$ $^{m}C_{ds}$ $^{m}C_{ds}$ $A_{ds}$ $G_{ds}$ $G_{eo}$ $A_{eo}$ $^{m}C_{es}$ $^{m}C_{es}$ $^{m}C_{e}$ | 68416 | 68435 | 86.1 | 146 |
| 628641 | $A_{es}$ $G_{eo}$ $G_{eo}$ $^{m}C_{eo}$ $A_{eo}$ $T_{ds}$ $^{m}C_{ds}$ $T_{ds}$ $T_{ds}$ $G_{ds}$ $A_{ds}$ $^{m}C_{ds}$ $A_{ds}$ $A_{ds}$ $G_{ds}$ $G_{eo}$ $A_{eo}$ $G_{es}$ $^{m}C_{es}$ $T_{e}$ | 68440 | 68459 | 81.0 | 147 |
| 628645 | $G_{es}$ $^{m}C_{eo}$ $^{m}C_{eo}$ $^{m}C_{eo}$ $^{m}C_{eo}$ $^{m}C_{ds}$ $T_{ds}$ $G_{ds}$ $G_{ds}$ $^{m}C_{ds}$ $G_{ds}$ $A_{ds}$ $A_{ds}$ $G_{ds}$ $T_{ds}$ $T_{eo}$ $T_{eo}$ $G_{es}$ $A_{es}$ $A_{e}$ | 68461 | 68480 | 29.6 | 148 |
| 628649 | $^{m}C_{es}$ $^{m}C_{eo}$ $^{m}C_{eo}$ $^{m}C_{eo}$ $A_{eo}$ $^{m}C_{ds}$ $^{m}C_{ds}$ $^{m}C_{ds}$ $^{m}C_{ds}$ $^{m}C_{ds}$ $^{m}C_{ds}$ $T_{ds}$ $^{m}C_{ds}$ $A_{ds}$ $G_{ds}$ $^{m}C_{eo}$ $^{m}C_{eo}$ $T_{es}$ $T_{es}$ $G_{e}$ | 68480 | 68499 | 39.9 | 149 |
| 628653 | $^{m}C_{es}$ $^{m}C_{eo}$ $A_{eo}$ $T_{eo}$ $G_{eo}$ $A_{ds}$ $^{m}C_{ds}$ $^{m}C_{ds}$ $T_{ds}$ $G_{ds}$ $G_{ds}$ $G_{ds}$ $T_{ds}$ $G_{ds}$ $G_{ds}$ $A_{eo}$ $T_{eo}$ $G_{es}$ $T_{es}$ $G_{e}$ | 68504 | 68523 | 39.7 | 150 |
| 628657 | $^{m}C_{es}$ $T_{eo}$ $G_{eo}$ $A_{eo}$ $G_{eo}$ $G_{ds}$ $G_{ds}$ $T_{ds}$ $^{m}C_{ds}$ $G_{ds}$ $G_{ds}$ $^{m}C_{ds}$ $^{m}C_{ds}$ $T_{ds}$ $^{m}C_{ds}$ $A_{eo}$ $G_{eo}$ $^{m}C_{es}$ $T_{es}$ $T_{e}$ | 68551 | 68570 | 28.6 | 151 |
| 628661 | $^{m}C_{es}$ $^{m}C_{eo}$ $^{m}C_{eo}$ $G_{eo}$ $G_{eo}$ $^{m}C_{ds}$ $T_{ds}$ $T_{ds}$ $T_{ds}$ $^{m}C_{ds}$ $G_{ds}$ $G_{ds}$ $^{m}C_{ds}$ $^{m}C_{ds}$ $^{m}C_{ds}$ $^{m}C_{eo}$ $G_{eo}$ $T_{es}$ $T_{es}$ $T_{e}$ | 68583 | 68602 | 37.3 | 152 |
| 628665 | $T_{es}$ $G_{eo}$ $G_{eo}$ $^{m}C_{eo}$ $^{m}C_{eo}$ $T_{ds}$ $^{m}C_{ds}$ $G_{ds}$ $G_{ds}$ $^{m}C_{ds}$ $G_{ds}$ $G_{ds}$ $^{m}C_{ds}$ $A_{ds}$ $G_{ds}$ $^{m}C_{eo}$ $G_{eo}$ $G_{es}$ $^{m}C_{es}$ $T_{e}$ | 68615 | 68634 | 38.2 | 153 |
| *628669 | $T_{es}$ $^{m}C_{eo}$ $G_{eo}$ $G_{eo}$ $A_{eo}$ $T_{ds}$ $A_{ds}$ $G_{ds}$ $A_{ds}$ $A_{ds}$ $G_{ds}$ $A_{ds}$ $^{m}C_{ds}$ $T_{ds}$ $^{m}C_{ds}$ $^{m}C_{eo}$ $T_{eo}$ $T_{es}$ $^{m}C_{es}$ $A_{e}$ | 68647 | 68666 | 66.3 | 154 |
| *628673 | $T_{es}$ $A_{eo}$ $^{m}C_{eo}$ $G_{eo}$ $G_{eo}$ $T_{ds}$ $^{m}C_{ds}$ $T_{ds}$ $^{m}C_{ds}$ $^{m}C_{ds}$ $T_{ds}$ $G_{ds}$ $^{m}C_{ds}$ $A_{ds}$ $^{m}C_{ds}$ $A_{eo}$ $G_{eo}$ $A_{es}$ $T_{es}$ $^{m}C_{e}$ | 68665 | 68684 | 83.3 | 155 |
| *628677 | $A_{es}$ $^{m}C_{eo}$ $^{m}C_{eo}$ $T_{eo}$ $^{m}C_{eo}$ $G_{ds}$ $A_{ds}$ $T_{ds}$ $G_{ds}$ $^{m}C_{ds}$ $T_{ds}$ $G_{ds}$ $A_{ds}$ $^{m}C_{ds}$ $^{m}C_{ds}$ $G_{eo}$ $T_{eo}$ $^{m}C_{es}$ $T_{es}$ $^{m}C_{e}$ | 68712 | 68731 | 70.8 | 156 |

TABLE 2-continued

Inhibition of human MECP2 by antisense oligonucleotides in vitro

| Isis No. | Sequence (5' to 3') | Start site | Stop site | % Inhibition | SEQ ID NO: |
|---|---|---|---|---|---|
| 628681 | $^{m}C_{es}$ $T_{eo}$ $T_{eo}$ $^{m}C_{eo}$ $T_{eo}$ $^{m}C_{ds}$ $A_{ds}$ $^{m}C_{ds}$ $^{m}C_{ds}$ $G_{ds}$ $A_{ds}$ $G_{ds}$ $G_{ds}$ $G_{ds}$ $T_{ds}$ $G_{eo}$ $G_{eo}$ $A_{es}$ $^{m}C_{es}$ $A_{e}$ | 68758 | 68777 | 24.2 | 157 |
| 628685 | $G_{es}$ $G_{eo}$ $G_{eo}$ $^{m}C_{eo}$ $T_{eo}$ $^{m}C_{ds}$ $T_{ds}$ $T_{ds}$ $A_{ds}$ $^{m}C_{ds}$ $A_{ds}$ $G_{ds}$ $G_{ds}$ $T_{ds}$ $^{m}C_{ds}$ $T_{eo}$ $T_{eo}$ $^{m}C_{es}$ $A_{es}$ $G_{e}$ | 68790 | 68809 | 62.3 | 158 |
| 628689 | $^{m}C_{es}$ $T_{eo}$ $G_{eo}$ $^{m}C_{eo}$ $T_{eo}$ $G_{ds}$ $^{m}C_{ds}$ $T_{ds}$ $G_{ds}$ $^{m}C_{ds}$ $G_{ds}$ $^{m}C_{ds}$ $^{m}C_{ds}$ $^{m}C_{ds}$ $^{m}C_{ds}$ $T_{eo}$ $T_{eo}$ $G_{es}$ $G_{es}$ $G_{e}$ | 68835 | 68854 | 73.7 | 159 |
| 628693 | $T_{es}$ $^{m}C_{eo}$ $G_{eo}$ $G_{eo}$ $G_{eo}$ $^{m}C_{ds}$ $T_{ds}$ $^{m}C_{ds}$ $A_{ds}$ $G_{ds}$ $G_{ds}$ $T_{ds}$ $G_{ds}$ $G_{ds}$ $A_{ds}$ $G_{eo}$ $G_{eo}$ $T_{es}$ $G_{es}$ $G_{e}$ | 68946 | 68965 | 13.0 | 160 |
| 628697 | $^{m}C_{es}$ $T_{eo}$ $G_{eo}$ $G_{eo}$ $G_{eo}$ $^{m}C_{ds}$ $A_{ds}$ $T_{ds}$ $^{m}C_{ds}$ $T_{ds}$ $T_{ds}$ $^{m}C_{ds}$ $T_{ds}$ $^{m}C_{ds}$ $^{m}C_{ds}$ $T_{eo}$ $^{m}C_{eo}$ $T_{es}$ $T_{es}$ $T_{e}$ | 69024 | 69043 | 59.0 | 161 |
| 628701 | $G_{es}$ $T_{eo}$ $^{m}C_{eo}$ $T_{eo}$ $T_{eo}$ $A_{ds}$ $G_{ds}$ $^{m}C_{ds}$ $T_{ds}$ $G_{ds}$ $G_{ds}$ $^{m}C_{ds}$ $T_{ds}$ $^{m}C_{ds}$ $^{m}C_{ds}$ $T_{eo}$ $T_{eo}$ $G_{es}$ $G_{es}$ $G_{e}$ | 69072 | 69091 | 63.7 | 162 |
| 628705 | $G_{es}$ $G_{eo}$ $T_{eo}$ $G_{eo}$ $G_{eo}$ $^{m}C_{ds}$ $A_{ds}$ $A_{ds}$ $^{m}C_{ds}$ $^{m}C_{ds}$ $G_{ds}$ $^{m}C_{ds}$ $G_{ds}$ $G_{ds}$ $G_{ds}$ $^{m}C_{eo}$ $T_{eo}$ $G_{es}$ $A_{es}$ $G_{e}$ | 69091 | 69110 | 59.5 | 163 |
| 628709 | $^{m}C_{es}$ $G_{eo}$ $G_{eo}$ $^{m}C_{eo}$ $^{m}C_{eo}$ $G_{ds}$ $T_{ds}$ $G_{ds}$ $G_{ds}$ $^{m}C_{ds}$ $G_{ds}$ $G_{ds}$ $^{m}C_{ds}$ $G_{ds}$ $G_{ds}$ $T_{eo}$ $G_{eo}$ $G_{es}$ $^{m}C_{es}$ $A_{e}$ | 69104 | 69123 | 39.5 | 164 |
| 628713 | $T_{es}$ $G_{eo}$ $T_{eo}$ $T_{eo}$ $T_{eo}$ $G_{ds}$ $T_{ds}$ $A_{ds}$ $^{m}C_{ds}$ $T_{ds}$ $T_{ds}$ $T_{ds}$ $T_{ds}$ $^{m}C_{ds}$ $T_{ds}$ $G_{eo}$ $^{m}C_{eo}$ $G_{es}$ $G_{es}$ $^{m}C_{e}$ | 69120 | 69139 | 58.1 | 165 |
| 628717 | $A_{es}$ $A_{eo}$ $A_{eo}$ $^{m}C_{eo}$ $A_{eo}$ $A_{ds}$ $T_{ds}$ $G_{ds}$ $T_{ds}$ $^{m}C_{ds}$ $T_{ds}$ $T_{ds}$ $T_{ds}$ $G_{ds}$ $^{m}C_{ds}$ $G_{eo}$ $^{m}C_{eo}$ $T_{es}$ $^{m}C_{es}$ $T_{e}$ | 69152 | 69171 | 59.3 | 166 |
| 628721 | $^{m}C_{es}$ $T_{eo}$ $^{m}C_{eo}$ $^{m}C_{eo}$ $T_{eo}$ $^{m}C_{ds}$ $T_{ds}$ $^{m}C_{ds}$ $T_{ds}$ $G_{ds}$ $T_{ds}$ $T_{ds}$ $T_{ds}$ $G_{ds}$ $G_{ds}$ $^{m}C_{eo}$ $^{m}C_{eo}$ $T_{es}$ $T_{es}$ $G_{e}$ | 69184 | 69203 | 61.6 | 167 |
| 628725 | $A_{es}$ $G_{eo}$ $T_{eo}$ $^{m}C_{eo}$ $A_{eo}$ $G_{ds}$ $^{m}C_{ds}$ $T_{ds}$ $A_{ds}$ $A_{ds}$ $^{m}C_{ds}$ $T_{ds}$ $^{m}C_{ds}$ $T_{ds}$ $^{m}C_{ds}$ $T_{eo}$ $^{m}C_{eo}$ $G_{es}$ $G_{es}$ $T_{e}$ | 69228 | 69247 | 66.3 | 168 |
| 628729 | $T_{es}$ $G_{eo}$ $T_{eo}$ $T_{eo}$ $G_{eo}$ $G_{ds}$ $T_{ds}$ $T_{ds}$ $T_{ds}$ $G_{ds}$ $^{m}C_{ds}$ $T_{ds}$ $T_{ds}$ $T_{ds}$ $G_{ds}$ $^{m}C_{eo}$ $A_{eo}$ $A_{es}$ $T_{es}$ $^{m}C_{e}$ | 69260 | 69279 | 79.7 | 169 |
| 628733 | $T_{es}$ $A_{eo}$ $A_{eo}$ $G_{eo}$ $G_{eo}$ $A_{ds}$ $G_{ds}$ $A_{ds}$ $A_{ds}$ $G_{ds}$ $A_{ds}$ $G_{ds}$ $A_{ds}$ $^{m}C_{ds}$ $A_{ds}$ $A_{eo}$ $^{m}C_{eo}$ $A_{es}$ $G_{es}$ $^{m}C_{e}$ | 69292 | 69311 | 35.1 | 170 |
| 628737 | $T_{es}$ $T_{eo}$ $A_{eo}$ $A_{eo}$ $T_{eo}$ $^{m}C_{ds}$ $G_{ds}$ $G_{ds}$ $G_{ds}$ $A_{ds}$ $A_{ds}$ $G_{ds}$ $^{m}C_{ds}$ $T_{ds}$ $T_{ds}$ $T_{eo}$ $G_{eo}$ $T_{es}$ $^{m}C_{es}$ $A_{e}$ | 69324 | 69343 | 78.1 | 171 |

Superscript "m" indicates 5-methylcytosine. Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

TABLE 3

Inhibition of human MECP2 by antisense oligonucleotides in vitro

| Isis No. | Sequence (5' to 3') | Start site | Stop site | % Inhibition | SEQ ID NO |
|---|---|---|---|---|---|
| 18078 | $G_{es}$ $T_{es}$ $G_{es}$ $^{m}C_{es}$ $G_{es}$ $C_{ds}$ $G_{ds}$ $C_{ds}$ $G_{ds}$ $A_{ds}$ $G_{ds}$ $C_{ds}$ $C_{ds}$ $C_{ds}$ $G_{es}$ $A_{es}$ $A_{es}$ $A_{es}$ $T_{es}$ $^{m}C_{e}$ | n/a | n/a | 0.6 | 15 |
| 628542 | $G_{es}$ $A_{eo}$ $G_{eo}$ $G_{eo}$ $A_{eo}$ $G_{ds}$ $G_{ds}$ $G_{ds}$ $A_{ds}$ $G_{ds}$ $^{m}C_{ds}$ $G_{ds}$ $^{m}C_{ds}$ $G_{ds}$ $^{m}C_{ds}$ $G_{eo}$ $^{m}C_{eo}$ $G_{es}$ $^{m}C_{es}$ $^{m}C_{e}$ | 1886 | 1905 | 23.9 | 172 |
| 628546 | $^{m}C_{es}$ $^{m}C_{eo}$ $G_{eo}$ $G_{eo}$ $A_{eo}$ $^{m}C_{ds}$ $G_{ds}$ $G_{ds}$ $^{m}C_{ds}$ $T_{ds}$ $T_{ds}$ $T_{ds}$ $T_{ds}$ $A_{ds}$ $^{m}C_{ds}$ $^{m}C_{eo}$ $A_{eo}$ $^{m}C_{es}$ $A_{es}$ $G_{e}$ | 1918 | 1937 | 60.4 | 173 |
| 628550 | $^{m}C_{es}$ $T_{eo}$ $^{m}C_{eo}$ $^{m}C_{eo}$ $T_{eo}$ $^{m}C_{ds}$ $^{m}C_{ds}$ $T_{ds}$ $^{m}C_{ds}$ $^{m}C_{ds}$ $G_{ds}$ $^{m}C_{ds}$ $T_{ds}$ $^{m}C_{ds}$ $G_{ds}$ $G_{eo}$ $^{m}C_{eo}$ $G_{es}$ $^{m}C_{es}$ $G_{e}$ | 1961 | 1980 | 67.0 | 174 |
| 628742 | $A_{es}$ $T_{eo}$ $G_{eo}$ $^{m}C_{eo}$ $T_{eo}$ $T_{ds}$ $^{m}C_{ds}$ $A_{ds}$ $T_{ds}$ $T_{ds}$ $T_{ds}$ $T_{ds}$ $T_{ds}$ $A_{ds}$ $^{m}C_{ds}$ $A_{eo}$ $G_{eo}$ $T_{es}$ $A_{es}$ $T_{e}$ | 3547 | 3566 | 82.9 | 175 |
| 628746 | $G_{es}$ $A_{eo}$ $G_{eo}$ $^{m}C_{eo}$ $^{m}C_{eo}$ $A_{ds}$ $G_{ds}$ $A_{ds}$ $G_{ds}$ $G_{ds}$ $^{m}C_{ds}$ $T_{ds}$ $G_{ds}$ $G_{ds}$ $G_{ds}$ $T_{eo}$ $G_{eo}$ $^{m}C_{es}$ $G_{es}$ $G_{e}$ | 6078 | 6097 | 38.7 | 176 |

TABLE 3-continued

| Isis No. | Sequence (5' to 3') | Start site | Stop site | % Inhibition | SEQ ID NO |
|---|---|---|---|---|---|
| Inhibition of human MECP2 by antisense oligonucleotides in vitro | | | | | |
| 628554 | $T_{es}\ G_{eo}\ A_{eo}\ G_{eo}\ T_{eo}\ {}^{m}C_{ds}\ T_{ds}\ G_{ds}\ T_{ds}\ A_{ds}\ T_{ds}\ T_{ds}\ T_{ds}\ T_{ds}\ T_{ds}\ A_{eo}\ T_{eo}\ G_{es}\ G_{es}\ A_{e}$ | 7300 | 7319 | 57.7 | 177 |
| 628558 | $G_{es}\ G_{eo}\ A_{eo}\ G_{eo}\ T_{eo}\ {}^{m}C_{ds}\ A_{ds}\ {}^{m}C_{ds}\ A_{ds}\ T_{ds}\ G_{ds}\ T_{ds}\ {}^{m}C_{ds}\ A_{ds}\ {}^{m}C_{ds}\ A_{eo}\ T_{eo}\ {}^{m}C_{es}\ A_{es}\ A_{e}$ | 7332 | 7351 | 82.8 | 178 |
| 628562 | $G_{es}\ A_{eo}\ A_{eo}\ T_{eo}\ {}^{m}C_{eo}\ {}^{m}C_{ds}\ T_{ds}\ G_{ds}\ T_{ds}\ T_{ds}\ G_{ds}\ G_{ds}\ A_{ds}\ G_{ds}\ {}^{m}C_{ds}\ T_{eo}\ G_{eo}\ G_{es}\ T_{es}\ {}^{m}C_{e}$ | 7375 | 7394 | 67.3 | 179 |
| 628566 | ${}^{m}C_{es}\ T_{eo}\ T_{eo}\ {}^{m}C_{eo}\ {}^{m}C_{eo}\ {}^{m}C_{ds}\ T_{ds}\ G_{ds}\ A_{ds}\ G_{ds}\ {}^{m}C_{ds}\ {}^{m}C_{ds}\ {}^{m}C_{ds}\ T_{ds}\ A_{ds}\ A_{eo}\ {}^{m}C_{eo}\ A_{es}\ T_{es}\ {}^{m}C_{e}$ | 7407 | 7426 | 32.1 | 180 |
| 628750 | ${}^{m}C_{es}\ {}^{m}C_{eo}\ {}^{m}C_{eo}\ A_{eo}\ {}^{m}C_{eo}\ A_{ds}\ G_{ds}\ {}^{m}C_{ds}\ A_{ds}\ G_{ds}\ T_{ds}\ A_{ds}\ A_{ds}\ A_{ds}\ A_{ds}\ G_{eo}\ A_{eo}\ G_{es}\ A_{es}\ A_{e}$ | 8615 | 8634 | 54.0 | 181 |
| 628754 | $A_{es}\ {}^{m}C_{eo}\ {}^{m}C_{eo}\ {}^{m}C_{eo}\ {}^{m}C_{eo}\ A_{ds}\ G_{ds}\ T_{ds}\ A_{ds}\ G_{ds}\ T_{ds}\ T_{ds}\ G_{ds}\ A_{ds}\ G_{ds}\ A_{eo}\ T_{eo}\ T_{es}\ A_{es}\ {}^{m}C_{e}$ | 11009 | 11028 | 40.8 | 182 |
| 628758 | $A_{es}\ T_{eo}\ A_{eo}\ G_{eo}\ T_{eo}\ A_{ds}\ G_{ds}\ T_{ds}\ T_{ds}\ G_{ds}\ {}^{m}C_{ds}\ {}^{m}C_{ds}\ A_{ds}\ G_{ds}\ A_{ds}\ G_{eo}\ G_{eo}\ G_{es}\ T_{es}\ G_{e}$ | 13862 | 13881 | 38.7 | 183 |
| 628762 | $G_{es}\ G_{eo}\ {}^{m}C_{eo}\ T_{eo}\ T_{eo}\ {}^{m}C_{ds}\ T_{ds}\ A_{ds}\ T_{ds}\ T_{ds}\ G_{ds}\ T_{ds}\ A_{ds}\ A_{ds}\ A_{ds}\ A_{eo}\ {}^{m}C_{eo}\ T_{es}\ A_{es}\ T_{e}$ | 16687 | 16706 | 95.8 | 184 |
| 628766 | $A_{es}\ {}^{m}C_{eo}\ T_{eo}\ G_{eo}\ G_{eo}\ T_{ds}\ T_{ds}\ T_{ds}\ T_{ds}\ T_{ds}\ A_{ds}\ A_{ds}\ G_{ds}\ A_{ds}\ G_{ds}\ A_{eo}\ T_{eo}\ G_{es}\ G_{es}\ G_{e}$ | 19134 | 19153 | 83.1 | 185 |
| 628770 | $T_{es}\ A_{eo}\ A_{eo}\ A_{eo}\ A_{eo}\ T_{ds}\ {}^{m}C_{ds}\ T_{ds}\ A_{ds}\ T_{ds}\ G_{ds}\ G_{ds}\ G_{ds}\ A_{ds}\ A_{ds}\ T_{eo}\ A_{eo}\ A_{es}\ A_{es}\ A_{e}$ | 21818 | 21837 | -7.4 | 186 |
| 628774 | $G_{es}\ A_{eo}\ A_{eo}\ A_{eo}\ T_{eo}\ G_{ds}\ T_{ds}\ G_{ds}\ G_{ds}\ G_{ds}\ {}^{m}C_{ds}\ T_{ds}\ T_{ds}\ G_{ds}\ G_{ds}\ {}^{m}C_{eo}\ A_{eo}\ T_{es}\ G_{es}\ G_{e}$ | 23936 | 23955 | 62.6 | 187 |
| 628778 | $A_{es}\ A_{eo}\ {}^{m}C_{eo}\ A_{eo}\ T_{eo}\ G_{ds}\ G_{ds}\ T_{ds}\ T_{ds}\ T_{ds}\ A_{ds}\ G_{ds}\ T_{ds}\ A_{ds}\ G_{ds}\ A_{eo}\ A_{eo}\ A_{es}\ {}^{m}C_{es}\ {}^{m}C_{e}$ | 26672 | 26691 | 72.8 | 188 |
| 628782 | $G_{es}\ G_{eo}\ T_{eo}\ A_{eo}\ T_{eo}\ T_{ds}\ A_{ds}\ T_{ds}\ A_{ds}\ A_{ds}\ T_{ds}\ T_{ds}\ T_{ds}\ T_{ds}\ G_{ds}\ T_{eo}\ A_{eo}\ A_{es}\ T_{es}\ T_{e}$ | 28682 | 28701 | 49.9 | 189 |
| 628786 | ${}^{m}C_{es}\ A_{eo}\ A_{eo}\ {}^{m}C_{eo}\ A_{eo}\ T_{ds}\ T_{ds}\ {}^{m}C_{ds}\ {}^{m}C_{ds}\ A_{ds}\ T_{ds}\ T_{ds}\ T_{ds}\ A_{ds}\ T_{ds}\ T_{eo}\ T_{eo}\ A_{es}\ G_{es}\ G_{e}$ | 31258 | 31277 | 90.5 | 190 |
| 628790 | $A_{es}\ T_{eo}\ T_{eo}\ T_{eo}\ T_{eo}\ {}^{m}C_{ds}\ A_{ds}\ {}^{m}C_{ds}\ {}^{m}C_{ds}\ {}^{m}C_{ds}\ T_{ds}\ T_{ds}\ T_{ds}\ A_{ds}\ A_{ds}\ A_{eo}\ A_{eo}\ A_{es}\ T_{es}\ {}^{m}C_{e}$ | 33773 | 33792 | 63.0 | 191 |
| 628794 | $T_{es}\ A_{eo}\ A_{eo}\ T_{eo}\ A_{eo}\ {}^{m}C_{ds}\ A_{ds}\ G_{ds}\ T_{ds}\ G_{ds}\ A_{ds}\ {}^{m}C_{d}s\ A_{ds}\ A_{ds}\ G_{ds}\ {}^{m}C_{eo}\ A_{eo}\ T_{es}\ {}^{m}C_{es}\ {}^{m}C_{e}$ | 35787 | 35806 | 68.0 | 192 |
| 628798 | $T_{es}\ {}^{m}C_{eo}\ {}^{m}C_{eo}\ A_{eo}\ T_{eo}\ {}^{m}C_{ds}\ T_{ds}\ T_{ds}\ G_{ds}\ {}^{m}C_{ds}\ A_{ds}\ G_{ds}\ G_{ds}\ T_{ds}\ G_{ds}\ G_{eo}\ A_{eo}\ G_{es}\ T_{es}\ A_{e}$ | 38549 | 38568 | 77.6 | 193 |
| 628802 | $G_{es}\ A_{eo}\ A_{eo}\ G_{eo}\ {}^{m}C_{eo}\ {}^{m}C_{ds}\ A_{ds}\ A_{ds}\ A_{ds}\ A_{ds}\ A_{ds}\ A_{ds}\ G_{ds}\ {}^{m}C_{ds}\ A_{ds}\ A_{eo}\ {}^{m}C_{eo}\ A_{es}\ A_{es}\ A_{e}$ | 40573 | 40592 | 60.5 | 194 |
| 628806 | ${}^{m}C_{es}\ {}^{m}C_{eo}\ A_{eo}\ A_{eo}\ G_{eo}\ A_{ds}\ {}^{m}C_{ds}\ A_{ds}\ A_{ds}\ G_{ds}\ G_{ds}\ A_{ds}\ A_{ds}\ A_{ds}\ A_{ds}\ A_{eo}\ {}^{m}C_{eo}\ G_{es}\ G_{es}\ G_{e}$ | 43080 | 43099 | 57.5 | 195 |
| 628810 | ${}^{m}C_{es}\ T_{eo}\ A_{eo}\ G_{eo}\ {}^{m}C_{eo}\ T_{ds}\ A_{ds}\ T_{ds}\ {}^{m}C_{ds}\ A_{ds}\ G_{ds}\ {}^{m}C_{ds}\ T_{ds}\ G_{ds}\ G_{ds}\ G_{eo}\ {}^{m}C_{eo}\ A_{es}\ T_{es}\ G_{e}$ | 45258 | 45277 | 66.7 | 196 |
| 628814 | $T_{es}\ G_{eo}\ {}^{m}C_{eo}\ {}^{m}C_{eo}\ T_{eo}\ T_{ds}\ G_{ds}\ T_{ds}\ T_{ds}\ G_{ds}\ G_{ds}\ G_{ds}\ T_{ds}\ A_{ds}\ G_{ds}\ T_{eo}\ A_{eo}\ {}^{m}C_{es}\ A_{es}\ G_{e}$ | 47334 | 47353 | 72.0 | 197 |
| 628818 | $G_{es}\ {}^{m}C_{eo}\ T_{eo}\ A_{eo}\ A_{eo}\ G_{ds}\ T_{ds}\ T_{ds}\ A_{ds}\ G_{ds}\ A_{ds}\ A_{ds}\ {}^{m}C_{ds}\ T_{ds}\ {}^{m}C_{ds}\ {}^{m}C_{eo}\ G_{eo}\ T_{es}\ G_{es}\ G_{e}$ | 49363 | 49382 | 49.4 | 198 |
| 628822 | $A_{es}\ {}^{m}C_{eo}\ A_{eo}\ {}^{m}C_{eo}\ G_{eo}\ {}^{m}C_{ds}\ {}^{m}C_{ds}\ T_{ds}\ G_{ds}\ T_{ds}\ A_{ds}\ A_{ds}\ T_{ds}\ {}^{m}C_{ds}\ {}^{m}C_{ds}\ T_{eo}\ G_{eo}\ {}^{m}C_{es}\ A_{es}\ T_{e}$ | 51552 | 51571 | 81.5 | 199 |
| 628826 | ${}^{m}C_{es}\ A_{eo}\ A_{eo}\ {}^{m}C_{eo}\ T_{eo}\ G_{ds}\ G_{ds}\ A_{ds}\ G_{ds}\ G_{ds}\ {}^{m}C_{ds}\ {}^{m}C_{ds}\ G_{ds}\ G_{ds}\ G_{ds}\ {}^{m}C_{eo}\ G_{eo}\ {}^{m}C_{es}\ G_{es}\ A_{e}$ | 54069 | 54088 | 9.7 | 200 |
| 628830 | $A_{es}\ G_{eo}\ {}^{m}C_{eo}\ {}^{m}C_{eo}\ {}^{m}C_{eo}\ A_{ds}\ {}^{m}C_{ds}\ A_{ds}\ {}^{m}C_{ds}\ A_{ds}\ G_{ds}\ {}^{m}C_{ds}\ T_{ds}\ G_{ds}\ T_{ds}\ {}^{m}C_{eo}\ T_{eo}\ {}^{m}C_{es}\ A_{es}\ G_{e}$ | 56096 | 56115 | 41.4 | 201 |

TABLE 3-continued

Inhibition of human MECP2 by antisense oligonucleotides in vitro

| Isis No. | Sequence (5' to 3') | Start site | Stop site | % Inhibition | SEQ ID NO |
|---|---|---|---|---|---|
| 628834 | $T_{es}$ $T_{eo}$ ${}^{m}C_{eo}$ ${}^{m}C_{eo}$ $T_{eo}$ ${}^{m}C_{ds}$ $A_{ds}$ $T_{ds}$ $G_{ds}$ $A_{ds}$ $A_{ds}$ $T_{ds}$ $G_{ds}$ $T_{ds}$ $G_{ds}$ $A_{eo}$ ${}^{m}C_{eo}$ ${}^{m}C_{es}$ $T_{es}$ $G_{e}$ | 58122 | 58141 | 47.6 | 202 |
| 628838 | $G_{es}$ $A_{eo}$ $G_{eo}$ $G_{eo}$ $A_{eo}$ $A_{ds}$ ${}^{m}C_{ds}$ $T_{ds}$ $T_{ds}$ $G_{ds}$ $T_{ds}$ ${}^{m}C_{ds}$ $T_{ds}$ $G_{ds}$ $A_{ds}$ $G_{eo}$ $A_{eo}$ $T_{es}$ ${}^{m}C_{es}$ $A_{e}$ | 60766 | 60785 | 68.3 | 203 |
| 628842 | ${}^{m}C_{es}$ $A_{eo}$ $G_{eo}$ ${}^{m}C_{eo}$ $T_{eo}$ $A_{ds}$ ${}^{m}C_{ds}$ $T_{ds}$ ${}^{m}C_{ds}$ $G_{ds}$ ${}^{m}C_{ds}$ $T_{ds}$ $A_{ds}$ $G_{ds}$ $A_{ds}$ $A_{eo}$ $A_{eo}$ $G_{es}$ $G_{es}$ $G_{e}$ | 62880 | 62899 | 70.8 | 204 |
| 628846 | ${}^{m}C_{es}$ $T_{eo}$ ${}^{m}C_{eo}$ ${}^{m}C_{eo}$ ${}^{m}C_{eo}$ ${}^{m}C_{ds}$ $A_{ds}$ $T_{ds}$ $A_{ds}$ $A_{ds}$ $A_{ds}$ $G_{ds}$ $G_{ds}$ $A_{ds}$ $G_{ds}$ $G_{eo}$ $G_{eo}$ $A_{es}$ $G_{es}$ $G_{e}$ | 64930 | 64949 | 1.6 | 205 |
| 628850 | ${}^{m}C_{es}$ ${}^{m}C_{eo}$ $A_{eo}$ $T_{eo}$ ${}^{m}C_{eo}$ $A_{ds}$ $T_{ds}$ $A_{ds}$ ${}^{m}C_{ds}$ $A_{ds}$ ${}^{m}C_{ds}$ $T_{ds}$ ${}^{m}C_{ds}$ $A_{ds}$ $G_{ds}$ $A_{eo}$ $T_{eo}$ ${}^{m}C_{es}$ $T_{es}$ $T_{e}$ | 66932 | 66951 | 62.6 | 206 |
| 628570 | $T_{es}$ $T_{eo}$ $G_{eo}$ $A_{eo}$ $G_{eo}$ $G_{ds}$ ${}^{m}C_{ds}$ ${}^{m}C_{ds}$ ${}^{m}C_{ds}$ $T_{ds}$ $G_{ds}$ $G_{ds}$ $A_{as}$ $G_{ds}$ $G_{ds}$ $T_{eo}$ ${}^{m}C_{eo}$ ${}^{m}C_{es}$ $T_{es}$ $G_{e}$ | 67074 | 67093 | 31.1 | 207 |
| 628574 | $T_{es}$ $T_{eo}$ ${}^{m}C_{eo}$ $T_{eo}$ $T_{eo}$ $T_{ds}$ ${}^{m}C_{ds}$ $T_{ds}$ $T_{ds}$ $A_{ds}$ $T_{ds}$ ${}^{m}C_{ds}$ $T_{ds}$ $T_{ds}$ $T_{ds}$ ${}^{m}C_{eo}$ $T_{eo}$ $T_{es}$ ${}^{m}C_{es}$ $A_{e}$ | 67120 | 67139 | 39.8 | 208 |
| 628578 | $G_{es}$ ${}^{m}C_{eo}$ ${}^{m}C_{eo}$ ${}^{m}C_{eo}$ $T_{eo}$ ${}^{m}C_{ds}$ $T_{ds}$ $T_{ds}$ $T_{ds}$ ${}^{m}C_{ds}$ $T_{ds}$ ${}^{m}C_{ds}$ $T_{ds}$ $T_{ds}$ ${}^{m}C_{ds}$ $T_{eo}$ $T_{eo}$ $T_{es}$ ${}^{m}C_{es}$ $T_{e}$ | 67132 | 67151 | 46.7 | 209 |
| 628582 | ${}^{m}C_{es}$ $T_{eo}$ $G_{eo}$ ${}^{m}C_{eo}$ $A_{eo}$ ${}^{m}C_{ds}$ $G_{ds}$ $G_{ds}$ $G_{ds}$ ${}^{m}C_{ds}$ $T_{ds}$ ${}^{m}C_{ds}$ $A_{ds}$ $T_{ds}$ $G_{ds}$ ${}^{m}C_{eo}$ $T_{eo}$ $T_{es}$ $G_{es}$ ${}^{m}C_{e}$ | 67150 | 67169 | 69.0 | 210 |
| 628586 | $G_{es}$ $T_{eo}$ $G_{eo}$ $G_{eo}$ $G_{eo}$ ${}^{m}C_{ds}$ $T_{ds}$ $G_{ds}$ $A_{ds}$ $T_{ds}$ $G_{ds}$ $G_{ds}$ ${}^{m}C_{ds}$ $T_{ds}$ $G_{ds}$ ${}^{m}C_{eo}$ $A_{eo}$ ${}^{m}C_{es}$ $G_{es}$ $G_{e}$ | 67162 | 67181 | 31.7 | 211 |
| 628590 | ${}^{m}C_{es}$ ${}^{m}C_{eo}$ $T_{eo}$ $G_{eo}$ ${}^{m}C_{eo}$ ${}^{m}C_{ds}$ $T_{ds}$ ${}^{m}C_{ds}$ $T_{ds}$ $G_{ds}$ ${}^{m}C_{ds}$ $G_{ds}$ $G_{ds}$ $G_{ds}$ ${}^{m}C_{ds}$ $T_{eo}$ ${}^{m}C_{eo}$ $A_{es}$ $G_{es}$ ${}^{m}C_{e}$ | 67188 | 67207 | 39.4 | 212 |
| 628594 | ${}^{m}C_{es}$ $G_{eo}$ $G_{eo}$ $A_{eo}$ $G_{eo}$ ${}^{m}C_{ds}$ ${}^{m}C_{ds}$ $T_{ds}$ $G_{ds}$ $A_{ds}$ ${}^{m}C_{ds}$ ${}^{m}C_{ds}$ ${}^{m}C_{ds}$ $T_{ds}$ $T_{ds}$ ${}^{m}C_{eo}$ $T_{eo}$ $G_{es}$ $A_{es}$ $T_{e}$ | 67220 | 67239 | 50.9 | 213 |
| 628598 | $G_{es}$ $G_{eo}$ $G_{eo}$ $A_{eo}$ $G_{eo}$ $G_{ds}$ ${}^{m}C_{ds}$ $A_{ds}$ $G_{ds}$ $A_{ds}$ $A_{ds}$ $G_{ds}$ ${}^{m}C_{ds}$ $T_{ds}$ $T_{ds}$ ${}^{m}C_{eo}$ ${}^{m}C_{eo}$ $G_{es}$ $G_{es}$ ${}^{m}C_{e}$ | 67250 | 67269 | 15.8 | 214 |
| 628602 | ${}^{m}C_{es}$ ${}^{m}C_{eo}$ $A_{eo}$ $G_{eo}$ ${}^{m}C_{eo}$ ${}^{m}C_{ds}$ $T_{ds}$ $T_{ds}$ ${}^{m}C_{ds}$ $A_{ds}$ $G_{ds}$ $G_{ds}$ ${}^{m}C_{ds}$ $A_{ds}$ $G_{ds}$ $G_{eo}$ $G_{eo}$ $T_{es}$ $G_{es}$ $G_{e}$ | 67321 | 67340 | 37.1 | 215 |
| 628606 | ${}^{m}C_{es}$ $G_{eo}$ $G_{eo}$ ${}^{m}C_{eo}$ ${}^{m}C_{eo}$ $A_{ds}$ $G_{ds}$ $A_{ds}$ $T_{ds}$ $T_{ds}$ $T_{ds}$ ${}^{m}C_{ds}$ ${}^{m}C_{ds}$ $T_{ds}$ $T_{ds}$ $T_{eo}$ $G_{eo}$ ${}^{m}C_{es}$ $T_{es}$ $T_{e}$ | 67353 | 67372 | 55.6 | 216 |
| 628610 | $T_{es}$ $G_{eo}$ $A_{eo}$ $T_{eo}$ ${}^{m}C_{eo}$ $A_{ds}$ $A_{ds}$ $A_{ds}$ $T_{ds}$ $A_{ds}$ ${}^{m}C_{ds}$ $A_{ds}$ ${}^{m}C_{ds}$ $A_{ds}$ $T_{ds}$ ${}^{m}C_{eo}$ $A_{eo}$ $T_{es}$ $A_{es}$ ${}^{m}C_{e}$ | 67385 | 67404 | 53.0 | 217 |
| 628614 | $G_{es}$ $T_{eo}$ $A_{eo}$ ${}^{m}C_{eo}$ $G_{eo}$ ${}^{m}C_{ds}$ $A_{ds}$ $A_{ds}$ $T_{ds}$ ${}^{m}C_{ds}$ $A_{ds}$ $A_{ds}$ ${}^{m}C_{ds}$ $T_{ds}$ ${}^{m}C_{ds}$ ${}^{m}C_{eo}$ $A_{eo}$ ${}^{m}C_{es}$ $T_{es}$ $T_{e}$ | 68188 | 68207 | 83.9 | 218 |
| 628618 | $T_{es}$ $G_{eo}$ $T_{eo}$ $G_{eo}$ $T_{eo}$ ${}^{m}C_{ds}$ $G_{ds}$ ${}^{m}C_{ds}$ ${}^{m}C_{ds}$ $T_{ds}$ $A_{ds}$ ${}^{m}C_{ds}$ ${}^{m}C_{ds}$ $T_{ds}$ $T_{ds}$ $T_{eo}$ $T_{eo}$ ${}^{m}C_{es}$ $G_{es}$ $A_{e}$ | 68209 | 68228 | 50.1 | 219 |
| 628622 | ${}^{m}C_{es}$ $A_{eo}$ $A_{eo}$ $A_{eo}$ $A_{eo}$ $T_{ds}$ ${}^{m}C_{ds}$ $A_{ds}$ $T_{ds}$ $T_{ds}$ $A_{ds}$ $G_{ds}$ $G_{ds}$ $G_{ds}$ $T_{ds}$ ${}^{m}C_{eo}$ ${}^{m}C_{eo}$ $A_{es}$ $G_{es}$ $G_{e}$ | 68231 | 68250 | 58.6 | 220 |
| 628626 | $T_{es}$ $T_{eo}$ $T_{eo}$ ${}^{m}C_{eo}$ $T_{eo}$ $G_{ds}$ ${}^{m}C_{ds}$ $T_{ds}$ ${}^{m}C_{ds}$ $T_{ds}$ ${}^{m}C_{ds}$ $G_{ds}$ ${}^{m}C_{ds}$ ${}^{m}C_{ds}$ $G_{ds}$ $G_{eo}$ $G_{eo}$ $A_{es}$ $G_{es}$ $G_{e}$ | 68278 | 68297 | 35.9 | 221 |
| 628630 | ${}^{m}C_{es}$ ${}^{m}C_{eo}$ $A_{eo}$ $G_{eo}$ $T_{eo}$ $T_{ds}$ ${}^{m}C_{ds}$ ${}^{m}C_{ds}$ $T_{ds}$ $G_{ds}$ $G_{ds}$ $A_{ds}$ $G_{ds}$ ${}^{m}C_{ds}$ $T_{ds}$ $T_{eo}$ $T_{eo}$ $G_{es}$ $G_{es}$ $G_{e}$ | 68319 | 68338 | 51.3 | 222 |
| 628634 | ${}^{m}C_{es}$ $A_{eo}$ ${}^{m}C_{eo}$ ${}^{m}C_{eo}$ $T_{eo}$ $G_{ds}$ ${}^{m}C_{ds}$ $A_{ds}$ ${}^{m}C_{ds}$ $A_{ds}$ ${}^{m}C_{ds}$ ${}^{m}C_{ds}$ ${}^{m}C_{ds}$ $T_{ds}$ ${}^{m}C_{ds}$ $T_{eo}$ $G_{eo}$ $A_{es}$ ${}^{m}C_{es}$ $G_{e}$ | 68392 | 68411 | 53.6 | 223 |
| 628638 | $G_{es}$ $A_{eo}$ $G_{eo}$ ${}^{m}C_{eo}$ $T_{eo}$ $T_{ds}$ ${}^{m}C_{ds}$ ${}^{m}C_{ds}$ ${}^{m}C_{ds}$ $A_{ds}$ $G_{ds}$ $G_{ds}$ $A_{ds}$ ${}^{m}C_{ds}$ $T_{ds}$ $T_{eo}$ $T_{eo}$ $T_{es}$ ${}^{m}C_{es}$ $T_{e}$ | 68425 | 68444 | 57.1 | 224 |
| 628642 | $G_{es}$ $T_{eo}$ $T_{eo}$ $T_{eo}$ $G_{eo}$ $A_{ds}$ $A_{ds}$ $A_{ds}$ $A_{ds}$ $G_{ds}$ $G_{ds}$ ${}^{m}C_{ds}$ $A_{ds}$ $T_{ds}$ ${}^{m}C_{ds}$ $T_{eo}$ $T_{eo}$ $G_{es}$ $A_{es}$ ${}^{m}C_{e}$ | 68448 | 68467 | 40.8 | 225 |
| 628646 | ${}^{m}C_{es}$ $T_{eo}$ $T_{eo}$ $G_{eo}$ ${}^{m}C_{eo}$ ${}^{m}C_{ds}$ ${}^{m}C_{ds}$ ${}^{m}C_{ds}$ ${}^{m}C_{ds}$ $T_{ds}$ $G_{ds}$ $G_{ds}$ ${}^{m}C_{ds}$ $G_{ds}$ $A_{ds}$ $A_{eo}$ $G_{eo}$ $T_{es}$ $T_{es}$ $T_{e}$ | 68464 | 68483 | 58.5 | 226 |

TABLE 3-continued

| Inhibition of human MECP2 by antisense oligonucleotides in vitro | | | | | |
|---|---|---|---|---|---|
| Isis No. | Sequence (5' to 3') | Start site | Stop site | % Inhibition | SEQ ID NO |
| 628650 | $T_{es}$ $G_{eo}$ $T_{eo}$ $G_{eo}$ $G_{eo}$ $T_{ds}$ $G_{ds}$ $G_{ds}$ $^{m}C_{ds}$ $^{m}C_{ds}$ $^{m}C_{ds}$ $^{m}C_{ds}$ $A_{ds}$ $^{m}C_{ds}$ $^{m}C_{ds}$ $^{m}C_{eo}$ $^{m}C_{eo}$ $^{m}C_{es}$ $^{m}C_{es}$ $T_{e}$ | 68488 | 68507 | 57.7 | 227 |
| 628654 | $T_{es}$ $T_{eo}$ $T_{eo}$ $G_{eo}$ $A_{eo}$ $T_{ds}$ $^{m}C_{ds}$ $A_{ds}$ $^{m}C_{ds}$ $^{m}C_{ds}$ $A_{ds}$ $T_{ds}$ $G_{ds}$ $A_{ds}$ $^{m}C_{ds}$ $^{m}C_{eo}$ $T_{eo}$ $G_{es}$ $G_{es}$ $G_{e}$ | 68512 | 68531 | 69.1 | 228 |
| 628658 | $G_{es}$ $G_{eo}$ $A_{eo}$ $A_{eo}$ $T_{eo}$ $G_{ds}$ $G_{ds}$ $^{m}C_{ds}$ $^{m}C_{ds}$ $T_{ds}$ $G_{ds}$ $A_{ds}$ $G_{ds}$ $G_{ds}$ $G_{ds}$ $T_{eo}$ $^{m}C_{eo}$ $G_{es}$ $G_{es}$ $^{m}C_{e}$ | 68559 | 68578 | 35.4 | 229 |
| 628662 | $^{m}C_{es}$ $^{m}C_{eo}$ $A_{eo}$ $^{m}C_{eo}$ $A_{eo}$ $^{m}C_{ds}$ $T_{ds}$ $^{m}C_{ds}$ $^{m}C_{ds}$ $^{m}C_{ds}$ $^{m}C_{ds}$ $G_{ds}$ $G_{ds}$ $^{m}C_{ds}$ $T_{ds}$ $T_{eo}$ $T_{eo}$ $^{m}C_{es}$ $G_{es}$ $G_{e}$ | 68591 | 68610 | 58.1 | 230 |
| 628666 | $T_{es}$ $T_{eo}$ $T_{eo}$ $^{m}C_{eo}$ $T_{eo}$ $T_{ds}$ $T_{ds}$ $T_{ds}$ $T_{ds}$ $G_{ds}$ $G_{ds}$ $^{m}C_{ds}$ $^{m}C_{ds}$ $T_{ds}$ $^{m}C_{ds}$ $G_{eo}$ $G_{eo}$ $^{m}C_{es}$ $G_{es}$ $G_{e}$ | 68623 | 68642 | 47.3 | 231 |
| 628670 | $^{m}C_{es}$ $T_{eo}$ $G_{eo}$ $^{m}C_{eo}$ $A_{eo}$ $^{m}C_{ds}$ $A_{ds}$ $G_{ds}$ $A_{ds}$ $T_{ds}$ $^{m}C_{ds}$ $G_{ds}$ $G_{ds}$ $A_{ds}$ $T_{ds}$ $A_{eo}$ $G_{eo}$ $A_{es}$ $A_{es}$ $G_{e}$ | 68656 | 68675 | 81.0 | 232 |
| *628674 | $G_{es}$ $T_{eo}$ $^{m}C_{eo}$ $T_{eo}$ $T_{eo}$ $G_{ds}$ $^{m}C_{ds}$ $G_{ds}$ $^{m}C_{ds}$ $T_{ds}$ $T_{ds}$ $^{m}C_{ds}$ $T_{ds}$ $T_{ds}$ $G_{ds}$ $A_{eo}$ $T_{eo}$ $G_{es}$ $G_{es}$ $G_{e}$ | 68688 | 68707 | 69.4 | 233 |
| *628678 | $^{m}C_{es}$ $T_{eo}$ $T_{eo}$ $^{m}C_{eo}$ $^{m}C_{eo}$ $T_{ds}$ $T_{ds}$ $G_{ds}$ $A_{ds}$ $^{m}C_{ds}$ $^{m}C_{ds}$ $T_{ds}$ $^{m}C_{ds}$ $G_{ds}$ $A_{ds}$ $T_{eo}$ $G_{eo}$ $^{m}C_{es}$ $T_{es}$ $G_{e}$ | 68720 | 68739 | 95.8 | 234 |
| 628682 | $T_{es}$ $T_{eo}$ $^{m}C_{eo}$ $^{m}C_{eo}$ $^{m}C_{eo}$ $G_{ds}$ $^{m}C_{ds}$ $T_{ds}$ $^{m}C_{ds}$ $T_{ds}$ $T_{ds}$ $^{m}C_{ds}$ $T_{ds}$ $^{m}C_{ds}$ $A_{ds}$ $^{m}C_{eo}$ $^{m}C_{eo}$ $G_{es}$ $A_{es}$ $G_{e}$ | 68766 | 68785 | 45.1 | 235 |
| 628686 | $T_{es}$ $^{m}C_{eo}$ $^{m}C_{eo}$ $G_{eo}$ $^{m}C_{eo}$ $^{m}C_{ds}$ $^{m}C_{ds}$ $A_{ds}$ $G_{ds}$ $G_{ds}$ $G_{ds}$ $^{m}C_{ds}$ $T_{ds}$ $^{m}C_{ds}$ $T_{ds}$ $T_{eo}$ $A_{eo}$ $^{m}C_{es}$ $A_{es}$ $G_{e}$ | 68798 | 68817 | 53.0 | 236 |
| 628690 | $T_{es}$ $G_{eo}$ $G_{eo}$ $T_{eo}$ $G_{eo}$ $G_{ds}$ $T_{ds}$ $G_{ds}$ $^{m}C_{ds}$ $T_{ds}$ $^{m}C_{ds}$ $^{m}C_{ds}$ $T_{ds}$ $T_{ds}$ $^{m}C_{ds}$ $T_{eo}$ $T_{eo}$ $G_{es}$ $G_{es}$ $G_{e}$ | 68868 | 68887 | 87.2 | 237 |
| 628694 | $^{m}C_{es}$ $G_{eo}$ $G_{eo}$ $A_{eo}$ $G_{eo}$ $^{m}C_{ds}$ $T_{ds}$ $^{m}C_{ds}$ $T_{ds}$ $^{m}C_{ds}$ $G_{ds}$ $G_{ds}$ $G_{ds}$ $^{m}C_{ds}$ $T_{ds}$ $^{m}C_{eo}$ $A_{eo}$ $G_{es}$ $G_{es}$ $T_{e}$ | 68954 | 68973 | 79.7 | 238 |
| 628698 | $A_{es}$ $G_{eo}$ $^{m}C_{eo}$ $^{m}C_{eo}$ $T_{eo}$ $^{m}C_{ds}$ $^{m}C_{ds}$ $T_{ds}$ $^{m}C_{ds}$ $T_{ds}$ $G_{ds}$ $G_{ds}$ $G_{ds}$ $^{m}C_{ds}$ $A_{ds}$ $T_{eo}$ $^{m}C_{eo}$ $T_{es}$ $T_{es}$ $^{m}C_{e}$ | 69032 | 69051 | 51.1 | 239 |
| 628702 | $^{m}C_{es}$ $G_{eo}$ $G_{eo}$ $G_{eo}$ $^{m}C_{eo}$ $T_{ds}$ $G_{ds}$ $A_{ds}$ $G_{ds}$ $T_{ds}$ $^{m}C_{ds}$ $T_{ds}$ $T_{ds}$ $A_{ds}$ $G_{ds}$ $^{m}C_{eo}$ $T_{eo}$ $G_{es}$ $G_{es}$ $^{m}C_{e}$ | 69080 | 69099 | 69.6 | 240 |
| 628706 | $G_{es}$ $G_{eo}$ $^{m}C_{eo}$ $G_{eo}$ $G_{eo}$ $T_{ds}$ $G_{ds}$ $G_{ds}$ $^{m}C_{ds}$ $A_{ds}$ $A_{ds}$ $^{m}C_{ds}$ $^{m}C_{ds}$ $G_{ds}$ $^{m}C_{ds}$ $G_{eo}$ $G_{eo}$ $G_{es}$ $^{m}C_{es}$ $T_{e}$ | 69094 | 69113 | 62.7 | 241 |
| 628710 | $T_{es}$ $^{m}C_{eo}$ $T_{eo}$ $G_{eo}$ $^{m}C_{eo}$ $G_{ds}$ $G_{ds}$ $^{m}C_{ds}$ $^{m}C_{ds}$ $G_{ds}$ $T_{ds}$ $G_{ds}$ $G_{ds}$ $^{m}C_{ds}$ $G_{ds}$ $G_{eo}$ $^{m}C_{eo}$ $G_{es}$ $G_{es}$ $T_{e}$ | 69108 | 69127 | 54.2 | 242 |
| 628714 | $^{m}C_{es}$ $^{m}C_{eo}$ $^{m}C_{eo}$ $^{m}C_{eo}$ $T_{eo}$ $^{m}C_{ds}$ $G_{ds}$ $G_{ds}$ $T_{ds}$ $G_{ds}$ $T_{ds}$ $T_{ds}$ $T_{ds}$ $G_{ds}$ $T_{ds}$ $A_{eo}$ $^{m}C_{eo}$ $T_{es}$ $T_{es}$ $T_{e}$ | 69128 | 69147 | 47.5 | 243 |
| 628718 | $G_{es}$ $G_{eo}$ $A_{eo}$ $G_{eo}$ $G_{eo}$ $A_{ds}$ $T_{ds}$ $G_{ds}$ $A_{ds}$ $A_{ds}$ $A_{ds}$ $^{m}C_{ds}$ $A_{ds}$ $A_{ds}$ $T_{ds}$ $G_{eo}$ $T_{eo}$ $^{m}C_{es}$ $T_{es}$ $T_{e}$ | 69160 | 69179 | 53.6 | 244 |
| 628722 | $T_{es}$ $^{m}C_{eo}$ $^{m}C_{eo}$ $A_{eo}$ $^{m}C_{eo}$ $A_{ds}$ $G_{ds}$ $G_{ds}$ $^{m}C_{ds}$ $T_{ds}$ $^{m}C_{ds}$ $^{m}C_{ds}$ $T_{ds}$ $^{m}C_{ds}$ $T_{ds}$ $^{m}C_{eo}$ $T_{eo}$ $G_{es}$ $T_{es}$ $T_{e}$ | 69192 | 69211 | 24.4 | 245 |
| 628726 | $^{m}C_{es}$ $^{m}C_{eo}$ $G_{eo}$ $T_{eo}$ $G_{eo}$ $T_{ds}$ $A_{ds}$ $A_{ds}$ $A_{ds}$ $G_{ds}$ $T_{ds}$ $^{m}C_{ds}$ $A_{ds}$ $G_{ds}$ $^{m}C_{ds}$ $T_{eo}$ $A_{eo}$ $A_{es}$ $^{m}C_{es}$ $T_{e}$ | 69236 | 69255 | 65.9 | 246 |
| 628730 | $T_{es}$ $T_{eo}$ $T_{eo}$ $A_{eo}$ $T_{eo}$ $T_{ds}$ $^{m}C_{ds}$ $T_{ds}$ $T_{ds}$ $G_{ds}$ $T_{ds}$ $T_{ds}$ $G_{ds}$ $G_{ds}$ $T_{ds}$ $T_{eo}$ $T_{eo}$ $G_{es}$ $^{m}C_{es}$ $T_{e}$ | 69268 | 69287 | 65.8 | 247 |
| 628734 | $^{m}C_{es}$ $^{m}C_{eo}$ $T_{eo}$ $A_{eo}$ $^{m}C_{eo}$ $^{m}C_{ds}$ $^{m}C_{ds}$ $A_{ds}$ $T_{ds}$ $A_{ds}$ $A_{ds}$ $G_{ds}$ $G_{ds}$ $A_{ds}$ $G_{ds}$ $A_{eo}$ $A_{eo}$ $G_{es}$ $A_{es}$ $G_{e}$ | 69300 | 69319 | 48.9 | 248 |
| 628738 | $T_{es}$ $A_{eo}$ $T_{eo}$ $T_{eo}$ $T_{eo}$ $^{m}C_{ds}$ $A_{ds}$ $G_{ds}$ $T_{ds}$ $T_{ds}$ $A_{ds}$ $A_{ds}$ $T_{ds}$ $^{m}C_{ds}$ $G_{ds}$ $G_{eo}$ $G_{eo}$ $A_{es}$ $A_{es}$ $G_{e}$ | 69332 | 69351 | 47.8 | 249 |

Superscript "m" indicates 5-methylcytosine. Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

TABLE 4

Inhibition or human MECP2 by antisense oligonucleotides in vitro

| Isis No. | Sequence (5' to 3') | Start site | Stop site | % Inhibi-tion | SEQ ID NO: |
|---|---|---|---|---|---|
| 18078 | $G_{es}$ $T_{es}$ $G_{es}$ ${}^{m}C_{es}$ $G_{es}$ $C_{ds}$ $G_{ds}$ $C_{ds}$ $G_{ds}$ $A_{ds}$ $G_{ds}$ $C_{ds}$ $C_{ds}$ $C_{ds}$ $G_{es}$ $A_{es}$ $A_{es}$ $A_{es}$ $T_{es}$ ${}^{m}C_{e}$ | n/a | n/a | -9.9 | 15 |
| 628544 | $A_{es}$ ${}^{m}C_{eo}$ $A_{eo}$ $G_{eo}$ ${}^{m}C_{eo}$ ${}^{m}C_{ds}$ $T_{ds}$ ${}^{m}C_{ds}$ $T_{ds}$ ${}^{m}C_{ds}$ $T_{ds}$ ${}^{m}C_{ds}$ ${}^{m}C_{ds}$ $G_{ds}$ $A_{eo}$ $G_{eo}$ $A_{es}$ $G_{es}$ $G_{e}$ | 1902 | 1921 | 45.6 | 250 |
| 628548 | ${}^{m}C_{es}$ $G_{eo}$ $G_{eo}$ ${}^{m}C_{eo}$ $G_{eo}$ $G_{ds}$ ${}^{m}C_{ds}$ $G_{ds}$ $G_{ds}$ ${}^{m}C_{ds}$ ${}^{m}C_{ds}$ $A_{ds}$ $T_{ds}$ $T_{ds}$ $T_{ds}$ $T_{eo}$ ${}^{m}C_{eo}$ ${}^{m}C_{es}$ $G_{es}$ $G_{e}$ | 1934 | 1953 | 69.6 | 251 |
| 628552 | $T_{es}$ $G_{eo}$ $G_{eo}$ $A_{eo}$ $G_{eo}$ ${}^{m}C_{ds}$ $A_{ds}$ $G_{ds}$ $T_{ds}$ ${}^{m}C_{ds}$ $T_{ds}$ ${}^{m}C_{ds}$ $T_{ds}$ ${}^{m}C_{ds}$ ${}^{m}C_{ds}$ $T_{eo}$ ${}^{m}C_{eo}$ ${}^{m}C_{es}$ $T_{es}$ ${}^{m}C_{e}$ | 1989 | 2008 | 40.3 | 252 |
| 628740 | $T_{es}$ $T_{eo}$ ${}^{m}C_{eo}$ $A_{eo}$ $T_{eo}$ $G_{ds}$ $G_{ds}$ $A_{ds}$ $A_{ds}$ $T_{ds}$ $G_{ds}$ $G_{ds}$ $G_{ds}$ ${}^{m}C_{ds}$ $G_{ds}$ $A_{eo}$ $G_{eo}$ $A_{es}$ $A_{es}$ $G_{e}$ | 2547 | 2566 | 23.4 | 253 |
| 628744 | $A_{es}$ ${}^{m}C_{eo}$ $A_{eo}$ $G_{eo}$ $A_{eo}$ $G_{ds}$ $G_{ds}$ ${}^{m}C_{ds}$ $A_{ds}$ $G_{ds}$ $G_{ds}$ $G_{ds}$ ${}^{m}C_{ds}$ $A_{ds}$ $G_{ds}$ $G_{eo}$ ${}^{m}C_{eo}$ $A_{es}$ ${}^{m}C_{es}$ $G_{e}$ | 4561 | 4580 | 62.6 | 254 |
| 628748 | $A_{es}$ $A_{eo}$ $G_{eo}$ $A_{eo}$ $T_{eo}$ $T_{ds}$ ${}^{m}C_{ds}$ $A_{ds}$ $T_{ds}$ $G_{ds}$ ${}^{m}C_{ds}$ $T_{ds}$ $T_{ds}$ $G_{ds}$ $T_{ds}$ $T_{eo}$ $A_{eo}$ $G_{es}$ $A_{es}$ $A_{e}$ | 7090 | 7109 | 39.7 | 255 |
| 628556 | $T_{es}$ ${}^{m}C_{eo}$ $A_{eo}$ $A_{eo}$ $A_{eo}$ $G_{ds}$ ${}^{m}C_{ds}$ $A_{ds}$ $G_{ds}$ $G_{ds}$ $A_{ds}$ $A_{ds}$ ${}^{m}C_{ds}$ $T_{ds}$ $G_{ds}$ $G_{eo}$ $T_{eo}$ $G_{es}$ $A_{es}$ $G_{e}$ | 7316 | 7335 | 40.7 | 256 |
| 628560 | $G_{es}$ $G_{eo}$ $T_{eo}$ ${}^{m}C_{eo}$ $T_{eo}$ $A_{ds}$ ${}^{m}C_{ds}$ $A_{ds}$ $G_{ds}$ $A_{ds}$ $A_{ds}$ $G_{ds}$ ${}^{m}C_{ds}$ $A_{ds}$ $A_{ds}$ $G_{eo}$ $G_{eo}$ $T_{es}$ $G_{es}$ $T_{e}$ | 7359 | 7378 | 76.3 | 257 |
| 628564 | ${}^{m}C_{es}$ $A_{eo}$ $T_{eo}$ ${}^{m}C_{eo}$ $T_{eo}$ ${}^{m}C_{ds}$ $A_{ds}$ $G_{ds}$ ${}^{m}C_{ds}$ $T_{ds}$ $A_{ds}$ ${}^{m}C_{ds}$ $C_{ds}$ $A_{ds}$ $T_{ds}$ $G_{eo}$ $G_{eo}$ $A_{es}$ $A_{es}$ $T_{e}$ | 7391 | 7410 | 63.3 | 258 |
| 628752 | ${}^{m}C_{es}$ $A_{eo}$ ${}^{m}C_{eo}$ ${}^{m}C_{eo}$ $A_{eo}$ $T_{ds}$ ${}^{m}C_{ds}$ ${}^{m}C_{ds}$ $T_{ds}$ $G_{ds}$ $A_{ds}$ $G_{ds}$ $G_{ds}$ ${}^{m}C_{ds}$ ${}^{m}C_{ds}$ $A_{eo}$ $G_{eo}$ $G_{es}$ ${}^{m}C_{es}$ $A_{e}$ | 9908 | 9927 | 86.2 | 259 |
| 628756 | $T_{es}$ $A_{eo}$ $A_{eo}$ ${}^{m}C_{eo}$ $T_{eo}$ $T_{ds}$ $T_{ds}$ $T_{ds}$ $T_{ds}$ $T_{ds}$ ${}^{m}C_{ds}$ $T_{ds}$ $A_{ds}$ $T_{ds}$ $T_{ds}$ $A_{eo}$ $T_{eo}$ $T_{cs}$ $A_{es}$ $T_{e}$ | 12623 | 12642 | 14 8 | 260 |
| 628760 | $A_{es}$ ${}^{m}C_{eo}$ $A_{eo}$ $G_{eO}$ $T_{eo}$ ${}^{m}C_{ds}$ $A_{ds}$ ${}^{m}C_{ds}$ $A_{ds}$ $G_{ds}$ $A_{ds}$ $A_{ds}$ ${}^{m}C_{ds}$ $A_{ds}$ $A_{ds}$ ${}^{m}C_{eo}$ $A_{eo}$ $A_{es}$ $A_{es}$ $G_{e}$ | 14890 | 14909 | 80.6 | 261 |
| 628764 | $G_{es}$ $G_{eo}$ ${}^{m}C_{eo}$ ${}^{m}C_{eo}$ $T_{eo}$ $A_{ds}$ $A_{ds}$ $T_{ds}$ $T_{ds}$ $T_{ds}$ $T_{ds}$ $T_{ds}$ $T_{ds}$ $A_{ds}$ $T_{ds}$ ${}^{m}C_{eo}$ $T_{eo}$ $T_{es}$ $T_{es}$ $G_{e}$ | 17865 | 17884 | 80.6 | 262 |
| 628768 | $A_{es}$ ${}^{m}C_{eo}$ $A_{eo}$ $G_{eo}$ $G_{eo}$ $G_{ds}$ $T_{ds}$ $T_{ds}$ $G_{ds}$ $T_{ds}$ $A_{ds}$ $G_{ds}$ ${}^{m}C_{ds}$ ${}^{m}C_{ds}$ $A_{ds}$ $T_{eo}$ ${}^{m}C_{eo}$ $A_{es}$ $G_{es}$ $T_{e}$ | 20758 | 20777 | 91.0 | 263 |
| 628772 | $G_{es}$ $A_{eo}$ $T_{eo}$ ${}^{m}C_{eo}$ $A_{eo}$ ${}^{m}C_{ds}$ $T_{ds}$ $G_{ds}$ $G_{ds}$ $A_{ds}$ $A_{ds}$ ${}^{m}C_{ds}$ $A_{ds}$ ${}^{m}C_{ds}$ $A_{ds}$ $A_{eo}$ $T_{eo}$ $G_{es}$ $G_{es}$ ${}^{m}C_{e}$ | 22839 | 22858 | 91.6 | 264 |
| 628776 | $G_{es}$ $G_{eo}$ $A_{eo}$ $A_{eo}$ $G_{eo}$ $A_{ds}$ $G_{ds}$ $A_{ds}$ $A_{ds}$ $A_{ds}$ $A_{ds}$ $G_{ds}$ $A_{ds}$ $A_{ds}$ $G_{ds}$ $G_{eo}$ $G_{eo}$ ${}^{m}C_{es}$ $A_{es}$ ${}^{m}C_{e}$ | 25437 | 25456 | 43.3 | 265 |
| 628780 | ${}^{m}C_{es}$ $A_{eo}$ $T_{eo}$ $T_{e}$ $T_{eo}$ $A_{ds}$ $A_{ds}$ $T_{ds}$ $A_{ds}$ $A_{ds}$ $A_{ds}$ $T_{ds}$ $A_{ds}$ $A_{ds}$ $A_{ds}$ $T_{eo}$ ${}^{m}C_{eo}$ ${}^{m}C_{es}$ ${}^{m}C_{es}$ $T_{e}$ | 27672 | 27691 | 21.9 | 266 |
| 628784 | $T_{es}$ $T_{eo}$ $T_{eo}$ $A_{eo}$ ${}^{m}C_{eo}$ ${}^{m}C_{ds}$ $A_{ds}$ $G_{ds}$ $T_{ds}$ $G_{ds}$ ${}^{m}C_{ds}$ ${}^{m}C_{ds}$ $A_{ds}$ $T_{ds}$ $T_{ds}$ $T_{eo}$ $T_{eo}$ $T_{es}$ ${}^{m}C_{es}$ ${}^{m}C_{e}$ | 30227 | 30246 | 58.2 | 267 |
| 628788 | ${}^{m}C_{es}$ $A_{eo}$ $G_{eo}$ ${}^{m}C_{eo}$ $A_{eo}$ $A_{ds}$ $A_{ds}$ $T_{ds}$ $T_{ds}$ $T_{ds}$ ${}^{m}C_{ds}$ $T_{ds}$ $G_{ds}$ $T_{ds}$ $G_{ds}$ $G_{eo}$ $T_{eo}$ $T_{es}$ $T_{es}$ $T_{e}$ | 32258 | 32277 | 94.0 | 268 |
| 628792 | $G_{es}$ ${}^{m}C_{eo}$ $T_{eo}$ ${}^{m}C_{eo}$ $T_{eo}$ ${}^{m}C_{ds}$ $A_{ds}$ $G_{ds}$ $A_{ds}$ ${}^{m}C_{ds}$ ${}^{m}C_{ds}$ $A_{ds}$ $G_{ds}$ $A_{ds}$ ${}^{m}C_{ds}$ ${}^{m}C_{eo}$ $A_{eo}$ $G_{es}$ $A_{es}$ ${}^{m}C_{e}$ | 34773 | 34792 | 78.3 | 269 |
| 628796 | $A_{es}$ ${}^{m}C_{eo}$ $A_{eo}$ $G_{eo}$ ${}^{m}C_{eo}$ $T_{ds}$ $G_{ds}$ $A_{ds}$ $T_{ds}$ $G_{ds}$ $A_{ds}$ $G_{ds}$ $G_{ds}$ $A_{ds}$ $G_{ds}$ $G_{eo}$ $G_{eo}$ $T_{es}$ $G_{es}$ $G_{e}$ | 37542 | 37561 | 11.6 | 270 |
| 628800 | $T_{es}$ $A_{eo}$ ${}^{m}C_{eo}$ $A_{eo}$ ${}^{m}C_{eo}$ $A_{ds}$ $A_{ds}$ $A_{ds}$ $T_{ds}$ $A_{ds}$ ${}^{m}C_{ds}$ $T_{ds}$ $A_{ds}$ $A_{ds}$ $G_{ds}$ ${}^{m}C_{eo}$ ${}^{m}C_{eo}$ $A_{es}$ ${}^{m}C_{es}$ $A_{e}$ | 39572 | 39591 | 76.1 | 271 |
| 628804 | $A_{es}$ ${}^{m}C_{eo}$ $T_{eo}$ $G_{eo}$ ${}^{m}C_{eo}$ ${}^{m}C_{ds}$ $A_{ds}$ ${}^{m}C_{ds}$ ${}^{m}C_{ds}$ $A_{ds}$ ${}^{m}C_{ds}$ ${}^{m}C_{ds}$ $A_{ds}$ $T_{ds}$ $G_{ds}$ $A_{eo}$ ${}^{m}C_{eo}$ $T_{es}$ $A_{es}$ $A_{e}$ | 41573 | 41592 | 63.7 | 272 |
| 628808 | $G_{es}$ $T_{eo}$ $T_{eo}$ $A_{eo}$ $G_{eo}$ $A_{ds}$ $A_{ds}$ $G_{ds}$ $T_{ds}$ $T_{ds}$ $G_{ds}$ $A_{ds}$ $T_{ds}$ $T_{ds}$ $T_{ds}$ $T_{eo}$ $T_{eo}$ $T_{es}$ ${}^{m}C_{es}$ $T_{e}$ | 44142 | 44161 | 80.7 | 273 |

TABLE 4-continued

Inhibition or human MECP2 by antisense oligonucleotides in vitro

| Isis No. | Sequence (5' to 3') | Start site | Stop site | % Inhibi-tion | SEQ ID NO: |
|---|---|---|---|---|---|
| 628812 | $A_{es}\ T_{eo}\ A_{eo}\ {}^{m}C_{eo}\ T_{eo}\ {}^{m}C_{ds}\ A_{ds}\ {}^{m}C_{ds}\ A_{ds}\ T_{ds}\ G_{ds}\ G_{ds}\ T_{ds}\ G_{ds}\ G_{ds}\ A_{eo}\ G_{eo}\ A_{es}\ A_{es}\ A_{e}$ | 46268 | 46287 | 52.5 | 274 |
| 628816 | $G_{qs}\ A_{eo}\ G_{eo}\ A_{eo}\ A_{eo}\ G_{ds}\ A_{ds}\ A_{ds}\ T_{ds}\ G_{ds}\ G_{ds}\ A_{ds}\ A_{ds}\ G_{ds}\ G_{ds}\ G_{eo}\ A_{eo}\ G_{es}\ A_{es}\ A_{e}$ | 48363 | 48382 | 21.0 | 275 |
| 628820 | $T_{es}\ A_{eo}\ G_{eo}\ A_{eo}\ G_{eo}\ G_{ds}\ G_{ds}\ T_{ds}\ T_{ds}\ G_{ds}\ G_{ds}\ A_{ds}\ G_{ds}\ G_{ds}\ A_{ds}\ A_{eo}\ {}^{m}C_{eo}\ A_{es}\ G_{es}\ G_{e}$ | 50365 | 50384 | 25.7 | 276 |
| 628824 | ${}^{m}C_{es}\ T_{eo}\ T_{eo}\ A_{eo}\ G_{eo}\ A_{ds}\ A_{ds}\ {}^{m}C_{ds}\ A_{ds}\ A_{ds}\ A_{ds}\ G_{ds}\ A_{ds}\ G_{ds}\ A_{ds}\ A_{eo}\ G_{eo}\ A_{es}\ A_{es}\ T_{e}$ | 53052 | 53071 | -5.2 | 277 |
| 628828 | $G_{es}\ A_{eo}\ {}^{m}C_{eo}\ A_{eo}\ {}^{m}C_{eo}\ T_{ds}\ G_{ds}\ A_{ds}\ {}^{m}C_{ds}\ A_{ds}\ {}^{m}C_{ds}\ T_{ds}\ G_{ds}\ T_{ds}\ G_{ds}\ {}^{m}C_{eo}\ A_{eo}\ T_{es}\ G_{es}\ A_{e}$ | 55069 | 55088 | 67.5 | 278 |
| 628832 | $G_{es}\ G_{eo}\ A_{eo}\ G_{eo}\ T_{eo}\ T_{ds}\ A_{ds}\ {}^{m}C_{ds}\ {}^{m}C_{ds}\ A_{ds}\ T_{ds}\ A_{ds}\ T_{ds}\ G_{ds}\ A_{ds}\ {}^{m}C_{eo}\ {}^{m}C_{eo}\ T_{es}\ G_{es}\ G_{e}$ | 57122 | 57141 | 68.6 | 279 |
| 628836 | ${}^{m}C_{es}\ G_{eo}\ T_{eo}\ A_{eo}\ A_{eo}\ G_{ds}\ {}^{m}C_{ds}\ T_{ds}\ T_{ds}\ {}^{m}C_{ds}\ T_{ds}\ A_{ds}\ G_{ds}\ {}^{m}C_{ds}\ A_{ds}\ A_{eo}\ G_{eo}\ G_{es}\ A_{es}\ G_{e}$ | 59723 | 59742 | 70.0 | 280 |
| 628840 | $G_{es}\ G_{eo}\ T_{eo}\ A_{eo}\ A_{eo}\ A_{ds}\ A_{ds}\ A_{ds}\ T_{ds}\ G_{ds}\ A_{ds}\ T_{ds}\ A_{ds}\ A_{ds}\ A_{ds}\ A_{eo}\ A_{eo}\ A_{es}\ {}^{m}C_{es}\ G_{e}$ | 61802 | 61821 | -9.7 | 281 |
| 628844 | $A_{es}\ G_{eo}\ {}^{m}C_{eo}\ {}^{m}C_{eo}\ T_{eo}\ T_{ds}\ {}^{m}C_{ds}\ T_{ds}\ {}^{m}C_{ds}\ {}^{m}C_{ds}\ T_{ds}\ G_{ds}\ {}^{m}C_{ds}\ {}^{m}C_{ds}\ T_{ds}\ {}^{m}C_{eo}\ A_{eo}\ G_{es}\ {}^{m}C_{es}\ T_{e}$ | 63907 | 63926 | 82.8 | 282 |
| 628848 | $A_{es}\ G_{eo}\ A_{eo}\ A_{eo}\ G_{eo}\ {}^{m}C_{ds}\ A_{ds}\ G_{ds}\ {}^{m}C_{ds}\ A_{ds}\ G_{ds}\ {}^{m}C_{ds}\ {}^{m}C_{ds}\ A_{ds}\ {}^{m}C_{ds}\ {}^{m}C_{eo}\ T_{eo}\ G_{es}\ {}^{m}C_{es}\ G_{e}$ | 65932 | 65951 | 14.3 | 283 |
| 628568 | $T_{es}\ G_{eo}\ G_{eo}\ T_{eo}\ {}^{m}C_{eo}\ T_{ds}\ T_{ds}\ {}^{m}C_{ds}\ T_{ds}\ G_{ds}\ A_{ds}\ {}^{m}C_{ds}\ T_{ds}\ T_{ds}\ T_{ds}\ T_{eo}\ {}^{m}C_{eo}\ T_{es}\ T_{es}\ {}^{m}C_{e}$ | 67056 | 67075 | 56.8 | 284 |
| 628572 | ${}^{m}C_{es}\ A_{eo}\ {}^{m}C_{eo}\ {}^{m}C_{eo}\ T_{eo}\ T_{ds}\ T_{ds}\ T_{ds}\ T_{ds}\ A_{ds}\ A_{ds}\ A_{ds}\ {}^{m}C_{ds}\ T_{ds}\ T_{ds}\ G_{eo}\ A_{eo}\ G_{es}\ G_{es}\ G_{e}$ | 67102 | 67121 | 74.9 | 285 |
| 628576 | $T_{eo}\ T_{eo}\ T_{eo}\ {}^{m}C_{eo}\ T_{eo}\ {}^{m}C_{ds}\ T_{ds}\ T_{ds}\ {}^{m}C_{ds}\ T_{ds}\ T_{ds}\ T_{ds}\ {}^{m}C_{ds}\ T_{ds}\ T_{ds}\ A_{eo}\ T_{eo}\ {}^{m}C_{es}\ T_{es}\ T_{e}$ | 67126 | 67145 | 47.3 | 286 |
| 628580 | $T_{es}\ {}^{m}C_{eo}\ A_{eo}\ T_{eo}\ G_{eo}\ {}^{m}C_{ds}\ T_{ds}\ T_{ds}\ G_{ds}\ {}^{m}C_{ds}\ {}^{m}C_{ds}\ {}^{m}C_{ds}\ T_{ds}\ {}^{m}C_{ds}\ T_{ds}\ T_{eo}\ T_{eo}\ {}^{m}C_{es}\ T_{es}\ {}^{m}C_{e}$ | 67140 | 67159 | 57.4 | 287 |
| 628584 | $T_{es}\ G_{eo}\ A_{eo}\ T_{eo}\ G_{eo}\ G_{ds}\ {}^{m}C_{ds}\ T_{ds}\ G_{ds}\ {}^{m}C_{ds}\ A_{ds}\ {}^{m}C_{ds}\ G_{ds}\ G_{ds}\ G_{ds}\ {}^{m}C_{eo}\ T_{eo}\ {}^{m}C_{es}\ A_{es}\ T_{e}$ | 67156 | 67175 | 58.1 | 288 |
| 628588 | ${}^{m}C_{es}\ A_{eo}\ G_{eo}\ {}^{m}C_{eo}\ A_{eo}\ G_{ds}\ A_{ds}\ G_{ds}\ T_{ds}\ G_{ds}\ G_{ds}\ T_{ds}\ G_{ds}\ G_{ds}\ G_{ds}\ {}^{m}C_{eo}\ T_{eo}\ G_{es}\ A_{es}\ T_{e}$ | 67172 | 67191 | 10.9 | 289 |
| 628592 | $T_{es}\ G_{eo}\ A_{eo}\ T_{eo}\ G_{eo}\ T_{ds}\ {}^{m}C_{ds}\ T_{ds}\ {}^{m}C_{ds}\ T_{ds}\ G_{ds}\ {}^{m}C_{ds}\ T_{ds}\ T_{ds}\ T_{ds}\ G_{eo}\ {}^{m}C_{eo}\ {}^{m}C_{es}\ T_{es}\ G_{e}$ | 67204 | 67223 | 37.9 | 290 |
| 628596 | ${}^{m}C_{es}\ A_{eo}\ G_{eo}\ A_{eo}\ A_{eo}\ G_{ds}\ {}^{m}C_{ds}\ T_{ds}\ T_{ds}\ {}^{m}C_{ds}\ {}^{m}C_{ds}\ G_{ds}\ G_{ds}\ {}^{m}C_{ds}\ A_{ds}\ {}^{m}C_{eo}\ A_{eo}\ G_{es}\ {}^{m}C_{es}\ {}^{m}C_{e}$ | 67244 | 67263 | 16.0 | 291 |
| 628600 | $G_{es}\ G_{eo}\ G_{eo}\ T_{eo}\ {}^{m}C_{eo}\ {}^{m}C_{ds}\ {}^{m}C_{ds}\ {}^{m}C_{ds}\ G_{ds}\ G_{ds}\ T_{ds}\ {}^{m}C_{ds}\ A_{ds}\ {}^{m}C_{ds}\ G_{ds}\ G_{eo}\ A_{eo}\ T_{es}\ G_{es}\ A_{e}$ | 67288 | 67307 | 50.5 | 292 |
| 628604 | $G_{es}\ {}^{m}C_{eo}\ T_{eo}\ T_{eo}\ A_{eo}\ A_{ds}\ G_{ds}\ {}^{m}C_{ds}\ T_{ds}\ T_{ds}\ {}^{m}C_{ds}\ {}^{m}C_{ds}\ G_{ds}\ T_{ds}\ G_{ds}\ T_{eo}\ {}^{m}C_{eo}\ {}^{m}C_{es}\ A_{es}\ G_{e}$ | 67337 | 67356 | 59.6 | 293 |
| 628608 | $A_{es}\ T_{eo}\ A_{eo}\ T_{eo}\ {}^{m}C_{eo}\ T_{ds}\ T_{ds}\ {}^{m}C_{ds}\ {}^{m}C_{ds}\ A_{ds}\ G_{ds}\ {}^{m}C_{ds}\ A_{ds}\ G_{ds}\ A_{ds}\ G_{eo}\ {}^{m}C_{eo}\ G_{es}\ G_{es}\ {}^{m}C_{e}$ | 67369 | 67388 | 19.9 | 294 |
| 628852 | $A_{es}\ G_{eo}\ {}^{m}C_{eo}\ A_{eo}\ A_{eo}\ {}^{m}C_{ds}\ {}^{m}C_{ds}\ A_{ds}\ A_{ds}\ A_{ds}\ G_{ds}\ A_{ds}\ G_{ds}\ T_{ds}\ {}^{m}C_{ds}\ A_{eo}\ G_{eo}\ G_{es}\ {}^{m}C_{es}\ {}^{m}C_{e}$ | 67934 | 67953 | 76.1 | 295 |
| 628612 | $A_{es}\ {}^{m}C_{eo}\ T_{eo}\ T_{eo}\ T_{eo}\ A_{ds}\ G_{ds}\ A_{ds}\ G_{ds}\ {}^{m}C_{ds}\ G_{ds}\ A_{ds}\ A_{ds}\ A_{ds}\ G_{ds}\ G_{eo}\ {}^{m}C_{eo}\ T_{es}\ T_{es}\ T_{e}$ | 68172 | 68191 | 36.2 | 296 |
| 628616 | $T_{es}\ T_{eo}\ T_{eo}\ T_{eo}\ {}^{m}C_{eo}\ G_{ds}\ A_{ds}\ A_{ds}\ G_{ds}\ T_{ds}\ A_{ds}\ {}^{m}C_{ds}\ G_{ds}\ {}^{m}C_{ds}\ A_{ds}\ A_{eo}\ T_{eo}\ {}^{m}C_{es}\ A_{es}\ A_{e}$ | 68196 | 68215 | 41.9 | 297 |

TABLE 4-continued

Inhibition or human MECP2 by antisense oligonucleotides in vitro

| Isis No. | Sequence (5' to 3') | Start site | Stop site | % Inhibi-tion | SEQ ID NO: |
|---|---|---|---|---|---|
| 628620 | $^{m}C_{es}\ ^{m}C_{eo}\ A_{eo}\ G_{eo}\ G_{eo}\ G_{ds}\ A_{ds}\ T_{ds}\ G_{ds}\ T_{ds}\ G_{ds}\ T_{ds}\ ^{m}C_{ds}\ G_{ds}\ ^{m}C_{ds}\ ^{m}C_{eo}\ T_{eo}\ A_{es}\ ^{m}C_{es}\ ^{m}C_{e}$ | 68216 | 68235 | 62.3 | 298 |
| 628624 | $^{m}C_{es}\ ^{m}C_{eo}\ A_{eo}\ G_{eo}\ T_{eo}\ T_{ds}\ A_{ds}\ ^{m}C_{ds}\ ^{m}C_{ds}\ G_{ds}\ T_{ds}\ G_{ds}\ A_{ds}\ A_{ds}\ G_{ds}\ T_{eo}\ ^{m}C_{eo}\ A_{es}\ A_{es}\ A_{e}$ | 68247 | 68266 | 40.4 | 299 |
| 628628 | $T_{es}\ G_{eo}\ G_{eo}\ G_{eo}\ ^{m}C_{eo}\ T_{ds}\ T_{ds}\ ^{m}C_{ds}\ T_{ds}\ T_{ds}\ A_{ds}\ G_{ds}\ G_{ds}\ T_{ds}\ G_{ds}\ G_{eo}\ T_{eo}\ T_{es}\ T_{es}\ ^{m}C_{e}$ | 68294 | 68313 | 53.5 | 300 |
| 628632 | $G_{es}\ T_{eo}\ G_{eo}\ G_{eo}\ T_{eo}\ G_{ds}\ ^{m}C_{ds}\ ^{m}C_{ds}\ G_{ds}\ ^{m}C_{ds}\ T_{ds}\ ^{m}C_{ds}\ ^{m}C_{ds}\ ^{m}C_{ds}\ T_{ds}\ T_{eo}\ T_{eo}\ G_{es}\ G_{es}\ G_{e}$ | 68355 | 68374 | 65.8 | 301 |
| 628636 | $T_{es}\ ^{m}C_{eo}\ T_{eo}\ ^{m}C_{eo}\ ^{m}C_{eo}\ A_{ds}\ G_{ds}\ G_{ds}\ A_{ds}\ ^{m}C_{ds}\ ^{m}C_{ds}\ ^{m}C_{ds}\ T_{ds}\ T_{ds}\ T_{ds}\ T_{eo}\ ^{m}C_{eo}\ A_{es}\ ^{m}C_{es}\ ^{m}C_{e}$ | 68408 | 68427 | 38.7 | 302 |
| 628640 | $G_{es}\ A_{eo}\ ^{m}C_{eo}\ A_{eo}\ A_{eo}\ G_{ds}\ G_{ds}\ A_{ds}\ G_{ds}\ ^{m}C_{ds}\ T_{ds}\ T_{ds}\ ^{m}C_{ds}\ ^{m}C_{ds}\ ^{m}C_{ds}\ A_{eo}\ G_{eo}\ G_{es}\ A_{es}\ ^{m}C_{e}$ | 68431 | 68450 | 57.4 | 303 |
| 628644 | $^{m}C_{es}\ ^{m}C_{eo}\ ^{m}C_{eo}\ T_{eo}\ G_{eo}\ G_{ds}\ ^{m}C_{ds}\ G_{ds}\ A_{ds}\ A_{ds}\ G_{ds}\ T_{ds}\ T_{ds}\ T_{ds}\ G_{ds}\ A_{eo}\ A_{eo}\ A_{es}\ A_{es}\ G_{e}$ | 68458 | 68477 | 37.8 | 304 |
| 628648 | $^{m}C_{es}\ ^{m}C_{eo}\ ^{m}C_{eo}\ ^{m}C_{eo}\ T_{eo}\ ^{m}C_{ds}\ A_{ds}\ G_{ds}\ ^{m}C_{ds}\ ^{m}C_{ds}\ T_{ds}\ T_{ds}\ G_{ds}\ ^{m}C_{ds}\ ^{m}C_{ds}\ ^{m}C_{eo}\ ^{m}C_{eo}\ ^{m}C_{es}\ T_{es}\ G_{e}$ | 68473 | 68492 | 25.0 | 305 |
| 628652 | $T_{es}\ G_{eo}\ G_{eo}\ G_{eo}\ T_{eo}\ G_{ds}\ G_{ds}\ A_{ds}\ T_{ds}\ G_{ds}\ T_{ds}\ G_{ds}\ G_{ds}\ T_{ds}\ G_{ds}\ G_{eo}\ ^{m}C_{eo}\ ^{m}C_{es}\ ^{m}C_{es}\ ^{m}C_{e}$ | 68496 | 68515 | 13.6 | 306 |
| 628656 | $^{m}C_{es}\ G_{eo}\ G_{eo}\ ^{m}C_{eo}\ ^{m}C_{eo}\ T_{ds}\ ^{m}C_{ds}\ A_{ds}\ G_{ds}\ ^{m}C_{ds}\ T_{ds}\ T_{ds}\ T_{ds}\ T_{ds}\ ^{m}C_{ds}\ G_{eo}\ ^{m}C_{eo}\ T_{es}\ T_{es}\ ^{m}C_{e}$ | 68543 | 68562 | 59.4 | 307 |
| 628660 | $T_{es}\ ^{m}C_{eo}\ G_{eo}\ G_{eo}\ ^{m}C_{eo}\ ^{m}C_{ds}\ ^{m}C_{ds}\ ^{m}C_{ds}\ G_{ds}\ T_{ds}\ T_{ds}\ T_{ds}\ ^{m}C_{ds}\ T_{ds}\ T_{ds}\ G_{eo}\ G_{eo}\ G_{es}\ A_{es}\ A_{e}$ | 68575 | 68594 | 33.8 | 308 |
| 628664 | $G_{es}\ ^{m}C_{eo}\ G_{eo}\ G_{eo}\ ^{m}C_{eo}\ A_{ds}\ G_{ds}\ ^{m}C_{ds}\ G_{ds}\ G_{ds}\ ^{m}C_{ds}\ T_{ds}\ G_{ds}\ ^{m}C_{ds}\ ^{m}C_{ds}\ A_{eo}\ ^{m}C_{eo}\ ^{m}C_{es}\ A_{es}\ ^{m}C_{e}$ | 68607 | 68626 | 31.0 | 309 |
| *628668 | $A_{es}\ A_{eo}\ G_{eo}\ A_{eo}\ ^{m}C_{eo}\ T_{ds}\ ^{m}C_{ds}\ ^{m}C_{ds}\ T_{ds}\ T_{ds}\ ^{m}C_{ds}\ A_{ds}\ ^{m}C_{ds}\ G_{ds}\ G_{ds}\ ^{m}C_{eo}\ T_{eo}\ T_{es}\ T_{es}\ ^{m}C_{e}$ | 68639 | 68658 | 69.2 | 310 |
| *628672 | $G_{es}\ G_{eo}\ T_{eo}\ ^{m}C_{eo}\ T_{eo}\ ^{m}C_{ds}\ ^{m}C_{ds}\ T_{ds}\ G_{ds}\ ^{m}C_{ds}\ A_{ds}\ ^{m}C_{ds}\ A_{ds}\ G_{ds}\ A_{ds}\ T_{eo}\ ^{m}C_{eo}\ G_{es}\ G_{es}\ A_{e}$ | 68662 | 68681 | 95.2 | 311 |
| *628676 | $G_{es}\ ^{m}C_{eo}\ T_{eo}\ G_{eo}\ A_{eo}\ ^{m}C_{ds}\ ^{m}C_{ds}\ G_{ds}\ T_{ds}\ ^{m}C_{ds}\ T_{ds}\ ^{m}C_{ds}\ ^{m}C_{ds}\ ^{m}C_{ds}\ G_{ds}\ G_{eo}\ G_{eo}\ T_{es}\ ^{m}C_{es}\ T_{e}$ | 68704 | 68723 | 40.4 | 312 |
| 628680 | $^{m}C_{es}\ G_{eo}\ A_{eo}\ G_{eo}\ G_{eo}\ G_{ds}\ T_{ds}\ G_{ds}\ G_{ds}\ A_{ds}\ ^{m}C_{ds}\ A_{ds}\ ^{m}C_{ds}\ ^{m}C_{ds}\ A_{ds}\ G_{eo}\ ^{m}C_{eo}\ A_{es}\ G_{es}\ G_{e}$ | 68750 | 68769 | 37.2 | 313 |
| 628684 | $A_{es}\ ^{m}C_{eo}\ A_{eo}\ G_{eo}\ G_{eo}\ T_{ds}\ ^{m}C_{ds}\ T_{ds}\ T_{ds}\ ^{m}C_{ds}\ A_{ds}\ G_{ds}\ T_{ds}\ ^{m}C_{ds}\ ^{m}C_{ds}\ T_{eo}\ T_{eo}\ T_{es}\ ^{m}C_{es}\ ^{m}C_{e}$ | 68782 | 68801 | 63.5 | 314 |
| 628688 | $^{m}C_{es}\ T_{eo}\ G_{eo}\ ^{m}C_{eo}\ T_{eo}\ ^{m}C_{ds}\ T_{ds}\ ^{m}C_{ds}\ ^{m}C_{ds}\ T_{ds}\ T_{ds}\ G_{ds}\ ^{m}C_{ds}\ T_{ds}\ T_{ds}\ T_{eo}\ T_{eo}\ ^{m}C_{es}\ ^{m}C_{es}\ G_{e}$ | 68814 | 68833 | 84.1 | 315 |
| 628692 | $^{m}C_{es}\ T_{eo}\ G_{eo}\ A_{eo}\ G_{eo}\ T_{ds}\ G_{ds}\ G_{ds}\ T_{ds}\ G_{ds}\ G_{ds}\ T_{ds}\ G_{ds}\ A_{ds}\ T_{ds}\ G_{eo}\ G_{eo}\ T_{es}\ G_{es}\ G_{e}$ | 68885 | 68904 | 11.9 | 316 |
| 628696 | $^{m}C_{es}\ T_{eo}\ T_{eo}\ ^{m}C_{eo}\ T_{eo}\ ^{m}C_{ds}\ ^{m}C_{ds}\ T_{ds}\ ^{m}C_{ds}\ T_{ds}\ T_{ds}\ T_{ds}\ G_{ds}\ ^{m}C_{ds}\ A_{ds}\ G_{eo}\ A_{eo}\ ^{m}C_{es}\ G_{es}\ ^{m}C_{e}$ | 69016 | 69035 | 70.9 | 317 |
| 628700 | $^{m}C_{es}\ ^{m}C_{eo}\ G_{eo}\ T_{eo}\ ^{m}C_{eo}\ G_{ds}\ ^{m}C_{ds}\ T_{ds}\ ^{m}C_{ds}\ T_{ds}\ ^{m}C_{ds}\ ^{m}C_{ds}\ A_{ds}\ G_{ds}\ T_{ds}\ G_{eo}\ A_{eo}\ G_{es}\ ^{m}C_{es}\ ^{m}C_{e}$ | 69048 | 69067 | 71.6 | 318 |
| 628704 | $G_{es}\ G_{eo}\ ^{m}C_{eo}\ A_{eo}\ A_{eo}\ ^{m}C_{ds}\ ^{m}C_{ds}\ G_{ds}\ ^{m}C_{ds}\ G_{ds}\ G_{ds}\ G_{ds}\ ^{m}C_{ds}\ T_{ds}\ G_{ds}\ A_{eo}\ G_{eo}\ T_{es}\ ^{m}C_{es}\ T_{e}$ | 69088 | 69107 | 72.3 | 319 |
| 628708 | $^{m}C_{es}\ ^{m}C_{eo}\ G_{eo}\ T_{eo}\ G_{eo}\ G_{ds}\ ^{m}C_{ds}\ G_{ds}\ G_{ds}\ ^{m}C_{ds}\ G_{ds}\ G_{ds}\ T_{ds}\ G_{ds}\ G_{ds}\ ^{m}C_{eo}\ A_{eo}\ A_{es}\ ^{m}C_{es}\ ^{m}C_{e}$ | 69101 | 69120 | 32.3 | 320 |
| 628712 | $T_{es}\ A_{eo}\ ^{m}C_{eo}\ T_{eo}\ T_{eo}\ T_{ds}\ T_{ds}\ ^{m}C_{ds}\ T_{ds}\ G_{ds}\ ^{m}C_{ds}\ G_{ds}\ G_{ds}\ ^{m}C_{ds}\ ^{m}C_{ds}\ G_{eo}\ T_{eo}\ G_{es}\ G_{es}\ ^{m}C_{e}$ | 69114 | 69133 | 55.9 | 321 |

TABLE 4-continued

| Inhibition or human MECP2 by antisense oligonucleotides in vitro | | | | | |
|---|---|---|---|---|---|
| Isis No. | Sequence (5' to 3') | Start site | Stop site | % Inhibi-tion | SEQ ID NO: |
| 628716 | $T_{es}\ {}^{m}C_{eo}\ T_{eo}\ T_{eo}\ T_{eo}\ G_{ds}\ {}^{m}C_{ds}\ G_{ds}\ {}^{m}C_{ds}\ T_{ds}\ {}^{m}C_{ds}\ T_{ds}\ {}^{m}C_{ds}\ {}^{m}C_{ds}\ {}^{m}C_{ds}\ T_{eo}\ {}^{m}C_{eo}\ {}^{m}C_{es}\ {}^{m}C_{es}\ {}^{m}C_{e}$ | 69144 | 69163 | 52.4 | 322 |
| 628720 | $T_{es}\ G_{eo}\ T_{eo}\ T_{eo}\ T_{eo}\ G_{ds}\ G_{ds}\ {}^{m}C_{ds}\ {}^{m}C_{ds}\ T_{ds}\ T_{ds}\ G_{ds}\ G_{ds}\ {}^{m}C_{ds}\ A_{ds}\ T_{eo}\ G_{eo}\ G_{es}\ A_{es}\ G_{e}$ | 69176 | 69195 | 55.1 | 323 |
| 628724 | $A_{es}\ A_{eo}\ {}^{m}C_{eo}\ T_{eo}\ {}^{m}C_{eo}\ T_{ds}\ {}^{m}C_{ds}\ T_{ds}\ {}^{m}C_{ds}\ G_{ds}\ G_{ds}\ T_{ds}\ {}^{m}C_{ds}\ A_{ds}\ {}^{m}C_{ds}\ G_{eo}\ G_{eo}\ G_{es}\ {}^{m}C_{es}\ G_{e}$ | 69220 | 69239 | 82.2 | 324 |
| 628728 | $T_{es}\ G_{eo}\ {}^{m}C_{eo}\ T_{eo}\ T_{eo}\ T_{ds}\ G_{ds}\ {}^{m}C_{ds}\ A_{ds}\ A_{ds}\ T_{ds}\ {}^{m}C_{ds}\ {}^{m}C_{ds}\ G_{ds}\ {}^{m}C_{ds}\ T_{eo}\ {}^{m}C_{eo}\ {}^{m}C_{es}\ G_{es}\ T_{e}$ | 69252 | 69271 | 77.9 | 325 |
| 628732 | $A_{es}\ G_{eo}\ A_{eo}\ G_{eo}\ A_{eo}\ {}^{m}C_{ds}\ A_{ds}\ A_{ds}\ {}^{m}C_{ds}\ A_{ds}\ G_{ds}\ {}^{m}C_{ds}\ T_{ds}\ G_{ds}\ {}^{m}C_{ds}\ {}^{m}C_{eo}\ T_{eo}\ T_{es}\ T_{es}\ A_{e}$ | 69284 | 69303 | 57.7 | 326 |
| 628736 | $G_{es}\ A_{eo}\ A_{eo}\ G_{eo}\ {}^{m}C_{eo}\ T_{ds}\ T_{ds}\ T_{ds}\ G_{ds}\ T_{ds}\ {}^{m}C_{ds}\ A_{ds}\ G_{ds}\ A_{ds}\ G_{ds}\ {}^{m}C_{eo}\ {}^{m}C_{eo}\ {}^{m}C_{es}\ T_{es}\ A_{e}$ | 69316 | 69335 | 90.1 | 327 |

Superscript "m" indicates 5-methylcytosine. Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

Example 2: Dose Response of Antisense Oligonucleotides Targeting MECP2 In Vitro MECP2 targeting antisense oligonucleotides selected from Tables 1-4 were tested for dose response analysis in HepG2 cells. Isis Number 141923 does not target MECP2 and was used as a negative control. Cells were electroporated with 0, 0.111, 0.333, 1.00, 3.00, or 9.00 μM antisense oligonucleotide, and MECP2 mRNA was analyzed as described in Example 1. Results are presented in Tables 5 and 6 below. Isis Numbers 141923 and 628749 were included in both data sets as references for comparison. The results show that the antisense oligonucleotides targeting MECP2 inhibited MECP2 mRNA expression in a dose dependent manner.

TABLE 5

| Dose repsonse in vitro | | | | | | |
|---|---|---|---|---|---|---|
| | % Inhibition | | | | | |
| Isis No. | 0.111 μM | 0.333 μM | 1.00 μM | 3.00 μM | 9.00 μM | SEQ ID NO: |
| 141923 | 101.7 | 124.0 | 97.3 | 105.3 | 70.6 | 328 |
| 628688 | 89.1 | 73.1 | 47.8 | 24.3 | 17.0 | 315 |
| 628724 | 83.6 | 76.8 | 41.2 | 17.4 | 14.1 | 324 |
| 628736 | 84.6 | 68.9 | 36.3 | 21.4 | 9.1 | 327 |
| 628749 | 63.8 | 36.4 | 19.3 | 7.7 | 3.7 | 103 |
| 628751 | 102.3 | 77.4 | 39.2 | 19.5 | 8.3 | 25 |
| 628752 | 76.0 | 77.0 | 47.4 | 28.0 | 18.4 | 259 |
| 628763 | 63.5 | 37.1 | 11.5 | 8.1 | 6.7 | 28 |
| 628767 | 82.2 | 56.7 | 33.0 | 16.0 | 12.0 | 29 |
| 628768 | 98.4 | 68.4 | 43.7 | 21.7 | 11.0 | 263 |
| 628772 | 84.3 | 60.6 | 34.4 | 13.7 | 5.4 | 264 |
| 628775 | 84.3 | 62.4 | 37.0 | 15.9 | 6.3 | 31 |
| 628787 | 81.8 | 60.5 | 38.6 | 26.6 | 10.0 | 34 |
| 628788 | 79.8 | 65.1 | 35.9 | 10.5 | 4.9 | 268 |
| 628811 | 69.1 | 46.8 | 20.6 | 22.1 | 4.2 | 40 |
| 628844 | 82.6 | 76.4 | 49.6 | 38.1 | 16.2 | 282 |

TABLE 6

| Dose repsonse in vitro | | | | | | |
|---|---|---|---|---|---|---|
| | % Inhibition | | | | | |
| Isis No. | 0.111 μM | 0.333 μM | 1.00 μM | 3.00 μM | 9.00 μM | SEQ ID NO: |
| 141923 | 116.6 | 123.1 | 120.7 | 119.6 | 119.0 | 328 |
| 628558 | 94.5 | 65.4 | 49.2 | 19.9 | 9.2 | 178 |
| 628614 | 85.8 | 84.4 | 60.5 | 28.9 | 15.3 | 218 |
| 628637 | 93.1 | 80.1 | 63.4 | 25.3 | 8.3 | 146 |
| 628641 | 100.4 | 81.8 | 55.3 | 24.3 | 11.2 | 147 |
| 628690 | 101.7 | 77.9 | 51.5 | 28.0 | 16.4 | 237 |
| 628694 | 101.6 | 86.5 | 50.6 | 25.1 | 13.9 | 238 |
| 628742 | 103.3 | 73.6 | 48.8 | 20.1 | 14.7 | 175 |
| 628749 | 78.3 | 45.6 | 15.8 | 9.1 | 9.9 | 103 |
| 628757 | 88.6 | 70.5 | 39.0 | 21.7 | 13.5 | 105 |
| 628762 | 67.5 | 47.3 | 22.8 | 8.1 | 18.2 | 184 |
| 628766 | 119.8 | 77.5 | 65.6 | 31.5 | 18.0 | 185 |
| 628785 | 72.5 | 45.8 | 25.8 | 15.1 | 18.9 | 112 |
| 628786 | 85.6 | 55.5 | 36.0 | 17.3 | 10.6 | 190 |
| 628822 | 88.4 | 84.3 | 45.8 | 36.6 | 11.5 | 199 |
| 628833 | 90.6 | 70.1 | 55.2 | 32.1 | 10.8 | 124 |

Example 3: Effect of Antisense Oligonucleotides Targeting MECP2 In Vivo

Antisense oligonucleotides (ASOs) that target human Methyl CpG Binding Protein 2 (MECP2), the complement of GENBANK accession number NT_167198.1 truncated from 4203000 to 4283000, SEQ ID NO: 2, were synthesized using standard solid phase oligonucleotide synthetic methods. They are chimeric oligonucleotides ("gapmers"), composed of a central "gap" region consisting of 2'-deoxynucleotides, which is flanked on both sides (5' and 3') by "wings" that are composed of modified nucleotides. The internucleoside (backbone) linkages are phosphorothioate or phosphodiester throughout the oligonucleotides. The sequences and structures of the antisense oligonucleotides and their start and stop sites along SEQ ID NO: 2 are shown in the table below.

TABLE 7

Antisense oligonucleotides targeted to human MECP2

| Isis No. | Sequence (5' to 3') | Start site | Stop site | SEQ ID NO. |
|---|---|---|---|---|
| 628724 | $A_{es}$ $A_{eo}$ $^{m}C_{eo}$ $T_{eo}$ $^{m}C_{eo}$ $T_{ds}$ $^{m}C_{ds}$ $T_{ds}$ $^{m}C_{ds}$ $G_{ds}$ $G_{ds}$ $T_{ds}$ $^{m}C_{ds}$ $A_{ds}$ $^{m}C_{ds}$ $G_{eo}$ $G_{eo}$ $G_{es}$ $^{m}C_{es}$ $G_{e}$ | 69220 | 69239 | 324 |
| 628749 | $^{m}C_{es}$ $A_{eo}$ $^{m}C_{eo}$ $A_{eo}$ $^{m}C_{eo}$ $T_{ds}$ $G_{ds}$ $A_{ds}$ $^{m}C_{ds}$ $^{m}C_{ds}$ $T_{ds}$ $T_{ds}$ $T_{ds}$ $^{m}C_{ds}$ $A_{ds}$ $G_{eo}$ $G_{eo}$ $G_{es}$ $^{m}C_{es}$ $T_{e}$ | 7615 | 7634 | 103 |
| 628772 | $G_{es}$ $A_{eo}$ $T_{eo}$ $^{m}C_{eo}$ $A_{eo}$ $^{m}C_{ds}$ $T_{ds}$ $G_{ds}$ $G_{ds}$ $A_{ds}$ $A_{ds}$ $^{m}C_{ds}$ $A_{ds}$ $^{m}C_{ds}$ $A_{ds}$ $A_{eo}$ $T_{eo}$ $G_{es}$ $G_{es}$ $T_{e}$ | 22839 | 22858 | 264 |
| 628775 | $^{m}C_{es}$ $G_{eo}$ $T_{eo}$ $G_{eo}$ $^{m}C_{eo}$ $^{m}C_{ds}$ $A_{ds}$ $T_{ds}$ $G_{ds}$ $G_{ds}$ $A_{ds}$ $A_{ds}$ $G_{ds}$ $T_{ds}$ $^{m}C_{ds}$ $^{m}C_{eo}$ $T_{eo}$ $T_{es}$ $^{m}C_{es}$ $^{m}C_{eo}$ | 24936 | 24955 | 31 |
| 628785 | $G_{es}$ $G_{eo}$ $T_{eo}$ $T_{eo}$ $T_{eo}$ $T_{ds}$ $T_{ds}$ $^{m}C_{ds}$ $T_{ds}$ $^{m}C_{ds}$ $^{m}C_{ds}$ $T_{ds}$ $T_{ds}$ $T_{ds}$ $A_{ds}$ $T_{eo}$ $T_{eo}$ $A_{es}$ $T_{es}$ $^{m}C_{eo}$ | 30744 | 30763 | 112 |

Superscript "m" indicates 5-methylcytosine. Subscripts: "o" indicates a phosphodiester internucleoside linkage, "s" indicates a phosphorothioate internucleoside linkage, "e" indicates a 2'-methoxyethyl modified nucleoside, and "d" indicates a 2'-deoxynucleoside.

The antisense oligonucleotides were analyzed for their effects on MECP2 mRNA and protein levels in transgenic MECP2 duplication mice that overexpress wild type human MECP2 (F1 hybrid MECP2-TG1 mice (FVB/N×129)(Samaco et al., *Nat Genet,* 2012). At 8 weeks of age, FVB/N×129 mice display hypoactivity in the open field test, increased anxiety in the open field and elevated plus maze tests, abnormal social behavior in the 3-chamber test, and increased motor coordination in the rotarod test. Seven week old MECP2-TG mice were given stereotactic intracerebral injection of 500 µg of an antisense oligonucleotide listed in Table 7 or saline into the right ventricle of the brain. Wild type mice were given stereotactic intracerebral injection of saline into the right ventricle of the brain as a control. Each group consisted of two or three mice. Two weeks following the injection, the mice were sacrificed, and cortical brain samples were collected for analysis of MECP2 mRNA and protein levels. MECP2 and GAPDH protein levels were analyzed by western blot performed on the cortical sample lysates. Rabbit antiserum raised against the N-terminus of MECP2 and mouse anti-GAPDH 6C5 (Advanced Immunochemicals, Long Beach, CA) were used as the primary antibodies. Western blot images were quanitifed using Image J software, and the MECP2 protein levels normalized to GAPDH levels are shown in Table 8 below.

Total MECP2 mRNA, human MECP2 mRNA (both the e1 and e2 isoforms), and mouse MECP2 mRNA (both the e1 and e2 isoforms) were separeately analyzed by RT-qPCR. The primers common to human and mouse used for total MECP2 mRNA were: 5'-TATTTGATCAATCCCCAGGG-3', SEQ ID NO: 3, and 5'-CTCCCTCTCCCAGTTACCGT-3', SEQ ID NO: 4. The human specific primers used for MECP2-e1 were 5'-AGGAGAGACTGGAAGAAAAGTC-3', SEQ ID NO: 5, and 5'-CTTGAGGGGTTTGTCCTTGA-3', SEQ ID NO: 6. The human specific primers used for MECP2-e2 were 5'-CTCACCAGTTCCTGCTTTGATGT-3', SEQ ID NO: 7, and 5'-CTTGAGGGGTTTGTCCTTGA-3', SEQ ID NO: 6. The mouse specific primers used for MECP2-e1 were 5'-AGGAGAGACTGGAGGAAAAGTC-3', SEQ ID NO: 8, and 5'-CTTAAACTTCAGTGGCTTGTCTCTG-3', SEQ ID NO: 9. The mouse specific primers used for MECP2-e2 were 5'-CTCACCAGTTCCTGCTTTGATGT-3', SEQ ID NO: 7, and 5'-CTTAAACTTCAGTGGCTTGTCTCTG-3', SEQ ID NO: 9. MECP2 mRNA levels were normalized to Hprt mRNA levels, which were analyzed using primer 5'-CGGGGGACATAAAAGTTATTG-3', SEQ ID NO: 10, and 5'-TGCATTGTTTTACCAGTGTCAA-3', SEQ ID NO: 11. Results are presented in Table 8 below as average normlized MECP2 mRNA levels relative to saline treated wild type (WT) mice. The results show that all of the antisense oligonucleotides tested inhibited MECP2 mRNA and protein levels in the transgenic mice, and human MECP2 mRNA levels were specifically inhibited, whereas mouse MECP2 mRNA levels were not inhibited. Isis Number 628785 was the most potent in the first experiments and was carried forward. Entries listed as "n/a" indicate that the corresponding experiment was not performed.

TABLE 8

MECP2 mRNA and protein levels in transgenic mice following ASO administration

| Mouse/Isis No. | MECP2 protein level | Total MECP2 mRNA | Human mRNA MECP2-e1 isoform | Human mRNA MECP2-e2 isoform | Mouse mRNA MECP2-e1 isoform | Mouse mRNA MECP2-e2 isoform | SEQ ID NO. |
|---|---|---|---|---|---|---|---|
| WT/PBS | 1.0 | 1.0 | 0.0 | 0.0 | 1.0 | 1.3 | |
| TG/PBS | 2.0 | 3.3 | 0.9 | 8.3 | 1.2 | 1.4 | |
| TG/628724 | 1.5 | 2.0 | n/a | n/a | n/a | n/a | 324 |
| TG/628749 | 1.6 | 2.5 | n/a | n/a | n/a | n/a | 103 |
| TG/628772 | 1.7 | 2.7 | n/a | n/a | n/a | n/a | 264 |
| TG/628775 | 1.4 | 2.1 | n/a | n/a | n/a | n/a | 31 |
| TG/628785 | 1.3 | 1.6 | 0.3 | 2.3 | 1.0 | 1.3 | 112 |

Example 4: Effect of Gradual Infusion of Antisense Oligonucleotide Targeting MECP2 In Vivo In order to gradually infuse antisense oligonucleotide into the right ventricle of the brain, micro-osmotic pumps (Alzet model 1004, Durect, Cupertino, CA) were filled with 500 μg of Isis No. 628785 or a control oligonucleotide that is not targeted to MECP2, dissolved in 100 μl saline. The pump was then connected through a plastic catheter to a cannula (Alzet Brain Infusion Kit 3, Durect, Cupertino, CA). The pump was designed to deliver the drug at a rate of 0.11 μl per hour for 28 days. The cannula and pump assembly was primed in sterile saline for two days at 37° C. Mice were anesthetized with isoflurane and placed on a computer-guided stereotaxic instrument (Angle Two Stereotaxic Instrument, Leica Microsystems, Bannockburn, IL). Anesthesia (isoflurane 3%) was continuously delivered via a small face mask. Ketoprofen 5 mg/kg was administered subcutaneously at the initiation of the surgery. After sterilizing the surgical site with betadine and 70% alcohol, a midline incision was made over the skull and a subcutaneous pocket was generated on the back of the animal. Next, the pump was inserted into the pocket and the cannula was stereotactically implanted to deliver the drug in the right ventricle using the following coordinates: AP=−0.2 mm, ML=1 mm, DV=−3 mm. The incision was sutured shut. Carprofen-containing food pellets were provided for 5 days after the surgery. 28 days after the initiation of the treatment the pump was disconnected from the cannula and removed. Two additional weeks were given to the animals to recover.

Isis No. 628785 was gradually infused into the right ventricles of the brains of 7-week old WT or TG mice using the micro-osmotic pumps. Each treatment group consisted of 4 or 5 animals. At the end of the four-week treatment period, western blot was performed as described in Example 3 to analyze MECP2 protein levels at 4, 8, and 12 weeks following the initiation of antisense oligonucleotide treatment. The results are shown in Table 9 below.

TABLE 9

MECP2 protein levels following antisense oligonucleotide infusion

| Mouse/Isis No. | MECP2 protein level (relative to WT/Control) 4 weeks | 8 weeks | 12 weeks |
|---|---|---|---|
| WT/Control | 1.0 | 1.0 | 1.0 |
| TG/Control | 2.9 | 2.7 | 2.3 |
| TG/628785 | 1.6 | 1.8 | 2.2 |

Example 5: Behavioral Effects of Antisense Oligonucleotide Targeting Human MECP2 In Vivo Following infusion of antisense oligonucleotide as described in Example 4, a battery of behavioral assays were performed to assess phenotypic effects of oligonucleotide treatment in TG mice treated with Isis No. 628785 or a control oligonucleotide and WT mice treated with a control oligonucleotide. Each treatment group contained at least 15 animals.

An open field test was performed two weeks and six weeks after the completion of the 4 week infusion by placing mice into the center of an open arena after habituation in the test room (40×40×30 cm). Their behavior was tracked by laser photobeam breaks for 30 min. Horizontal locomotor activity, rearing activity, time spent in the center of the arena, and entries to the center were analyzed using AccuScan Fusion software (Omnitech, Columbus, OH). The results are reported in table 10 below. The results show that the TG mice displayed hypoactivity in the open field test relative to WT mice at both time points, and treatment of TG mice with Isis No. 628785 restored activity close to WT levels.

TABLE 10

Open field test

| Mouse/Isis No. | Horizontal activity (activity counts) 2 weeks | 6 weeks | Rearing episodes 2 weeks | 6 weeks | Time in center (s) 2 weeks | 6 weeks | Entries to center 2 weeks | 6 weeks |
|---|---|---|---|---|---|---|---|---|
| WT/Control | 7134 | 5632 | 277 | 236 | 179 | n/a | 147 | 103 |
| TG/Control | 4116 | 3493 | 156 | 106 | 105 | n/a | 65 | 45 |
| TG/628785 | 5550 | 6114 | 170 | 205 | 93 | n/a | 75 | 99 |

Mice were tested in an elevated plus maze two weeks and six weeks after the completion of the 4 week infusion. After habituation in the test room, mice were placed in the center part of the maze facing one of the two open arms. Mouse behavior was video-tracked for 10 minutes, and the time the mice spent in the open arms and the entries to the open arms were recorded and analyzed using ANY-maze system (Stoelting, Wood Dale, IL). The results are shown in Table 11 below. The results show that the TG mice displayed increased anxiety in the elevated plus maze test relative to WT mice at both time points, and treatment of TG mice with Isis No. 628785 restored anxiety levels close to WT levels.

TABLE 11

| Elevated plus maze | | | | |
|---|---|---|---|---|
| Mouse/Isis | Time in open arms (s) | | Entries into open arms | |
| No. | 2 weeks | 6 weeks | 2 weeks | 6 weeks |
| WT/Control | 139 | 81 | 21 | 12 |
| TG/Control | 76 | 13 | 12 | 2 |
| TG/628785 | 91 | 55 | 11 | 7 |

Mice were assessed in a three-chamber social interaction test three weeks and seven weeks after the completion of the 4 week infusion. The apparatus comprised a clear Plexiglas box with removable partitions that separated the box into three chambers: left, central, and right. In the left and right chambers a cylindrical wire cup was placed with the open side down. Age and gender-matched mice were used as novel partners. Two days before the test, the novel partner mice were habituated to the wire cups (3 inches diameter by 4 inches in height) for 1 hour per day. After habituation in the test room, each mouse was placed in the central chamber and allowed to explore the three chambers for 10 minutes (habituation phase). The time spent in each chamber during the habituation phase was recorded automatically and analyzed using ANY-maze system (Stoelting, Wood Dale, IL). Next, a novel partner mouse was placed under a wire cup in either the left or the right chamber. An inanimate object was placed as a control under the wire cup of the opposite chamber. The location of the novel mouse was randomized between the left and right chambers for each test mouse to control for side preference. The mouse tested was allowed to explore again for an additional 10 minutes. The time spent investigating the novel partner (defined by rearing, sniffing or pawing at the wire cup) and the time spent investigating the inanimate object were measured manually. The results are shown in Table 12 below. The results show that the TG mice displayed hypoactivity and decreased social interaction in the three-chamber social interaction test relative to WT mice at both time points, and treatment of TG mice with Isis No. 628785 restored social interaction with a novel partner to WT levels at the 6 week time point.

TABLE 12

| Three-chamber social interaction test | | | | | | | | |
|---|---|---|---|---|---|---|---|---|
| | Time spent investigating chambers during habituation phase (s) | | | | Time spent investigating novel partner or inanimate object (s) | | | |
| Mouse/Isis | Left | | Right | | Novel partner | | Inanimate object | |
| No. | 2 weeks | 6 weeks | 2 weeks | 6 weeks | 2 weeks | 6 weeks | 2 weeks | 6 weeks |
| WT/Control | 52.4 | n/a | 44.1 | n/a | 141 | 107 | 38 | 37 |
| TG/Control | 35.5 | n/a | 29.9 | n/a | 106 | 59 | 33 | 28 |
| TG/628785 | 37.7 | n/a | 23.0 | n/a | 94 | 106 | 27 | 28 |

Mice were assessed in an accelerating rotarod test three weeks after the completion of the 4 week infusion. After habituation in the test room, motor coordination was measured using an accelerating rotarod apparatus (Ugo Basile, Varese, Italy). Mice were tested 2 consecutive days, 4 trials each, with an interval of 60 minutes between trials to rest. Each trial lasted for a maximum of 10 minutes; mice that never fell were given a measurement of 600 seconds. The rod accelerated from 4 to 40 r.p.m. in the first 5 minutes. The time that it took for each mouse to fall from the rod (latency to fall) was recorded. Results are shown in Table 13 below. The results show that the TG mice displayed increased performance in the rotarod test relative to WT mice, and treatment of TG mice with Isis No. 628785 restored performance to WT levels.

TABLE 13

Accelerating rotarod test

| Mouse/Isis | Latency to fall (s) | |
|---|---|---|
| No. | Day 1 | Day 2 |
| WT/Control | 174 | 300 |
| TG/Control | 275 | 400 |
| TG/628785 | 183 | 282 |

The results in tables 10-13 above show that treatment with Isis No. 628785 targeting MECP2 reversed behavioral phenotypes of the TG mice. The TG mice treated with Isis No. 628785 performed similarly to WT mice in the rotarod test 3-4 weeks after completion of the infusion. By 6-7 weeks after completion of the infusion, the hypoactivity, anxiety-like behaviors and social behavior of the TG mice were reversed, as evidenced by the open field, elevated plus maze and three-chamber tests, respectively.

Example 6: Dose Response of Antisense Oligonucleotide Targeting Human MECP2 in Patient Cells In order to test for a dose dependent effect of Isis No. 628785 on human cells, B-lymphoblast cells from two individuals affected with MECP2-duplication symdrome and age-matched control cells were cultured in suspension in RPMI 1640 medium with L-glutamine, penicillin-streptomycin, and 10% (v/v) fetal bovice serum. A day before transfection, cells were seeded in triplicate for each treatment in 6-well plates at $10^6$ cells per well in a total volume of 2 mL medium. Cells were transfected with Isis No. 628785 or control oligonucleotide at a concentration listed in Table 14 below with TurboFect transfection reagent (Thermo Scientific, Carlsbad, CA). Cells were harvested and RNA was extracted 48 hours after transfection, and MECP2 mRNA levels were analyzed as described in Example 1. Results are presented in Table 14 below as average normlized MECP2 mRNA levels for both patients' cells relative to untreated control cells. The results show that Isis No. 628785 inhibited MECP2 expression in human MECP2 duplication patient cells.

TABLE 14

Antisense oligonucleotide treatment of patient lymphoblasts

| Cell type/Isis No. | Concentration (nM) | Total relative MECP2 mRNA |
|---|---|---|
| Control/Control | 600 | 1.0 |
| Patient/Control | 600 | 3.1 |
| Patient/628785 | 150 | 2.2 |
| Patient/628785 | 300 | 1.6 |
| Patient/628785 | 600 | 1.3 |

Example 7: Reduction of Seizure Activity with an Antisense Oligonucleotide Targeting Human MECP2 In Vivo Without treatment, seizures and accompanying abnormal electrographic discharges occur in MECP2-TG1 mice as they age. In order to test the effect of antisense oligonucleotide treatment on seizure activity in MECP2-TG1 mice, electrocephalography recordings were performed and behavioral seizure activity was observed.

25-35 week old MECP2-TG1 mice that had been treated as described in Example 4 were anaesthetized with isoflurane and mounted in a stereotaxic frame for the surgical implantation of three recording electrodes (Teflon-coated silver wire, 125 μm in diameter) in the subdural space of the left frontal cortex, the left parietal cortex, and the right parietal cortex, with a reference electrode placed in the occipital region of the skull. After 3-5 days of surgical recovery, cortical EEG activity and behavior were recorded for 2 h per day over 3-5 days. Strong electrographic seizure events were typically accompanied by behavioral seizures. FIG. 1 displays representative EEG traces for WT mice, MECP2-TG1 mice without Isis No. 628785 treatment, and MECP2-TG1 mice that received treatment with Isis No. 628785. Treatment of MECP2-TG1 mice with Isis No. 628785 eliminated both behavioral seizures and abnormal EEG discharges.

What is claimed is:

1. A compound, comprising a modified antisense oligonucleotide consisting of 13 to 30 linked nucleosides and having a nucleobase sequence comprising at least 13 consecutive nucleobases of a nucleobase sequence selected from of SEQ ID NOs: 16-24, 112, 190, and 268.

2. The compound of claim 1, wherein the nucleobase sequence of the modified antisense oligonucleotide is at least 80% complementary to SEQ ID NO: 1 or SEQ ID NO: 2.

3. The compound of claim 1, consisting of a single-stranded modified antisense oligonucleotide.

4. The compound of claim 1, wherein at least one internucleoside linkage is a modified internucleoside linkage.

5. The compound of claim 4, wherein at least one modified internucleoside linkage is a phosphorothioate internucleoside linkage.

6. The compound of claim 4, wherein each modified internucleoside linkage is a phosphorothioate internucleoside linkage.

7. The compound of claim 1, wherein at least one internucleoside linkage is a phosphodiester internucleoside linkage.

8. The compound of claim 1, wherein at least one internucleoside linkage is a phosphorothioate linkage and at least one internucleoside linkage is a phosphodiester linkage.

9. The compound of claim 1, wherein at least one nucleoside comprises a modified nucleobase.

10. The compound of claim 9, wherein the modified nucleobase is a 5-methylcytosine.

11. The compound of claim 1, wherein at least one nucleoside of the modified antisense oligonucleotide comprises a modified sugar moiety.

12. The compound of claim 11, wherein the at least one modified sugar moiety is a bicyclic sugar moiety.

13. The compound of claim 12, wherein the bicyclic sugar moiety comprises a 4'-CH(R)-O-2' bridge wherein R is, independently, H, $C_1$-$C_{12}$ alkyl, or a protecting group.

14. The compound of claim 13, wherein R is methyl.

15. The compound of claim 13, wherein R is H.

16. The compound of claim 11, wherein the at least one modified sugar moiety is a 2'-MOE modified sugar moiety.

17. The compound of claim 1, wherein the modified antisense oligonucleotide comprises:

a gap segment consisting of 10 linked deoxynucleosides;
a 5' wing segment consisting of 5 linked nucleosides; and
a 3' wing segment consisting of 5 linked nucleosides;
wherein the gap segment is positioned between the 5' wing segment and the 3' wing segment and wherein each nucleoside of each wing segment comprises a modified sugar.

18. The compound of claim 1, wherein the modified antisense oligonucleotide consists of 20 linked nucleosides.

19. A composition comprising the compound of claim 1 or salt thereof and at least one of a pharmaceutically acceptable carrier or diluent.

20. The compound of claim 1, wherein the modified antisense oligonucleotide consists of 16 to 30 linked nucleosides and has a nucleobase sequence comprising at least 16 consecutive nucleobases of a nucleobase sequence selected from SEQ ID NOs: 16-24, 112, 190, and 268.

21. The compound of claim 1, wherein the modified antisense oligonucleotide consists of 18 to 30 linked nucleosides and has a nucleobase sequence comprising at least 18 consecutive nucleobases of a nucleobase sequence selected from SEQ ID NOs: 16-24, 112, 190, and 268.

22. The compound of claim 1, wherein the modified antisense oligonucleotide consists of 20 to 30 linked nucleosides and has a nucleobase sequence comprising at least 20 consecutive nucleobases of a nucleobase sequence selected from SEQ ID NOs: 16-24, 112, 190, and 268.

23. The compound of claim 2, wherein the nucleobase sequence of the modified antisense oligonucleotide is at least 85% complementary to SEQ ID NO: 1 or SEQ ID NO: 2.

24. The compound of claim 2, wherein the nucleobase sequence of the modified antisense oligonucleotide is at least 95% complementary to SEQ ID NO: 1 or SEQ ID NO: 2.

25. The compound of claim 2, wherein the nucleobase sequence of the modified antisense oligonucleotide is 100% complementary to SEQ ID NO: 1 or SEQ ID NO: 2.

* * * * *

UNITED STATES PATENT AND TRADEMARK OFFICE

CERTIFICATE OF CORRECTION

PATENT NO. : 12,343,357 B2
APPLICATION NO. : 17/408920
DATED : July 1, 2025
INVENTOR(S) : Susan M. Freier It is certified that error appears in the above-identified patent and that said Letters Patent is hereby corrected as shown below:

In the Claims

In Claim 1, Column 249, Lines 50-51, "sequence selected from of SEQ ID NOs:" should be changed to --sequence selected from SEQ ID NOs:--.

Signed and Sealed this
Thirtieth Day of September, 2025

John A. Squires
*Director of the United States Patent and Trademark Office*